US011692036B2

(12) United States Patent
Luo et al.

(10) Patent No.: US 11,692,036 B2
(45) Date of Patent: *Jul. 4, 2023

(54) ANTI-CTLA4 ANTIBODIES AND METHODS OF MAKING AND USING THE SAME

(71) Applicant: Adagene Inc., Grand Cayman (KY)

(72) Inventors: Peter Peizhi Luo, San Mateo, CA (US); Fangyong Du, Jiangsu (CN); Zhongzong Pan, Jiangsu (CN); Guizhong Liu, Jiangsu (CN)

(73) Assignee: Adagene Inc., Grand Cayman (KY)

( * ) Notice: Subject to any disclaimer, the term of this patent is extended or adjusted under 35 U.S.C. 154(b) by 207 days.

This patent is subject to a terminal disclaimer.

(21) Appl. No.: 16/966,844

(22) PCT Filed: Feb. 2, 2019

(86) PCT No.: PCT/CN2019/074580
§ 371 (c)(1),
(2) Date: Jul. 31, 2020

(87) PCT Pub. No.: WO2019/149281
PCT Pub. Date: Aug. 8, 2019

(65) Prior Publication Data
US 2021/0206855 A1 Jul. 8, 2021

(30) Foreign Application Priority Data
Feb. 2, 2018 (WO) ............... PCT/CN2018/075064

(51) Int. Cl.
| C07K 16/28 | (2006.01) |
| A61K 39/00 | (2006.01) |
| C12N 5/10 | (2006.01) |
| A61K 31/713 | (2006.01) |
| C12N 15/63 | (2006.01) |
| A61P 35/00 | (2006.01) |
| C12N 5/0783 | (2010.01) |
| C12N 5/071 | (2010.01) |
| G01N 33/574 | (2006.01) |
| A61K 45/06 | (2006.01) |

(52) U.S. Cl.
CPC ........ C07K 16/2818 (2013.01); A61K 31/713 (2013.01); A61P 35/00 (2018.01); C07K 16/2809 (2013.01); C12N 5/0638 (2013.01); C12N 5/0682 (2013.01); C12N 5/10 (2013.01); C12N 15/63 (2013.01); G01N 33/574 (2013.01); A61K 45/06 (2013.01); A61K 2039/505 (2013.01); A61K 2039/507 (2013.01); C07K 2317/21 (2013.01); C07K 2317/33 (2013.01); C07K 2317/34 (2013.01); C07K 2317/51 (2013.01); C07K 2317/55 (2013.01); C07K 2317/56 (2013.01); C07K 2317/70 (2013.01); C07K 2317/622 (2013.01); C07K 2317/732 (2013.01); C07K 2317/76 (2013.01); C07K 2317/92 (2013.01); C07K 2317/94 (2013.01); C07K 2319/30 (2013.01); C07K 2319/50 (2013.01); C07K 2319/70 (2013.01)

(58) Field of Classification Search
None
See application file for complete search history.

(56) References Cited

U.S. PATENT DOCUMENTS

| 4,399,216 | A | 8/1983 | Axel et al. |
| 4,634,665 | A | 1/1987 | Axel et al. |
| 4,816,567 | A | 3/1989 | Cabilly et al. |
| 5,179,017 | A | 1/1993 | Axel et al. |
| 5,648,237 | A | 7/1997 | Carter |
| 5,677,425 | A | 10/1997 | Axel et al. |
| 5,789,199 | A | 8/1998 | Joly et al. |
| 5,840,523 | A | 11/1998 | Simmons et al. |
| 5,959,177 | A | 9/1999 | Hein et al. |
| 5,994,619 | A | 11/1999 | Axel et al. |
| 6,040,498 | A | 3/2000 | Stomp et al. |
| 6,172,197 | B1 | 1/2001 | McCafferty et al. |
| 6,291,158 | B1 | 9/2001 | Bodmer et al. |
| 6,417,429 | B1 | 7/2002 | Hein et al. |
| 6,420,548 | B1 | 7/2002 | Vezina et al. |
| 6,582,915 | B1 | 6/2003 | Stice et al. |
| 6,593,081 | B1 | 7/2003 | McCafferty et al. |
| 6,696,245 | B2 | 2/2004 | Winter et al. |
| 6,765,087 | B1 | 7/2004 | Casterman et al. |
| 6,838,254 | B1 | 1/2005 | Hamers et al. |
| 6,933,368 | B2 | 8/2005 | Co et al. |

(Continued)

FOREIGN PATENT DOCUMENTS

| AU | 2013202755 A1 | 5/2013 |
| CN | 102482347 A | 5/2012 |

(Continued)

OTHER PUBLICATIONS

Committee for Medicinal Products for Human Use (CHMP). Assessment Report For Yervoy (ipilimumab). CHMP assessment report EMNCHMP/557664/2011. May 19, 2011(May 19, 2011) pp. 1-71.
Ferrara et al., (2018). "Anti-CTLA-4 immunotherapy does not deplete FOXP3+ regulatory T cells (Tregs) in human cancers-Letter," Clin. Cancer Res, 25(11):3468.
Gerspach et al., (2006). "Target-selective activation of a TNF prodrug by urokinase-type plasminogen activator (uPA) mediated proteolytic processing at the cell surface," Cancer Immunol Immunother, 55(12):1590-1600.

(Continued)

Primary Examiner — Laura B Goddard
(74) Attorney, Agent, or Firm — Morrison & Foerster LLP

(57) ABSTRACT

Provided herein are cross-reactive antibodies (or antigen binding fragments thereof) that bind to human CTLA4, activatable antibodies that bind to human CTLA4, nucleic acid molecules encoding the same, pharmaceutical compositions thereof, and methods of their therapeutic use (e.g., for treatment of cancer).

28 Claims, 74 Drawing Sheets

Specification includes a Sequence Listing.

(56) References Cited

U.S. PATENT DOCUMENTS

| | | | |
|---|---|---|---|
| 7,125,978 | B1 | 10/2006 | Vezina et al. |
| 11,078,281 | B2* | 8/2021 | Wang ............ C12N 15/63 |
| 2006/0153808 | A1 | 7/2006 | Cristofanilli et al. |
| 2007/0117809 | A1 | 5/2007 | Fridman |
| 2016/0145604 | A1 | 5/2016 | Du et al. |
| 2019/0241662 | A1 | 8/2019 | Luo et al. |
| 2019/0241886 | A1 | 8/2019 | Luo et al. |

FOREIGN PATENT DOCUMENTS

| | | |
|---|---|---|
| CN | 105296433 A | 2/2016 |
| CN | 106163556 A | 11/2016 |
| EP | 368684 B1 | 3/1994 |
| EP | 338841 A1 | 3/1995 |
| EP | 616640 B1 | 9/2004 |
| WO | WO-1987004462 A1 | 7/1987 |
| WO | WO-1989001036 A1 | 2/1989 |
| WO | WO-2002053596 A2 | 7/2002 |
| WO | WO-2002055106 A2 | 7/2002 |
| WO | WO-2003002609 A2 | 1/2003 |
| WO | WO-2003015711 A2 | 2/2003 |
| WO | WO-2003040170 A2 | 5/2003 |
| WO | WO-2003048731 A2 | 6/2003 |
| WO | WO-2003074678 A2 | 9/2003 |
| WO | WO-2004003019 A2 | 1/2004 |
| WO | WO-2004016805 A2 | 2/2004 |
| WO | WO-2004058821 A2 | 7/2004 |
| WO | WO-2004081026 A2 | 9/2004 |
| WO | WO-2004101790 A1 | 11/2004 |
| WO | WO-2005035572 A2 | 4/2005 |
| WO | WO-2006066568 A2 | 6/2006 |
| WO | WO-2006079372 A1 | 8/2006 |
| WO | WO-2006129163 A1 | 12/2006 |
| WO | WO-2007059782 A1 | 5/2007 |
| WO | WO-2009022215 A1 | 2/2009 |
| WO | WO-2009025846 A2 | 2/2009 |
| WO | WO-2009079335 A1 | 6/2009 |
| WO | WO-2010081173 A2 | 7/2010 |
| WO | WO-2016130898 A2 | 8/2016 |
| WO | WO-2016130986 A1 | 8/2016 |
| WO | WO-2016200645 A1 | 12/2016 |
| WO | WO-2017011580 A3 | 1/2017 |
| WO | WO-2017106372 A1 | 6/2017 |
| WO | WO-2017194265 A1 | 11/2017 |
| WO | WO-2018202649 A1 | 11/2018 |
| WO | WO-2018209701 A1 | 11/2018 |
| WO | WO-2019036842 A1 | 2/2019 |
| WO | WO-2019036855 A1 | 2/2019 |
| WO | WO-2019036856 A1 | 2/2019 |

OTHER PUBLICATIONS

Ha et al., (2019). "Differential control of human Treg and effector T cells in tumor immunity by Fc-engineered anti-CTLA-4 antibody," PNAS, 116(2):609-618.

He et al., (2017). "Remarkably similar CTLA-4 binding properties of therapeutic ipilimumab and tremelimumab antibodies," Oncotarget 8:67129-67139.

Hurwitz et al., (1998). "CTLA-4 blockade synergizes with tumor-derived granulocyte-macrophage colony-stimulating factor for treatment of an experimental mammary carcinoma," Proc Natl Acad Sci USA 95 (17): 10067-71.

International Search Report and Written Opinion of the International Searching Authority dated Apr. 28, 2019, issued for PCT/CN2019/074580, filed Feb. 2, 2019, 15 pages.

International Search Report and Written Opinion of the International Searching Authority dated May 8, 2019, issued for PCT/CN2019/074581, filed Feb. 2, 2019, 13 pages.

International Search Report and Written Opinion of the International Searching Authority dated Nov. 6, 2018, issued for PCT/CN2018/075065, filed Feb. 2, 2018, 16 pages.

International Search Report and Written Opinion of the International Searching Authority dated Nov. 7, 2018, issued for PCT/CN2018/075064, filed Feb. 2, 2018, 17 pages.

Jiang et al., (2004). "Tumor imaging by means of proteolytic activation of cell-penetrating peptides," Proc Natl Acad Sci USA 101 (51):17867-72.

Ke et al., (1997). "Optimal Subsite Occupancy and Design of a Selective Inhibitor of Urokinase," J Biol Chem 272(33):20456-62.

Keler et al., (2003). "Activity and Safety of CTLA-4 Blockade Combined with Vaccines in Cynomolgus," The Journal of Immunology, 171:6251-59.

Kwon et al., (1997). "Manipulation of T cell costimulatory and inhibitory signals for immunotherapy of prostate cancer," Proc Natl Acad Sci USA, 94(15):8099-103.

Lee et al., (2016). "Structural basis of checkpoint blockade by monoclonal antibodies in cancer immunotherapy," Nat Commun 7(13354):1-10.

Lei et al., (1987). "Characterization of the Erwinia carotovora pelB gene and its product pectate lyase," J. Bacteriol., 169:4379-83.

Ramagopal et al., (2017). "Structural basis for cancer immunotherapy by the first-in-class checkpoint inhibitor ipilimumab," Proc Natl Acad Sci USA 114(21): 4223-4232.

Ribas et al., (2007). "Tremelimumab (CP-675, 206), a Cytotoxic T 1-61 Lymphocyte-Associated Antigen 4 Blocking Monoclonal Antibody in Clinical Development for Patients with Cancer," The Oncologist, 12:873-883.

Schwartz et al., (2001). "Structural basis for co-stimulation by the human CTLA-4/B7-2 complex," Nature 410(6828): 604-608.

Sharma et al., (2019; epub 2018). "Anti-CTLA-4 Immunotherapy Does Not Deplete FOXP3+ Regulatory T Cells (Tregs) in Human Cancers," Clin. Cancer Res., 25:1233-1238.

Stamper et al., (2001). "Crystal structure of the B7-1/CTLA-4 complex that inhibits human immune responses," Nature 410(6828): 608-611.

Xu et al., (2012). "Preparation and characterization of a chimeric anti-human CTLA-4 monoclonal antibody," Current Immunology, 5(32):359-364. English Abstract Only.

Yang et al., (1997). "Enhanced induction of antitumor T-cell responses by cytotoxic T Tymphocyte-associated molecule-4 blockade: the effect is manifested only at the restricted tumor-bearing stages," Cancer Res 57(18):4036-41.

* cited by examiner

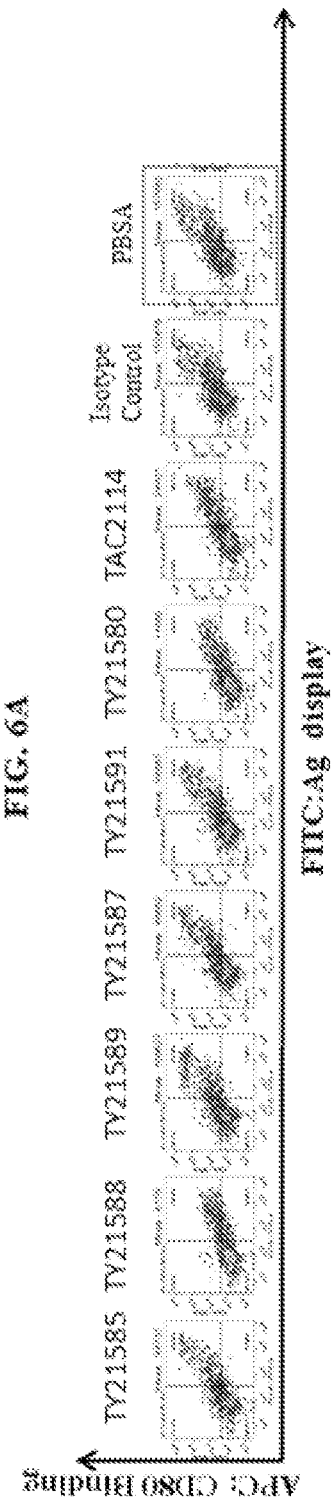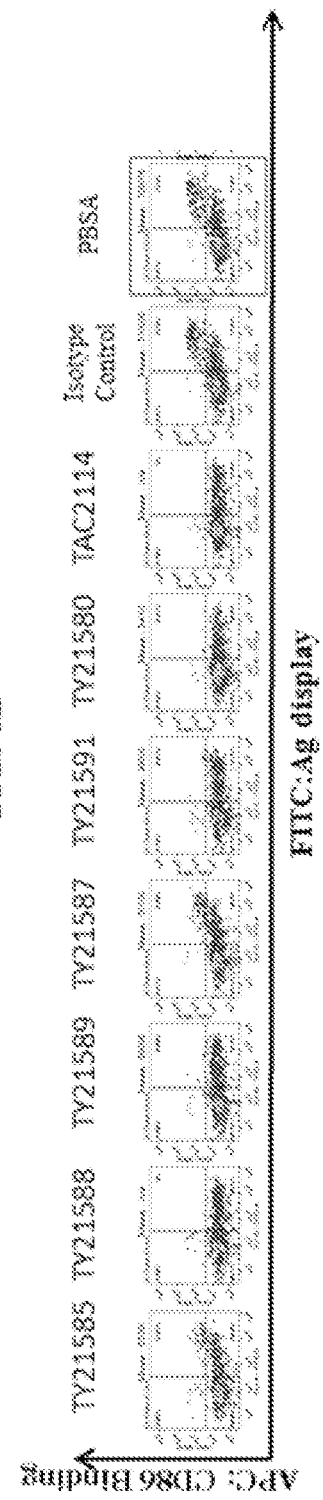

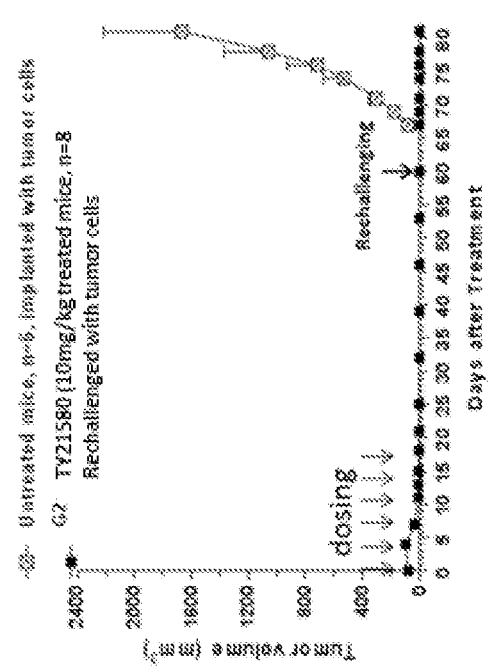
FIG. 15A
FIG. 15C
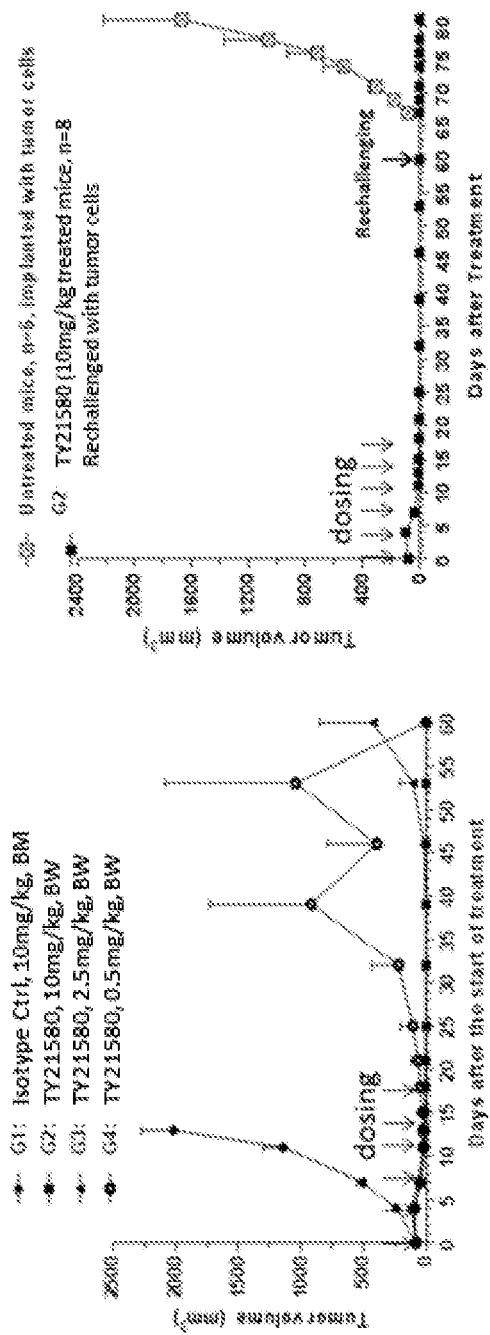
FIG. 15B
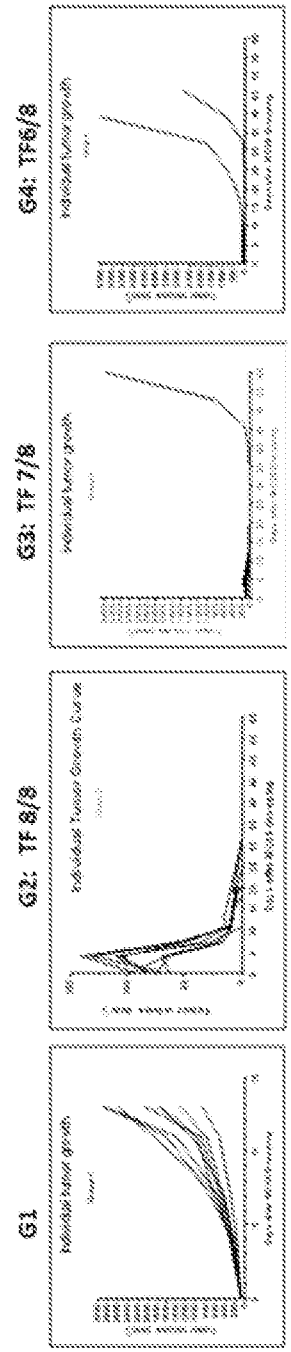

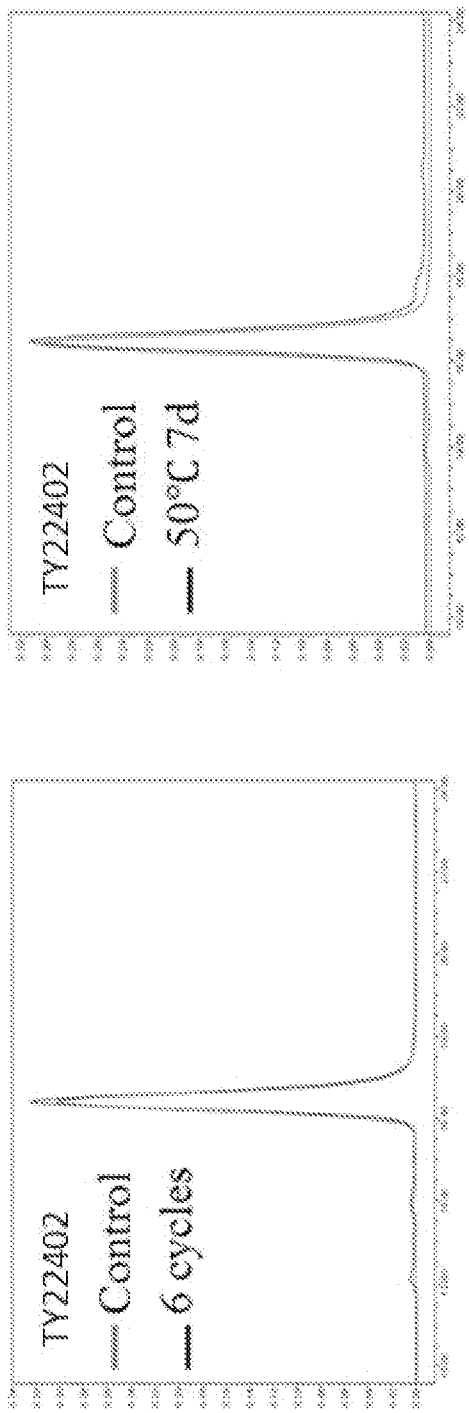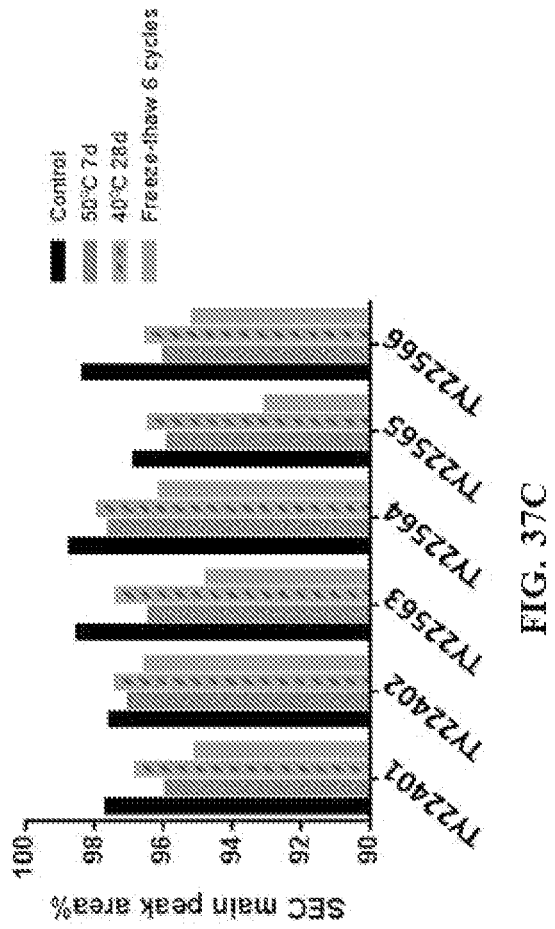
FIG. 37A
FIG. 37B
FIG. 37C

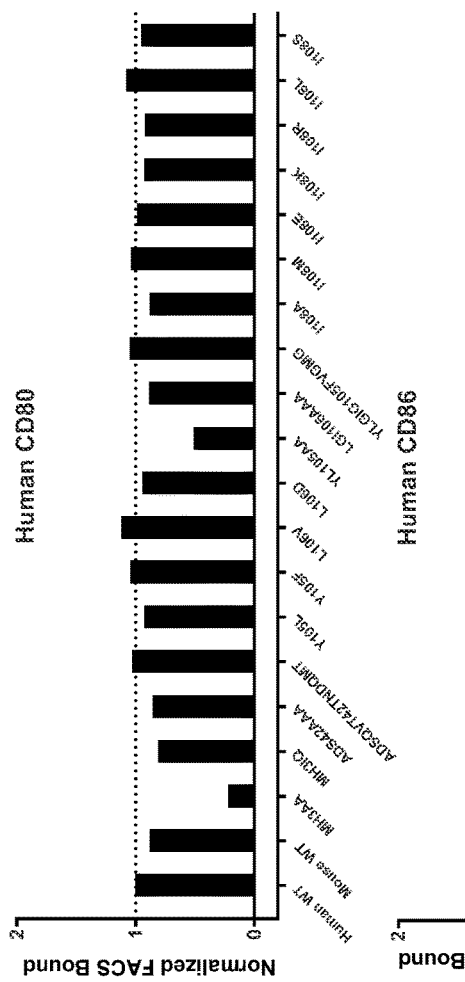
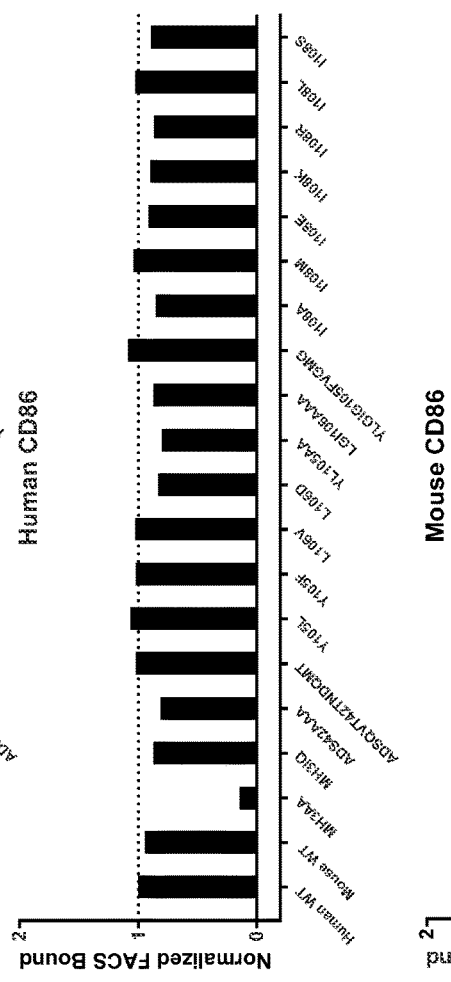
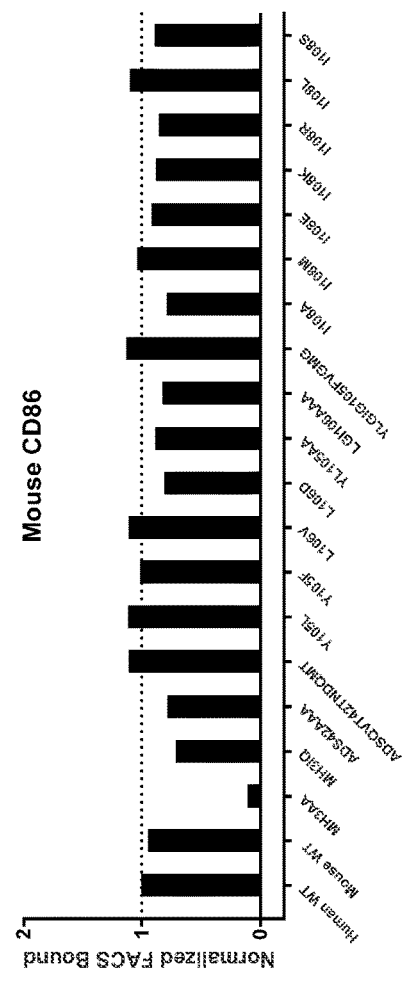
FIG. 56C
FIG. 56D
FIG. 56E

SEQUENCE LISTING

```
<160> NUMBER OF SEQ ID NOS: 230

<210> SEQ ID NO 1
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Phe or Tyr
<220> FEATURE:
<221> NAME/KEY: VARIANT
<222> LOCATION: 5
<223> OTHER INFORMATION: Xaa = Asp or Gly
<220> FEATURE:
<221> NAME/KEY: VARIANT
<222> LOCATION: 7
<223> OTHER INFORMATION: Xaa = Ala, Gly or Trp

<400> SEQUENCE: 1

Xaa Thr Phe Ser Xaa Tyr Xaa Ile His Trp Val
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Ser or Thr
<220> FEATURE:
<221> NAME/KEY: VARIANT
<222> LOCATION: 7, 8
<223> OTHER INFORMATION: Xaa = His or Tyr
<220> FEATURE:
<221> NAME/KEY: VARIANT
<222> LOCATION: 10
<223> OTHER INFORMATION: Xaa = Ala, Asp, or Ser

<400> SEQUENCE: 2

Tyr Ser Ile Xaa Ser Gly Xaa Xaa Trp Xaa Trp Ile
1               5                   10
```

```
<210> SEQ ID NO 3
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 11
<223> OTHER INFORMATION: Xaa = Gly or Ser

<400> SEQUENCE: 3

Phe Ser Leu Ser Thr Gly Gly Val Ala Val Xaa Trp Ile
1               5                   10

<210> SEQ ID NO 4
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Asp or Glu
<220> FEATURE:
<221> NAME/KEY: VARIANT
<222> LOCATION: 5
<223> OTHER INFORMATION: Xaa = Ser or Tyr
<220> FEATURE:
<221> NAME/KEY: VARIANT
<222> LOCATION: 14
<223> OTHER INFORMATION: Xaa = Pro or Gln

<400> SEQUENCE: 4

Ile Gly Xaa Ile Xaa His Ser Gly Ser Thr Tyr Tyr Ser Xaa Ser Leu
1               5                   10                  15

Lys Ser Arg Val
            20

<210> SEQ ID NO 5
<211> LENGTH: 21
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Ile or Trp
<220> FEATURE:
<221> NAME/KEY: VARIANT
<222> LOCATION: 8, 10
<223> OTHER INFORMATION: Xaa = Gly or Ser
<220> FEATURE:
<221> NAME/KEY: VARIANT
<222> LOCATION: 12
<223> OTHER INFORMATION: Xaa = Lys or Asn

<400> SEQUENCE: 5

Ile Gly Xaa Ile Ser Pro Ser Xaa Gly Xaa Thr Xaa Tyr Ala Gln Lys
1               5                   10                  15

Phe Gln Gly Arg Val
            20

<210> SEQ ID NO 6
<211> LENGTH: 21
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Ala, Gly, or Ser
<220> FEATURE:
<221> NAME/KEY: VARIANT
<222> LOCATION: 7
<223> OTHER INFORMATION: Xaa = Ser or Tyr
<220> FEATURE:
<221> NAME/KEY: VARIANT
<222> LOCATION: 9
<223> OTHER INFORMATION: Xaa = Gly or Ser
<220> FEATURE:
<221> NAME/KEY: VARIANT
<222> LOCATION: 10
<223> OTHER INFORMATION: Xaa = Ser or Thr

<400> SEQUENCE: 6

Val Ser Xaa Ile Ser Gly Xaa Gly Xaa Xaa Thr Tyr Tyr Ala Asp Ser
1               5                   10                  15

Val Lys Gly Arg Phe
            20

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Gly, Arg, or Ser
<220> FEATURE:
<221> NAME/KEY: VARIANT
<222> LOCATION: 4
<223> OTHER INFORMATION: Xaa = Ala, Ile, or Tyr
<220> FEATURE:
<221> NAME/KEY: VARIANT
<222> LOCATION: 5
<223> OTHER INFORMATION: Xaa = Asp, Val, or Tyr
<220> FEATURE:
<221> NAME/KEY: VARIANT
<222> LOCATION: 6
<223> OTHER INFORMATION: Xaa = Ala, Glu, or Tyr
<220> FEATURE:
<221> NAME/KEY: VARIANT
<222> LOCATION: 9
<223> OTHER INFORMATION: Xaa = Ile or Tyr

<400> SEQUENCE: 7

Ala Arg Xaa Xaa Xaa Xaa Phe Asp Xaa
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Asp or Leu
<220> FEATURE:
<221> NAME/KEY: VARIANT
<222> LOCATION: 5
<223> OTHER INFORMATION: Xaa = Phe or Tyr
<220> FEATURE:
<221> NAME/KEY: VARIANT
<222> LOCATION: 10
<223> OTHER INFORMATION: Xaa = Val or Tyr
```

```
<400> SEQUENCE: 8

Ala Arg Xaa Gly Xaa Gly Tyr Phe Asp Xaa
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Leu or Arg
<220> FEATURE:
<221> NAME/KEY: VARIANT
<222> LOCATION: 4
<223> OTHER INFORMATION: Xaa = Ile or Pro
<220> FEATURE:
<221> NAME/KEY: VARIANT
<222> LOCATION: 5
<223> OTHER INFORMATION: Xaa = Ala or Tyr
<220> FEATURE:
<221> NAME/KEY: VARIANT
<222> LOCATION: 6
<223> OTHER INFORMATION: Xaa = Ser or Thr
<220> FEATURE:
<221> NAME/KEY: VARIANT
<222> LOCATION: 8
<223> OTHER INFORMATION: Xaa = Thr or Tyr
<220> FEATURE:
<221> NAME/KEY: VARIANT
<222> LOCATION: 9
<223> OTHER INFORMATION: Xaa = Ala or Tyr

<400> SEQUENCE: 9

Ala Arg Xaa Xaa Xaa Xaa Ala Xaa Xaa Phe Asp Tyr
1               5                   10

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Ile or Val
<220> FEATURE:
<221> NAME/KEY: VARIANT
<222> LOCATION: 5
<223> OTHER INFORMATION: Xaa = Ala or His
<220> FEATURE:
<221> NAME/KEY: VARIANT
<222> LOCATION: 6
<223> OTHER INFORMATION: Xaa = Pro or Ser
<220> FEATURE:
<221> NAME/KEY: VARIANT
<222> LOCATION: 13
<223> OTHER INFORMATION: Xaa = Asp or Tyr
<220> FEATURE:
<221> NAME/KEY: VARIANT
<222> LOCATION: 17
<223> OTHER INFORMATION: Xaa = Phe or Val

<400> SEQUENCE: 10

Ala Arg Asp Xaa Xaa Xaa Gly Ser Ser Gly Tyr Tyr Xaa Gly Phe Asp
1               5                   10                  15

Xaa
```

```
<210> SEQ ID NO 11
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5, 7
<223> OTHER INFORMATION: Xaa = Gly or Ser
<220> FEATURE:
<221> NAME/KEY: VARIANT
<222> LOCATION: 6
<223> OTHER INFORMATION: Xaa = Ile or Val
<220> FEATURE:
<221> NAME/KEY: VARIANT
<222> LOCATION: 9
<223> OTHER INFORMATION: Xaa = Ser or Tyr
<220> FEATURE:
<221> NAME/KEY: VARIANT
<222> LOCATION: 11
<223> OTHER INFORMATION: Xaa = Ala or Asn

<400> SEQUENCE: 11

Arg Ala Ser Gln Xaa Xaa Xaa Ser Xaa Leu Xaa
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Ser or Thr
<220> FEATURE:
<221> NAME/KEY: VARIANT
<222> LOCATION: 7
<223> OTHER INFORMATION: Xaa = Phe, Arg, or Ser
<220> FEATURE:
<221> NAME/KEY: VARIANT
<222> LOCATION: 8
<223> OTHER INFORMATION: Xaa = Gly or Ser
<220> FEATURE:
<221> NAME/KEY: VARIANT
<222> LOCATION: 10
<223> OTHER INFORMATION: Xaa = Phe or Tyr

<400> SEQUENCE: 12

Arg Ala Ser Gln Xaa Val Xaa Xaa Arg Xaa Leu Ala
1               5                   10

<210> SEQ ID NO 13
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Glu or Gln
<220> FEATURE:
<221> NAME/KEY: VARIANT
<222> LOCATION: 9
<223> OTHER INFORMATION: Xaa = Asp, Phe, His, or Tyr
<220> FEATURE:
<221> NAME/KEY: VARIANT
<222> LOCATION: 11
<223> OTHER INFORMATION: Xaa = Phe, Ile, or Lys
<220> FEATURE:
<221> NAME/KEY: VARIANT
<222> LOCATION: 15
```

<223> OTHER INFORMATION: Xaa = Ala, Asp, or His

<400> SEQUENCE: 13

Arg Ala Ser Xaa Ser Val Asp Phe Xaa Gly Xaa Ser Phe Leu Xaa
1               5                   10                  15

<210> SEQ ID NO 14
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Ala or Asp
<220> FEATURE:
<221> NAME/KEY: VARIANT
<222> LOCATION: 4
<223> OTHER INFORMATION: Xaa = Asn, Ser or Thr
<220> FEATURE:
<221> NAME/KEY: VARIANT
<222> LOCATION: 5
<223> OTHER INFORMATION: Xaa = Leu or Arg
<220> FEATURE:
<221> NAME/KEY: VARIANT
<222> LOCATION: 6
<223> OTHER INFORMATION: Xaa = Ala, Glu, or Gln
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 9
<223> OTHER INFORMATION: Xaa = Ile or Val

<400> SEQUENCE: 14

Xaa Ala Ser Xaa Xaa Xaa Xaa Gly Xaa
1               5

<210> SEQ ID NO 15
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Glu, Gln, or Val
<220> FEATURE:
<221> NAME/KEY: VARIANT
<222> LOCATION: 4
<223> OTHER INFORMATION: Xaa = His or Gln
<220> FEATURE:
<221> NAME/KEY: VARIANT
<222> LOCATION: 5
<223> OTHER INFORMATION: Xaa = Ala, Gly, His, Arg, or Ser
<220> FEATURE:
<221> NAME/KEY: VARIANT
<222> LOCATION: 6
<223> OTHER INFORMATION: Xaa = Asp, Leu, Ser, or Tyr
<220> FEATURE:
<221> NAME/KEY: VARIANT
<222> LOCATION: 7
<223> OTHER INFORMATION: Xaa = Glu, Gly, Pro, Gln, or Ser
<220> FEATURE:
<221> NAME/KEY: VARIANT
<222> LOCATION: 8
<223> OTHER INFORMATION: Xaa = Leu, Thr, Val, or Trp
<220> FEATURE:
<221> NAME/KEY: VARIANT
<222> LOCATION: 10
<223> OTHER INFORMATION: Xaa = Phe, Leu, Pro, Trp, or Tyr

```
<400> SEQUENCE: 15

Tyr Cys Xaa Xaa Xaa Xaa Xaa Xaa Pro Xaa Thr
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Ser or Tyr
<220> FEATURE:
<221> NAME/KEY: VARIANT
<222> LOCATION: 6
<223> OTHER INFORMATION: Xaa = Asp or Tyr
<220> FEATURE:
<221> NAME/KEY: VARIANT
<222> LOCATION: 7
<223> OTHER INFORMATION: Xaa = Gln or Tyr

<400> SEQUENCE: 16

Tyr Cys Gln Gln Xaa Xaa Xaa Trp Pro Pro Trp Thr
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = His or Gln
<220> FEATURE:
<221> NAME/KEY: VARIANT
<222> LOCATION: 6
<223> OTHER INFORMATION: Xaa = Thr or Val
<220> FEATURE:
<221> NAME/KEY: VARIANT
<222> LOCATION: 11
<223> OTHER INFORMATION: Xaa = Glu or Val

<400> SEQUENCE: 17

Tyr Cys Gln Xaa Tyr Xaa Ser Ser Pro Pro Xaa Tyr Thr
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic Construct

<400> SEQUENCE: 18

Phe Thr Phe Ser Asp Tyr Ala Ile His Trp Val
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic Construct

<400> SEQUENCE: 19
```

Tyr Ser Ile Thr Ser Gly Tyr Tyr Trp Ala Trp Ile
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic Construct

<400> SEQUENCE: 20

Phe Thr Phe Ser Asp Tyr Gly Ile His Trp Val
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic Construct

<400> SEQUENCE: 21

Tyr Ser Ile Ser Ser Gly Tyr His Trp Asp Trp Ile
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic Construct

<400> SEQUENCE: 22

Phe Thr Phe Ser Asp Tyr Trp Ile His Trp Val
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic Construct

<400> SEQUENCE: 23

Tyr Ser Ile Ser Ser Gly Tyr His Trp Ser Trp Ile
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Synthetic Construct

<400> SEQUENCE: 24

Phe Ser Leu Ser Thr Gly Gly Val Ala Val Ser Trp Ile
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic Construct

<400> SEQUENCE: 25

Phe Ser Leu Ser Thr Gly Gly Val Ala Val Gly Trp Ile

```
1               5                   10
```

<210> SEQ ID NO 26
<211> LENGTH: 11
<212> TYPE: PRT
<213> ORGANISM: Artificial Sequence
<220> FEATURE:
<223> OTHER INFORMATION: Synthetic Construct

<400> SEQUENCE: 26

```
Phe Thr Phe Ser Gly Tyr Ala Ile His Trp Val
1               5                   10
```

<210> SEQ ID NO 27
<211> LENGTH: 11
<212> TYPE: PRT
<213> ORGANISM: Artificial Sequence
<220> FEATURE:
<223> OTHER INFORMATION: Synthetic Construct

<400> SEQUENCE: 27

```
Tyr Thr Phe Ser Gly Tyr Gly Ile His Trp Val
1               5                   10
```

<210> SEQ ID NO 28
<211> LENGTH: 11
<212> TYPE: PRT
<213> ORGANISM: Artificial Sequence
<220> FEATURE:
<223> OTHER INFORMATION: Synthetic Construct

<400> SEQUENCE: 28

```
Tyr Thr Phe Ser Gly Tyr Ala Ile His Trp Val
1               5                   10
```

<210> SEQ ID NO 29
<211> LENGTH: 12
<212> TYPE: PRT
<213> ORGANISM: Artificial Sequence
<220> FEATURE:
<223> OTHER INFORMATION: Synthetic Construct

<400> SEQUENCE: 29

```
Tyr Ser Ile Thr Ser Gly His Tyr Trp Ser Trp Ile
1               5                   10
```

<210> SEQ ID NO 30
<211> LENGTH: 21
<212> TYPE: PRT
<213> ORGANISM: Artificial Sequence
<220> FEATURE:
<223> OTHER INFORMATION: Synthetic Construct

<400> SEQUENCE: 30

```
Ile Gly Ile Ile Ser Pro Ser Ser Gly Ser Thr Asn Tyr Ala Gln Lys
1               5                   10                  15

Phe Gln Gly Arg Val
            20
```

<210> SEQ ID NO 31
<211> LENGTH: 21
<212> TYPE: PRT
<213> ORGANISM: Artificial Sequence
<220> FEATURE:
<223> OTHER INFORMATION: Synthetic Construct

<400> SEQUENCE: 31

```
Val Ser Ser Ile Ser Gly Ser Gly Ser Thr Thr Tyr Tyr Ala Asp Ser
1               5                   10                  15

Val Lys Gly Arg Phe
            20

<210> SEQ ID NO 32
<211> LENGTH: 20
<212> TYPE: PRT
<213> ORGANISM: Artificial Sequence
<220> FEATURE:
<223> OTHER INFORMATION: Synthetic Construct

<400> SEQUENCE: 32

Ile Gly Glu Ile Tyr His Ser Gly Ser Thr Tyr Tyr Ser Pro Ser Leu
1               5                   10                  15

Lys Ser Arg Val
            20

<210> SEQ ID NO 33
<211> LENGTH: 21
<212> TYPE: PRT
<213> ORGANISM: Artificial Sequence
<220> FEATURE:
<223> OTHER INFORMATION: Synthetic Construct

<400> SEQUENCE: 33

Val Ser Gly Ile Ser Gly Tyr Gly Gly Ser Thr Tyr Tyr Ala Asp Ser
1               5                   10                  15

Val Lys Gly Arg Phe
            20

<210> SEQ ID NO 34
<211> LENGTH: 21
<212> TYPE: PRT
<213> ORGANISM: Artificial Sequence
<220> FEATURE:
<223> OTHER INFORMATION: Synthetic Construct

<400> SEQUENCE: 34

Ile Gly Trp Ile Ser Pro Ser Gly Gly Thr Lys Tyr Ala Gln Lys
1               5                   10                  15

Phe Gln Gly Arg Val
            20

<210> SEQ ID NO 35
<211> LENGTH: 20
<212> TYPE: PRT
<213> ORGANISM: Artificial Sequence
<220> FEATURE:
<223> OTHER INFORMATION: Synthetic Construct

<400> SEQUENCE: 35

Leu Ala Arg Ile Asp Trp Asp Asp Asp Lys Tyr Tyr Ser Thr Ser Leu
1               5                   10                  15

Lys Ser Arg Leu
            20

<210> SEQ ID NO 36
<211> LENGTH: 21
<212> TYPE: PRT
<213> ORGANISM: Artificial Sequence
<220> FEATURE:
<223> OTHER INFORMATION: Synthetic Construct
```

```
<400> SEQUENCE: 36

Val Ser Ala Ile Ser Gly Tyr Gly Ser Thr Thr Tyr Tyr Ala Asp Ser
1               5                   10                  15

Val Lys Gly Arg Phe
            20

<210> SEQ ID NO 37
<211> LENGTH: 21
<212> TYPE: PRT
<213> ORGANISM: Artificial Sequence
<220> FEATURE:
<223> OTHER INFORMATION: Synthetic Construct

<400> SEQUENCE: 37

Ile Gly Ile Ile Ser Pro Ser Gly Gly Thr Lys Tyr Ala Gln Lys
1               5                   10                  15

Phe Gln Gly Arg Val
            20

<210> SEQ ID NO 38
<211> LENGTH: 21
<212> TYPE: PRT
<213> ORGANISM: Artificial Sequence
<220> FEATURE:
<223> OTHER INFORMATION: Synthetic Construct

<400> SEQUENCE: 38

Ile Gly Ile Ile Ser Pro Ser Gly Gly Ser Thr Lys Tyr Ala Gln Lys
1               5                   10                  15

Phe Gln Gly Arg Val
            20

<210> SEQ ID NO 39
<211> LENGTH: 20
<212> TYPE: PRT
<213> ORGANISM: Artificial Sequence
<220> FEATURE:
<223> OTHER INFORMATION: Synthetic Construct

<400> SEQUENCE: 39

Ile Gly Asp Ile Ser His Ser Gly Ser Thr Tyr Tyr Ser Gln Ser Leu
1               5                   10                  15

Lys Ser Arg Val
            20

<210> SEQ ID NO 40
<211> LENGTH: 17
<212> TYPE: PRT
<213> ORGANISM: Artificial Sequence
<220> FEATURE:
<223> OTHER INFORMATION: Synthetic Construct

<400> SEQUENCE: 40

Ala Arg Asp Ile His Ser Gly Ser Ser Gly Tyr Tyr Tyr Gly Phe Asp
1               5                   10                  15

Val

<210> SEQ ID NO 41
<211> LENGTH: 10
<212> TYPE: PRT
<213> ORGANISM: Artificial Sequence
<220> FEATURE:
<223> OTHER INFORMATION: Synthetic Construct
```

```
<400> SEQUENCE: 41

Ala Arg Asp Gly Phe Gly Tyr Phe Asp Tyr
1               5                   10

<210> SEQ ID NO 42
<211> LENGTH: 17
<212> TYPE: PRT
<213> ORGANISM: Artificial Sequence
<220> FEATURE:
<223> OTHER INFORMATION: Synthetic Construct

<400> SEQUENCE: 42

Ala Arg Asp Val Ala Pro Gly Ser Ser Gly Tyr Tyr Asp Gly Phe Asp
1               5                   10                  15

Phe

<210> SEQ ID NO 43
<211> LENGTH: 13
<212> TYPE: PRT
<213> ORGANISM: Artificial Sequence
<220> FEATURE:
<223> OTHER INFORMATION: Synthetic Construct

<400> SEQUENCE: 43

Ala Arg His Ser Tyr Tyr Gly Ser Gly Asn Phe Asp Tyr
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Synthetic Construct

<400> SEQUENCE: 44

Ala Arg Gly Ala Tyr Glu Phe Asp Tyr
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Construct

<400> SEQUENCE: 45

Ala Arg Ser Tyr Val Tyr Phe Asp Tyr
1               5

<210> SEQ ID NO 46
<211> LENGTH: 12
<212> TYPE: PRT
<213> ORGANISM: Artificial Sequence
<220> FEATURE:
<223> OTHER INFORMATION: Synthetic Construct

<400> SEQUENCE: 46

Ala Arg Arg Ile Ala Thr Ala Thr Tyr Phe Asp Tyr
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Synthetic Construct
```

```
<400> SEQUENCE: 47

Ala Arg Leu Pro Tyr Ser Ala Tyr Ala Phe Asp Tyr
1               5                   10

<210> SEQ ID NO 48
<211> LENGTH: 7
<212> TYPE: PRT
<213> ORGANISM: Artificial Sequence
<220> FEATURE:
<223> OTHER INFORMATION: Synthetic Construct

<400> SEQUENCE: 48

Ala Arg His Pro Phe Ala Tyr
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic Construct

<400> SEQUENCE: 49

Ala Arg Arg Ile Asp Ala Phe Asp Ile
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic Construct

<400> SEQUENCE: 50

Ala Arg Leu Tyr Asp Val Ala Tyr
1               5

<210> SEQ ID NO 51
<211> LENGTH: 10
<212> TYPE: PRT
<213> ORGANISM: Artificial Sequence
<220> FEATURE:
<223> OTHER INFORMATION: Synthetic Construct

<400> SEQUENCE: 51

Ala Arg Leu Gly Tyr Gly Tyr Phe Asp Val
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic Construct

<400> SEQUENCE: 52

Ala Arg Gly Ser Arg Thr Gly Tyr Phe Asp Tyr
1               5                   10

<210> SEQ ID NO 53
<211> LENGTH: 15
<212> TYPE: PRT
<213> ORGANISM: Artificial Sequence
<220> FEATURE:
<223> OTHER INFORMATION: Synthetic Construct
```

<400> SEQUENCE: 53

Arg Ala Ser Glu Ser Val Asp Phe Phe Gly Ile Ser Phe Leu Ala
1               5                   10                  15

<210> SEQ ID NO 54
<211> LENGTH: 10
<212> TYPE: PRT
<213> ORGANISM: Artificial Sequence
<220> FEATURE:
<223> OTHER INFORMATION: Synthetic Construct

<400> SEQUENCE: 54

Ser Ala Ser Ser Ser Val Ser Tyr Val Tyr
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Synthetic Construct

<400> SEQUENCE: 55

Arg Ala Ser Gln Gly Ile Gly Ser Ser Leu Ala
1               5                   10

<210> SEQ ID NO 56
<211> LENGTH: 15
<212> TYPE: PRT
<213> ORGANISM: Artificial Sequence
<220> FEATURE:
<223> OTHER INFORMATION: Synthetic Construct

<400> SEQUENCE: 56

Arg Ala Ser Glu Ser Val Asp Phe Phe Gly Lys Ser Phe Leu His
1               5                   10                  15

<210> SEQ ID NO 57
<211> LENGTH: 12
<212> TYPE: PRT
<213> ORGANISM: Artificial Sequence
<220> FEATURE:
<223> OTHER INFORMATION: Synthetic Construct

<400> SEQUENCE: 57

Arg Ala Ser Gln Ser Val Ser Ser Arg Phe Leu Ala
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetic Construct

<400> SEQUENCE: 58

Arg Ala Ser Gln Ser Val Arg Gly Arg Phe Leu Ala
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic Construct

<400> SEQUENCE: 59

Arg Ala Ser Gln Thr Val Phe Ser Arg Tyr Leu Ala
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Synthetic Construct

<400> SEQUENCE: 60

Arg Ala Ser Gln Gly Val Ser Ser Tyr Leu Ala
1               5                   10

<210> SEQ ID NO 61
<211> LENGTH: 15
<212> TYPE: PRT
<213> ORGANISM: Artificial Sequence
<220> FEATURE:
<223> OTHER INFORMATION: Synthetic Construct

<400> SEQUENCE: 61

Arg Ala Ser Gln Ser Val Asp Phe Tyr Gly Ile Ser Phe Leu Asp
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Synthetic Construct

<400> SEQUENCE: 62

Arg Ala Ser Gln Ser Val Asp Phe Asp Gly Phe Ser Phe Leu His
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Synthetic Construct

<400> SEQUENCE: 63

Arg Ala Ser Gln Ser Val Asp Phe His Gly Lys Ser Phe Leu His
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Synthetic Construct

<400> SEQUENCE: 64

Arg Ala Ser Gln Ser Val Asp Phe Tyr Gly Ile Ser Phe Leu His
1               5                   10                  15

<210> SEQ ID NO 65
<211> LENGTH: 11
<212> TYPE: PRT
<213> ORGANISM: Artificial Sequence
<220> FEATURE:
<223> OTHER INFORMATION: Synthetic Construct

<400> SEQUENCE: 65

```
Arg Ala Ser Gln Ser Ile Ser Ser Tyr Leu Asn
1               5                   10

<210> SEQ ID NO 66
<211> LENGTH: 9
<212> TYPE: PRT
<213> ORGANISM: Artificial Sequence
<220> FEATURE:
<223> OTHER INFORMATION: Synthetic Construct

<400> SEQUENCE: 66

Asp Ala Ser Asn Arg Ala Thr Gly Ile
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic Construct

<400> SEQUENCE: 67

Asp Ala Ser Ser Leu Glu Ser Gly Val
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic Construct

<400> SEQUENCE: 68

Asp Ala Ser Asn Leu Glu Thr Gly Val
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic Construct

<400> SEQUENCE: 69

Ala Ala Ser Thr Leu Gln Ser Gly Val
1               5

<210> SEQ ID NO 70
<211> LENGTH: 13
<212> TYPE: PRT
<213> ORGANISM: Artificial Sequence
<220> FEATURE:
<223> OTHER INFORMATION: Synthetic Construct

<400> SEQUENCE: 70

Tyr Cys Gln His Tyr Thr Ser Ser Pro Pro Val Tyr Thr
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Synthetic Construct

<400> SEQUENCE: 71

Tyr Cys Val Gln Gly Leu Gln Thr Pro Trp Thr
```

```
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Synthetic Construct

<400> SEQUENCE: 72

Tyr Cys Gln Gln Tyr Asp Gln Trp Pro Pro Trp Thr
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Synthetic Construct

<400> SEQUENCE: 73

Tyr Cys Gln Gln Ser Tyr Ser Trp Pro Pro Thr
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthetic Construct

<400> SEQUENCE: 74

Tyr Cys Gln Gln Ser Tyr Pro Thr Pro Leu Thr
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Synthetic Construct

<400> SEQUENCE: 75

Tyr Cys Gln Gln Ser Ser Ser Trp Pro Pro Thr
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Synthetic Construct

<400> SEQUENCE: 76

Tyr Cys Gln Gln Ser Tyr Tyr Trp Pro Pro Trp Thr
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Synthetic Construct

<400> SEQUENCE: 77

Tyr Cys Gln His His Tyr Gly Thr Pro Leu Thr
1               5                   10
```

<210> SEQ ID NO 78
<211> LENGTH: 13
<212> TYPE: PRT
<213> ORGANISM: Artificial Sequence
<220> FEATURE:
<223> OTHER INFORMATION: Synthetic Construct

<400> SEQUENCE: 78

Tyr Cys Gln Gln Tyr Val Ser Ser Pro Pro Glu Tyr Thr
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Synthetic Construct

<400> SEQUENCE: 79

Tyr Cys Gln Gln Arg Asp Ser Trp Pro Tyr Thr
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Synthetic Construct

<400> SEQUENCE: 80

Tyr Cys Glu Gln Ser Leu Glu Val Pro Phe Thr
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Synthetic Construct

<400> SEQUENCE: 81

Tyr Cys Val Gln Ala Leu Gln Leu Pro Leu Thr
1               5                   10

<210> SEQ ID NO 82
<211> LENGTH: 124
<212> TYPE: PRT
<213> ORGANISM: Artificial Sequence
<220> FEATURE:
<223> OTHER INFORMATION: Synthetic Construct

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Ile His Trp Val Arg Gln Ala Pro Gly Lys Gly Leu Glu Trp Ile
        35                  40                  45

Gly Ile Ile Ser Pro Ser Ser Gly Ser Thr Asn Tyr Ala Gln Lys Phe
    50                  55                  60

Gln Gly Arg Val Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys 85                  90                  95

Ala Arg Asp Ile His Ser Gly Ser Ser Gly Tyr Tyr Tyr Gly Phe Asp
            100                 105                 110

Val Trp Gly Gln Gly Thr Leu Val Thr Val Ser Ser
            115                 120

<210> SEQ ID NO 83
<211> LENGTH: 118
<212> TYPE: PRT
<213> ORGANISM: Artificial Sequence
<220> FEATURE:
<223> OTHER INFORMATION: Synthetic Construct

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Ser Gly
            20                  25                  30

Tyr Tyr Trp Ala Trp Ile Arg Gln Ala Pro Gly Lys Gly Leu Glu Trp
        35                  40                  45

Val Ser Ser Ile Ser Gly Ser Gly Ser Thr Thr Tyr Tyr Ala Asp Ser
50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Asp Gly Phe Gly Tyr Phe Asp Tyr Trp Gly Gln Gly Thr
            100                 105                 110

Leu Val Thr Val Ser Ser
            115

<210> SEQ ID NO 84
<211> LENGTH: 123
<212> TYPE: PRT
<213> ORGANISM: Artificial Sequence
<220> FEATURE:
<223> OTHER INFORMATION: Synthetic Construct

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Ile
        35                  40                  45

Gly Glu Ile Tyr His Ser Gly Ser Thr Tyr Tyr Ser Pro Ser Leu Lys
50                  55                  60

Ser Arg Val Thr Ile Ser Arg Asp Asn Ser Lys Asn Thr Leu Tyr Leu
65                  70                  75                  80

Gln Leu Asn Ser Leu Arg Ala Glu Asp Thr Ala Val Tyr Tyr Cys Ala
                85                  90                  95

Arg Asp Val Ala Pro Gly Ser Ser Gly Tyr Tyr Asp Gly Phe Asp Phe
            100                 105                 110

Trp Gly Gln Gly Thr Leu Val Thr Val Ser Ser
            115                 120

<210> SEQ ID NO 85
<211> LENGTH: 121

<212> TYPE: PRT
<213> ORGANISM: Artificial Sequence
<220> FEATURE:
<223> OTHER INFORMATION: Synthetic Construct

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30

Tyr His Trp Asp Trp Ile Arg Gln Ala Pro Gly Lys Gly Leu Glu Trp
        35                  40                  45

Val Ser Gly Ile Ser Gly Tyr Gly Gly Ser Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg His Ser Tyr Tyr Gly Ser Gly Asn Phe Asp Tyr Trp Gly
            100                 105                 110

Gln Gly Thr Leu Val Thr Val Ser Ser
        115                 120

<210> SEQ ID NO 86
<211> LENGTH: 116
<212> TYPE: PRT
<213> ORGANISM: Artificial Sequence
<220> FEATURE:
<223> OTHER INFORMATION: Synthetic Construct

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Ile His Trp Val Arg Gln Ala Pro Gly Lys Gly Leu Glu Trp Ile
        35                  40                  45

Gly Trp Ile Ser Pro Ser Gly Gly Thr Lys Tyr Ala Gln Lys Phe
    50                  55                  60

Gln Gly Arg Val Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Gly Ala Tyr Glu Phe Asp Tyr Trp Gly Gln Gly Thr Leu Val
            100                 105                 110

Thr Val Ser Ser
        115

<210> SEQ ID NO 87
<211> LENGTH: 116
<212> TYPE: PRT
<213> ORGANISM: Artificial Sequence
<220> FEATURE:
<223> OTHER INFORMATION: Synthetic Construct

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly

```
                    20                  25                  30
Tyr His Trp Ser Trp Ile Arg Gln Ala Pro Gly Lys Gly Leu Glu Trp
            35                  40                  45
Leu Ala Arg Ile Asp Trp Asp Asp Lys Tyr Tyr Ser Thr Ser Leu
50                  55                  60
Lys Ser Arg Leu Thr Ile Ser Arg Asp Asn Ser Lys Asn Thr Leu Tyr
65                  70                  75                  80
Leu Gln Leu Asn Ser Leu Arg Ala Glu Asp Thr Ala Val Tyr Tyr Cys
                85                  90                  95
Ala Arg Ser Tyr Val Tyr Phe Asp Tyr Trp Gly Gln Gly Thr Leu Val
            100                 105                 110
Thr Val Ser Ser
            115

<210> SEQ ID NO 88
<211> LENGTH: 120
<212> TYPE: PRT
<213> ORGANISM: Artificial Sequence
<220> FEATURE:
<223> OTHER INFORMATION: Synthetic Construct

<400> SEQUENCE: 88

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Ser Leu Ser Thr Gly
                20                  25                  30
Gly Val Ala Val Ser Trp Ile Arg Gln Ala Pro Gly Lys Gly Leu Glu
            35                  40                  45
Trp Ile Gly Glu Ile Tyr His Ser Gly Ser Thr Tyr Tyr Ser Pro Ser
        50                  55                  60
Leu Lys Ser Arg Val Thr Ile Ser Arg Asp Asn Ser Lys Asn Thr Leu
65                  70                  75                  80
Tyr Leu Gln Leu Asn Ser Leu Arg Ala Glu Asp Thr Ala Val Tyr Tyr
                85                  90                  95
Cys Ala Arg Arg Ile Ala Thr Thr Tyr Phe Asp Tyr Trp Gly Gln
            100                 105                 110
Gly Thr Leu Val Thr Val Ser Ser
        115                 120

<210> SEQ ID NO 89
<211> LENGTH: 121
<212> TYPE: PRT
<213> ORGANISM: Artificial Sequence
<220> FEATURE:
<223> OTHER INFORMATION: Synthetic Construct

<400> SEQUENCE: 89

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Ser Leu Ser Thr Gly
                20                  25                  30
Gly Val Ala Val Gly Trp Ile Arg Gln Ala Pro Gly Lys Gly Leu Glu
            35                  40                  45
Trp Val Ser Ala Ile Ser Gly Tyr Gly Ser Thr Thr Tyr Tyr Ala Asp
        50                  55                  60
Ser Val Lys Gly Arg Phe Thr Ile Ser Arg Asp Asn Ser Lys Asn Thr
65                  70                  75                  80
```

Leu Tyr Leu Gln Leu Asn Ser Leu Arg Ala Glu Asp Thr Ala Val Tyr
            85                  90                  95

Tyr Cys Ala Arg Leu Pro Tyr Ser Ala Tyr Ala Phe Asp Tyr Trp Gly
            100                 105                 110

Gln Gly Thr Leu Val Thr Val Ser Ser
            115                 120

<210> SEQ ID NO 90
<211> LENGTH: 114
<212> TYPE: PRT
<213> ORGANISM: Artificial Sequence
<220> FEATURE:
<223> OTHER INFORMATION: Synthetic Construct

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Ile His Trp Val Arg Gln Ala Pro Gly Lys Gly Leu Glu Trp Ile
            35                  40                  45

Gly Ile Ile Ser Pro Ser Gly Gly Thr Lys Tyr Ala Gln Lys Phe
        50                  55                  60

Gln Gly Arg Val Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
            85                  90                  95

Ala Arg His Pro Phe Ala Tyr Trp Gly Gln Gly Thr Leu Val Thr Val
            100                 105                 110

Ser Ser

<210> SEQ ID NO 91
<211> LENGTH: 115
<212> TYPE: PRT
<213> ORGANISM: Artificial Sequence
<220> FEATURE:
<223> OTHER INFORMATION: Synthetic Construct

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Gly Tyr
            20                  25                  30

Gly Ile His Trp Val Arg Gln Ala Pro Gly Lys Gly Leu Glu Trp Ile
            35                  40                  45

Gly Glu Ile Tyr His Ser Gly Ser Thr Tyr Tyr Ser Pro Ser Leu Lys
            50                  55                  60

Ser Arg Val Thr Ile Ser Arg Asp Asn Ser Lys Asn Thr Leu Tyr Leu
65                  70                  75                  80

Gln Leu Asn Ser Leu Arg Ala Glu Asp Thr Ala Val Tyr Tyr Cys Ala
            85                  90                  95

Arg Arg Ile Asp Ala Phe Asp Ile Trp Gly Gln Gly Thr Leu Val Thr
            100                 105                 110

Val Ser Ser
        115

<210> SEQ ID NO 92
<211> LENGTH: 115

```
<212> TYPE: PRT
<213> ORGANISM: Artificial Sequence
<220> FEATURE:
<223> OTHER INFORMATION: Synthetic Construct

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Gly Tyr
            20                  25                  30

Ala Ile His Trp Val Arg Gln Ala Pro Gly Lys Gly Leu Glu Trp Ile
        35                  40                  45

Gly Ile Ile Ser Pro Ser Gly Gly Thr Lys Tyr Ala Gln Lys Phe
    50                  55                  60

Gln Gly Arg Val Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Leu Tyr Asp Val Ala Tyr Trp Gly Gln Gly Thr Leu Val Thr
            100                 105                 110

Val Ser Ser
        115

<210> SEQ ID NO 93
<211> LENGTH: 117
<212> TYPE: PRT
<213> ORGANISM: Artificial Sequence
<220> FEATURE:
<223> OTHER INFORMATION: Synthetic Construct

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Ile His Trp Val Arg Gln Ala Pro Gly Lys Gly Leu Glu Trp Ile
        35                  40                  45

Gly Ile Ile Ser Pro Ser Gly Gly Ser Thr Lys Tyr Ala Gln Lys Phe
    50                  55                  60

Gln Gly Arg Val Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Leu Gly Tyr Gly Tyr Phe Asp Val Trp Gly Gln Gly Thr Leu
            100                 105                 110

Val Thr Val Ser Ser
        115

<210> SEQ ID NO 94
<211> LENGTH: 118
<212> TYPE: PRT
<213> ORGANISM: Artificial Sequence
<220> FEATURE:
<223> OTHER INFORMATION: Synthetic Construct

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Ser Gly
```

```
                 20                  25                  30

His Tyr Trp Ser Trp Ile Arg Gln Ala Pro Gly Lys Gly Leu Glu Trp
            35                  40                  45

Ile Gly Asp Ile Ser His Ser Gly Ser Thr Tyr Tyr Ser Gln Ser Leu
 50                  55                  60

Lys Ser Arg Val Thr Ile Ser Arg Asp Asn Ser Lys Asn Thr Leu Tyr
 65                  70                  75                  80

Leu Gln Leu Asn Ser Leu Arg Ala Glu Asp Thr Ala Val Tyr Tyr Cys
                85                  90                  95

Ala Arg Gly Ser Arg Thr Gly Tyr Phe Asp Tyr Trp Gly Gln Gly Thr
               100                 105                 110

Leu Val Thr Val Ser Ser
               115

<210> SEQ ID NO 95
<211> LENGTH: 114
<212> TYPE: PRT
<213> ORGANISM: Artificial Sequence
<220> FEATURE:
<223> OTHER INFORMATION: Synthetic Construct

<400> SEQUENCE: 95

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Glu Ser Val Asp Phe Phe
                20                  25                  30

Gly Ile Ser Phe Leu Ala Trp Tyr Gln Gln Lys Pro Gly Lys Ala Pro
            35                  40                  45

Lys Leu Leu Ile Tyr Asp Ala Ser Asn Arg Ala Thr Gly Ile Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln His Tyr Thr
                85                  90                  95

Ser Ser Pro Pro Val Tyr Thr Phe Gly Gln Gly Thr Lys Val Glu Ile
               100                 105                 110

Lys Arg

<210> SEQ ID NO 96
<211> LENGTH: 107
<212> TYPE: PRT
<213> ORGANISM: Artificial Sequence
<220> FEATURE:
<223> OTHER INFORMATION: Synthetic Construct

<400> SEQUENCE: 96

Asp Ile Gln Leu Thr Gln Ser Pro Ser Ser Leu Ser Ala Ser Val Gly
 1               5                  10                  15

Asp Arg Val Thr Ile Thr Cys Ser Ala Ser Ser Ser Val Ser Tyr Val
                20                  25                  30

Tyr Trp Tyr Gln Gln Lys Pro Gly Lys Ala Pro Lys Leu Leu Ile Tyr
            35                  40                  45

Asp Ala Ser Ser Leu Glu Ser Gly Val Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Val Gln Gly Leu Gln Thr Pro Trp Thr
```

```
                        85                  90                  95

Phe Gly Gln Gly Thr Lys Val Glu Ile Lys Arg
                100                 105

<210> SEQ ID NO 97
<211> LENGTH: 109
<212> TYPE: PRT
<213> ORGANISM: Artificial Sequence
<220> FEATURE:
<223> OTHER INFORMATION: Synthetic Construct

<400> SEQUENCE: 97

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Ser
            20                  25                  30

Leu Ala Trp Tyr Gln Gln Lys Pro Gly Lys Ala Pro Lys Leu Leu Ile
        35                  40                  45

Tyr Asp Ala Ser Asn Arg Ala Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Gln Trp Pro Pro
                85                  90                  95

Trp Thr Phe Gly Gln Gly Thr Lys Val Glu Ile Lys Arg
                100                 105

<210> SEQ ID NO 98
<211> LENGTH: 112
<212> TYPE: PRT
<213> ORGANISM: Artificial Sequence
<220> FEATURE:
<223> OTHER INFORMATION: Synthetic Construct

<400> SEQUENCE: 98

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Phe Phe
            20                  25                  30

Gly Lys Ser Phe Leu His Trp Tyr Gln Gln Lys Pro Gly Lys Ala Pro
        35                  40                  45

Lys Leu Leu Ile Tyr Asp Ala Ser Asn Leu Glu Thr Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Tyr
                85                  90                  95

Ser Trp Pro Pro Thr Phe Gly Gln Gly Thr Lys Val Glu Ile Lys Arg
                100                 105                 110

<210> SEQ ID NO 99
<211> LENGTH: 109
<212> TYPE: PRT
<213> ORGANISM: Artificial Sequence
<220> FEATURE:
<223> OTHER INFORMATION: Synthetic Construct

<400> SEQUENCE: 99

Asp Ile Gln Leu Thr Gln Ser Pro Ser Ser Leu Ser Ala Ser Val Gly
1               5                   10                  15
```

```
Asp Arg Val Thr Ile Thr Cys Arg Ala Ser Gln Ser Val Ser Ser Arg
            20                  25                  30

Phe Leu Ala Trp Tyr Gln Gln Lys Pro Gly Lys Ala Pro Lys Leu Leu
        35                  40                  45

Ile Tyr Asp Ala Ser Asn Arg Ala Thr Gly Ile Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Pro Thr Pro
                85                  90                  95

Leu Thr Phe Gly Gln Gly Thr Lys Val Glu Ile Lys Arg
                100                 105

<210> SEQ ID NO 100
<211> LENGTH: 109
<212> TYPE: PRT
<213> ORGANISM: Artificial Sequence
<220> FEATURE:
<223> OTHER INFORMATION: Synthetic Construct

<400> SEQUENCE: 100

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Arg Gly Arg
            20                  25                  30

Phe Leu Ala Trp Tyr Gln Gln Lys Pro Gly Lys Ala Pro Lys Leu Leu
        35                  40                  45

Ile Tyr Asp Ala Ser Asn Arg Ala Thr Gly Ile Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Ser Ser Trp Pro
                85                  90                  95

Pro Thr Phe Gly Gln Gly Thr Lys Val Glu Ile Lys Arg
                100                 105

<210> SEQ ID NO 101
<211> LENGTH: 110
<212> TYPE: PRT
<213> ORGANISM: Artificial Sequence
<220> FEATURE:
<223> OTHER INFORMATION: Synthetic Construct

<400> SEQUENCE: 101

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Thr Val Phe Ser Arg
            20                  25                  30

Tyr Leu Ala Trp Tyr Gln Gln Lys Pro Gly Lys Ala Pro Lys Leu Leu
        35                  40                  45

Ile Tyr Asp Ala Ser Asn Arg Ala Thr Gly Ile Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Tyr Trp Pro
                85                  90                  95

Pro Trp Thr Phe Gly Gln Gly Thr Lys Val Glu Ile Lys Arg
```

<210> SEQ ID NO 102
<211> LENGTH: 108
<212> TYPE: PRT
<213> ORGANISM: Artificial Sequence
<220> FEATURE:
<223> OTHER INFORMATION: Synthetic Construct

<400> SEQUENCE: 102

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Leu
                85                  90                  95

Thr Phe Gly Gln Gly Thr Lys Val Glu Ile Lys Arg
            100                 105

<210> SEQ ID NO 103
<211> LENGTH: 114
<212> TYPE: PRT
<213> ORGANISM: Artificial Sequence
<220> FEATURE:
<223> OTHER INFORMATION: Synthetic Construct

<400> SEQUENCE: 103

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe Tyr
            20                  25                  30

Gly Ile Ser Phe Leu Asp Trp Tyr Gln Gln Lys Pro Gly Lys Ala Pro
        35                  40                  45

Lys Leu Leu Ile Tyr Asp Ala Ser Asn Arg Ala Thr Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Tyr Val
                85                  90                  95

Ser Ser Pro Pro Glu Tyr Thr Phe Gly Gln Gly Thr Lys Val Glu Ile
            100                 105                 110

Lys Arg

<210> SEQ ID NO 104
<211> LENGTH: 112
<212> TYPE: PRT
<213> ORGANISM: Artificial Sequence
<220> FEATURE:
<223> OTHER INFORMATION: Synthetic Construct

<400> SEQUENCE: 104

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe Asp
                20                  25                  30

Gly Phe Ser Phe Leu His Trp Tyr Gln Gln Lys Pro Gly Lys Ala Pro
        35                  40                  45

Lys Leu Leu Ile Tyr Asp Ala Ser Ser Leu Glu Ser Gly Val Pro Ser
 50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Arg Asp
                85                  90                  95

Ser Trp Pro Tyr Thr Phe Gly Gln Gly Thr Lys Val Glu Ile Lys Arg
            100                 105                 110

<210> SEQ ID NO 105
<211> LENGTH: 112
<212> TYPE: PRT
<213> ORGANISM: Artificial Sequence
<220> FEATURE:
<223> OTHER INFORMATION: Synthetic Construct

<400> SEQUENCE: 105

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe His
                20                  25                  30

Gly Lys Ser Phe Leu His Trp Tyr Gln Gln Lys Pro Gly Lys Ala Pro
        35                  40                  45

Lys Leu Leu Ile Tyr Asp Ala Ser Ser Leu Glu Ser Gly Val Pro Ser
 50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Glu Gln Ser Leu
                85                  90                  95

Glu Val Pro Phe Thr Phe Gly Gln Gly Thr Lys Val Glu Ile Lys Arg
            100                 105                 110

<210> SEQ ID NO 106
<211> LENGTH: 112
<212> TYPE: PRT
<213> ORGANISM: Artificial Sequence
<220> FEATURE:
<223> OTHER INFORMATION: Synthetic Construct

<400> SEQUENCE: 106

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe Tyr
                20                  25                  30

Gly Ile Ser Phe Leu His Trp Tyr Gln Gln Lys Pro Gly Lys Ala Pro
        35                  40                  45

Lys Leu Leu Ile Tyr Asp Ala Ser Ser Leu Glu Ser Gly Val Pro Ser
 50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Val Gln Ala Leu
                85                  90                  95

Gln Leu Pro Leu Thr Phe Gly Gln Gly Thr Lys Val Glu Ile Lys Arg
            100                 105                 110

<210> SEQ ID NO 107
<211> LENGTH: 108
<212> TYPE: PRT
<213> ORGANISM: Artificial Sequence
<220> FEATURE:
<223> OTHER INFORMATION: Synthetic Construct

<400> SEQUENCE: 107

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Leu
                85                  90                  95

Thr Phe Gly Gln Gly Thr Lys Val Glu Ile Lys Arg
            100                 105

<210> SEQ ID NO 108
<211> LENGTH: 372
<212> TYPE: DNA
<213> ORGANISM: Artificial Sequence
<220> FEATURE:
<223> OTHER INFORMATION: Synthetic Construct

<400> SEQUENCE: 108
gaggttcagc tggtggagtc tggcggtggc ctggtgcagc caggggctc actccgtttg      60 tcctgtgcag cttccggatt caccttctcc gactacgcta ttcactgggt gcgtcaggcc    120
ccgggtaagg gactcgagtg gatcggtatc atctccccat ctagcggttc tactaactac    180
gcccagaagt tccagggtcg tgtgactata agtcgcgaca attcgaaaaa cacactgtac    240
ctacaactga acagcttaag agctgaggac actgccgtct attattgcgc cagagacatt    300
cactctggtt cttctggtta ctactacggt ttcgacgtct ggggtcaagg aacactagtc    360
accgtctcct cg                                                        372

<210> SEQ ID NO 109
<211> LENGTH: 354
<212> TYPE: DNA
<213> ORGANISM: Artificial Sequence
<220> FEATURE:
<223> OTHER INFORMATION: Synthetic Construct

<400> SEQUENCE: 109
gaggttcagc tggtggagtc tggcggtggc ctggtgcagc caggggctc actccgtttg      60 tcctgtgcag cttccggata ctctatcacc tctggttact actgggcctg gattcgtcag    120
gccccgggta agggcctcga gtgggtgtct ccatctctg gttccggttc tactacctac    180
tacgccgact ctgtcaaggg ccgtttcact ataagtcgcg acaattcgaa aaacacactg    240
tacctacaac tgaacagctt aagagctgag gacactgccg tctattattg cgccagagat    300
ggtttcggct acttcgacta ctgggggtca aggaacactag tcaccgtctc ctcg         354

<210> SEQ ID NO 110
<211> LENGTH: 369
<212> TYPE: DNA
<213> ORGANISM: Artificial Sequence
<220> FEATURE:
<223> OTHER INFORMATION: Synthetic Construct

<400> SEQUENCE: 110

```
gaggttcagc tggtggagtc tggcggtggc ctggtgcagc caggggctc actccgtttg      60
tcctgtgcag cttccggatt caccttctcc gactacggta ttcactgggt gcgtcaggcc    120
ccgggtaagg gcctcgagtg gatcggtgaa atctaccact ctggttctac ctactactct    180
ccatctctga gtctcgtgt gactataagt cgcgacaatt cgaaaaacac actgtaccta    240
caactgaaca gcttaagagc tgaggacact gccgtctatt attgcgccag agacgttgcc    300
cctggttctt ctggttacta cgacggtttc gacttctggg gtcaaggaac actagtcacc    360
gtctcctcg                                                             369
```

<210> SEQ ID NO 111
<211> LENGTH: 363
<212> TYPE: DNA
<213> ORGANISM: Artificial Sequence
<220> FEATURE:
<223> OTHER INFORMATION: Synthetic Construct

<400> SEQUENCE: 111

```
gaggttcagc tggtggagtc tggcggtggc ctggtgcagc caggggctc actccgtttg      60
tcctgtgcag cttccggata ctctatctcc tctggttacc actgggactg gattcgtcag    120
gccccgggta agggcctcga gtgggtgtct ggtatctctg gttacggtgg ttctacctac    180
tacgccgact ctgtcaaggg ccgtttcact ataagtcgcg acaattcgaa aaacacactg    240
tacctacaac tgaacagctt aagagctgag gacactgccg tctattattg cgccagacac    300
agttattacg gttccggtaa tttcgactac tggggtcaag gaacactagt caccgtctcc    360
tcg                                                                    363
```

<210> SEQ ID NO 112
<211> LENGTH: 348
<212> TYPE: DNA
<213> ORGANISM: Artificial Sequence
<220> FEATURE:
<223> OTHER INFORMATION: Synthetic Construct

<400> SEQUENCE: 112

```
gaggttcagc tggtggagtc tggcggtggc ctggtgcagc caggggctc actccgtttg      60
tcctgtgcag cttccggatt caccttctcc gactactgga ttcactgggt gcgtcaggcc    120
ccgggtaagg gcctcgagtg gatcggttgg atctccccat ctggcggtgg tactaagtac    180
gcccagaagt tccagggtcg tgtgactata agtcgcgaca attcgaaaaa cactgtac      240
ctacaactga acagcttaag agctgaggac actgccgtct attattgcgc cagagggct    300
tacgaatttg actactgggg tcaaggaaca ctagtcaccg tctcctcg                  348
```

<210> SEQ ID NO 113
<211> LENGTH: 348
<212> TYPE: DNA
<213> ORGANISM: Artificial Sequence
<220> FEATURE:
<223> OTHER INFORMATION: Synthetic Construct

<400> SEQUENCE: 113

```
gaggttcagc tggtggagtc tggcggtggc ctggtgcagc caggggctc actccgtttg      60 tcctgtgcag cttccggata ctctatctcc tctggttacc actggagctg gattcgtcag    120
gccccgggta agggcctcga gtggctggcc cggatcgact gggacgatga caagtactac    180
tctacctctc tgaagtctcg tctgactata agtcgcgaca attcgaaaaa cacactgtac    240
ctacaactga acagcttaag agctgaggac actgccgtct attattgcgc cagatcgtac    300
gtgtacttcg actactgggg tcaaggaaca ctagtcaccg tctcctcg                 348
```

<210> SEQ ID NO 114
<211> LENGTH: 360
<212> TYPE: DNA
<213> ORGANISM: Artificial Sequence
<220> FEATURE:
<223> OTHER INFORMATION: Synthetic Construct

<400> SEQUENCE: 114

```
gaggttcagc tggtggagtc tggcggtggc ctggtgcagc caggggctc actccgtttg      60 tcctgtgcag cttccggatt ctctctgtct accggcggtg tggctgtgag ctggattcgt    120
caggccccgg gtaagggcct cgagtggatc ggtgaaatct accactctgg ttctacctac    180
tactctccat ctctgaagtc tcgtgtgact ataagtcgcg acaattcgaa aaacacactg    240
tacctacaac tgaacagctt aagagctgag gacactgccg tctattattg cgcccgtcgt    300
atcgccaccg ctacttactt cgactactgg ggtcaaggaa cactagtcac cgtctcctcg    360
```

<210> SEQ ID NO 115
<211> LENGTH: 363
<212> TYPE: DNA
<213> ORGANISM: Artificial Sequence
<220> FEATURE:
<223> OTHER INFORMATION: Synthetic Construct

<400> SEQUENCE: 115

```
gaggttcagc tggtggagtc tggcggtggc ctggtgcagc caggggctc actccgtttg      60 tcctgtgcag cttccggatt ctctctgtct accggcggtg tggctgtggg ctggattcgt    120
caggccccgg gtaagggcct cgagtgggtg tctgctatct ctggttacgg ttctactacc    180
tactacgccg actctgtcaa gggccgtttc actataagtc gcgacaattc gaaaaacaca    240
ctgtacctac aactgaacag cttaagagct gaggacactg ccgtctatta ttgcgccaga    300
ttgccatact ccgcctacgc tttcgactac tggggtcaag gaacactagt caccgtctcc    360
tcg                                                                  363
```

<210> SEQ ID NO 116
<211> LENGTH: 342
<212> TYPE: DNA
<213> ORGANISM: Artificial Sequence
<220> FEATURE:
<223> OTHER INFORMATION: Synthetic Construct

<400> SEQUENCE: 116

```
gaggttcagc tggtggagtc tggcggtggc ctggtgcagc caggggctc actccgtttg      60 tcctgtgcag cttccggatt caccttctcc ggctacgcta ttcactgggt gcgtcaggcc    120
ccgggtaagg gcctcgagtg gatcggtatc atctccccat ctggcggtgg tactaagtac    180
gcccagaagt tccagggtcg tgtgactata agtcgcgaca attcgaaaaa cacactgtac    240
ctacaactga acagcttaag agctgaggac actgccgtct attattgcgc cagacaccca    300
ttcgcctact ggggtcaagg aacactagtc accgtctcct cg                       342
```

<210> SEQ ID NO 117
<211> LENGTH: 345
<212> TYPE: DNA
<213> ORGANISM: Artificial Sequence
<220> FEATURE:
<223> OTHER INFORMATION: Synthetic Construct

<400> SEQUENCE: 117

| | | | | | |
|---|---|---|---|---|---|
| gaggttcagc | tggtggagtc | tggcggtggc | ctggtgcagc | caggggggctc | actccgtttg | 60 |
| tcctgtgcag | cttccggata | caccttctcc | ggctacggta | ttcactgggt | gcgtcaggcc | 120 |
| ccgggtaagg | gcctcgagtg | gatcggtgaa | atctaccact | ctggttctac | ctactactct | 180 |
| ccatctctga | agtctcgtgt | gactataagt | cgcgacaatt | cgaaaaacac | actgtaccta | 240 |
| caactgaaca | gcttaagagc | tgaggacact | gccgtctatt | attgcgccag | aagaattgac | 300 |
| gccttcgaca | tctggggtca | aggaacacta | gtcaccgtct | cctcg | | 345 |

<210> SEQ ID NO 118
<211> LENGTH: 345
<212> TYPE: DNA
<213> ORGANISM: Artificial Sequence
<220> FEATURE:
<223> OTHER INFORMATION: Synthetic Construct

<400> SEQUENCE: 118

| | | | | | |
|---|---|---|---|---|---|
| gaggttcagc | tggtggagtc | tggcggtggc | ctggtgcagc | caggggggctc | actccgtttg | 60 |
| tcctgtgcag | cttccggata | caccttctcc | ggctacgcta | ttcactgggt | gcgtcaggcc | 120 |
| ccgggtaagg | gcctcgagtg | gatcggtatc | atctcccccat | ctggcggtgg | tactaagtac | 180 |
| gcccagaagt | tccagggtcg | tgtgactata | agtcgcgaca | attcgaaaaa | cacactgtac | 240 |
| ctacaactga | acagcttaag | agctgaggac | actgccgtct | attattgcgc | cagactctat | 300 |
| gacgttgcct | actggggtca | aggaacacta | gtcaccgtct | cctcg | | 345 |

<210> SEQ ID NO 119
<211> LENGTH: 351
<212> TYPE: DNA
<213> ORGANISM: Artificial Sequence
<220> FEATURE:
<223> OTHER INFORMATION: Synthetic Construct

<400> SEQUENCE: 119

| | | | | | |
|---|---|---|---|---|---|
| gaggttcagc | tggtggagtc | tggcggtggc | ctggtgcagc | caggggggctc | actccgtttg | 60 |
| tcctgtgcag | cttccggatt | caccttctcc | gactacgcta | ttcactgggt | gcgtcaggcc | 120 |
| ccgggtaagg | gcctcgagtg | gatcggtatc | atctcccccat | ctggcggttc | tactaagtac | 180 |
| gcccagaagt | tccagggtcg | tgtgactata | agtcgcgaca | attcgaaaaa | cacactgtac | 240 |
| ctacaactga | acagcttaag | agctgaggac | actgccgtct | attattgcgc | cagactcggt | 300 |
| tacgggtact | tcgacgtctg | gggtcaagga | acactagtca | ccgtctcctc | g | 351 |

<210> SEQ ID NO 120
<211> LENGTH: 354
<212> TYPE: DNA
<213> ORGANISM: Artificial Sequence
<220> FEATURE:
<223> OTHER INFORMATION: Synthetic Construct

<400> SEQUENCE: 120

| | | | | | |
|---|---|---|---|---|---|
| gaggttcagc | tggtggagtc | tggcggtggc | ctggtgcagc | caggggggctc | actccgtttg | 60 |

```
tcctgtgcag cttccggata ctctatcacc tctggtcact actggagctg gattcgtcag    120
gccccgggta agggcctcga gtggatcggt gacatctccc actctggttc tacctactac    180
tctcaatctc tgaagtctcg tgtgactata agtcgcgaca attcgaaaaa cacactgtac    240
ctacaactga acagcttaag agctgaggac actgccgtct attattgcgc gcgtggtagt    300
aggaccggct acttcgacta ttggggtcaa ggaacactag tcaccgtctc ctcg          354

<210> SEQ ID NO 121
<211> LENGTH: 342
<212> TYPE: DNA
<213> ORGANISM: Artificial Sequence
<220> FEATURE:
<223> OTHER INFORMATION: Synthetic Construct

<400> SEQUENCE: 121
gatatccagt tgacccagtc cccgagttcc ctgtccgcct ctgtgggcga tcgggtcacc     60
atcacctgcc gtgcctctga gtctgtggac ttcttcggta tctctttcct ggcctggtat    120
caacagaaac caggaaaagc tccgaagctt ctgatctacg acgcctctaa ccgtgccacc    180
ggtatcccat ctcgcttctc tggatccggt tccgggacgg atttcactct gaccatcagc    240
agtctgcagc cggaagactt cgcaacttat tactgccagc actacaccct ttcgccacca    300
gtgtacacct tcggacaggg taccaaggtg gagatcaaac ga                       342

<210> SEQ ID NO 122
<211> LENGTH: 321
<212> TYPE: DNA
<213> ORGANISM: Artificial Sequence
<220> FEATURE:
<223> OTHER INFORMATION: Synthetic Construct

<400> SEQUENCE: 122
gatatccagt tgacccagtc cccgagttcc ctgtccgcct ctgtgggcga tcgggtcacc     60
atcacctgct ctgcctcttc tagcgtgagc tacgtgtact ggtatcaaca gaaaccagga    120
aaagctccga agcttctgat ctacgacgcc tcttctctgg aatctggtgt gccatctcgc    180
ttctctggat ccggttccgg gacggatttc actctgacca tcagcagtct gcagccggaa    240
gacttcgcaa cttattactg cgtgcagggt cttcagaccc cttggacctt cggacagggt    300
accaaggtgg agatcaaacg a                                              321

<210> SEQ ID NO 123
<211> LENGTH: 327
<212> TYPE: DNA
<213> ORGANISM: Artificial Sequence
<220> FEATURE:
<223> OTHER INFORMATION: Synthetic Construct

<400> SEQUENCE: 123
gatatccagt tgacccagtc cccgagttcc ctgtccgcct ctgtgggcga tcgggtcacc     60
atcacctgcc gtgcctctca gggtattggc tcttccctgg cttggtatca acagaaacca    120
ggaaaagctc cgaagcttct gatctacgac gcctctaacc gtgccaccgg tatcccatct    180
cgcttctctg gatccggttc cgggacggat ttcactctga ccatcagcag tctgcagccg    240
gaagacttcg caacttatta ctgccagcag tacgaccaat ggccaccttg gaccttcgga    300
cagggtacca aggtggagat caaacga                                        327

<210> SEQ ID NO 124
<211> LENGTH: 336
```

```
<212> TYPE: DNA
<213> ORGANISM: Artificial Sequence
<220> FEATURE:
<223> OTHER INFORMATION: Synthetic Construct

<400> SEQUENCE: 124
gatatccagt tgacccagtc cccgagttcc ctgtccgcct ctgtgggcga tcgggtcacc    60
atcacctgcc gtgcctctga gtctgtggac ttcttcggta agtctttcct gcactggtat   120
caacagaaac caggaaaagc tccgaagctt ctgatctacg acgcctctaa cctggaaacc   180
ggtgtgccat ctcgcttctc tggatccggt tccgggacgg atttcactct gaccatcagc   240
agtctgcagc cggaagactt cgcaacttat tactgccagc agtcctactc ctggcctccg   300
accttcggac agggtaccaa ggtggagatc aaacga                             336

<210> SEQ ID NO 125
<211> LENGTH: 327
<212> TYPE: DNA
<213> ORGANISM: Artificial Sequence
<220> FEATURE:
<223> OTHER INFORMATION: Synthetic Construct

<400> SEQUENCE: 125
gatatccagt tgacccagtc cccgagttcc ctgtccgcct ctgtgggcga tcgggtcacc    60
atcacctgcc gtgcctctca gtctgtgagc agccgtttcc tggcctggta tcaacagaaa   120
ccaggaaaag ctccgaagct tctgatctac gacgcctcta accgtgccac cggtatccca   180
tctcgcttct ctggatccgg ttccgggacg gatttcactc tgaccatcag cagtctgcag   240
ccggaagact tcgcaactta ttactgccag cagtcctacc ccacccctct taccttcgga   300
cagggtacca aggtggagat caaacga                                       327

<210> SEQ ID NO 126
<211> LENGTH: 327
<212> TYPE: DNA
<213> ORGANISM: Artificial Sequence
<220> FEATURE:
<223> OTHER INFORMATION: Synthetic Construct

<400> SEQUENCE: 126
gatatccagt tgacccagtc cccgagttcc ctgtccgcct ctgtgggcga tcgggtcacc    60
atcacctgcc gtgcctctca gtctgtgcgc ggccgtttcc tggcctggta tcaacagaaa   120
ccaggaaaag ctccgaagct tctgatctac gacgcctcta accgtgccac cggtatccca   180
tctcgcttct ctggatccgg ttccgggacg gatttcactc tgaccatcag cagtctgcag   240
ccggaagact tcgcaactta ttactgccag cagtcctcct cctggcctcc gaccttcgga   300
cagggtacca aggtggagat caaacga                                       327

<210> SEQ ID NO 127
<211> LENGTH: 330
<212> TYPE: DNA
<213> ORGANISM: Artificial Sequence
<220> FEATURE:
<223> OTHER INFORMATION: Synthetic Construct

<400> SEQUENCE: 127
gatatccagt tgacccagtc cccgagttcc ctgtccgcct ctgtgggcga tcgggtcacc    60
atcacctgcc gtgcctctca gaccgtgttc tctcgttacc tggcttggta tcaacagaaa   120
ccaggaaaag ctccgaagct tctgatctac gacgcctcta accgtgccac cggtatccca   180
```

```
tctcgcttct ctggatccgg ttccgggacg gatttcactc tgaccatcag cagtctgcag      240
ccggaagact tcgcaactta ttactgccag cagtcctact actggccacc ttggaccttc      300
ggacagggta ccaaggtgga gatcaaacga                                       330

<210> SEQ ID NO 128
<211> LENGTH: 324
<212> TYPE: DNA
<213> ORGANISM: Artificial Sequence
<220> FEATURE:
<223> OTHER INFORMATION: Synthetic Construct

<400> SEQUENCE: 128
gatatccagt tgacccagtc cccgagttcc ctgtccgcct ctgtgggcga tcgggtcacc       60
atcacctgcc gtgcctctca gggtgtgtct tcttacctgg cctggtatca acagaaacca      120
ggaaaagctc cgaagcttct gatctacgcc gcctctacct tgcagtctgg tgtgccatct      180
cgcttctctg gatccggttc cgggacggat ttcactctga ccatcagcag tctgcagccg      240
gaagacttcg caacttacta ctgccagcac cactacggca ccccactgac cttcggtcag      300
ggtaccaagg tggagatcaa acga                                             324

<210> SEQ ID NO 129
<211> LENGTH: 342
<212> TYPE: DNA
<213> ORGANISM: Artificial Sequence
<220> FEATURE:
<223> OTHER INFORMATION: Synthetic Construct

<400> SEQUENCE: 129
gatatccagt tgacccagtc cccgagttcc ctgtccgcct ctgtgggcga tcgggtcacc       60
atcacctgcc gtgcctctca gtctgtggac ttctacggta tctctttcct ggactggtat      120
caacagaaac caggaaaagc tccgaagctt ctgatctacg acgcctctaa ccgtgccacc      180
ggtatcccat ctcgcttctc tggatccggt tccgggacgg atttcactct gaccatcagc      240
agtctgcagc cggaagactt cgcaacttat tactgccagc agtacgtctc ttcgccacca      300
gagtacacct tcggacaggg taccaaggtg gagatcaaac ga                         342

<210> SEQ ID NO 130
<211> LENGTH: 336
<212> TYPE: DNA
<213> ORGANISM: Artificial Sequence
<220> FEATURE:
<223> OTHER INFORMATION: Synthetic Construct

<400> SEQUENCE: 130
gatatccagt tgacccagtc cccgagttcc ctgtccgcct ctgtgggcga tcgggtcacc       60
atcacctgcc gtgcctctca gtctgtggac ttcgacggtt tctctttcct gcactggtat      120
caacagaaac caggaaaagc tccgaagctt ctgatctacg acgcctcttc tctggaatct      180
ggtgtgccat ctcgcttctc tggatccggt tccgggacgg atttcactct gaccatcagc      240
agtctgcagc cggaagactt cgcaacttat tactgccagc agcgtgactc ctggccttac      300
accttcggac agggtaccaa ggtggagatc aaacga                                336

<210> SEQ ID NO 131
<211> LENGTH: 336
<212> TYPE: DNA
<213> ORGANISM: Artificial Sequence
<220> FEATURE:
<223> OTHER INFORMATION: Synthetic Construct
```

<400> SEQUENCE: 131

```
gatatccagt tgacccagtc cccgagttcc ctgtccgcct ctgtgggcga tcgggtcacc    60
atcacctgcc gtgcctctca gtctgtggac ttccacggta agtctttcct gcactggtat   120
caacagaaac caggaaaagc tccgaagctt ctgatctacg acgcctcttc tctggaatct   180
ggtgtgccat ctcgcttctc tggatccggt tccgggacgg atttcactct gaccatcagc   240
agtctgcagc cggaagactt cgcaacttat tactgcgagc aatccctgga agtcccattc   300
accttcggac agggtaccaa ggtggagatc aaacga                             336
```

<210> SEQ ID NO 132
<211> LENGTH: 336
<212> TYPE: DNA
<213> ORGANISM: Artificial Sequence
<220> FEATURE:
<223> OTHER INFORMATION: Synthetic Construct

<400> SEQUENCE: 132

```
gatatccagt tgacccagtc cccgagttcc ctgtccgcct ctgtgggcga tcgggtcacc    60
atcacctgcc gtgcctctca gtctgtggac ttctacggta tctctttcct gcactggtat   120
caacagaaac caggaaaagc tccgaagctt ctgatctacg acgcctcttc tctggaatct   180
ggtgtgccat ctcgcttctc tggatccggt tccgggacgg atttcactct gaccatcagc   240
agtctgcagc cggaagactt cgcaacttat tactgcgtgc aggctcttca gttgcctctt   300
accttcggac agggtaccaa ggtggagatc aaacga                             336
```

<210> SEQ ID NO 133
<211> LENGTH: 324
<212> TYPE: DNA
<213> ORGANISM: Artificial Sequence
<220> FEATURE:
<223> OTHER INFORMATION: Synthetic Construct

<400> SEQUENCE: 133

```
gatatccagt tgacccagtc cccgagttcc ctgtccgcct ctgtgggcga tcgggtcacc    60
atcacctgcc gtgcctctca gtctatctct tcttacctga actggtatca acagaaacca   120
ggaaaagctc cgaagcttct gatctacgac gcctctaacc tggaaaccgg tgtgccatct   180
cgcttctctg gatccggttc cggacggat ttcactctga ccatcagcag tctgcagccg    240
gaagacttcg caacttacta ctgccagcac cactacggca ccccactgac cttcggtcag   300
ggtaccaagg tggagatcaa acga                                          324
```

<210> SEQ ID NO 134
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Present in repeats of at least two and up to
      ten
<220> FEATURE:
<221> NAME/KEY: VARIANT
<222> LOCATION: 3
<223> OTHER INFORMATION: Present in repeats of at least three and up to
      ten
<220> FEATURE:
<221> NAME/KEY: VARIANT
<222> LOCATION: 1, 3

```
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr
<220> FEATURE:
<221> NAME/KEY: VARIANT
<222> LOCATION: 5
<223> OTHER INFORMATION: Present in repeats of at least one and up to
      ten
<220> FEATURE:
<221> NAME/KEY: VARIANT
<222> LOCATION: 5
<223> OTHER INFORMATION: Xaa = Asp, Ala, Tyr, Ser, Thr, Asn, Ile, Leu,
      Phe, Val, His, or Pro

<400> SEQUENCE: 134

Xaa Cys Xaa Cys Xaa
1               5

<210> SEQ ID NO 135
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Present in repeats of at least two and up to
      ten
<220> FEATURE:
<221> NAME/KEY: VARIANT
<222> LOCATION: 3
<223> OTHER INFORMATION: Present in repeats of at least three and up to
      ten
<220> FEATURE:
<221> NAME/KEY: VARIANT
<222> LOCATION: 5
<223> OTHER INFORMATION: Present in repeats of at least one and up to
      ten
<220> FEATURE:
<221> NAME/KEY: VARIANT
<222> LOCATION: 1, 3, 5
<223> OTHER INFORMATION: Xaa = Asp, Ala, Tyr, Ser, Thr, Asn, Ile, Leu,
      Phe, Val, His, or Pro

<400> SEQUENCE: 135

Xaa Cys Xaa Cys Xaa
1               5

<210> SEQ ID NO 136
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3
<223> OTHER INFORMATION: Present in repeats of at least two and up to
      ten
<220> FEATURE:
<221> NAME/KEY: misc_feature
<222> LOCATION: 7, 8, 9
<223> OTHER INFORMATION: Present in repeats of at least three and up to
      ten
<220> FEATURE:
<221> NAME/KEY: misc_feature
<222> LOCATION: 13, 14, 15
<223> OTHER INFORMATION: Present in repeats of at least one and up to
      ten
<220> FEATURE:
<221> NAME/KEY: misc_feature
<222> LOCATION: 1, 2, 7, 8, 13
<223> OTHER INFORMATION: n = A,T,C or G
<220> FEATURE:
<221> NAME/KEY: misc_feature
```

```
<222> LOCATION: 3, 9
<223> OTHER INFORMATION: n = T or G
<220> FEATURE:
<221> NAME/KEY: misc_feature
<222> LOCATION: 6, 12
<223> OTHER INFORMATION: n = T or C
<220> FEATURE:
<221> NAME/KEY: misc_feature
<222> LOCATION: 14
<223> OTHER INFORMATION: n = A,T, or C

<400> SEQUENCE: 136
nnntgnnnnt gnnnc                                              15

<210> SEQ ID NO 137
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 15, 16
<223> OTHER INFORMATION: Xaa = Asp, Ala, Tyr, Ser, Thr, Asn, Ile, Leu,
      Phe, Val, His, or Pro
<220> FEATURE:
<221> NAME/KEY: VARIANT
<222> LOCATION: 8, 9, 10, 11, 12, 13
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr

<400> SEQUENCE: 137

Xaa Xaa Xaa Xaa Xaa Xaa Cys Xaa Xaa Xaa Xaa Xaa Xaa Cys Xaa Xaa
1               5                   10                  15

<210> SEQ ID NO 138
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 17, 18
<223> OTHER INFORMATION: Xaa = Asp, Ala, Tyr, Ser, Thr, Asn, Ile, Leu,
      Phe, Val, His, or Pro
<220> FEATURE:
<221> NAME/KEY: VARIANT
<222> LOCATION: 8, 9, 10, 11, 12, 13, 14, 15
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr

<400> SEQUENCE: 138

Xaa Xaa Xaa Xaa Xaa Xaa Cys Xaa Xaa Xaa Xaa Xaa Xaa Xaa Xaa Cys
1               5                   10                  15

Xaa Xaa

<210> SEQ ID NO 139
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 8, 9, 10, 11, 12, 13, 15, 16
<223> OTHER INFORMATION: Xaa = Asp, Ala, Tyr, Ser, Thr, Asn, Ile, Leu,
      Phe, Val, His, or Pro

<400> SEQUENCE: 139

Xaa Xaa Xaa Xaa Xaa Xaa Cys Xaa Xaa Xaa Xaa Xaa Cys Xaa Xaa
```

<210> SEQ ID NO 140
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 8, 9, 10, 11, 12, 13, 14, 15, 17, 18
<223> OTHER INFORMATION: Xaa = Asp, Ala, Tyr, Ser, Thr, Asn, Ile, Leu,
      Phe, Val, His, or Pro

<400> SEQUENCE: 140

Xaa Xaa Xaa Xaa Xaa Xaa Cys Xaa Xaa Xaa Xaa Xaa Xaa Xaa Xaa Cys
1               5                   10                  15

Xaa Xaa

<210> SEQ ID NO 141
<211> LENGTH: 16
<212> TYPE: PRT
<213> ORGANISM: Artificial Sequence
<220> FEATURE:
<223> OTHER INFORMATION: Synthetic Construct

<400> SEQUENCE: 141

Asn Phe Val Ala Asp Ser Cys Pro Asp His Pro Tyr Pro Cys Ser Ala
1               5                   10                  15

<210> SEQ ID NO 142
<211> LENGTH: 16
<212> TYPE: PRT
<213> ORGANISM: Artificial Sequence
<220> FEATURE:
<223> OTHER INFORMATION: Synthetic Construct

<400> SEQUENCE: 142

Ile Val His His Ser Asp Cys Asp Ala Phe Tyr Pro Tyr Cys Asp Ser
1               5                   10                  15

<210> SEQ ID NO 143
<211> LENGTH: 16
<212> TYPE: PRT
<213> ORGANISM: Artificial Sequence
<220> FEATURE:
<223> OTHER INFORMATION: Synthetic Construct

<400> SEQUENCE: 143

Tyr Ser Ala Tyr Pro Ala Cys Asp Ser His Tyr Pro Tyr Cys Asn Ser
1               5                   10                  15

<210> SEQ ID NO 144
<211> LENGTH: 16
<212> TYPE: PRT
<213> ORGANISM: Artificial Sequence
<220> FEATURE:
<223> OTHER INFORMATION: Synthetic Construct

<400> SEQUENCE: 144

Pro Asn Pro Ser Ser Asp Cys Val Pro Tyr Tyr Tyr Ala Cys Ala Tyr
1               5                   10                  15

<210> SEQ ID NO 145
<211> LENGTH: 16
<212> TYPE: PRT
<213> ORGANISM: Artificial Sequence

```
<220> FEATURE:
<223> OTHER INFORMATION: Synthetic Construct

<400> SEQUENCE: 145

Tyr Ser Ala Tyr Pro Ala Cys Asp Ser His Tyr Pro Tyr Cys Gln Ser
1               5                   10                  15

<210> SEQ ID NO 146
<211> LENGTH: 16
<212> TYPE: PRT
<213> ORGANISM: Artificial Sequence
<220> FEATURE:
<223> OTHER INFORMATION: Synthetic Construct

<400> SEQUENCE: 146

Pro Gln Pro Ser Ser Asp Cys Val Pro Tyr Tyr Tyr Ala Cys Ala Tyr
1               5                   10                  15

<210> SEQ ID NO 147
<211> LENGTH: 16
<212> TYPE: PRT
<213> ORGANISM: Artificial Sequence
<220> FEATURE:
<223> OTHER INFORMATION: Synthetic Construct

<400> SEQUENCE: 147

Pro Asn Pro Ala Ser Asp Cys Val Pro Tyr Tyr Tyr Ala Cys Ala Tyr
1               5                   10                  15

<210> SEQ ID NO 148
<211> LENGTH: 5
<212> TYPE: PRT
<213> ORGANISM: Artificial Sequence
<220> FEATURE:
<223> OTHER INFORMATION: Synthetic Construct

<400> SEQUENCE: 148

Glu Val Gly Ser Tyr
1               5

<210> SEQ ID NO 149
<211> LENGTH: 5
<212> TYPE: PRT
<213> ORGANISM: Artificial Sequence
<220> FEATURE:
<223> OTHER INFORMATION: Synthetic Construct

<400> SEQUENCE: 149

Ser Gly Arg Ser Ala
1               5

<210> SEQ ID NO 150
<211> LENGTH: 6
<212> TYPE: PRT
<213> ORGANISM: Artificial Sequence
<220> FEATURE:
<223> OTHER INFORMATION: Synthetic Construct

<400> SEQUENCE: 150

Pro Leu Gly Leu Ala Gly
1               5

<210> SEQ ID NO 151
<211> LENGTH: 7
<212> TYPE: PRT
<213> ORGANISM: Artificial Sequence
<220> FEATURE:
```

<223> OTHER INFORMATION: Synthetic Construct

<400> SEQUENCE: 151

Glu Asn Leu Tyr Phe Gln Gly
1               5

<210> SEQ ID NO 152
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6, 7, 8, 9, 10, 11, 13, 14, 15, 16, 17, 18, 20, 21
<223> OTHER INFORMATION: Xaa = Asp, Ala, Tyr, Ser, Thr, Asn, Ile, Leu,
      Phe, Val, His, or Pro

<400> SEQUENCE: 152

Glu Val Gly Ser Tyr Xaa Xaa Xaa Xaa Xaa Xaa Cys Xaa Xaa Xaa Xaa
1               5                   10                  15

Xaa Xaa Cys Xaa Xaa Ser Gly Arg Ser Ala
            20                  25

<210> SEQ ID NO 153
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6, 7, 8, 9, 10, 11, 20, 21
<223> OTHER INFORMATION: Xaa = Asp, Ala, Tyr, Ser, Thr, Asn, Ile, Leu,
      Phe, Val, His, or Pro
<220> FEATURE:
<221> NAME/KEY: VARIANT
<222> LOCATION: 13, 14, 15, 16, 17, 18
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr

<400> SEQUENCE: 153

Glu Val Gly Ser Tyr Xaa Xaa Xaa Xaa Xaa Xaa Cys Xaa Xaa Xaa Xaa
1               5                   10                  15

Xaa Xaa Cys Xaa Xaa Ser Gly Arg Ser Ala
            20                  25

<210> SEQ ID NO 154
<211> LENGTH: 28
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6, 7, 8, 9, 10, 11, 13, 14, 15, 16, 17, 18, 19, 20, 22,
      23
<223> OTHER INFORMATION: Xaa = Asp, Ala, Tyr, Ser, Thr, Asn, Ile, Leu,
      Phe, Val, His, or Pro

<400> SEQUENCE: 154

Glu Val Gly Ser Tyr Xaa Xaa Xaa Xaa Xaa Xaa Cys Xaa Xaa Xaa Xaa
1               5                   10                  15

Xaa Xaa Xaa Xaa Cys Xaa Xaa Ser Gly Arg Ser Ala
            20                  25

<210> SEQ ID NO 155
<211> LENGTH: 28

```
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6, 7, 8, 9, 10, 11, 22, 23
<223> OTHER INFORMATION: Xaa = Asp, Ala, Tyr, Ser, Thr, Asn, Ile, Leu,
      Phe, Val, His, or Pro
<220> FEATURE:
<221> NAME/KEY: VARIANT
<222> LOCATION: 13, 14, 15, 16, 17, 18, 19, 20
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr

<400> SEQUENCE: 155

Glu Val Gly Ser Tyr Xaa Xaa Xaa Xaa Xaa Xaa Cys Xaa Xaa Xaa Xaa
1               5                   10                  15

Xaa Xaa Xaa Xaa Cys Xaa Xaa Ser Gly Arg Ser Ala
            20                  25

<210> SEQ ID NO 156
<211> LENGTH: 5
<212> TYPE: PRT
<213> ORGANISM: Artificial Sequence
<220> FEATURE:
<223> OTHER INFORMATION: Synthetic Construct

<400> SEQUENCE: 156

Gly Gly Gly Gly Ser
1               5

<210> SEQ ID NO 157
<211> LENGTH: 4
<212> TYPE: PRT
<213> ORGANISM: Artificial Sequence
<220> FEATURE:
<223> OTHER INFORMATION: Synthetic Construct

<400> SEQUENCE: 157

Ser Gly Gly Ser
1

<210> SEQ ID NO 158
<211> LENGTH: 4
<212> TYPE: PRT
<213> ORGANISM: Artificial Sequence
<220> FEATURE:
<223> OTHER INFORMATION: Synthetic Construct

<400> SEQUENCE: 158

Gly Gly Ser Gly
1

<210> SEQ ID NO 159
<211> LENGTH: 5
<212> TYPE: PRT
<213> ORGANISM: Artificial Sequence
<220> FEATURE:
<223> OTHER INFORMATION: Synthetic Construct

<400> SEQUENCE: 159

Gly Gly Ser Gly Gly
1               5

<210> SEQ ID NO 160
<211> LENGTH: 5
<212> TYPE: PRT
```

<213> ORGANISM: Artificial Sequence
<220> FEATURE:
<223> OTHER INFORMATION: Synthetic Construct

<400> SEQUENCE: 160

Gly Ser Gly Ser Gly
1               5

<210> SEQ ID NO 161
<211> LENGTH: 5
<212> TYPE: PRT
<213> ORGANISM: Artificial Sequence
<220> FEATURE:
<223> OTHER INFORMATION: Synthetic Construct

<400> SEQUENCE: 161

Gly Ser Gly Gly Gly
1               5

<210> SEQ ID NO 162
<211> LENGTH: 5
<212> TYPE: PRT
<213> ORGANISM: Artificial Sequence
<220> FEATURE:
<223> OTHER INFORMATION: Synthetic Construct

<400> SEQUENCE: 162

Gly Gly Gly Ser Gly
1               5

<210> SEQ ID NO 163
<211> LENGTH: 5
<212> TYPE: PRT
<213> ORGANISM: Artificial Sequence
<220> FEATURE:
<223> OTHER INFORMATION: Synthetic Construct

<400> SEQUENCE: 163

Gly Ser Ser Ser Gly
1               5

<210> SEQ ID NO 164
<211> LENGTH: 42
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Ala, Asp, Ile, Asn, Pro, or Tyr
<220> FEATURE:
<221> NAME/KEY: VARIANT
<222> LOCATION: 7
<223> OTHER INFORMATION: Xaa = Ala, Phe, Asn, Ser, or Val
<220> FEATURE:
<221> NAME/KEY: VARIANT
<222> LOCATION: 8
<223> OTHER INFORMATION: Xaa = Ala, His, Leu, Pro, Ser, Val, or Tyr
<220> FEATURE:
<221> NAME/KEY: VARIANT
<222> LOCATION: 9
<223> OTHER INFORMATION: Xaa = Ala, His, Ser, or Tyr
<220> FEATURE:
<221> NAME/KEY: VARIANT
<222> LOCATION: 10
<223> OTHER INFORMATION: Xaa = Ala, Asp, Pro, Ser, Val, or Tyr
<220> FEATURE:
<221> NAME/KEY: VARIANT
<222> LOCATION: 11
<223> OTHER INFORMATION: Xaa = Ala, Asp, Leu, Ser, or Tyr

```
<220> FEATURE:
<221> NAME/KEY: VARIANT
<222> LOCATION: 13
<223> OTHER INFORMATION: Xaa = Asp, Pro, or Val
<220> FEATURE:
<221> NAME/KEY: VARIANT
<222> LOCATION: 14
<223> OTHER INFORMATION: Xaa = Ala, Asp, His, Pro, Ser, or Thr
<220> FEATURE:
<221> NAME/KEY: VARIANT
<222> LOCATION: 15
<223> OTHER INFORMATION: Xaa = Ala, Asp, Phe, His, Pro, or Tyr
<220> FEATURE:
<221> NAME/KEY: VARIANT
<222> LOCATION: 16
<223> OTHER INFORMATION: Xaa =  Leu, Pro, or Tyr
<220> FEATURE:
<221> NAME/KEY: VARIANT
<222> LOCATION: 17
<223> OTHER INFORMATION: Xaa = Phe, Pro, or Tyr
<220> FEATURE:
<221> NAME/KEY: VARIANT
<222> LOCATION: 18
<223> OTHER INFORMATION: Xaa = Ala, Pro, Ser, or Tyr
<220> FEATURE:
<221> NAME/KEY: VARIANT
<222> LOCATION: 20
<223> OTHER INFORMATION: Xaa = Ala, Asp, Asn, Ser, Thr, or Tyr
<220> FEATURE:
<221> NAME/KEY: VARIANT
<222> LOCATION: 21
<223> OTHER INFORMATION: Xaa = Ala, Ser, or Tyr

<400> SEQUENCE: 164

Glu Val Gly Ser Tyr Xaa Xaa Xaa Xaa Xaa Xaa Cys Xaa Xaa Xaa Xaa
1               5                   10                  15

Xaa Xaa Cys Xaa Xaa Ser Gly Arg Ser Ala Gly Gly Gly Thr Glu
            20                  25                  30

Asn Leu Tyr Phe Gln Gly Ser Gly Gly Ser
        35                  40

<210> SEQ ID NO 165
<211> LENGTH: 42
<212> TYPE: PRT
<213> ORGANISM: Artificial Sequence
<220> FEATURE:
<223> OTHER INFORMATION: Synthetic Construct

<400> SEQUENCE: 165

Glu Val Gly Ser Tyr Asp Ala Leu His Tyr Ala Cys Pro Pro Asp Tyr
1               5                   10                  15

Tyr Ala Cys Tyr Tyr Ser Gly Arg Ser Ala Gly Gly Gly Thr Glu
            20                  25                  30

Asn Leu Tyr Phe Gln Gly Ser Gly Gly Ser
        35                  40

<210> SEQ ID NO 166
<211> LENGTH: 42
<212> TYPE: PRT
<213> ORGANISM: Artificial Sequence
<220> FEATURE:
<223> OTHER INFORMATION: Synthetic Construct

<400> SEQUENCE: 166

Glu Val Gly Ser Tyr Asn Ser Tyr His Ala Tyr Cys Pro His Pro Leu
1               5                   10                  15

Tyr Pro Cys Thr Ala Ser Gly Arg Ser Ala Gly Gly Gly Thr Glu
            20                  25                  30
```

-continued

```
Asn Leu Tyr Phe Gln Gly Ser Gly Gly Ser
        35                  40

<210> SEQ ID NO 167
<211> LENGTH: 42
<212> TYPE: PRT
<213> ORGANISM: Artificial Sequence
<220> FEATURE:
<223> OTHER INFORMATION: Synthetic Construct

<400> SEQUENCE: 167

Glu Val Gly Ser Tyr Ala Ser Ser Ala Val Leu Cys Val Thr Ala Tyr
1               5                   10                  15

Phe Ser Cys Asn Ser Ser Gly Arg Ser Ala Gly Gly Gly Thr Glu
            20                  25                  30

Asn Leu Tyr Phe Gln Gly Ser Gly Gly Ser
        35                  40

<210> SEQ ID NO 168
<211> LENGTH: 41
<212> TYPE: PRT
<213> ORGANISM: Artificial Sequence
<220> FEATURE:
<223> OTHER INFORMATION: Synthetic Construct

<400> SEQUENCE: 168

Glu Val Gly Ser Tyr Asn Phe Val Ala Asp Ser Cys Pro Asp His Pro
1               5                   10                  15

Tyr Pro Cys Ser Ala Ser Gly Arg Ser Ala Gly Gly Gly Ser Pro
            20                  25                  30

Leu Gly Leu Ala Gly Ser Gly Gly Ser
        35                  40

<210> SEQ ID NO 169
<211> LENGTH: 42
<212> TYPE: PRT
<213> ORGANISM: Artificial Sequence
<220> FEATURE:
<223> OTHER INFORMATION: Synthetic Construct

<400> SEQUENCE: 169

Glu Val Gly Ser Tyr Asn Phe Val Ala Asp Ser Cys Pro Asp His Pro
1               5                   10                  15

Tyr Pro Cys Ser Ala Ser Gly Arg Ser Ala Gly Gly Gly Thr Glu
            20                  25                  30

Asn Leu Tyr Phe Gln Gly Ser Gly Gly Ser
        35                  40

<210> SEQ ID NO 170
<211> LENGTH: 41
<212> TYPE: PRT
<213> ORGANISM: Artificial Sequence
<220> FEATURE:
<223> OTHER INFORMATION: Synthetic Construct

<400> SEQUENCE: 170

Glu Val Gly Ser Tyr Ile Val His His Ser Asp Cys Asp Ala Phe Tyr
1               5                   10                  15

Pro Tyr Cys Asp Ser Ser Gly Arg Ser Ala Gly Gly Gly Ser Pro
            20                  25                  30

Leu Gly Leu Ala Gly Ser Gly Gly Ser
        35                  40
```

```
<210> SEQ ID NO 171
<211> LENGTH: 42
<212> TYPE: PRT
<213> ORGANISM: Artificial Sequence
<220> FEATURE:
<223> OTHER INFORMATION: Synthetic Construct

<400> SEQUENCE: 171

Glu Val Gly Ser Tyr Ile Val His His Ser Asp Cys Asp Ala Phe Tyr
1               5                   10                  15

Pro Tyr Cys Asp Ser Ser Gly Arg Ser Ala Gly Gly Gly Thr Glu
            20                  25                  30

Asn Leu Tyr Phe Gln Gly Ser Gly Gly Ser
        35                  40

<210> SEQ ID NO 172
<211> LENGTH: 41
<212> TYPE: PRT
<213> ORGANISM: Artificial Sequence
<220> FEATURE:
<223> OTHER INFORMATION: Synthetic Construct

<400> SEQUENCE: 172

Glu Val Gly Ser Tyr Tyr Ser Ala Tyr Pro Ala Cys Asp Ser His Tyr
1               5                   10                  15

Pro Tyr Cys Asn Ser Ser Gly Arg Ser Ala Gly Gly Gly Gly Ser Pro
            20                  25                  30

Leu Gly Leu Ala Gly Ser Gly Gly Ser
        35                  40

<210> SEQ ID NO 173
<211> LENGTH: 42
<212> TYPE: PRT
<213> ORGANISM: Artificial Sequence
<220> FEATURE:
<223> OTHER INFORMATION: Synthetic Construct

<400> SEQUENCE: 173

Glu Val Gly Ser Tyr Tyr Ser Ala Tyr Pro Ala Cys Asp Ser His Tyr
1               5                   10                  15

Pro Tyr Cys Asn Ser Ser Gly Arg Ser Ala Gly Gly Gly Gly Thr Glu
            20                  25                  30

Asn Leu Tyr Phe Gln Gly Ser Gly Gly Ser
        35                  40

<210> SEQ ID NO 174
<211> LENGTH: 41
<212> TYPE: PRT
<213> ORGANISM: Artificial Sequence
<220> FEATURE:
<223> OTHER INFORMATION: Synthetic Construct

<400> SEQUENCE: 174

Glu Val Gly Ser Tyr Pro Asn Pro Ser Ser Asp Cys Val Pro Tyr Tyr
1               5                   10                  15

Tyr Ala Cys Ala Tyr Ser Gly Arg Ser Ala Gly Gly Gly Gly Ser Pro
            20                  25                  30

Leu Gly Leu Ala Gly Ser Gly Gly Ser
        35                  40

<210> SEQ ID NO 175
<211> LENGTH: 42
```

```
<212> TYPE: PRT
<213> ORGANISM: Artificial Sequence
<220> FEATURE:
<223> OTHER INFORMATION: Synthetic Construct

<400> SEQUENCE: 175

Glu Val Gly Ser Tyr Pro Asn Pro Ser Ser Asp Cys Val Pro Tyr Tyr
1               5                   10                  15

Tyr Ala Cys Ala Tyr Ser Gly Arg Ser Ala Gly Gly Gly Thr Glu
            20                  25                  30

Asn Leu Tyr Phe Gln Gly Ser Gly Gly Ser
        35                  40

<210> SEQ ID NO 176
<211> LENGTH: 41
<212> TYPE: PRT
<213> ORGANISM: Artificial Sequence
<220> FEATURE:
<223> OTHER INFORMATION: Synthetic Construct

<400> SEQUENCE: 176

Glu Val Gly Ser Tyr Tyr Ser Ala Tyr Pro Ala Cys Asp Ser His Tyr
1               5                   10                  15

Pro Tyr Cys Gln Ser Ser Gly Arg Ser Ala Gly Gly Gly Ser Pro
            20                  25                  30

Leu Gly Leu Ala Gly Ser Gly Gly Ser
        35                  40

<210> SEQ ID NO 177
<211> LENGTH: 41
<212> TYPE: PRT
<213> ORGANISM: Artificial Sequence
<220> FEATURE:
<223> OTHER INFORMATION: Synthetic Construct

<400> SEQUENCE: 177

Glu Val Gly Ser Tyr Tyr Ser Ala Tyr Pro Ala Cys Asp Ser His Tyr
1               5                   10                  15

Pro Tyr Cys Asn Ser Ala Gly Arg Ser Ala Gly Gly Gly Ser Pro
            20                  25                  30

Leu Gly Leu Ala Gly Ser Gly Gly Ser
        35                  40

<210> SEQ ID NO 178
<211> LENGTH: 41
<212> TYPE: PRT
<213> ORGANISM: Artificial Sequence
<220> FEATURE:
<223> OTHER INFORMATION: Synthetic Construct

<400> SEQUENCE: 178

Glu Val Gly Ser Tyr Pro Gln Pro Ser Ser Asp Cys Val Pro Tyr Tyr
1               5                   10                  15

Tyr Ala Cys Ala Tyr Ser Gly Arg Ser Ala Gly Gly Gly Ser Pro
            20                  25                  30

Leu Gly Leu Ala Gly Ser Gly Gly Ser
        35                  40

<210> SEQ ID NO 179
<211> LENGTH: 41
<212> TYPE: PRT
<213> ORGANISM: Artificial Sequence
<220> FEATURE:
```

```
<223> OTHER INFORMATION: Synthetic Construct

<400> SEQUENCE: 179

Glu Val Gly Ser Tyr Pro Asn Pro Ala Ser Asp Cys Val Pro Tyr Tyr
1               5                   10                  15

Tyr Ala Cys Ala Tyr Ser Gly Arg Ser Ala Gly Gly Gly Ser Pro
                20                  25                  30

Leu Gly Leu Ala Gly Ser Gly Gly Ser
        35                  40

<210> SEQ ID NO 180
<211> LENGTH: 20
<212> TYPE: PRT
<213> ORGANISM: Artificial Sequence
<220> FEATURE:
<223> OTHER INFORMATION: Synthetic Construct

<400> SEQUENCE: 180

Ser Gly Arg Ser Ala Gly Gly Gly Ser Pro Leu Gly Leu Ala Gly
1               5                   10                  15

Ser Gly Gly Ser
            20

<210> SEQ ID NO 181
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Present in repeats of at least two and up to
      ten
<220> FEATURE:
<221> NAME/KEY: VARIANT
<222> LOCATION: 1, 10, 11
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr

<400> SEQUENCE: 181

Xaa Cys Pro Asp His Pro Tyr Pro Cys Xaa Xaa
1               5                   10

<210> SEQ ID NO 182
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Present in repeats of at least two and up to
      ten
<220> FEATURE:
<221> NAME/KEY: VARIANT
<222> LOCATION: 1, 10, 11
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr

<400> SEQUENCE: 182

Xaa Cys Asp Ala Phe Tyr Pro Tyr Cys Xaa Xaa
1               5                   10

<210> SEQ ID NO 183
<211> LENGTH: 11
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Present in repeats of at least two and up to
      ten
<220> FEATURE:
<221> NAME/KEY: VARIANT
<222> LOCATION: 1, 10, 11
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr

<400> SEQUENCE: 183

Xaa Cys Asp Ser His Tyr Pro Tyr Cys Xaa Xaa
1               5                   10

<210> SEQ ID NO 184
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Present in repeats of at least two and up to
      ten
<220> FEATURE:
<221> NAME/KEY: VARIANT
<222> LOCATION: 1, 10, 11
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr

<400> SEQUENCE: 184

Xaa Cys Val Pro Tyr Tyr Tyr Ala Cys Xaa Xaa
1               5                   10

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189
<211> LENGTH: 21
<212> TYPE: PRT
<213> ORGANISM: Artificial Sequence
<220> FEATURE:
<223> OTHER INFORMATION: Synthetic Construct

<400> SEQUENCE: 189
```

```
Glu Val Gly Ser Tyr Asn Phe Val Ala Asp Ser Cys Pro Asp His Pro
1               5                   10                  15

Tyr Pro Cys Ser Ala
            20

<210> SEQ ID NO 190
<211> LENGTH: 21
<212> TYPE: PRT
<213> ORGANISM: Artificial Sequence
<220> FEATURE:
<223> OTHER INFORMATION: Synthetic Construct

<400> SEQUENCE: 190

Glu Val Gly Ser Tyr Ile Val His His Ser Asp Cys Asp Ala Phe Tyr
1               5                   10                  15

Pro Tyr Cys Asp Ser
            20

<210> SEQ ID NO 191
<211> LENGTH: 21
<212> TYPE: PRT
<213> ORGANISM: Artificial Sequence
<220> FEATURE:
<223> OTHER INFORMATION: Synthetic Construct

<400> SEQUENCE: 191

Glu Val Gly Ser Tyr Tyr Ser Ala Tyr Pro Ala Cys Asp Ser His Tyr
1               5                   10                  15

Pro Tyr Cys Asn Ser
            20

<210> SEQ ID NO 192
<211> LENGTH: 21
<212> TYPE: PRT
<213> ORGANISM: Artificial Sequence
<220> FEATURE:
<223> OTHER INFORMATION: Synthetic Construct

<400> SEQUENCE: 192

Glu Val Gly Ser Tyr Pro Asn Pro Ser Ser Asp Cys Val Pro Tyr Tyr
1               5                   10                  15

Tyr Ala Cys Ala Tyr
            20

<210> SEQ ID NO 193
<211> LENGTH: 21
<212> TYPE: PRT
<213> ORGANISM: Artificial Sequence
<220> FEATURE:
<223> OTHER INFORMATION: Synthetic Construct

<400> SEQUENCE: 193

Glu Val Gly Ser Tyr Tyr Ser Ala Tyr Pro Ala Cys Asp Ser His Tyr
1               5                   10                  15

Pro Tyr Cys Gln Ser
            20

<210> SEQ ID NO 194

<400> SEQUENCE: 194

000
```

```
<210> SEQ ID NO 195
<211> LENGTH: 21
<212> TYPE: PRT
<213> ORGANISM: Artificial Sequence
<220> FEATURE:
<223> OTHER INFORMATION: Synthetic Construct

<400> SEQUENCE: 195

Glu Val Gly Ser Tyr Pro Gln Pro Ser Ser Asp Cys Val Pro Tyr Tyr
1               5                   10                  15

Tyr Ala Cys Ala Tyr
            20

<210> SEQ ID NO 196
<211> LENGTH: 21
<212> TYPE: PRT
<213> ORGANISM: Artificial Sequence
<220> FEATURE:
<223> OTHER INFORMATION: Synthetic Construct

<400> SEQUENCE: 196

Glu Val Gly Ser Tyr Pro Asn Pro Ala Ser Asp Cys Val Pro Tyr Tyr
1               5                   10                  15

Tyr Ala Cys Ala Tyr
            20

<210> SEQ ID NO 197
<211> LENGTH: 41
<212> TYPE: PRT
<213> ORGANISM: Artificial Sequence
<220> FEATURE:
<223> OTHER INFORMATION: Synthetic Construct

<400> SEQUENCE: 197

Glu Val Gly Ser Tyr Ile Val His His Ser Asp Cys Asp Ala Phe Tyr
1               5                   10                  15

Pro Tyr Cys Asp Ser Ser Gly Arg Ser Ala Gly Gly Gly Thr Pro
            20                  25                  30

Leu Gly Leu Ala Gly Ser Gly Gly Ser
        35                  40

<210> SEQ ID NO 198
<211> LENGTH: 36
<212> TYPE: PRT
<213> ORGANISM: Artificial Sequence
<220> FEATURE:
<223> OTHER INFORMATION: Synthetic Construct

<400> SEQUENCE: 198

Glu Val Gly His Ser Asp Cys Asp Ala Phe Tyr Pro Tyr Cys Asp Ser
1               5                   10                  15

Ser Gly Arg Ser Ala Gly Gly Gly Thr Pro Leu Gly Leu Ala Gly
            20                  25                  30

Ser Gly Gly Ser
        35

<210> SEQ ID NO 199
<211> LENGTH: 32
<212> TYPE: PRT
<213> ORGANISM: Artificial Sequence
<220> FEATURE:
<223> OTHER INFORMATION: Synthetic Construct

<400> SEQUENCE: 199
```

Glu Asp Cys Asp Ala Phe Tyr Pro Tyr Cys Asp Ser Ser Gly Arg Ser
1               5                   10                  15

Ala Gly Gly Gly Gly Thr Pro Leu Gly Leu Ala Gly Ser Gly Gly Ser
            20                  25                  30

<210> SEQ ID NO 200
<211> LENGTH: 41
<212> TYPE: PRT
<213> ORGANISM: Artificial Sequence
<220> FEATURE:
<223> OTHER INFORMATION: Synthetic Construct

<400> SEQUENCE: 200

Glu Val Gly Ser Tyr Pro Asn Pro Ser Ser Asp Cys Val Pro Tyr Tyr
1               5                   10                  15

Tyr Ala Cys Ala Tyr Ser Gly Arg Ser Ala Gly Gly Gly Gly Thr Pro
            20                  25                  30

Leu Gly Leu Ala Gly Ser Gly Gly Ser
            35                  40

<210> SEQ ID NO 201
<211> LENGTH: 36
<212> TYPE: PRT
<213> ORGANISM: Artificial Sequence
<220> FEATURE:
<223> OTHER INFORMATION: Synthetic Construct

<400> SEQUENCE: 201

Glu Val Gly Ser Ser Asp Cys Val Pro Tyr Tyr Tyr Ala Cys Ala Tyr
1               5                   10                  15

Ser Gly Arg Ser Ala Gly Gly Gly Gly Thr Pro Leu Gly Leu Ala Gly
            20                  25                  30

Ser Gly Gly Ser
        35

<210> SEQ ID NO 202
<211> LENGTH: 32
<212> TYPE: PRT
<213> ORGANISM: Artificial Sequence
<220> FEATURE:
<223> OTHER INFORMATION: Synthetic Construct

<400> SEQUENCE: 202

Glu Asp Cys Val Pro Tyr Tyr Tyr Ala Cys Ala Tyr Ser Gly Arg Ser
1               5                   10                  15

Ala Gly Gly Gly Gly Thr Pro Leu Gly Leu Ala Gly Ser Gly Gly Ser
            20                  25                  30

<210> SEQ ID NO 203
<211> LENGTH: 118
<212> TYPE: PRT
<213> ORGANISM: Artificial Sequence
<220> FEATURE:
<223> OTHER INFORMATION: Synthetic Construct

<400> SEQUENCE: 203

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
            35                  40                  45

```
Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Ala Gln Ile
                100                 105                 110

Tyr Val Ile Asp Pro Glu
        115
```

<210> SEQ ID NO 204
<211> LENGTH: 118
<212> TYPE: PRT
<213> ORGANISM: Artificial Sequence
<220> FEATURE:
<223> OTHER INFORMATION: Synthetic Construct

<400> SEQUENCE: 204

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
                100                 105                 110

Tyr Val Ile Asp Pro Glu
        115
```

<210> SEQ ID NO 205
<211> LENGTH: 115
<212> TYPE: PRT
<213> ORGANISM: Artificial Sequence
<220> FEATURE:
<223> OTHER INFORMATION: Synthetic Construct

<400> SEQUENCE: 205

```
Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
                20                  25                  30

Glu Val Arg Val Thr Val Leu Arg Gln Ala Asp Ser Gln Val Thr Glu
            35                  40                  45

Val Cys Ala Ala Thr Tyr Met Met Gly Asn Glu Leu Thr Phe Ile Cys
    50                  55                  60

Thr Gly Thr Ser Ser Gly Asn Gln Val Asn Leu Thr Ile Gln Gly Leu
65                  70                  75                  80

Arg Ala Met Asp Thr Gly Leu Tyr Ile Cys Lys Val Glu Leu Met Tyr
                85                  90                  95

Pro Pro Pro Tyr Tyr Leu Gly Ile Gly Asn Gly Thr Gln Ile Tyr Val
                100                 105                 110
```

```
Ile Asp Pro
        115

<210> SEQ ID NO 206
<211> LENGTH: 114
<212> TYPE: PRT
<213> ORGANISM: Artificial Sequence
<220> FEATURE:
<223> OTHER INFORMATION: Synthetic Construct

<400> SEQUENCE: 206

Ala Met His Val Ala Gln Pro Ala Val Val Leu Ala Ser Ser Arg Gly
1               5                   10                  15

Ile Ala Ser Phe Val Cys Glu Tyr Ala Ser Pro Gly Lys Ala Thr Glu
            20                  25                  30

Val Arg Val Thr Val Leu Arg Gln Ala Asp Ser Gln Val Thr Glu Val
        35                  40                  45

Cys Ala Ala Thr Tyr Met Met Gly Asn Glu Leu Thr Phe Asp Ser Ile
    50                  55                  60

Cys Thr Gly Thr Ser Ser Gly Asn Gln Val Asn Leu Thr Ile Gln Gly
65                  70                  75                  80

Leu Arg Ala Met Asp Thr Gly Leu Tyr Ile Cys Lys Val Glu Leu Met
                85                  90                  95

Tyr Pro Pro Pro Tyr Tyr Leu Gly Ile Gly Asn Gly Thr Gln Ile Tyr
            100                 105                 110

Val Ile

<210> SEQ ID NO 207
<211> LENGTH: 120
<212> TYPE: PRT
<213> ORGANISM: Homo sapiens

<400> SEQUENCE: 207

Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu
        115                 120

<210> SEQ ID NO 208
<211> LENGTH: 120
<212> TYPE: PRT
<213> ORGANISM: Mus musculus

<400> SEQUENCE: 208

Glu Ala Ile Gln Val Thr Gln Pro Ser Val Val Leu Ala Ser Ser His
1               5                   10                  15
```

Gly Val Ala Ser Phe Pro Cys Glu Tyr Ser Pro Ser His Asn Thr Asp
                20                  25                  30

Glu Val Arg Val Thr Val Leu Arg Gln Thr Asn Asp Gln Met Thr Glu
             35                  40                  45

Val Cys Ala Thr Thr Phe Thr Glu Lys Asn Thr Val Gly Phe Leu Asp
 50                  55                  60

Tyr Pro Phe Cys Ser Gly Thr Phe Asn Glu Ser Arg Val Asn Leu Thr
 65                  70                  75                  80

Ile Gln Gly Leu Arg Ala Val Asp Thr Gly Leu Tyr Leu Cys Lys Val
                 85                  90                  95

Glu Leu Met Tyr Pro Pro Pro Tyr Phe Val Gly Met Gly Asn Gly Thr
            100                 105                 110

Gln Ile Tyr Val Ile Asp Pro Glu
            115                 120

<210> SEQ ID NO 209
<211> LENGTH: 31
<212> TYPE: PRT
<213> ORGANISM: Artificial Sequence
<220> FEATURE:
<223> OTHER INFORMATION: Synthetic Construct

<400> SEQUENCE: 209

Glu Val Gly Ser Tyr Pro Asn Pro Ser Ser Asp Cys Val Pro Tyr Tyr
 1               5                  10                  15

Tyr Ala Cys Ala Tyr Ser Gly Arg Ser Ala Pro Leu Gly Leu Ala
                20                  25                  30

<210> SEQ ID NO 210
<211> LENGTH: 22
<212> TYPE: PRT
<213> ORGANISM: Artificial Sequence
<220> FEATURE:
<223> OTHER INFORMATION: Synthetic Construct

<400> SEQUENCE: 210

Glu Asp Cys Val Pro Tyr Tyr Tyr Ala Cys Ala Tyr Ser Gly Arg Ser
 1               5                  10                  15

Ala Pro Leu Gly Leu Ala
            20

<210> SEQ ID NO 211
<211> LENGTH: 17
<212> TYPE: PRT
<213> ORGANISM: Artificial Sequence
<220> FEATURE:
<223> OTHER INFORMATION: Synthetic Construct

<400> SEQUENCE: 211

Glu Asp Cys Val Pro Tyr Tyr Tyr Ala Cys Ala Tyr Ser Gly Arg Ser
 1               5                  10                  15

Ala

<210> SEQ ID NO 212
<211> LENGTH: 17
<212> TYPE: PRT
<213> ORGANISM: Artificial Sequence
<220> FEATURE:
<223> OTHER INFORMATION: Synthetic Construct

<400> SEQUENCE: 212

Glu Asp Cys Val Pro Tyr Tyr Tyr Ala Cys Ala Tyr Pro Leu Gly Leu
1               5                   10                  15

Ala

<210> SEQ ID NO 213
<211> LENGTH: 12
<212> TYPE: PRT
<213> ORGANISM: Artificial Sequence
<220> FEATURE:
<223> OTHER INFORMATION: Synthetic Construct

<400> SEQUENCE: 213

Glu Asp Cys Val Pro Tyr Tyr Tyr Ala Cys Ala Tyr
1               5                   10

<210> SEQ ID NO 214
<211> LENGTH: 16
<212> TYPE: PRT
<213> ORGANISM: Artificial Sequence
<220> FEATURE:
<223> OTHER INFORMATION: Synthetic Construct

<400> SEQUENCE: 214

Glu Val Gly Ser Ser Asp Cys Val Pro Tyr Tyr Tyr Ala Cys Ala Tyr
1               5                   10                  15

<210> SEQ ID NO 215
<211> LENGTH: 12
<212> TYPE: PRT
<213> ORGANISM: Artificial Sequence
<220> FEATURE:
<223> OTHER INFORMATION: Synthetic Construct

<400> SEQUENCE: 215

Glu Asp Cys Asp Ala Phe Tyr Pro Tyr Cys Asp Ser
1               5                   10

<210> SEQ ID NO 216
<211> LENGTH: 16
<212> TYPE: PRT
<213> ORGANISM: Artificial Sequence
<220> FEATURE:
<223> OTHER INFORMATION: Synthetic Construct

<400> SEQUENCE: 216

Glu Val Gly His Ser Asp Cys Asp Ala Phe Tyr Pro Tyr Cys Asp Ser
1               5                   10                  15

<210> SEQ ID NO 217
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Present in repeats of at least one and up to 11
<220> FEATURE:
<221> NAME/KEY: VARIANT
<222> LOCATION: 5, 6, 7, 8, 9, 10, 11, 12
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr
<220> FEATURE:
<221> NAME/KEY: VARIANT
<222> LOCATION: 3, 14, 15
<223> OTHER INFORMATION: Xaa = Asp, Ala, Tyr, Ser, Thr, Asn, Ile, Leu,
      Phe, Val, His, or Pro

```
<400> SEQUENCE: 217

Glu Val Xaa Cys Xaa Xaa Xaa Xaa Xaa Xaa Xaa Cys Xaa Xaa Ser
1               5                   10                  15

Gly Arg Ser Ala
            20

<210> SEQ ID NO 218
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4, 5, 6, 7, 8, 9, 11, 12
<223> OTHER INFORMATION: Xaa = Asp, Ala, Tyr, Ser, Thr, Asn, Ile, Leu,
      Phe, Val, His, or Pro

<400> SEQUENCE: 218

Glu Asp Cys Xaa Xaa Xaa Xaa Xaa Xaa Cys Xaa Xaa Ser Gly Arg Ser
1               5                   10                  15

Ala

<210> SEQ ID NO 219
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4, 5, 6, 7, 8, 9, 11, 12
<223> OTHER INFORMATION: Xaa = Asp, Ala, Tyr, Ser, Thr, Asn, Ile, Leu,
      Phe, Val, His, or Pro

<400> SEQUENCE: 219

Glu Asp Cys Xaa Xaa Xaa Xaa Xaa Xaa Cys Xaa Xaa Pro Leu Gly Leu
1               5                   10                  15

Ala

<210> SEQ ID NO 220
<211> LENGTH: 21
<212> TYPE: PRT
<213> ORGANISM: Artificial Sequence
<220> FEATURE:
<223> OTHER INFORMATION: Synthetic Construct

<400> SEQUENCE: 220

Ser Gly Arg Ser Ala Gly Gly Gly Gly Thr Glu Asn Leu Tyr Phe Gln
1               5                   10                  15

Gly Ser Gly Gly Ser
            20

<210> SEQ ID NO 221
<211> LENGTH: 20
<212> TYPE: PRT
<213> ORGANISM: Artificial Sequence
<220> FEATURE:
<223> OTHER INFORMATION: Synthetic Construct

<400> SEQUENCE: 221

Ser Gly Arg Ser Ala Gly Gly Gly Gly Thr Pro Leu Gly Leu Ala Gly
1               5                   10                  15

Ser Gly Gly Ser
            20
```

<210> SEQ ID NO 222
<211> LENGTH: 10
<212> TYPE: PRT
<213> ORGANISM: Artificial Sequence
<220> FEATURE:
<223> OTHER INFORMATION: Synthetic Construct

<400> SEQUENCE: 222

Ser Gly Arg Ser Ala Pro Leu Gly Leu Ala
1               5                   10

<210> SEQ ID NO 223
<211> LENGTH: 13
<212> TYPE: PRT
<213> ORGANISM: Artificial Sequence
<220> FEATURE:
<223> OTHER INFORMATION: Synthetic Construct

<400> SEQUENCE: 223

Phe Ser Leu Ser Thr Gly Gly Val Gly Val Gly Trp Ile
1               5                   10

<210> SEQ ID NO 224
<211> LENGTH: 20
<212> TYPE: PRT
<213> ORGANISM: Artificial Sequence
<220> FEATURE:
<223> OTHER INFORMATION: Synthetic Construct

<400> SEQUENCE: 224

Leu Ala Leu Ile Asp Trp Ala Asp Asp Lys Tyr Tyr Ser Pro Ser Leu
1               5                   10                  15

Lys Ser Arg Leu
            20

<210> SEQ ID NO 225
<211> LENGTH: 15
<212> TYPE: PRT
<213> ORGANISM: Artificial Sequence
<220> FEATURE:
<223> OTHER INFORMATION: Synthetic Construct

<400> SEQUENCE: 225

Ala Arg Gly Gly Ser Asp Thr Val Ile Gly Asp Trp Phe Ala Tyr
1               5                   10                  15

<210> SEQ ID NO 226
<211> LENGTH: 11
<212> TYPE: PRT
<213> ORGANISM: Artificial Sequence
<220> FEATURE:
<223> OTHER INFORMATION: Synthetic Construct

<400> SEQUENCE: 226

Arg Ala Ser Gln Ser Ile Gly Ser Tyr Leu Ala
1               5                   10

<210> SEQ ID NO 227
<211> LENGTH: 9
<212> TYPE: PRT
<213> ORGANISM: Artificial Sequence
<220> FEATURE:
<223> OTHER INFORMATION: Synthetic Construct

<400> SEQUENCE: 227

```
Asp Ala Ser Asn Leu Glu Thr Gly Val
1               5
```

<210> SEQ ID NO 228
<211> LENGTH: 10
<212> TYPE: PRT
<213> ORGANISM: Artificial Sequence
<220> FEATURE:
<223> OTHER INFORMATION: Synthetic Construct

<400> SEQUENCE: 228

```
Tyr Cys Gln Gln Gly Tyr Tyr Leu Trp Thr
1               5                   10
```

<210> SEQ ID NO 229
<211> LENGTH: 123
<212> TYPE: PRT
<213> ORGANISM: Artificial Sequence
<220> FEATURE:
<223> OTHER INFORMATION: Synthetic Construct

<400> SEQUENCE: 229

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Gly
            20                  25                  30

Gly Val Gly Val Gly Trp Ile Arg Gln Ala Pro Gly Lys Gly Leu Glu
        35                  40                  45

Trp Leu Ala Leu Ile Asp Trp Ala Asp Asp Lys Tyr Tyr Ser Pro Ser
    50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Gly Ser Asp Thr Val Ile Gly Asp Trp Phe Ala Tyr
            100                 105                 110

Trp Gly Gln Gly Thr Leu Val Thr Val Ser Ser
        115                 120
```

<210> SEQ ID NO 230
<211> LENGTH: 106
<212> TYPE: PRT
<213> ORGANISM: Artificial Sequence
<220> FEATURE:
<223> OTHER INFORMATION: Synthetic Construct

<400> SEQUENCE: 230

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Gly Tyr Tyr Leu Trp Thr
                85                  90                  95

Phe Gly Gln Gly Thr Lys Val Glu Ile Lys
               100                 105
```

ANTI-CTLA4 ANTIBODIES AND METHODS OF MAKING AND USING THE SAME

CROSS REFERENCE TO RELATED APPLICATIONS

This application is a national stage application under 35 U.S.C. § 371 of International Application No. PCT/CN2019/074580, filed internationally on Feb. 2, 2019, which claims the priority benefit of International Application No. PCT/CN2018/075064, filed on Feb. 2, 2018, each of which is incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 695402000500SUBSEQLIST.TXT, date recorded: Dec. 18, 2020, size: 102 KB).

FIELD OF THE INVENTION

The present disclosure relates to cross-reactive antibodies that bind to human Cytotoxic T-lymphocyte Protein 4 (CTLA4), precision/context-dependent activatable antibodies that bind to human CTLA4, nucleic acids encoding the same, pharmaceutical compositions thereof, and their therapeutic use.

BACKGROUND

CTLA4 is a member of the immunoglobulin (Ig) superfamily of proteins that acts to downregulate T-cell activation and maintain immunogenic homeostasis. It has been shown that in vivo antibody-mediated blockade of CTLA4 enhanced anti-cancer immune responses in a syngeneic murine prostate cancer model (Kwon et al. (1997) Proc Natl Acad Sci USA, 94(15):8099-103). In addition, blockade of CTLA4 function was shown to enhance anti-tumor T cell responses at various stages of tumor growth in tumor-bearing mice (Yang et al. (1997) Cancer Res 57(18):4036-41; Hurwitz et al. (1998) Proc Natl Acad Sci USA 95 (17): 10067-7). However, the development of antibody-based therapeutics suitable for human use remains difficult, as translation from pre-clinical animal models to human safety is often poor. Accordingly, a need exists for anti-CTLA4 antibodies that are cross-reactive among different species, such as humans and experimental animals (e.g., mouse, monkey, rat, etc.), to concurrently enable animal model studies and provide suitable human therapeutic candidates. In addition, a need exists for the development of safer anti-CTLA4 antibodies that are only active in certain contexts, such as in the protease-rich tumor microenvironment.

All references cited herein, including patent applications, patent publications, non-patent literature, and UniProtKB/Swiss-Prot/GenBank Accession numbers are herein incorporated by reference in their entirety, as if each individual reference were specifically and individually indicated to be incorporated by reference.

BRIEF SUMMARY

To meet the above and other needs, disclosed herein are antibodies (e.g., cross-reactive antibodies), and antigen binding fragments thereof, that bind to human CTLA4. The anti-CTLA4 antibodies, or antigen binding fragments thereof, of the present disclosure possessed at least one (e.g., one, some, or all) of the following functional properties: (a) bind to human, cynomolgus monkey, mouse, rat, and/or dog CTLA4 with a $K_D$ of 500 nM or less; (b) have antagonist activity on human CTLA4; (c) do not bind to human PD-1, PD-L1, PD-L2, LAG3, TIM3, B7-H3, CD95, CD120a, OX40, CD40, BTLA, VISTA, ICOS, and/or B7-H4 at concentration up to 100 nM; (d) are cross-reactive with monkey, mouse, rat, and/or dog CTLA4; (e) induces ADCC effects (e.g., on Tregs); (0 activates human PBMCs (e.g., stimulates secretion of IL-2 and/or IFNγ); (g) are capable of inhibiting tumor cell growth and establishing immune memory against tumor cells; (h) have therapeutic effect on a cancer; and (i) block binding of human CTLA4 to human CD80 and/or human CD86 (see Examples 1-5 below).

Disclosed herein are precision/context-dependent activatable antibodies that bind to human CTLA4 when in active form but not in inactive form, i.e., the activatable antibodies bound to CTLA4 (were active) only after cleavage of the cleavable moiety (CM) to remove the masking moiety (MM). In some embodiments, the discovered masking moieties (MMs) described herein were capable of efficiently masking antibody activity and/or reducing or completely inhibiting antigen binding, while in some embodiments being devoid of the chemically labile residues methionine and/or tryptophan. Furthermore, the activatable antibodies identified and described herein are as efficient at treating multiple cancer types as their parental antibody, while having significantly reduced cytotoxicity in susceptible animals (NOD mice).

Accordingly, in one aspect, provided herein is an anti-CTLA4 antibody (e.g., human antibodies) that binds human CTLA4 and is cross-reactive with a CTLA4 polypeptide from at least one non-human animal selected from the group consisting of cynomolgus monkey, mouse, rat, and dog. In some embodiments, the antibody binds to cynomolgus monkey CTLA4 and mouse CTLA4. In some embodiments that may be combined with any of the preceding embodiments, the antibody binds to human CTLA4, cynomolgus monkey CTLA4, mouse CTLA4, rat CTLA4, and/or dog CTLA4 with a dissociation constant ($K_D$) of about 350 nM or less (e.g., about 300 nM or less, about 200 nM or less, about 100 nM or less, about 50 nM or less, or about 10 nM or less). In some embodiments, the $K_D$ is measured by surface plasmon resonance (SPR). In some embodiments, binding of the antibody to CTLA4 induces antibody-dependent cell cytotoxicity (ADCC) against a CTLA4-expressing cell. In some embodiments, binding of the antibody to CTLA4 induces ADCC against a Treg cell. In some embodiments, binding of the anti-CTLA4 antibody described herein induces antibody-dependent cell cytotoxicity (ADCC) against a CTLA4-expressing human cell or a human Treg cell, wherein the ADCC activity of the anti-CTL4 antibody is higher than the ADCC activity of ipilimumab in vitro, and wherein both antibodies comprise wild type human IgG1 Fc region. In some embodiments, binding of the anti-CTLA4 antibody described herein induces antibody-dependent cell cytotoxicity (ADCC) against a CTLA4-expressing human cell or a human Treg cell, wherein the ADCC activity of the anti-CTLA4 antibody is two times or higher than the ADCC activity of ipilimumab in vitro, and wherein both antibodies comprise wild type human IgG1 Fc region. In some embodiments, the EC50 of the anti-CTL4 antibody ADCC activity is 50% or less than the EC50 of ipilimumab ADCC activity in vitro. Assays for measuring ADCC activities are described in Examples 3 and 15. In some embodiments, the anti-CTLA4 antibody depletes Treg cells selectively in tumor microenvironment (e.g., reducing percentage of Treg cells in tumor infiltrating lymphocytes), as compared to PBMC or spleen in a mouse cancer model. See, e.g., Example 18.

In some embodiments that may be combined with any of the preceding embodiments, the antibody specifically binds to an epitope comprising amino acid residues at a ligand binding site of human CTLA4, such as CD80 and/or CD86 binding site of human CTLA4. In some embodiments, the antibody specifically binds to an epitope similar to a ligand binding site of human CTLA4, such as CD80 and/or CD86 binding site of human CTLA4. In some embodiments, the antibody specifically binds to an epitope comprising amino acid residues Y105 and L106 of human CTLA4, wherein the numbering of the amino acid residues is according to SEQ ID NO: 207. In some embodiments, the antibody does not bind to residue I108 of human CTLA4, wherein the numbering of the amino acid residues is according to SEQ ID NO: 207. In some embodiments, the anti-CTLA4 antibody blocks binding of CD80 and/or CD86 to human CTLA4. In some embodiments, the anti-CTLA4 antibody has an IC50 higher than the IC50 of ipilimumab for blocking binding of CD80 and/or CD86 to human CTLA4. In some embodiments, the anti-CTLA4 antibody has an IC50 that is 3.5 times or higher (including 3.9 times or higher) than the IC50 of ipilimumab for blocking binding of CD80 and/or CD86 to human CTLA4 in an assay that CD86 or CD80 is plate bound and CTLA4 is in solution or CTLA4 displayed on cell surface. See Example 13, Table 23, FIGS. 57A-57D and 58. Assays for testing antibody's blocking activities (ligand competition) and IC50 are described in Examples 3 and 13.

In some embodiments that may be combined with any of the preceding embodiments, the antibody comprises a heavy chain variable region and a light chain variable region, a) wherein the heavy chain variable region comprises an HVR-H1, an HVR-H2, and an HVR-H3, wherein the HVR-H1 comprises an amino acid sequence according to a formula selected from the group consisting of: Formula (I): X1TFSX2YX3IHWV (SEQ ID NO: 1), wherein X1 is F or Y, X2 is D or G, and X3 is A, G, or W; Formula (II): YSIX1SGX2X3WX4WI (SEQ ID NO: 2), wherein X1 is S or T, X2 is H or Y, X3 is H or Y, and X4 is A, D, or S; and Formula (III): FSLSTGGVAVX1WI (SEQ ID NO: 3), wherein X1 is G or S; wherein the HVR-H2 comprises an amino acid sequence according to a formula selected from the group consisting of: Formula (IV): IGX1IX2HSGSTYYSX3SLKSRV (SEQ ID NO: 4), wherein X1 is D or E, X2 is S or Y, and X3 is P or Q; Formula (V): IGX1ISPSX2GX3TX4YAQKFQGRV (SEQ ID NO: 5), wherein X1 is I or W, X2 is G or S, X3 is G or S, and X4 is K or N; and Formula (VI): VSX1ISGX2GX3X4TYYADSVKGRF (SEQ ID NO: 6), wherein X1 is A, G, or S, X2 is S or Y, X3 is G or S, and X4 is S or T; and wherein the HVR-H3 comprises an amino acid sequence according to a formula selected from the group consisting of: Formula (VII): ARX1X2X3X4FDX5 (SEQ ID NO: 7), wherein X1 is G, R, or S, X2 is A, I, or Y, X3 is D, V, or Y, X4 is A, E, or Y, and X5 is I or Y; Formula (VIII): ARX1GX2GYFDX3 (SEQ ID NO: 8), wherein X1 is D or L, X2 is F or Y, and X3 is V or Y; Formula (IX): ARX1X2X3X4AX5X6FDY (SEQ ID NO: 9), wherein X1 is L or R, X2 is I or P, X3 is A or Y, X4 is S or T, X5 is T or Y, and X6 is A or Y; Formula (X): ARDX1X2X3GSSGYYX4GFDX5 (SEQ ID NO: 10), wherein X1 is I or V, X2 is A or H, X3 is P or S, X4 is D or Y, and X5 is F or V; and b) wherein the light chain variable region comprises an HVR-L1, an HVR-L2, and an HVR-L3, wherein the HVR-L1 comprises an amino acid sequence according to a formula selected form the group consisting of: Formula (XI): RASQX1X2X3SX4LX5 (SEQ ID NO: 11), wherein X1 is G or S, X2 is I or V, X3 is G or S, X4 is S or Y, and X5 is A or N; Formula (XII): RASQX1VX2X3RX4LA (SEQ ID NO: 12), wherein X1 is S or T, X2 is F, R, or S, X3 is G or S, and X4 is F or Y; and Formula (XIII): RASX1SVDFX2GX3SFLX4 (SEQ ID NO: 13), wherein X1 is E or Q, X2 is D, F, H, or Y, X3 is F, I, or K, and X4 is A, D, or H; wherein the HVR-L2 comprises an amino acid sequence according to Formula (XIV): X1ASX2X3X4X5GX6 (SEQ ID NO: 14), wherein X1 is A or D, X2 is N, S, or T, X3 is L or R, X4 is A, E, or Q, X5 is S or T, and X6 is I or V; and wherein the HVR-L3 comprises an amino acid sequence according to a formula selected from the group consisting of: Formula (XV): YCX1X2X3X4X5X6PX7T (SEQ ID NO: 15), wherein X1 is E, Q, or V, X2 is H or Q, X3 is A, G, H, R, or S, X4 is D, L, S, or Y, X5 is E, G, P, Q, or S, X6 is L, T, V, or W, and X7 is F, L, P, W, or Y; Formula (XVI): YCQQX1X2X3WPPWT (SEQ ID NO: 16), wherein X1 is S or Y, X2 is D or Y, and X3 is Q or Y; and Formula (XVII): YCQX1YX2SSPPX3YT (SEQ ID NO: 17), wherein X1 is H or Q, X2 is T or V, and X3 is E or V. In some embodiments, the HVR-H1 comprises an amino acid sequence selected from the group consisting of SEQ ID NOS: 18-29, the HVR-H2 comprises an amino acid sequence selected from the group consisting of SEQ ID NOS: 30-39, the HVR-H3 comprises an amino acid sequence selected from the group consisting of SEQ ID NOS: 40-52, the HVR-L1 comprises an amino acid sequence selected from the group consisting of SEQ ID NOS: 53-65, the HVR-L2 comprises an amino acid sequence selected from the group consisting of SEQ ID NOS: 66-69, and the HVR-L3 comprises an amino acid sequence selected from the group consisting of SEQ ID NOS: 70-81. In some embodiments, the antibody comprises: a) an HVR-H1 comprising the amino acid sequence of SEQ ID NO: 18, an HVR-H2 comprising the amino acid sequence of SEQ ID NO: 30, an HVR-H3 comprising the amino acid sequence of SEQ ID NO: 40, an HVR-L1 comprising the amino acid sequence of SEQ ID NO: 53, an HVR-L2 comprising the amino acid sequence of SEQ ID NO: 66, and an HVR-L3 comprising the amino acid sequence of SEQ ID NO: 70; b) an HVR-H1 comprising the amino acid sequence of SEQ ID NO: 19, an HVR-H2 comprising the amino acid sequence of SEQ ID NO: 31, an HVR-H3 comprising the amino acid sequence of SEQ ID NO: 41, an HVR-L1 comprising the amino acid sequence of SEQ ID NO: 54, an HVR-L2 comprising the amino acid sequence of SEQ ID NO: 67, and an HVR-L3 comprising the amino acid sequence of SEQ ID NO: 71; c) an HVR-H1 comprising the amino acid sequence of SEQ ID NO: 20, an HVR-H2 comprising the amino acid sequence of SEQ ID NO: 32, an HVR-H3 comprising the amino acid sequence of SEQ ID NO: 42, an HVR-L1 comprising the amino acid sequence of SEQ ID NO: 55, an HVR-L2 comprising the amino acid sequence of SEQ ID NO: 66, and an HVR-L3 comprising the amino acid sequence of SEQ ID NO: 72; d) an HVR-H1 comprising the amino acid sequence of SEQ ID NO: 21 an HVR-H2 comprising the amino acid sequence of SEQ ID NO: 33, an HVR-H3 comprising the amino acid sequence of SEQ ID NO: 43, an HVR-L1 comprising the amino acid sequence of SEQ ID NO: 56, an HVR-L2 comprising the amino acid sequence of SEQ ID NO: 68, and an HVR-L3 comprising the amino acid sequence of SEQ ID NO: 73; e)

an HVR-H1 comprising the amino acid sequence of SEQ ID NO: 22, an HVR-H2 comprising the amino acid sequence of SEQ ID NO: 34, an HVR-H3 comprising the amino acid sequence of SEQ ID NO: 44, an HVR-L1 comprising the amino acid sequence of SEQ ID NO: 57, an HVR-L2 comprising the amino acid sequence of SEQ ID NO: 66, and an HVR-L3 comprising the amino acid sequence of SEQ ID NO: 74; f) an HVR-H1 comprising the amino acid sequence of SEQ ID NO: 23, an HVR-H2 comprising the amino acid sequence of SEQ ID NO: 35, an HVR-H3 comprising the amino acid sequence of SEQ ID NO: 45, an HVR-L1 comprising the amino acid sequence of SEQ ID NO: 58, an HVR-L2 comprising the amino acid sequence of SEQ ID NO: 66, and an HVR-L3 comprising the amino acid sequence of SEQ ID NO: 75; g) an HVR-H1 comprising the amino acid sequence of SEQ ID NO: 24, an HVR-H2 comprising the amino acid sequence of SEQ ID NO: 32, an HVR-H3 comprising the amino acid sequence of SEQ ID NO: 46, an HVR-L1 comprising the amino acid sequence of SEQ ID NO: 59, an HVR-L2 comprising the amino acid sequence of SEQ ID NO: 66, and an HVR-L3 comprising the amino acid sequence of SEQ ID NO: 76; h) an HVR-H1 comprising the amino acid sequence of SEQ ID NO: 25, an HVR-H2 comprising the amino acid sequence of SEQ ID NO: 36, an HVR-H3 comprising the amino acid sequence of SEQ ID NO: 47, an HVR-L1 comprising the amino acid sequence of SEQ ID NO: 60, an HVR-L2 comprising the amino acid sequence of SEQ ID NO: 69, and an HVR-L3 comprising the amino acid sequence of SEQ ID NO: 77; i) an HVR-H1 comprising the amino acid sequence of SEQ ID NO: 26, an HVR-H2 comprising the amino acid sequence of SEQ ID NO: 37, an HVR-H3 comprising the amino acid sequence of SEQ ID NO: 48, an HVR-L1 comprising the amino acid sequence of SEQ ID NO: 61, an HVR-L2 comprising the amino acid sequence of SEQ ID NO: 66, and an HVR-L3 comprising the amino acid sequence of SEQ ID NO: 78; j) an HVR-H1 comprising the amino acid sequence of SEQ ID NO: 27, an HVR-H2 comprising the amino acid sequence of SEQ ID NO: 32, an HVR-H3 comprising the amino acid sequence of SEQ ID NO: 49, an HVR-L1 comprising the amino acid sequence of SEQ ID NO: 62, an HVR-L2 comprising the amino acid sequence of SEQ ID NO: 67, and an HVR-L3 comprising the amino acid sequence of SEQ ID NO: 79; k) an HVR-H1 comprising the amino acid sequence of SEQ ID NO: 28, an HVR-H2 comprising the amino acid sequence of SEQ ID NO: 37, an HVR-H3 comprising the amino acid sequence of SEQ ID NO: 50, an HVR-L1 comprising the amino acid sequence of SEQ ID NO: 63, an HVR-L2 comprising the amino acid sequence of SEQ ID NO: 67, and an HVR-L3 comprising the amino acid sequence of SEQ ID NO: 80; l) an HVR-H1 comprising the amino acid sequence of SEQ ID NO: 18, an HVR-H2 comprising the amino acid sequence of SEQ ID NO: 38, an HVR-H3 comprising the amino acid sequence of SEQ ID NO: 51, an HVR-L1 comprising the amino acid sequence of SEQ ID NO: 64, an HVR-L2 comprising the amino acid sequence of SEQ ID NO: 67, and an HVR-L3 comprising the amino acid sequence of SEQ ID NO: 81; or m) an HVR-H1 comprising the amino acid sequence of SEQ ID NO: 29, an HVR-H2 comprising the amino acid sequence of SEQ ID NO: 39, an HVR-H3 comprising the amino acid sequence of SEQ ID NO: 52, an HVR-L1 comprising the amino acid sequence of SEQ ID NO: 65, an HVR-L2 comprising the amino acid sequence of SEQ ID NO: 68, and an HVR-L3 comprising the amino acid sequence of SEQ ID NO: 77. In some embodiments that may be combined with any of the preceding embodiments, the heavy chain variable region comprises an amino acid sequence selected from the group consisting of SEQ ID NOS: 82-94, and/or the light chain variable region comprises an amino acid sequence selected from the group consisting of SEQ ID NOS: 95-107. In some embodiments that may be combined with any of the preceding embodiments, the antibody comprises: a) a heavy chain variable region comprising the amino acid sequence of SEQ ID NO: 82 or a variant thereof having at least about 90% (e.g., at least about 92%, 95%, 98%, 99% or more) sequence identity to the amino acid sequence of SEQ ID NO: 82, and a light chain variable region comprising the amino acid sequence of SEQ ID NO: 95 or a variant thereof having at least about 90% (e.g., at least about 92%, 95%, 98%, 99% or more) sequence identity to the amino acid sequence of SEQ ID NO: 95; b) a heavy chain variable region comprising the amino acid sequence of SEQ ID NO: 83 or a variant thereof having at least about 90% (e.g., at least about 92%, 95%, 98%, 99% or more) sequence identity to the amino acid sequence of SEQ ID NO: 83, and a light chain variable region comprising the amino acid sequence of SEQ ID NO: 96 or a variant thereof having at least about 90% (e.g., at least about 92%, 95%, 90%, 99% or more) sequence identity to the amino acid sequence of SEQ ID NO: 96; c) a heavy chain variable region comprising the amino acid sequence of SEQ ID NO: 84 or a variant thereof having at least about 90% (e.g., at least about 92%, 95%, 98%, 99% or more) sequence identity to the amino acid sequence of SEQ ID NO: 84, and a light chain variable region comprising the amino acid sequence of SEQ ID NO: 97 or a variant thereof having at least about 90% (e.g., at least about 92%, 95%, 98%, 99% or more) sequence identity to the amino acid sequence of SEQ ID NO: 97; d) a heavy chain variable region comprising the amino acid sequence of SEQ ID NO: 85 or a variant thereof having at least about 90% (e.g., at least about 92%, 95%, 98%, 99% or more) sequence identity to the amino acid sequence of SEQ ID NO: 85, and a light chain variable region comprising the amino acid sequence of SEQ ID NO: 98 or a variant thereof having at least about 90% (e.g., at least about 92%, 95%, 98%, 99% or more) sequence identity to the amino acid sequence of SEQ ID NO: 98; e) a heavy chain variable region comprising the amino acid sequence of SEQ ID NO: 86 or a variant thereof having at least about 90% (e.g., at least about 92%, 95%, 98%, 99% or more) sequence identity to the amino acid sequence of SEQ ID NO: 86, and a light chain variable region comprising the amino acid sequence of SEQ ID NO: 99 or a variant thereof having at least about 90% (e.g., at least about 92%, 95%, 98%, 99% or more) sequence identity to the amino acid sequence of SEQ ID NO: 99; f) a heavy chain variable region comprising the amino acid sequence of SEQ ID NO: 87 or a variant thereof having at least about 90% (e.g., at least about 92%, 95%, 98%, 99% or more) sequence identity to the amino acid sequence of SEQ ID NO: 87, and a light chain variable region comprising the amino acid sequence of SEQ ID NO: 100 or a variant thereof having at least about 90% (e.g., at least about 92%, 95%, 98%, 99% or more) sequence identity to the amino acid sequence of SEQ ID NO: 100; g) a heavy chain variable region comprising the amino acid sequence of SEQ ID NO: 88 or a variant thereof having at least about 90% (e.g., at least about 92%, 95%, 98%, 99% or more) sequence identity to the amino acid sequence of SEQ ID NO: 88, and a light chain variable region comprising the amino acid sequence of SEQ ID NO: 101 or a variant thereof having at least about 90% (e.g., at least about 92%, 95%, 98%, 99% or more) sequence identity to the amino acid sequence of SEQ ID NO: 101; h) a heavy chain variable region comprising the amino acid sequence of SEQ ID NO: 89 or a variant thereof having at least about 90% (e.g., at least about 92%, 95%, 98%, 99% or more) sequence identity to the amino acid sequence of SEQ ID NO: 89, and a light chain variable region comprising the amino acid sequence of SEQ ID NO: 102 or a variant thereof having at least about 90% (e.g., at least about 92%, 95%, 98%, 99% or more) sequence identity to the amino acid sequence of SEQ ID NO: 102; i) a heavy chain variable region comprising the amino acid sequence of SEQ ID NO: 90 or a variant thereof having at least about 90% (e.g., at least about 92%, 95%, 98%, 99% or more) sequence identity to the amino acid sequence of SEQ ID NO: 90, and a light chain variable region comprising the amino acid sequence of SEQ ID NO: 103 or a variant thereof having at least about 90% (e.g., at least about 92%, 95%, 98%, 99% or more) sequence identity to the amino acid sequence of SEQ ID NO: 103; j) a heavy chain variable region comprising the amino acid sequence of SEQ ID NO: 91 or a variant thereof having at least about 90% (e.g., at least about 92%, 95%, 98%, 99% or more) sequence identity to the amino acid sequence of SEQ ID NO: 91, and a light chain variable region comprising the amino acid sequence of SEQ ID NO: 104 or a variant thereof having at least about 90% (e.g., at least about 92%, 95%, 98%, 99% or more) sequence identity to the amino acid sequence of SEQ ID NO: 104; k) a heavy chain variable region comprising the amino acid sequence of SEQ ID NO: 92 or a variant thereof having at least about 90% (e.g., at least about 92%, 95%, 98%, 99% or more) sequence identity to the amino acid sequence of SEQ ID NO: 92, and a light chain variable region comprising the amino acid sequence of SEQ ID NO: 105 or a variant thereof having at least about 90% (e.g., at least about 92%, 95%, 98%, 99% or more) sequence identity to the amino acid sequence of SEQ ID NO: 105; l) a heavy chain variable region comprising the amino acid sequence of SEQ ID NO: 93 or a variant thereof having at least about 90% (e.g., at least about 92%, 95%, 98%, 99% or more) sequence identity to the amino acid sequence of SEQ ID NO: 93, and a light chain variable region comprising the amino acid sequence of SEQ ID NO: 106 or a variant thereof having at least about 90% (e.g., at least about 92%, 95%, 98%, 99% or more) sequence identity to the amino acid sequence of SEQ ID NO: 106; or m) a heavy chain variable region comprising the amino acid sequence of SEQ ID NO: 94 or a variant thereof having at least about 90% (e.g., at least about 92%, 95%, 98%, 99% or more) sequence identity to the amino acid sequence of SEQ ID NO: 94, and a light chain variable region comprising the amino acid sequence of SEQ ID NO: 107 or a variant thereof having at least about 90% (e.g., at least about 92%, 95%, 98%, 99% or more) sequence identity to the amino acid sequence of SEQ ID NO: 107.

In some embodiments, the anti-CTLA4 antibody described herein comprises a heavy chain variable region and a light chain variable region, wherein one, two, three, four, five, or six HVRs of the antibody comprise a HVR sequence shown in Table A. In some embodiments, the anti-CTLA4 antibody comprises a heave chain variable region comprising an HVR-H1, an HVR-H2, and an HVR-H3, wherein the HVR-H1 comprises the amino acid sequence of SEQ ID NO: 23, or the HVR-H2 comprises the amino acid sequence of SEQ ID NO: 35, or the HVR-H3 comprises the amino acid sequence of SEQ ID NO: 45. In some embodiments, the anti-CTLA4 antibody comprises a light chain variable region comprising an HVR-L1, an HVR-L2, and an HVR-L3, wherein the HVR-L1 comprises the amino acid sequence of SEQ ID NO: 58, or the HVR-L2 comprises the antibody comprises the amino acid sequence of SEQ ID NO: 66, or the HVR-L3 comprises the amino acid sequence of SEQ ID NO: 75. In some embodiments, the HVR-H2 of the antibody comprises the amino acid sequence of SEQ ID NO: 35. In some embodiments, the anti-CTLA4 antibody comprises (a) a heavy chain variable region comprising an HVR-H1 comprising the amino acid sequence of SEQ ID NO: 23, an HVR-H2 comprising the amino acid sequence of SEQ ID NO: 35, and an HVR-H3 comprising the amino acid sequence of SEQ ID NO: 45, and/or a light chain variable region comprising an HVR-L1 comprising the amino acid sequence of SEQ ID NO: 58, an HVR-L2 comprising the amino acid sequence of SEQ ID NO: 66, and an HVR-L3 comprising the amino acid sequence of SEQ ID NO: 75. In some embodiments, one, two, three, four, five or six of the HVRs of the antibody may comprise one, two or three conservative amino acid substitutions in the HVRs. In some embodiments, the anti-CTLA4 antibody comprises (b) a heavy chain variable region comprising the amino acid sequence of SEQ ID NO: 87 or an amino acid sequence having at least 90% (e.g., 91%, 92%, 93%, 95%, 96%, 97%, 98%, or 99%) sequence identity to the amino acid sequence of SEQ ID NO: 87, and/or a light chain variable region comprising the amino acid sequence of SEQ ID NO: 100 or an amino acid sequence having at least 90% (e.g., 91%, 92%, 93%, 95%, 96%, 97%, 98%, or 99%) sequence identity to the amino acid sequence of SEQ ID NO: 100.

In some embodiments that may be combined with any of the preceding embodiments, the antibody is an antibody fragment. In some embodiments, the fragment is a Fab, Fab', Fab'-SH, F(ab')$_2$, Fv or scFv fragment. In some embodiments that may be combined with any of the preceding embodiments, the antibody comprises an IgG1, IgG2, IgG3, or IgG4 Fc region (such as human IgG1, IgG2, IgG3, or IgG4 Fc region). In some embodiments, the antibody comprising a human IgG1 or a variant that has enhanced ADCC activity. In some embodiments, the antibody comprises a human IgG1 with reduced fucosylation (or non-fucosylated). In some embodiments, the antibody is a human antibody.

Other aspects of the present disclosure relate to an antibody that competes or cross-competes for binding to human CTLA4 with any of the antibodies described herein. Also provided herein are antibodies that bind to the same epitope and/or essentially the same epitope as any of the antibodies described herein.

Other aspects of the present disclosure relate to an activatable antibody comprising: a) a first polypeptide comprising, from N-terminus to C-terminus, a masking moiety (MM), a cleavable moiety (CM), and a target binding moiety (TBM), wherein the MM comprises an amino acid sequence according to Formula (XVIII): $X_mCX_nCZ_o$ (SEQ ID NO: 134), wherein m is from 2-10, n is from 3-10, and o is from 1-10, wherein each X is independently an amino acid selected from the group consisting of A, C, D, E, F, G, H, I, K, L, M, N, P, Q, R, S, T, V, W, and Y, and wherein each Z is independently an amino acid selected from the group consisting of D, A, Y, S, T, N, I, L, F, V, H, and P; wherein the MM inhibits the binding of the activatable antibody to human CTLA4 when the CM is not cleaved; wherein the CM comprises at least a first cleavage site; and wherein the TBM comprises an antibody heavy chain variable region (VH); and b) a second polypeptide comprising an antibody light chain variable region (VL); and wherein the activatable antibody binds to human CTLA4 via the VH and VL when the CM is cleaved. In some embodiments, m is from 3-10.

Other aspects of the present disclosure relate to an activatable antibody comprising: a) a polypeptide comprising, from N-terminus to C-terminus, a masking moiety (MM), a cleavable moiety (CM), and a target binding moiety (TBM), wherein the MM comprises an amino acid sequence according to Formula (XVIII): $X_mCX_nCZ_o$ (SEQ ID NO: 134), wherein m is from 2-10, n is from 3-10, and o is from 1-10, wherein each X is independently an amino acid selected from the group consisting of A, C, D, E, F, G, H, I, K, L, M, N, P, Q, R, S, T, V, W, and Y, and wherein each Z is independently an amino acid selected from the group consisting of D, A, Y, S, T, N, I, L, F, V, H, and P; wherein the MM inhibits the binding of the activatable antibody to human CTLA4 when the CM is not cleaved; wherein the CM comprises at least a first cleavage site; and wherein the TBM comprises an antibody light chain variable region (VL); and b) a second polypeptide comprising an antibody heavy chain variable region (VH); and wherein the activatable antibody binds to human CTLA4 via the VH and VL when the CM is cleaved. In some embodiments, m is from 3-10.

Other aspects of the present disclosure relate to an activatable antibody comprising: a polypeptide comprising, from N-terminus to C-terminus, a masking moiety (MM), a cleavable moiety (CM), and a target binding moiety (TBM), wherein the MM comprises an amino acid sequence according to Formula (XVIII): $X_mCX_nCZ_o$ (SEQ ID NO: 134), wherein m is from 2-10, n is from 3-10, and o is from 1-10, wherein each X is independently an amino acid selected from the group consisting of A, C, D, E, F, G, H, I, K, L, M, N, P, Q, R, S, T, V, W, and Y, and wherein each Z is independently an amino acid selected from the group consisting of D, A, Y, S, T, N, I, L, F, V, H, and P; wherein the MM inhibits the binding of the activatable antibody to human CTLA4 when the CM is not cleaved; wherein the CM comprises at least a first cleavage site; wherein the TBM comprises from the N-terminus to the C-terminus, an antibody light chain variable region (VL) and an antibody heavy chain variable region (VH); and wherein the activatable antibody binds to human CTLA4 via the VH and VL when the CM is cleaved. In some embodiments, m is from 3-10.

Other aspects of the present disclosure relate to an activatable antibody comprising: a polypeptide comprising, from N-terminus to C-terminus, a masking moiety (MM), a cleavable moiety (CM), and a target binding moiety (TBM), wherein the MM comprises an amino acid sequence according to Formula (XVIII): $X_mCX_nCZ_o$ (SEQ ID NO: 134), wherein m is from 2-10, n is from 3-10, and o is from 1-10, wherein each X is independently an amino acid selected from the group consisting of A, C, D, E, F, G, H, I, K, L, M, N, P, Q, R, S, T, V, W, and Y, and wherein each Z is independently an amino acid selected from the group consisting of D, A, Y, S, T, N, I, L, F, V, H, and P; wherein the MM inhibits the binding of the activatable antibody to human CTLA4 when the CM is not cleaved; wherein the CM comprises at least a first cleavage site; wherein the TBM comprises from the N-terminus to the C-terminus, an antibody heavy chain variable region (VH) and an antibody light chain variable region (VL); and wherein the activatable antibody binds to human CTLA4 via the VH and VL when the CM is cleaved.

In some embodiments according to any one of the activatable antibodies described above, m is 2, 3, 4, 5, or 6. In some embodiments, m is 6. In some embodiments, n is from 6-8. In some embodiments, n is 6. In some embodiments, o is from 1-2. In some embodiments, o is 2. In some embodiments that may be combined with any of the preceding embodiments, each X is not M, W, or C. In some embodiments that may be combined with any of the preceding embodiments, each X in $X_m$ of Formula (XVIII) is independently an amino acid selected from the group consisting of D, A, Y, S, T, N, I, L, F, V, H, and P. In some embodiments that may be combined with any of the preceding embodiments, each X in $X_n$ of Formula (XVIII) is independently an amino acid selected from the group consisting of D, A, Y, S, T, N, I, L, F, V, H, and P. In some embodiments, the MM comprises an amino acid sequence selected from the group consisting of $X_m$CPDHPYPCXX (SEQ ID NO:181), $X_m$CDAFYPYCXX (SEQ ID NO:182), $X_m$CDSHYPYCXX (SEQ ID NO:183), and $X_m$CVPYYYACXX (SEQ ID NO:184), where m is from 2-10, and where each X is independently an amino acid selected from the group consisting of A, C, D, E, F, G, H, I, K, L, M, N, P, Q, R, S, T, V, W, and Y. In some embodiments, each X is not M, W, or C. In some embodiments, each X is independently an amino acid selected from the group consisting of D, A, Y, S, T, N, I, L, F, V, H, and P. In some embodiments that may be combined with any of the preceding embodiments, the masking moiety (MM) comprises an amino acid sequence selected from SEQ ID NOS: 141-147. In some embodiments that may be combined with any of the preceding embodiments, the MM further comprises, at its N-terminus, an additional amino acid sequence. In some embodiments, the additional amino acid sequence comprises the amino acid sequence of SEQ ID NO: 148.

In some embodiments that may be combined with any of the preceding embodiments, the first cleavage site is a protease cleavage site for a protease selected from the group consisting of urokinase-type plasminogen activator (uPA), matrix metalloproteinase-1 (MMP-1), MMP-2, MMP-3, MMP-8, MMP-9, MMP-14, Tobacco Etch Virus (TEV) protease, plasmin, Thrombin, Factor X, PSA, PSMA, Cathepsin D, Cathepsin K, Cathepsin S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE. In some embodiments that may be combined with any of the preceding embodiments, the CM further comprises a first linker ($L_1$) C-terminal to the first cleavage site. In some embodiments, the $L_1$ comprises an amino acid sequence selected from the group consisting of SEQ ID NOS: 156-163. In some embodiments that may be combined with any of the preceding embodiments, the CM further comprises a second cleavage site. In some embodiments, the second cleavage site is C-terminal to the $L_1$. In some embodiments, the second cleavage site is a protease cleavage site for a protease selected from the group consisting of urokinase-type plasminogen activator (uPA), matrix metalloproteinase-1 (MMP-1), MMP-2, MMP-3, MMP-8, MMP-9, MMP-14, Tobacco Etch Virus (TEV) protease, plasmin, Thrombin, Factor X, PSA, PSMA, Cathepsin D, Cathepsin K, Cathepsin S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE. In some embodiments, the first and second cleavage sites are different. In some embodiments that may be combined with any of the preceding embodiments, the CM further comprises a second linker ($L_2$) C-terminal to the second cleavage site. In some embodiments, the $L_2$ comprises an amino acid sequence selected from the group consisting of SEQ ID NOS: 156-163. In some embodiments that may be combined with any of the preceding embodiments, the CM further comprises a third linker ($L_3$) N-terminal to the first cleavage site. In some embodiments that may be combined with any of the preceding embodiments, the CM comprises at least a first protease cleavage site and is cleaved with one or more proteases selected from the group consisting of urokinase-type plasminogen activator (uPA), matrix metalloproteinase-1 (MMP-1), MMP-2, MMP-3, MMP-8, MMP-9, MMP-14, Tobacco Etch Virus (TEV) protease, plasmin, Thrombin, Factor X, PSA, PSMA, Cathepsin D, Cathepsin K, Cathepsin S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE.

In some embodiments that may be combined with any of the preceding embodiments, the activatable antibody comprises a masking moiety (MM) and cleavable moiety (CM) comprising an amino acid sequence according to Formula (XXIX): EVGSYX1X2X3X4X5X6CX7X8X9X10X11X12C X13X14SGRSAGGGGTENLYFQGSGGS (SEQ ID NO: 164), wherein X1 is A, D, I, N, P, or Y, X2 is A, F, N, S, or V, X3 is A, H, L, P, S, V, or Y, X4 is A, H, S, or Y, X5 is A, D, P, S, V, or Y, X6 is A, D, L, S, or Y, X7 is D, P, or V, X8 is A, D, H, P, S, or T, X9 is A, D, F, H, P, or Y, X10 is L, P, or Y, X11 is F, P, or Y, X12 is A, P, S, or Y, X13 is A, D, N, S, T, or Y, and X14 is A, S, or Y. In some embodiments that may be combined with any of the preceding embodiments, the activatable antibody comprises an amino acid sequence selected from the group consisting of SEQ ID NOS: 165-179.

In some embodiments that may be combined with any of the preceding embodiments, the VL comprises an HVR-L1 comprising the amino acid sequence of SEQ ID NO: 58, an HVR-L2 comprising the amino acid sequence of SEQ ID NO: 66, and an HVR-L3 comprising the amino acid sequence of SEQ ID NO: 75. In some embodiments that may be combined with any of the preceding embodiments, the VL comprises the amino acid sequence of SEQ ID NO: 100, or a variant thereof having at least about 90% (e.g., at least about 92%, 95%, 98%, 99% or more) sequence identity to the amino acid sequence of SEQ ID NO: 100. In some embodiments that may be combined with any of the preceding embodiments, the VH comprises an HVR-H1 comprising the amino acid sequence of SEQ ID NO: 23, an HVR-H2 comprising the amino acid sequence of SEQ ID NO: 35, and an HVR-H3 comprising the amino acid sequence of SEQ ID NO: 45. In some embodiments that may be combined with any of the preceding embodiments, the VH comprises the amino acid sequence of SEQ ID NO: 87, or a variant thereof having at least about 90% (e.g., at least about 92%, 95%, 98%, 99% or more) sequence identity to the amino acid sequence of SEQ ID NO: 87.

Other aspects of the present disclosure relate to a pharmaceutical composition comprising any of the antibodies and/or activatable antibodies described herein and a pharmaceutically acceptable carrier.

Other aspects of the present disclosure relate to a polynucleotide encoding any of the antibodies and/or activatable antibodies described herein. In some embodiments, the polynucleotide comprises a sequence selected from SEQ ID NOS: 108-133.

Other aspects of the present disclosure relate to a vector comprising any of the polynucleotides described herein. In some embodiments, the vector is an expression vector and/or a display vector.

Other aspects of the present disclosure relate to a host cell comprising any of the polynucleotides and/or vectors described herein. In some embodiments, the host cell is a eukaryotic cell. In some embodiments, the host cell is a Chinese Hamster Ovary (CHO) cell.

Other aspects of the present disclosure relate to a method of making an antibody or activatable antibody comprising culturing any of the host cells described herein under conditions suitable for producing the antibody or activatable antibody. In some embodiments, the method further comprises recovering the antibody or activatable antibody produced by the cell.

Other aspects of the present disclosure relate to a method of treating or delaying progression of cancer in a subject in need thereof comprising administering to the subject an effective amount of any of the antibodies, activatable antibodies, and/or pharmaceutical compositions descried herein. In some embodiments, the cancer is liver cancer, a cancer of the digestive system (e.g., colon cancer, colorectal cancer), lung cancer, bone cancer, heart cancer, brain cancer, kidney cancer, bladder cancer, a hematological cancer (e.g., leukemia), skin cancer, breast cancer, thyroid cancer, pancreatic cancer, a head and/or neck cancer, an eye-related cancer, a male reproductive system cancer (e.g., prostate cancer, testicular cancer), or a female reproductive system cancer (e.g., uterine cancer, cervical cancer). Other aspects of the present disclosure relate to a method of reducing size of a solid tumor in a subject in need thereof, wherein the solid tumor has a size of about 400-1000 mm$^3$, the method comprises comprising administering to the subject an effective amount of any of the antibodies, activatable antibodies, and/or pharmaceutical compositions descried herein. In some embodiments, the solid tumor has a size of about 400-800 mm$^3$. In some embodiments, the method further comprises administering to the subject an effective amount of at least one additional therapeutic agent. In some embodiments, the at least one additional therapeutic agent is selected from the group consisting of viral gene therapy, immune checkpoint inhibitors, target therapies, radiation therapies, vaccination therapies, and chemotherapies. In some embodiments, the at least one additional therapeutic agent is selected from the group consisting of pomalyst, revlimid, lenalidomide, pomalidomide, thalidomide, a DNA-alkylating platinum-containing derivative, cisplatin, 5-fluorouracil, cyclophosphamide, an anti-CD137 antibody, an anti-PD-1 antibody, an anti-PD-L1 antibody, an anti-CD20 antibody, an anti-CD40 antibody, an anti-DR5 antibody, an anti-CD1d antibody, an anti-TIM3 antibody, an anti-SLAMF7 antibody, an anti-KIR receptor antibody, an anti-OX40 antibody, an anti-HER2 antibody, an anti-ErbB-2 antibody, an anti-EGFR antibody, cetuximab, rituximab, trastuzumab, pembrolizumab, radiotherapy, single dose radiation, fractionated radiation, focal radiation, whole organ radiation, IL-12, IFNα, GM-CSF, a chimeric antigen receptor, adoptively transferred T cells, an anti-cancer vaccine, and an oncolytic virus. In some embodiments, the method comprises administering to the subject an effective amount of the anti-CTLA4 antibody, the activatable antibody or the pharmaceutical composition described herein prior to a surgery or after a surgery to remove the tumor in the subject. In some embodiments, the anti-CD137 antibody comprises an antibody heavy chain variable region comprising an HVR-H1 comprising the amino acid sequence FSLSTGGVGVGWI (SEQ ID NO: 223), an HVR-H2 comprising the amino acid sequence LALIDWADDKYYSPSLKSRL (SEQ ID NO:224), and an HVR-H3 comprising the amino acid sequence ARGGSDTVIGDWFAY (SEQ ID NO: 225), and an antibody light chain variable region comprising an HVR-L1 comprising the amino acid sequence RASQSIGSYLA (SEQ ID NO: 226), an HVR-L2 comprising the amino acid sequence DASNLETGV (SEQ ID NO: 227), and an HVR-L3 comprising the amino acid sequence YCQQGYYLWT (SEQ ID NO: 228). In some embodiments, the anti-CD137 antibody comprises an antibody heavy chain variable region comprising the amino acid sequence of SEQ ID NO: 229 or a sequence having at least 90% (e.g., 91%, 92%, 93%, 94%, 95%, 96%, 97%, 98% or 99%) to the sequence of SEQ ID NO: 229; and/or an antibody light chain variable region comprising the amino acid sequence of SEQ ID NO: 230 or a sequence having at least 90% (e.g., 91%, 92%, 93%, 94%, 95%, 96%, 97%, 98% or 99%) to the sequence of SEQ ID NO: 230.

```
                                              (SEQ ID NO: 229)
EVQLVESGGGLVQPGGSLRLSCAASGFSLSTGGVGVGWIRQAPGKGLEW
LALIDWADDKYYSPSLKSRLTISRDNSKNTLYLQLNSLRAEDTAVYYCA
RGGSDTVIGDWFAYWGQGTLVTVSS (SEQ ID NO: 230)
DIQLTQSPSSLSASVGDRVTITCRASQSIGSYLAWYQQKPGKAPKLLIY
DASNLETGVPSRFSGSGSGTDFTLTISSLQPEDFATYYCQQGYYLWTFG
QGTKVEIK
```

It is to be understood that one, some, or all of the properties of the various embodiments described above and herein may be combined to form other embodiments of the present disclosure. These and other aspects of the present disclosure will become apparent to one of skill in the art. These and other embodiments of the present disclosure are further described by the detailed description that follows.

BRIEF DESCRIPTION OF THE DRAWINGS

FIG. 1A shows binding of the indicated antibodies to human CTLA4. FIG. 1B shows binding of the indicated antibodies to canine CTLA4.

FIG. 4A shows binding of the indicated antibodies, or isotype control, to HEK293F cells transiently overexpressing human PD-1, CTLA4, LAG3, TIM3, B7-H3, or empty vector (293F). FIG. 4B shows binding of the indicated antibodies, isotype control, or vehicle (PBSA) to HEK293F cells transiently overexpressing human CD95, CD120a, OX40, CD40, CTLA4, or empty vector (pIRES). FIG. 4C shows binding of the indicated antibodies, isotype control, or vehicle (PBSA) to HEK293F cells transiently overexpressing human TIM3, CTLA4, PD-L1, LAG3, BTLA, VISTA, PD-L2, ICOS, B7-H4, PD-1, B7-H3, or empty vector (pIRES).

FIG. 5A shows the ability of antibodies TY21687, TY21689, TY21680, and TY21691 to block human CD80 binding to human CTLA4. FIG. 5B shows the ability of antibodies TAC2114, TY21585, TY21587, TY21588, TY21589, TY21580, and TY21591 to block human CD80 binding to human CTLA4. FIG. 5C shows the ability of antibodies TY21687, TY21689, TY21680, and TY21691 to block human CD86 binding to human CTLA4. FIG. 5D shows the ability of antibodies TAC2114, TY21585, TY21587, TY21588, TY21589, TY21580, and TY21591 to block human CD86 binding to human CTLA4.

FIGS. 6A-B show the blocking capabilities of the antibodies, as determined by FACS. FIG. 6A shows the ability of the indicated antibodies, isotype control, or vehicle (PBSA) to block human CD80 binding to HEK293F cells transiently overexpressing human CTLA4. FIG. 6B shows the ability of the indicated antibodies, isotype control, or vehicle (PBSA) to block human CD86 binding to HEK293F cells transiently overexpressing human CTLA4.

FIG. 8A shows the effect on IL-2 secretion from CD3-stimulated human PBMCs treated with antibody TY21580 or isotype control. FIG. 8B shows the effect on IFNγ secretion from CD3-stimulated human PBMCs treated with antibody TY21580 or isotype control.

FIG. 11A shows the ADCC activity of antibody TY21580, or isotype control, on HEK293F cells transiently overexpressing human CTLA4 and incubated with human natural killer (NK) cells. FIG. 11B shows the ADCC activity of antibody TY21580, TAC2114, or isotype control on HEK293F cells transiently overexpressing human CTLA4 and incubated with human NK cells.

FIG. 12A shows the ADCC activity of antibody TY21580, TAC2114, or isotype control on human Treg cells (from donor #96) incubated with human NK cells. FIG. 12B shows the ADCC activity of antibody TY21580, TAC2114, or isotype control on human Treg cells (from donor #12) incubated with human NK cells.

FIGS. 15A-C show the in vivo anti-tumor efficacy of antibody TY21580, or isotype control, in an MC38 syngeneic mouse colorectal tumor model. FIG. 15A shows the tumor growth curves of different treatment groups of female C57BL/6 mice bearing MC38-established tumors. Data points represent group mean; error bars represent SEM. FIG. 15B shows individual tumor growth curves for each group tested. FIG. 15C shows re-challenge studies indicating the long lasting memory of immunity against MC38 tumor cells.

FIG. 20A shows the tumor growth curves of different treatment groups of female C57BL/6 mice bearing 3LL-established tumors. Data points represent group mean; error bars represent SEM. FIG. 20B shows individual tumor growth curves for each group tested.

FIG. 25A shows the average spleen weight of male BALB/c mice after repeat intraperitoneal administration of either antibody TY21580 or vehicle control on days 1, 4, 7, and 11. FIG. 25B shows the average spleen weight of female BALB/c mice after repeat intraperitoneal administration of either antibody TY21580 or vehicle control on days 1, 4, 7, and 11.

FIG. 27A shows the size exclusion chromatography (SEC) profile of antibody TY21586 after storage at >100 mg/mL. FIG. 27B shows the SEC profile of antibody TY21580 after storage at >100 mg/mL.

FIG. 31A shows functional display of Fabs targeting CTLA4 on the surface of yeast. FIG. 31B shows functional display of scFvs targeting CTLA4 on the surface of yeast.

FIG. 33A shows binding affinity of CTLA4 activatable antibody clones in the scFv format, including the CTLA4 activatable antibody clone B13287 with the masking peptide intact, or with the masking peptide cleaved by the TEV protease, as compared to the scFv fragment of the target antibody with no masking peptide.
FIG. 33B shows CTLA4 binding affinity of CTLA4 activatable antibody clones in the Fab format, including the CTLA4 activatable antibody clone B13189 with the masking peptide intact, or with the masking peptide cleaved by the TEV protease, as compared to the Fab fragment of the target antibody with no masking peptide.

FIG. 34A shows the association and dissociation curves of the indicated activatable antibodies as compared to the parental antibody TY21580, as determined by the ForteBio system. FIG. 34B shows a graph of the relative ratio of bound activatable antibodies, as compared to the parental antibody TY21580.

FIG. 35A shows a first batch of ELISA data indicating binding of CTLA4 activatable antibodies TY22401, TY22402, TY22403, TY22404 to recombinant human CTLA4-Fc, as compared to the parental antibody TY21580. FIG. 35B shows binding of CTLA4 activatable antibodies TY22563, TY22564, TY22565, TY22566 to recombinant human CTLA4-Fc, as compared to the parental antibody TY21580.

FIG. 36A shows SDS-PAGE results of activatable antibody TY22404 with no treatment, treated with the protease uPA, or treated with 5 or 10 units of the protease MMP-9. FIG. 36B shows binding of activatable antibody TY22404 with no treatment, treated with the protease uPA, or treated with the protease MMP-9, as compared to the parental antibody TY21580, determined by ELISA.

FIGS. 37A-C show the size-exclusion chromatography (SEC) profiles of exemplary activatable antibodies under accelerated stress conditions. FIG. 37A shows the SEC profiles of activatable antibody TY22402 after six cycles of freezing and thawing, as compared to the control condition.

FIG. 37B shows the SEC profiles of activatable antibody TY22402 after seven days at 50° C., as compared to the control condition. FIG. 37C shows the percentages of SEC main peak area of the exemplary activatable antibodies after seven days at 50° C., after storage at 40° C. for up to 28 days, or after six cycles of freezing and thawing, as compared to the control condition.

FIG. 40A shows the effect on IL-2 secretion from CD3-primed human PBMCs stimulated with isotype control antibody, parental antibody TY21580, and exemplary CTLA4 activatable antibodies TY22401, TY22402, or TY22404. FIG. 40B shows the effect on IFNγ secretion from CD3-primed human PBMCs stimulated with isotype control antibody, parental antibody TY21580, and exemplary CTLA4 activatable antibodies TY22401, TY22402, or TY22404.

FIG. 42A shows the tumor growth curves of different treatment groups of female C57BL/6 mice bearing MC38-established tumors. Data points represent group mean; error bars represent SEM. FIG. 42B shows individual tumor growth curves for the groups treated with TY21580, TY22401, TY22402, and TY22566.

FIG. 45A shows the tumor growth curves of different treatment groups of female C57BL/6 mice bearing 3LL-established tumors. Data points represent group mean; error bars represent SEM. FIG. 45B shows individual tumor growth curves for the groups treated with TY21580, TY22401, TY22402, and TY22566.

FIG. 46A shows a time course of the blood concentrations of the activatable antibody TY22401 intravenously administered at a concentration of 10 mg/kg to female BALB/c mice, as compared to the parental antibody TY21580. FIG. 46B shows a time course of the blood concentrations of the activatable antibody TY22402 intravenously administered at a concentration of 10 mg/kg to female BALB/c mice, as compared to the parental antibody TY21580. FIG. 46C shows a time course of the blood concentrations of the activatable antibody TY22404 intravenously administered at a concentration of 10 mg/kg to female BALB/c mice, as compared to the parental antibody TY21580.

FIG. 48A shows the average spleen weight of BALB/c mice after repeat intraperitoneal administration of activatable antibody TY22402, parental antibody TY21580, or isotype control on days 1, 4, 7, and 11. FIG. 48B shows the average spleen weight of BALB/c mice after repeat intraperitoneal administration of activatable antibody TY22566, parental antibody TY21580, or isotype control on days 1, 4, 7, and 11. FIG. 48C shows the average spleen weight of BALB/c mice after repeat intraperitoneal administration of activatable antibody TY22401, parental antibody TY21580, or isotype control on days 1, 4, 7, and 11.

FIGS. 56A-56E depict results from epitope mapping experiments, showing binding capacity of TY21580 (FIG. 56A), Ipilimumab (FIG. 56B), human CD80 (FIG. 56C), human CD86 (FIG. 56D), and mouse CD86 (FIG. 56E) to human CTLA4, mouse CTLA4, and CTLA4 mutants by flow cytometry.

FIGS. 57A and 57B show binding curves of human CD80 (FIG. 57A) or CD86 (FIG. 57B) to plate-bound human recombinant CTLA4 proteins in the presence of serial dilutions of TY21580, Ipilimumab, or an isotype control antibody, as measured by ELISA. FIGS. 57C-57D show binding curves of human recombinant CTLA4 proteins to plate-bound human CD80 (FIG. 57C) or CD86 (FIG. 57D) in the presence of serial dilutions of TY21580, Ipilimumab, or an isotype control antibody, as measured by ELISA.

FIG. 60A depicts group averaged tumor growth over time in MC38 tumor bearing mice treated with an isotype control antibody (1 mg/kg BIW), TY21580 (1 mg/kg or 0.2 mg/kg BIW), or Ipilimumab (1 mg/kg or 0.2 mg/kg BIW). Data points represent mean values; error bars represent standard error of the mean (SEM). FIG. 60B depicts tumor growth over time in individual MC38 tumor bearing mice treated with an isotype control antibody (Group-1), TY21580 (Group-2 and Group-3), or Ipilimumab (Group-4 and Group-5).

FIG. 61A shows the percentages of T regulatory (Treg) cells (CD4+CD25+) in CD4+ T cells isolated from the tumors. FIG. 61B depicts the ratio of cytotoxic T lymphocytes (CD8+ T cells) to Treg cells (i.e., the CD8+/Treg ratio) in CD4+ T cell subpopulations isolated from the tumors. Each data point represents the data from one mouse. Statistical analyses were done with Prism 7 (GraphPad Software). P-values were calculated using Multiple T test. ns: P>0.05; : 0.001<P<0.01, *: P<0.001.

FIG. 62A shows the percentages of T regulatory (Treg) cells (CD4+CD25+) in CD4+ T cells isolated from the tumors. FIG. 62B depicts the ratio of cytotoxic T lymphocytes (CD8+ T cells) to Treg cells (i.e., the CD8+/Treg ratio) in CD4+ T cell subpopulations isolated from the tumors. Each data point represents the data from one mouse. Statistical analyses were done with Prism 7 (GraphPad Software). P-values were calculated using Multiple T test. ns: P>0.05; : 0.001<P<0.01, *: P<0.001.

FIG. 64A depicts group averaged tumor growth with TY21580 treatment beginning when tumors reached 500 mm$^3$ or 800 mm$^3$, or with isotype control antibody treatment beginning when tumors reached 500 mm$^3$. Data points represent mean values of tumors from 8 mice/group, error bars represent standard error of the mean (SEM). FIGS. 64B-64D depict individual tumor growth in each mouse. FIG. 64B depicts tumor growth in mice treated with an isotype control antibody, with treatment beginning when tumors reached 500 mm$^3$; FIG. 64C depicts tumor growth in mice treated with TY21580, with treatment beginning when tumors reached 500 mm$^3$; FIG. 64D depicts tumor growth in mice treated with TY21580, with treatment beginning when tumors reached 800 mm$^3$.

FIGS. 65A and 65B represent two experiments set up using the same experimental methods to test various activatable anti-CTLA4 antibodies.

DETAILED DESCRIPTION

I. General Techniques

Figure 1A:
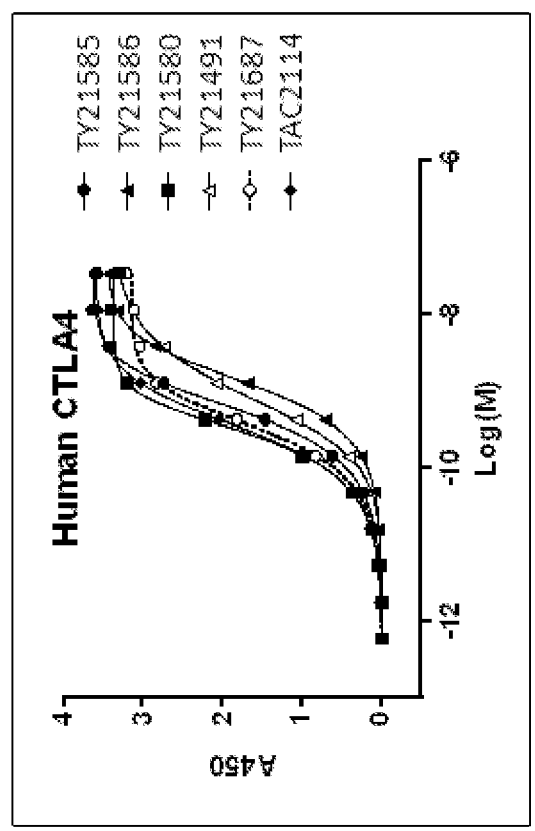
FIGS. 1A-B show antibody binding to CTLA4, as determined by ELISA.

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual, and Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press;

Animal Cell Culture (R.I. Freshney), ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993).

II. Definitions

Before describing the present disclosure in detail, it is to be understood that this present disclosure is not limited to particular compositions or biological systems, which can, of course, vary. It is also to be understood that the terminology used herein is for the purpose of describing particular embodiments only, and is not intended to be limiting.

As used herein, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the present disclosure described herein include "comprising," "consisting," and "consisting essentially of" aspects and embodiments.

The term "and/or" as used herein a phrase such as "A and/or B" is intended to include both A and B; A or B; A (alone); and B (alone). Likewise, the term "and/or" as used herein a phrase such as "A, B, and/or C" is intended to encompass each of the following embodiments: A, B, and C; A, B, or C; A or C; A or B; B or C; A and C; A and B; B and C; A (alone); B (alone); and C (alone).

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. The term "amino acid analogs" refers to compounds that have the same basic chemical structure as a naturally occurring amino acid but the C-terminal carboxy group, the N-terminal amino group, or side chain functional group has been chemically modified to another functional group. The term "amino acid mimetics" refers to chemical compounds that have a structure that is different from the general chemical structure of an amino acid, but that functions similarly to a naturally occurring amino acid. As used herein, the twenty conventional amino acids and their abbreviations follow conventional usage. See e.g., Immunology—A Synthesis (2nd Edition, E. S. Golub and D. R. Gren, Eds., Sinauer Associates, Sunderland, Mass. (1991)).

The terms "polypeptide," "protein," and "peptide" are used interchangeably herein and may refer to polymers of two or more amino acids.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "isolated nucleic acid" refers to a nucleic acid molecule of genomic, cDNA, or synthetic origin, or a combination thereof, which is separated from other nucleic acid molecules present in the natural source of the nucleic acid. For example, with regard to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid of interest.

The term "antibody" is used herein in the broadest sense and specifically covers monoclonal antibodies (including full length monoclonal antibodies), polyclonal antibodies, multispecific antibodies (e.g., bispecific antibodies, trispecific antibodies), and antibody fragments (e.g., Fab, Fab', Fab'-SH, F(ab')$_2$, Fv and/or a single-chain variable fragment or scFv) so long as they exhibit the desired biological activity.

In some embodiments, the term "antibody" refers to an antigen-binding protein (i.e., immunoglobulin) having a basic four-polypeptide chain structure consisting of two identical heavy (H) chains and two identical light (L) chains. Each L chain is linked to an H chain by one covalent disulfide bond, while the two H chains are linked to each other by one or more disulfide bonds depending on the H chain isotype. Each heavy chain has, at the N-terminus, a variable region (abbreviated herein as $V_H$) followed by a constant region. The heavy chain constant region is comprised of three domains, $C_{H1}$, $C_{H2}$ and $C_{H3}$. Each light chain has, at the N-terminus, a variable region (abbreviated herein as $V_L$) followed by a constant region at its other end. The light chain constant region is comprised of one domain, $C_L$. The $V_L$ is aligned with the $V_H$ and the $C_L$ is aligned with the first constant domain of the heavy chain (CH1). The pairing of a $V_H$ and $V_L$ together forms a single antigen-binding site. An IgM antibody consists of 5 of the basic heterotetramer units along with an additional polypeptide called J chain, and therefore contains 10 antigen binding sites, while secreted IgA antibodies can polymerize to form polyvalent assemblages comprising 2-5 of the basic 4-chain units along with J chain.

The $V_H$ and $V_L$ regions can be further subdivided into regions of hypervariability, termed hyper-variable regions (HVR) based on structural and sequence analysis. HVRs are interspersed with regions that are more conserved, termed framework regions (FW) (see e.g., Chen et al. (1999) J. Mol. Biol. (1999) 293, 865-881). Each $V_H$ and $V_L$ is composed of three HVRs and four FWs, arranged from amino-terminus to carboxy-terminus in the following order: FW-1_HVR-1_FW-2_HVR-2_FW-3_HVR-3_FW4. Throughout the present disclosure, the three HVRs of the heavy chain are referred to as HVR-H1, HVR-H2, and HVR-H3. Similarly, the three HVRs of the light chain are referred to as HVR-L1, HVR-L2, and HVR-L3.

The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. Within light and heavy chains, the variable and constant regions are joined by a "J" region of about 12 or more amino acids, with the heavy chain also including a "D" region of about 10 or more amino acids (see e.g., Fundamental Immunology Ch. 7 (Paul, W., ed., 2$^{nd}$ ed. Raven Press, N.Y). (1989)).

The L chain from any vertebrate species can be assigned to one of two clearly distinct types, called kappa and lambda, based on the amino acid sequences of their constant domains. Depending on the amino acid sequence of the constant domain of their heavy chains (CH), antibodies can be assigned to different classes or isotypes. There are five classes of antibodies: IgA, IgD, IgE, IgG, and IgM, having heavy chains designated α (alpha), δ (delta), ε (epsilon), γ (gamma), and μ (mu), respectively. The IgG class of antibody can be further classified into four subclasses IgG1, IgG2, IgG3, and IgG4 by the gamma heavy chains, Y1-Y4, respectively.

The term "antibody derivative" or "derivative" of an antibody refers to a molecule that is capable of binding to the same antigen (e.g., CTLA4) that the antibody binds to and comprises an amino acid sequence of the antibody linked to an additional molecular entity. The amino acid sequence of the antibody that is contained in the antibody derivative may be a full-length heavy chain, a full-length light chain, any portion or portions of a full-length heavy chain, any portion or portions of the full-length light chain of the antibody, any other fragment(s) of an antibody, or the complete antibody. The additional molecular entity may be a chemical or biological molecule. Examples of additional molecular entities include chemical groups, amino acids, peptides, proteins (such as enzymes, antibodies), and chemical compounds. The additional molecular entity may have any utility, such as for use as a detection agent, label, marker, pharmaceutical or therapeutic agent. The amino acid sequence of an antibody may be attached or linked to the additional molecular entity by chemical coupling, genetic fusion, noncovalent association, or otherwise. The term "antibody derivative" also encompasses chimeric antibodies, humanized antibodies, and molecules that are derived from modifications of the amino acid sequences of a CTLA4 antibody, such as conservation amino acid substitutions, additions, and insertions.

The term "antigen-binding fragment" or "antigen binding portion" of an antibody refers to one or more portions of an antibody that retain the ability to bind to the antigen that the antibody bonds to (e.g., CTLA4). Examples of "antigen-binding fragments" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., Nature 341:544-546 (1989)), which consists of a $V_H$ domain; and (vi) an isolated complementarity determining region (CDR).

The term "binding molecule" encompasses (1) antibody, (2) antigen-binding fragment of an antibody, and (3) derivative of an antibody, each as defined herein.

The term "CTLA4" is used in the present application, and includes the human CTLA4 (e.g., UniProt accession number P16410), as well as variants, isoforms, and species homologs thereof (e.g., mouse CTLA4 (UniProt accession number P09793), rat CTLA4 (UniProt accession number Q9Z1A7), dog CTLA4 (UniProt accession number Q9XSI1), cynomolgus monkey CTLA4 (UniProt accession number G7PL88), etc.). Accordingly, a binding molecule (e.g., an antibody or activatable antibody), as defined and disclosed herein, may also bind CTLA4 from species other than human. In other cases, a binding molecule may be completely specific for the human CTLA4 and may not exhibit species or other types of cross-reactivity.

The term "CTLA4 antibody" refers to an antibody, as defined herein, capable of binding to human CTLA4.

The term "chimeric antibody" refers to an antibody that comprises amino acid sequences derived from different animal species, such as those having a variable region derived from a human antibody and a murine immunoglobulin constant region.

The term "compete for binding" refers to the interaction of two antibodies in their binding to a binding target. A first antibody competes for binding with a second antibody if binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not, be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope, whether to the same, greater, or lesser extent, the antibodies are said to "cross-compete" with each other for binding of their respective epitope(s).

The term "epitope" refers to a part of an antigen to which an antibody (or antigen-binding fragment thereof) binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope can include various numbers of amino acids in a unique spatial conformation. Methods of determining spatial conformation of epitopes include, for example, x-ray crystallography, 2-dimensional nuclear magnetic resonance, deuterium and hydrogen exchange in combination with mass spectrometry, or site-directed mutagenesis, or all methods used in combination with computational modeling of antigen and its complex structure with its binding antibody and its variants (see e.g., Epitope Mapping Protocols in Methods in Molecular Biology, Vol. 66, G. E. Morris, Ed. (1996)). Once a desired epitope of an antigen is determined, antibodies to that epitope can be generated, e.g., using the techniques described herein. The generation and characterization of antibodies may also elucidate information about desirable epitopes. From this information, it is then possible to competitively screen antibodies for binding to the same epitope. An approach to achieve this is to conduct cross-competition studies to find antibodies that competitively bind with one another, i.e., the antibodies compete for binding to the antigen. A high throughput process for "binning" antibodies based upon their cross-competition is described in PCT Publication No. WO 03/48731.

The term "germline" refers to the nucleotide sequences of the antibody genes and gene segments as they are passed from parents to offspring via the germ cells. The germline sequence is distinguished from the nucleotide sequences encoding antibodies in mature B cells which have been altered by recombination and hypermutation events during the course of B cell maturation.

The term "glycosylation sites" refers to amino acid residues which are recognized by a eukaryotic cell as locations for the attachment of sugar residues. The amino acids where carbohydrate, such as oligosaccharide, is attached are typically asparagine (N-linkage), serine (O-linkage), and threonine (O-linkage) residues. The specific site of attachment is typically signaled by a sequence of amino acids, referred to herein as a "glycosylation site sequence". The glycosylation site sequence for N-linked glycosylation is: -Asn-X-Ser- or -Asn-X-Thr-, where X may be any of the conventional amino acids, other than proline. The terms "N-linked" and "O-linked" refer to the chemical group that serves as the attachment site between the sugar molecule and the amino acid residue. N-linked sugars are attached through an amino group; O-linked sugars are attached through a hydroxyl group. The term "glycan occupancy" refers to the existence of a carbohydrate moiety linked to a glycosylation site (i.e., the glycan site is occupied). Where there are at least two potential glycosylation sites on a polypeptide, either none (0-glycan site occupancy), one (1-glycan site occupancy) or both (2-glycan site occupancy) sites can be occupied by a carbohydrate moiety.

The term "host cell" refers to a cellular system which can be engineered to generate proteins, protein fragments, or peptides of interest. Host cells include, without limitation, cultured cells, e.g., mammalian cultured cells derived from rodents (rats, mice, guinea pigs, or hamsters) such as CHO, BHK, NSO, SP2/0, YB2/0; human cells (e.g., HEK293F cells, HEK293T cells; or human tissues or hybridoma cells, yeast cells, insect cells (e.g., S2 cells), bacterial cells (e.g., E. coli cells) and cells comprised within a transgenic animal or cultured tissue. The term encompasses not only the particular subject cell but also the progeny of such a cell. Because certain modifications may occur in succeeding generations due to either mutation or environmental influences, such progeny may not be identical to the parent cell, but are still included within the scope of the term "host cell."

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "humanized antibody" refers to a chimeric antibody that contains amino acid residues derived from human antibody sequences. A humanized antibody may contain some or all of the CDRs or HVRs from a non-human animal or synthetic antibody while the framework and constant regions of the antibody contain amino acid residues derived from human antibody sequences.

The term "illustrative antibody" refers to any one of the antibodies described in the disclosure and designated as those listed in Tables A and B, and any antibodies comprising the 6 HVRs and/or the VH and VLs of the antibodies listed in Tables A and B. These antibodies may be in any class (e.g., IgA, IgD, IgE, IgG, and IgM). Thus, each antibody identified above encompasses antibodies in all five classes that have the same amino acid sequences for the $V_L$ and $V_H$ regions. Further, the antibodies in the IgG class may be in any subclass (e.g., IgG1 IgG2, IgG3, and IgG4). Thus, each antibody identified above in the IgG subclass encompasses antibodies in all four subclasses that have the same amino acid sequences for the $V_L$ and $V_H$ regions. The amino acid sequences of the heavy chain constant regions of human antibodies in the five classes, as well as in the four IgG subclasses, are known in the art.

An "isolated" antibody or binding molecule (e.g., activatable antibody) is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see e.g., Flatman et al., J. Chromatogr. B 848:79-87 (2007).

The term "$K_a$" refers to the association rate constant of a particular binding molecule-antigen interaction, where the term "$k_d$" refers to the dissociation rate constant of a particular binding molecule-antigen interaction.

The term "$K_D$" refers to the equilibrium dissociation constant of a particular antibody-antigen interaction. It is obtained from the ratio of $k_d$ to $k_a$ (i.e., $k_d/k_a$) and is expressed as a molar concentration (M). $K_D$ is used as a measure for the affinity of an antibody's binding to its binding partner. The smaller the $K_D$, the more tightly bound the antibody is, or the higher the affinity between antibody and the antigen. For example, an antibody with a nanomolar (nM) dissociation constant binds more tightly to a particular antigen than an antibody with a micromolar (µM) dissociation constant. $K_D$ values for antibodies can be determined using methods well established in the art. One method for determining the $K_D$ of an antibody is by using surface plasmon resonance, typically using a biosensor system such as a Biacore® system. For example, an assay procedure using the BIACORE™ system (BIAcore assay) is described in at least Example 3 of the present disclosure.

The term "mammal" refers to any animal species of the Mammalia class. Examples of mammals include: humans; laboratory animals such as rats, mice, hamsters, rabbits, non-human primates, and guinea pigs; domestic animals such as cats, dogs, cattle, sheep, goats, horses, and pigs; and captive wild animals such as lions, tigers, elephants, and the like.

The term "prevent" or "preventing," with reference to a certain disease condition in a mammal, refers to preventing or delaying the onset of the disease, or preventing the manifestation of clinical or subclinical symptoms thereof.

As used herein, "sequence identity" between two polypeptide sequences indicates the percentage of amino acids that are identical between the sequences. The amino acid sequence identity of polypeptides can be determined conventionally using known computer programs such as Bestfit, FASTA, or BLAST (see e.g., Pearson, *Methods Enzymol.* 183:63-98 (1990); Pearson, *Methods Mol. Biol.* 132:185-219 (2000); Altschul et al., *J. Mol. Biol.* 215:403-410 (1990); Altschul et al., *Nucleic Acids Res.* 25:3389-3402 (1997)). When using Bestfit or any other sequence alignment program to determine whether a particular sequence is, for instance, 95% identical to a reference amino acid sequence, the parameters are set such that the percentage of identity is calculated over the full length of the reference amino acid sequence and that gaps in homology of up to 5% of the total number of amino acid residues in the reference sequence are allowed. This aforementioned method in determining the percentage of identity between polypeptides is applicable to all proteins, fragments, or variants thereof disclosed herein.

As used herein, the term "binds", "binds to", "specifically binds" "specifically binds to" or is "specific for" refers to measurable and reproducible interactions such as binding between a target and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 µM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

The term "treat", "treating", or "treatment", with reference to a certain disease condition in a mammal, refers to causing a desirable or beneficial effect in the mammal having the disease condition. The desirable or beneficial effect may include reduced frequency or severity of one or more symptoms of the disease (i.e., tumor growth and/or metastasis, or other effect mediated by the numbers and/or activity of immune cells, and the like), or arrest or inhibition of further development of the disease, condition, or disorder. In the context of treating cancer in a mammal, the desirable or beneficial effect may include inhibition of further growth or spread of cancer cells, death of cancer cells, inhibition of reoccurrence of cancer, reduction of pain associated with the cancer, or improved survival of the mammal. The effect can be either subjective or objective. For example, if the mammal is human, the human may note improved vigor or vitality or decreased pain as subjective symptoms of improvement or response to therapy. Alternatively, the clinician may notice a decrease in tumor size or tumor burden based on physical exam, laboratory parameters, tumor markers or radiographic findings. Some laboratory signs that the clinician may observe for response to treatment include normalization of tests, such as white blood cell count, red blood cell count, platelet count, erythrocyte sedimentation rate, and various enzyme levels. Additionally, the clinician may observe a decrease in a detectable tumor marker. Alternatively, other tests can be used to evaluate objective improvement, such as sonograms, nuclear magnetic resonance testing and positron emissions testing.

The term "vector" refers to a nucleic acid molecule capable of transporting a foreign nucleic acid molecule. The foreign nucleic acid molecule is linked to the vector nucleic acid molecule by a recombinant technique, such as ligation or recombination. This allows the foreign nucleic acid molecule to be multiplied, selected, further manipulated or expressed in a host cell or organism. A vector can be a plasmid, phage, transposon, cosmid, chromosome, virus, or virion. One type of vectors can be integrated into the genome of a host cell upon introduction into the host cell, and thereby are replicated along with the host genome (e.g., non-episomal mammalian vectors). Another type of vector is capable of autonomous replication in a host cell into which it is introduced (e.g., bacterial vectors having a bacterial origin of replication and episomal mammalian vectors). Another specific type of vector capable of directing the expression of expressible foreign nucleic acids to which they are operatively linked is commonly referred to as "expression vectors." Expression vectors generally have control sequences that drive expression of the expressible foreign nucleic acids. Simpler vectors, known as "transcription vectors," are only capable of being transcribed but not translated: they can be replicated in a target cell but not expressed. The term "vector" encompasses all types of vectors regardless of their function. Vectors capable of directing the expression of expressible nucleic acids to which they are operatively linked are commonly referred to "expression vectors." Other examples of "vectors" may include display vectors (e.g., vectors that direct expression and display of an encoded polypeptide on the surface of a virus or cell (such as a bacterial cell, yeast cell, insect cell, and/or mammalian cell).

As used herein, a "subject", "patient", or "individual" may refer to a human or a non-human animal. A "non-human animal" may refer to any animal not classified as a human, such as domestic, farm, or zoo animals, sports, pet animals (such as dogs, horses, cats, cows, etc.), as well as animals used in research. Research animals may refer without limitation to nematodes, arthropods, vertebrates, mammals, frogs, rodents (e.g., mice or rats), fish (e.g., zebrafish or pufferfish), birds (e.g., chickens), dogs, cats, and non-human primates (e.g., rhesus monkeys, cynomolgus monkeys, chimpanzees, etc.). In some embodiments, the subject, patient, or individual is a human.

An "effective amount" refers to at least an amount effective, at dosages and for periods of time necessary, to achieve one or more desired or indicated effects, including a therapeutic or prophylactic result. An effective amount can be provided in one or more administrations. For purposes of the present disclosure, an effective amount of antibody, drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition (e.g., an effective amount as administered as a monotherapy or combination therapy). Thus, an "effective amount" may be considered in the context of administering one or more therapeutic agents, and a single agent may be considered to be given in an effective amount if, in conjunction with one or more other agents, a desirable result may be or is achieved.

III. Binding Molecules that Bind to Human CTLA4

The present disclosure relates, in part, to isolated binding molecules that bind to human CTLA4, including CTLA4 antibodies, antigen-binding fragments of the CTLA4 antibodies, and derivatives of the CTLA4 antibodies. In some embodiments, the binding molecules are any of the antibodies described herein, including antibodies described with reference to specific amino acid sequences of HVRs, variable regions (VL, VH), and light and heavy chains (e.g., IgG1, IgG2, IgG4). In some embodiments, the antibodies are human antibodies. In some embodiments, the antibodies are humanized antibodies and/or chimeric antibodies. In some embodiments, the present disclosure relates to binding molecules that bind to human CTLA4, and have at least one (e.g., at least one, at least two, at least three, at least four, at least five, at least six, at least seven, at least eight, or all nine) of the following functional properties: (a) bind to human, cynomolgus monkey, mouse, rat, and/or dog CTLA4 with a $K_D$ of 500 nM or less; (b) have antagonist activity on human CTLA4; (c) do not bind to human PD-1, PD-L1, PD-L2, LAG3, TIM3, B7-H3, CD95, CD120a, OX40, CD40, BTLA, VISTA, ICOS, and/or B7-H4 at concentration up to 100 nM; (d) are cross-reactive with monkey, mouse, rat, and/or dog CTLA4; (e) induces ADCC effects (e.g., on Tregs); (1) activates human PBMCs (e.g., stimulates secretion of IL-2 and/or IFNγ); (g) are capable of inhibiting tumor cell growth; (h) have therapeutic effect on a cancer; and (i) block binding of human CTLA4 to human CD80 and/or human CD86. In some embodiments, the anti-CTLA4 antibodies described herein have lower activity in blocking binding of CD80 and/or CD86 to human CTLA4 as compared to ipilimumab in an assay wherein either when human CD80 and/or CD86 are immobilized (or plate bound) or when human CTLA4 protein is present on cell surface. See FIGS. 57C and 57D and 58. In some embodiments, the anti-CTLA4 antibodies described herein deplete Treg cells selectively in tumor microenvironment as compared to Treg depletions in PBMC or spleen. In some embodiments, the anti-CTLA4 antibodies described herein have higher Treg depletion activity in tumor microenvironment as compared to ipilimumab. See FIGS. 61A-B, 62A-B, and 63. Also provided herein are one or more anti-CTLA4 antibodies or antigen-binding fragments that cross-compete for binding to human CTLA4 with one or more of the antibodies or antigen-binding fragments described herein.

In some embodiments, the antibodies or antigen-binding fragments bind to human, cynomolgus monkey, mouse, rat, and/or dog CTLA4 with a $K_D$ of about 500 nM or less (e.g., about 500 nM or less, about 450 nM or less, about 400 nM or less, about 350 nM or less, about 300 nM or less, about 250 nM or less, about 200 nM or less, about 150 nM or less, about 100 nM or less, about 90 nM or less, about 80 nM or less, about 70 nM or less, about 60 nM or less, about 50 nM or less, about 40 nM or less, about 30 nM or less, about 25 nM or less, about 20 nM or less, about 10 nM or less, about 1 nM or less, about 0.1 nM or less, etc.) In some embodiments, the antibodies or antigen-binding fragments bind to human, cynomolgus monkey, mouse, rat, and/or dog CTLA4 with a $K_D$ of about 350 nM or less. In some embodiments, the antibodies or antigen-binding fragments bind to human CTLA4 with a $K_D$ of about 100 nM or less. In some embodiments, the antibodies or antigen-binding fragments bind to human CTLA4 with a $K_D$ of about 50 nM or less. In some embodiments, the antibodies or antigen-binding fragments bind to human CTLA4 with a $K_D$ of about 10 nM or less. Methods of measuring the $K_D$ of an antibody or antigen-binding fragment may be carried out using any method known in the art, including for example, by surface plasmon resonance, an ELISA, isothermal titration calorimetry, a filter binding assay, an EMSA, etc. In some embodiments, the $K_D$ is measured by surface plasmon resonance or an ELISA (see e.g., Example 3 below).

In some embodiments, the antibodies or antigen-binding fragments described herein have antagonist activity on human CTLA4. In some embodiments, the antibodies or antigen-binding fragments repress one or more activities of human CTLA4 when a cell (e.g., a human cell) expressing human CTLA4 is contacted by the antibody or antigen binding fragment (e.g., CTLA4 blockade as measured by an increase in a reporter gene signal using a CLA4 blockage reporter gene assay).

In some embodiments, the antibodies or antigen-binding fragments are cross-reactive with monkey (e.g., cynomolgus monkey), mouse, rat, and/or dog CTLA4. In some embodiments, the antibodies or antigen-binding fragments are cross-reactive with monkey CTLA4. In some embodiments, the antibodies or antigen-binding fragments are cross-reactive with mouse CTLA4. In some embodiments, the antibodies or antigen-binding fragments are cross-reactive with rat CTLA4. In some embodiments, the antibodies or antigen-binding fragments are cross-reactive with dog CTLA4. In some embodiments, the antibodies or antigen binding fragments are cross reactive with monkey and mouse CTLA4; monkey and rat CTLA4; monkey and dog CTLA4; mouse and rat CTLA4; mouse and dog CTLA4; rat and dog CTLA4; monkey, mouse, and rat CTLA4; monkey, mouse, and dog CTLA4; monkey, rat, and dog CTLA4; mouse, rat, and dog CTLA4; or monkey, mouse, and dog CTLA4. In some embodiments, the antibodies or antigen binding fragments are cross-reactive if the antibodies or antigen-binding fragments binds to a non-human CTLA4 molecule with a $K_D$ less than about 500 nM (e.g., less than about 1 nM, less than about 10 nM, less than about 25 nM, less than about 50 nM, less than about 75 nM, less than about 100 nM, less than about 150 nM, less than about 200 nM, less than about 250 nM, less than about 300 nM, less than about 350 nM, etc.). Methods of measuring antibody cross-reactivity are known in the art, including, without limitation, surface plasmon resonance, an ELISA, isothermal titration calorimetry, a filter binding assay, an EMSA, etc. In some embodiments, the cross-reactivity is measured by ELISA (see e.g., Example 3 below).

In some embodiments, the antibodies induce ADCC effects against a CTLA4 expressing cell (e.g., against CTLA4-expressing human cells such as Tregs) after the antibody binds to the cell-expressed CTLA4. Methods of measuring ADCC effects (e.g., in vitro methods) are known in the art, including, without limitation, via the methods described in Example 3 below. In some embodiments, the antibodies induce ADCC effects by more than about 10% (e.g., induce ADCC by more than about 10%, more than about 15%, more than about 20%, more than about 25%, more than about 30%, more than about 35%, more than about 40%, etc.) relative to a control (e.g., an isotype control or ipilimumab).

In some embodiments, the antibodies or antigen-binding fragments are capable of inhibiting tumor cell growth and/or proliferation. In some embodiments, the tumor cell growth and/or proliferation is inhibited by at least about 5% (e.g., at least about 5%, at least about 10%, at least about 20%, at least about 30%, at least about 40%, at least about 50%, at least about 60%, at least about 70%, at least about 80%, at least about 90%, or at least about 99%) when contacted with the antibodies or antigen-binding fragments relative to corresponding tumor cells not contacted with the antibodies or antigen-binding fragments (or relative to corresponding tumor cells contacted with an isotype control antibody). In some embodiments, the antibodies or antigen-binding fragments are capable of reducing tumor volume in a subject when the subject is administered the antibodies or antigen-binding fragments. In some embodiments, the antibodies or antigen-binding fragments are capable of reducing tumor volume in a subject by at least about 5% (e.g., at least about 5%, at least about 10%, at least about 20%, at least about 30%, at least about 40%, at least about 50%, at least about 60%, at least about 70%, at least about 80%, at least about 90%, or at least about 99%) relative to the initial tumor volume in the subject (e.g., prior to administration of the antibodies or antigen-binding fragments; as compared to a corresponding tumor in a subject administered an isotype control antibody). Methods of monitoring tumor cell growth/proliferation, tumor volume, and/or tumor inhibition are known in the art, including, for example, via the methods described in Example 4 below.

In some embodiments, the antibodies or antigen-binding fragments have therapeutic effect on a cancer. In some embodiments, the antibodies or antigen-binding fragments reduce one or more signs or symptoms of a cancer. In some embodiments, a subject suffering from a cancer goes into partial or complete remission when administered the antibodies or antigen-binding fragments.

In another aspect, the disclosure provides isolated antibodies that compete or cross-compete for binding to human CTLA4 with any of the illustrative antibodies of the disclosure, such as TY21585, TY21586, TY21587, TY21588, TY21589, TY21580, TY21591, TY21686, TY21687, TY21689, TY21680, TY21691, and/or TY21692. In a particular embodiment, the present disclosure provides isolated antibodies that compete or cross-compete for binding to the same epitope on the human CTLA4 with any of the illustrative antibodies of the disclosure. The ability of an antibody to compete or cross-compete for binding with another antibody can be determined using standard binding assays known in the art, such as BIAcore analysis, ELISA assays, or flow cytometry. For example, one can allow an illustrative antibody of the disclosure to bind to human CTLA4 under saturating conditions and then measure the ability of the test antibody to bind to the CTLA4. If the test antibody is able to bind to the CTLA4 at the same time as the illustrative antibody, then the test antibody binds to a different epitope as the illustrative antibody. However, if the test antibody is not able to bind to the CTLA4 at the same time, then the test antibody binds to the same epitope, an overlapping epitope, or an epitope that is in close proximity to the epitope bound by the illustrative antibody. This experiment can be performed using various methods, such as ELISA, RIA, FACS or surface plasmon resonance.

In some embodiments, the antibodies or antigen-binding fragments block the binding between CTLA4 and one or more of its binding partners (e.g., human CTLA4 and human CD80, human CTLA4 and human CD86). In some embodiments, the antibodies or antigen-binding fragments block the binding between CTLA4 and its ligand in vitro. In some embodiments, the antibody or antigen-binding fragment has a half maximal inhibitory concentration ($IC_{50}$) of about 500 nM or less (e.g., about 500 nM or less, about 400 nM or less, about 300 nM or less, about 200 nM or less, about 100 nM or less, about 50 nM or less, about 25 nM or less, about 10 nM or less, about 1 nM or less, etc.) for blocking binding of CTLA4 to CD80 and/or CD86. In some embodiments, the antibody or antigen-binding fragment has a half maximal inhibitory concentration ($IC_{50}$) of about 100 nM or less for blocking binding of CTLA4 to CD80 and/or CD86. In some embodiments, the antibody or antigen-binding fragment completely blocks binding of human CTLA4 to CD80 and/or CD86 when provided at a concentration of about 100 nM or greater (e.g., about 100 nM or greater, about 500 nM or greater, about 1 μM or greater, about 10 μM or greater, etc.). As used herein, the term "complete blocking" or "completely blocks" refers to the antibody or antigen-binding fragment's ability to reduce binding between a first protein and a second protein by at least about 80% (e.g., at least about 80%, at least about 85%, at least about 90%, at least about 95%, at least about 99%, etc.). Methods of measuring the ability of an antibody or antigen-binding fragment to block binding of a first protein (e.g., human CTLA4) and a second protein (e.g., human CD80 or human CD86) are known in the art, including, without limitation, via BIAcore analysis, ELISA assays, and flow cytometry (see e.g., Example 3 below). In some embodiments, the anti-CTLA4 antibodies described herein have lower activity in blocking ligand binding than ipilimumab.

CTLA4 Antibodies

In some aspects, the present disclosure provides an isolated antibody that binds to human CTLA4. In some embodiments, the antibody binds human CTLA4 with a $K_D$ of 1000 nM or less (e.g., 50 nM or less, 10 nM or less) as measured by surface plasmon resonance. In some embodiments, the antibody is cross-reactive with at least one non-human species selected from cynomolgus monkey, mouse, rat, and dog.

In some aspects, the present disclosure provides an isolated antibody that specifically binds to an epitope similar to a ligand binding site of human CTLA4. In some embodiments, the antibody specifically binds to an epitope similar to CD80 binding site of human CTLA4. In some embodiments, the antibody specifically binds to an epitope similar to CD86 binding site of human CTLA4. In some embodiments, the antibody specifically binds to an epitope comprising one or more amino acid residues in a ligand binding site (e.g., CD80 and/or CD86 binding site) of human CTLA4. In some embodiments, the antibody specifically binds to an epitope on human CTLA4 that is different from the epitope of ipilimumab. In some embodiments, the epitope does not comprise amino acid residues in the CC' loop motif of human CTLA4. In some embodiments, the epitope does not comprise amino acid residue L106 or I108 of human CTLA4. In some embodiments, the antibody specifically binds to an epitope comprising amino acid residues Y105 and L106, but not I108 of human CTLA4, wherein the numbering of the amino acid residues is according to SEQ ID NO: 207.

```
                                         (SEQ ID NO: 207)
KAMHVAQPAVVLASSRGIASFVCEYASPGKATEVRVTVLRQADSQVTEVCA
ATYMMGNELTFLDDSICTGTSSGNQVNLTIQGLRAMDTGLYICKVELMYPP
PYYLGIGNGTQIYVIDPE
```

In one aspect, the present disclosure provides an isolated antibody comprising a heavy chain variable region and a light chain variable region, a) where the heavy chain variable region comprises an HVR-H1, an HVR-H2, and an HVR-H3, where the HVR-H1 comprises an amino acid sequence according to a formula selected from: Formula (I): X1TFSX2YX3IHWV (SEQ ID NO: 1), where X1 is F or Y, X2 is D or G, and X3 is A, G, or W; Formula (II): YSIX1SGX2X3WX4WI (SEQ ID NO: 2), where X1 is S or T, X2 is H or Y, X3 is H or Y, and X4 is A, D, or S; and Formula (III): FSLSTGGVAVX1WI (SEQ ID NO: 3), where X1 is G or S; the HVR-H2 comprises an amino acid sequence according to a formula selected from: Formula (IV): IGX1IX2HSGSTYYSX3SLKSRV (SEQ ID NO: 4), where X1 is D or E, X2 is S or Y, and X3 is P or Q; Formula (V): IGX1ISPSX2GX3TX4YAQKFQGRV (SEQ ID NO: 5), where X1 is I or W, X2 is G or S, X3 is G or S, and X4 is K or N; and Formula (VI): VSX1ISGX2GX3X4TYYADSVKGRF (SEQ ID NO: 6), where X1 is A, G, or S, X2 is S or Y, X3 is G or S, and X4 is S or T; and the HVR-H3 comprises an amino acid sequence according to a formula selected from: Formula (VII): ARX1X2X3X4FDX5 (SEQ ID NO: 7), where X1 is G, R, or S, X2 is A, I, or Y, X3 is D, V, or Y, X4 is A, E, or Y, and X5 is I or Y; Formula (VIII): ARX1GX2GYFDX3 (SEQ ID NO: 8), where X1 is D or L, X2 is F or Y, and X3 is V or Y; Formula (IX): ARX1X2X3X4AX5X6FDY (SEQ ID NO: 9), where X1 is L or R, X2 is I or P, X3 is A or Y, X4 is S or T, X5 is T or Y, and X6 is A or Y; and Formula (X): ARDX1X2X3GSSGYYX4GFDX5 (SEQ ID NO: 10), where X1 is I or V, X2 is A or H, X3 is P or S, X4 is D or Y, and X5 is F or V; and/or b) where the light chain variable region comprises an HVR-L1, an HVR-L2, and an HVR-L3, where the HVR-L1 comprises an amino acid sequence according to a formula selected from: Formula (XI): RASQX1X2X3SX4LX5 (SEQ ID NO: 11), where X1 is G or S, X2 is I or V, X3 is G or S, X4 is S or Y, and X5 is A or N; Formula (XII): RASQX1VX2X3RX4LA (SEQ ID NO: 12), where X1 is S or T, X2 is F, R, or S, X3 is G or S, and X4 is F or Y; and Formula (XIII): RASX1SVDFX2GX3SFLX4 (SEQ ID NO: 13), where X1 is E or Q, X2 is D, F, H, or Y, X3 is F, I, or K, and X4 is A, D, or H; the HVR-L2 comprises an amino acid sequence according to Formula (XIV): X1ASX2X3X4X5GX6 (SEQ ID NO: 14), where X1 is A or D, X2 is N, S, or T, X3 is L or R, X4 is A, E, or Q, X5 is S or T, and X6 is I or V; and the HVR-L3 comprises an amino acid sequence according to a formula selected from: Formula (XV): YCX1X2X3X4X5X6PX7T (SEQ ID NO: 15), where X1 is E, Q, or V, X2 is H or Q, X3 is A, G, H, R, or S, X4 is D, L, S, or Y, X5 is E, G, P, Q, or S, X6 is L, T, V, or W, and X7 is F, L, P, W, or Y; Formula (XVI): YCQQX1X2X3WPPWT (SEQ ID NO: 16), where X1 is S or Y, X2 is D or Y, and X3 is Q or Y; and Formula (XVII): YCQX1YX2SSPPX3YT (SEQ ID NO: 17), where X1 is H or Q, X2 is T or V, and X3 is E or V.

In some embodiments, the antibody comprises: a) an HVR-H1 comprising an amino acid sequence selected from SEQ ID NOS: 18-29; an HVR-H2 comprising an amino acid sequence selected from SEQ ID NOS: 30-39; and an HVR-H3 comprising an amino acid sequence selected from SEQ ID NOS: 40-52; and/or b) an HVR-L1 comprising an amino acid sequence selected from SEQ ID NOS: 53-65; an HVR-L2 comprising an amino acid sequence selected from SEQ ID NOS: 66-69; and an HVR-L3 comprising an amino acid sequence selected from SEQ ID NOS: 70-81. In some embodiments, the antibody comprises one, two, three, four, five, or all six of the HVRs shown for any of the exemplary antibodies described in Table A below.

TABLE A anti-CTLA4 HVR sequences

| Ab name: | HVR-H1 | HVR-H2 | HVR-H3 | HVR-L1 | HVR-L2 | HVR-L3 |
|---|---|---|---|---|---|---|
| TY21585 | FTFSDYAIH WV (SEQ ID NO: 18) | IGIISPSSGSTNYAQ KFQGRV (SEQ ID NO: 30) | ARDIHSGSSGY YYGFDV (SEQ ID NO: 40) | RASESVDFFG ISFLA (SEQ ID NO: 53) | DASNR ATGI (SEQ ID NO: 66) | YCQHYTSS PPVYT (SEQ ID NO: 70) |
| TY21586 | YSITSGYY WAWI (SEQ ID NO: 19) | VSSISGSGSTTYYA DSVKGRF (SEQ ID NO: 31) | ARDGFGYFDY (SEQ ID NO: 41) | SASSSVSYVY (SEQ ID NO: 54) | DASSLE SGV (SEQ ID NO: 67) | YCVQGLQT PWT (SEQ ID NO: 71) |
| TY21587 | FTFSDYGIH WV (SEQ ID NO: 20) | IGEIYHSGSTYYSP SLKSRV (SEQ ID NO: 32) | ARDVAPGSSGY YDGFDF (SEQ ID NO: 42) | RASQGIGSSL A (SEQ ID NO: 55) | DASNR ATGI (SEQ ID NO: 66) | YCQQYDQ WPPWT (SEQ ID NO: 72) |
| TY21588 | YSISSGYH WDWI (SEQ ID NO: 21) | VSGISGYGGSTYY ADSVKGRF (SEQ ID NO: 33) | ARHSYYGSGNF DY (SEQ ID NO: 43) | RASESVDFFG KSFLH (SEQ ID NO: 56) | DASNL ETGV (SEQ ID NO: 68) | YCQQSYS WPPT (SEQ ID NO: 73) |

TABLE A-continued anti-CTLA4 HVR sequences

| Ab name: | HVR-H1 | HVR-H2 | HVR-H3 | HVR-L1 | HVR-L2 | HVR-L3 |
|---|---|---|---|---|---|---|
| TY21589 | FTFSDYWI HWV (SEQ ID NO: 22) | IGWISPSGGGTKYA QKFQGRV (SEQ ID NO: 34) | ARGAYEFDY (SEQ ID NO: 44) | RASQSVSSRF LA (SEQ ID NO: 57) | DASNR ATGI (SEQ ID NO: 66) | YCQQSYPT PLT (SEQ ID NO: 74) |
| TY21580 | YSISSGYH WSWI (SEQ ID NO: 23) | LARIDWDDDKYYS TSLKSRL (SEQ ID NO: 35) | ARSYVYFDY (SEQ ID NO: 45) | RASQSVRGR FLA (SEQ ID NO: 58) | DASNR ATGI (SEQ ID NO: 66) | YCQQSSSW PPT (SEQ ID NO: 75) |
| TY21591 | FSLSTGGV AVSWI (SEQ ID NO: 24) | IGEIYHSGSTYYSP SLKSRV (SEQ ID NO: 32) | ARRIATATYFD Y (SEQ ID NO: 46) | RASQTVFSR YLA (SEQ ID NO: 59) | DASNR ATGI (SEQ ID NO: 66) | YCQQSYY WPPWT (SEQ ID NO: 76) |
| TY21686 | FSLSTGGV AVGWI (SEQ ID NO: 25) | VSAISGYGSTTYY ADSVKGRF (SEQ ID NO: 36) | ARLPYSAYAFD Y (SEQ ID NO: 47) | RASQGVSSY LA (SEQ ID NO: 60) | AASTL QSGV (SEQ ID NO: 69) | YCQHHYG TPLT (SEQ ID NO: 77) |
| TY21687 | FTFSGYAIH WV (SEQ ID NO: 26) | IGIISPSGGGTKYA QKFQGRV (SEQ ID NO: 37) | ARHPFAY (SEQ ID NO: 48) | RASQSVDFY GISFLD (SEQ ID NO: 61) | DASNR ATGI (SEQ ID NO: 66) | YCQQYVSS PPEYT (SEQ ID NO: 78) |
| TY21689 | YTFSGYGI HWV (SEQ ID NO: 27) | IGEIYHSGSTYYSP SLKSRV (SEQ ID NO: 32) | ARRIDAFDI (SEQ ID NO: 49) | RASQSVDFD GFSFLH (SEQ ID NO: 62) | DASSLE SGV (SEQ ID NO: 67) | YCQQRDS WPYT (SEQ ID NO: 79) |
| TY21680 | YTFSGYAI HWV (SEQ ID NO: 28) | IGIISPSGGGTKYA QKFQGRV (SEQ ID NO: 37) | ARLYDVAY (SEQ ID NO: 50) | RASQSVDFH GKSFLH (SEQ ID NO: 63) | DASSLE SGV (SEQ ID NO: 67) | YCEQSLEV PFT (SEQ ID NO: 80) |
| TY21691 | FTFSDYAIH WV (SEQ ID NO: 18) | IGIISPSGGSTKYAQ KFQGRV (SEQ ID NO: 38) | ARLGYGYFDV (SEQ ID NO: 51) | RASQSVDFY GISFLH (SEQ ID NO: 64) | DASSLE SGV (SEQ ID NO: 67) | YCVQALQL PLT (SEQ ID NO: 81) |
| TY21692 | YSITSGHY WSWI (SEQ ID NO: 29) | IGDISHSGSTYYSQ SLKSRV (SEQ ID NO: 39) | ARGSRTGYFDY (SEQ ID NO: 52) | RASQSISSYL N (SEQ ID NO: 65) | DASNL ETGV (SEQ ID NO: 68) | YCQHHYG TPLT (SEQ ID NO: 77) |

In some embodiments, the antibody comprises an HVR-H1 comprising the amino acid sequence of SEQ ID NO: 18, an HVR-H2 comprising the amino acid sequence of SEQ ID NO: 30, an HVR-H3 comprising the amino acid sequence of SEQ ID NO: 40, an HVR-L1 comprising the amino acid sequence of SEQ ID NO: 53, an HVR-L2 comprising the amino acid sequence of SEQ ID NO: 66, and an HVR-L3 comprising the amino acid sequence of SEQ ID NO: 70. In some embodiments, the antibody comprises an HVR-H1 comprising the amino acid sequence of SEQ ID NO: 19, an HVR-H2 comprising the amino acid sequence of SEQ ID NO: 31, an HVR-H3 comprising the amino acid sequence of SEQ ID NO: 41, an HVR-L1 comprising the amino acid sequence of SEQ ID NO: 54, an HVR-L2 comprising the amino acid sequence of SEQ ID NO: 67, and an HVR-L3 comprising the amino acid sequence of SEQ ID NO: 71. In some embodiments, the antibody comprises an HVR-H1 comprising the amino acid sequence of SEQ ID NO: 20, an HVR-H2 comprising the amino acid sequence of SEQ ID NO: 32, an HVR-H3 comprising the amino acid sequence of SEQ ID NO: 42, an HVR-L1 comprising the amino acid sequence of SEQ ID NO: 55, an HVR-L2 comprising the amino acid sequence of SEQ ID NO: 66, and an HVR-L3 comprising the amino acid sequence of SEQ ID NO: 72. In some embodiments, the antibody comprises an HVR-H1 comprising the amino acid sequence of SEQ ID NO: 21 an HVR-H2 comprising the amino acid sequence of SEQ ID NO: 33, an HVR-H3 comprising the amino acid sequence of SEQ ID NO: 43, an HVR-L1 comprising the amino acid sequence of SEQ ID NO: 56, an HVR-L2 comprising the amino acid sequence of SEQ ID NO: 68, and an HVR-L3 comprising the amino acid sequence of SEQ ID NO: 73. In some embodiments, the antibody comprises an HVR-H1 comprising the amino acid sequence of SEQ ID NO: 22, an HVR-H2 comprising the amino acid sequence of SEQ ID NO: 34, an HVR-H3 comprising the amino acid sequence of SEQ ID NO: 44, an HVR-L1 comprising the amino acid sequence of SEQ ID NO: 57, an HVR-L2 comprising the amino acid sequence of SEQ ID NO: 66, and an HVR-L3 comprising the amino acid sequence of SEQ ID NO: 74. In some embodiments, the antibody comprises an HVR-H1 comprising the amino acid sequence of SEQ ID NO: 23, an HVR-H2 comprising the amino acid sequence of SEQ ID NO: 35, an HVR-H3 comprising the amino acid sequence of SEQ ID NO: 45, an HVR-L1 comprising the amino acid sequence of SEQ ID NO: 58, an HVR-L2 comprising the amino acid sequence of SEQ ID NO: 66, and an HVR-L3 comprising the amino acid sequence of SEQ ID NO: 75. In some embodiments, the antibody comprises an HVR-H1 comprising the amino acid sequence of SEQ ID NO: 24, an HVR-H2 comprising the amino acid sequence of SEQ ID NO: 32, an HVR-H3 comprising the amino acid sequence of SEQ ID NO: 46, an HVR-L1 comprising the amino acid sequence of SEQ ID NO: 59, an HVR-L2 comprising the amino acid sequence of SEQ ID NO: 66, and an HVR-L3 comprising the amino acid sequence of SEQ ID NO: 76. In some embodiments, the antibody comprises an HVR-H1 comprising the amino acid sequence of SEQ ID NO: 25, an HVR-H2 comprising the amino acid sequence of SEQ ID NO: 36, an HVR-H3 comprising the amino acid sequence of SEQ ID NO: 47, an HVR-L1 comprising the amino acid sequence of SEQ ID NO: 60, an HVR-L2 comprising the amino acid sequence of SEQ ID NO: 69, and an HVR-L3 comprising the amino acid sequence of SEQ ID NO: 77. In some embodiments, the antibody comprises an HVR-H1 comprising the amino acid sequence of SEQ ID NO: 26, an HVR-H2 comprising the amino acid sequence of SEQ ID NO: 37, an HVR-H3 comprising the amino acid sequence of SEQ ID NO: 48, an HVR-L1 comprising the amino acid sequence of SEQ ID NO: 61, an HVR-L2 comprising the amino acid sequence of SEQ ID NO: 66, and an HVR-L3 comprising the amino acid sequence of SEQ ID NO: 78. In some embodiments, the antibody comprises an HVR-H1 comprising the amino acid sequence of SEQ ID NO: 27, an HVR-H2 comprising the amino acid sequence of SEQ ID NO: 32, an HVR-H3 comprising the amino acid sequence of SEQ ID NO: 49, an HVR-L1 comprising the amino acid sequence of SEQ ID NO: 62, an HVR-L2 comprising the amino acid sequence of SEQ ID NO: 67, and an HVR-L3 comprising the amino acid sequence of SEQ ID NO: 79. In some embodiments, the antibody comprises an HVR-H1 comprising the amino acid sequence of SEQ ID NO: 28, an HVR-H2 comprising the amino acid sequence of SEQ ID NO: 37, an HVR-H3 comprising the amino acid sequence of SEQ ID NO: 50, an HVR-L1 comprising the amino acid sequence of SEQ ID NO: 63, an HVR-L2 comprising the amino acid sequence of SEQ ID NO: 67, and an HVR-L3 comprising the amino acid sequence of SEQ ID NO: 80. In some embodiments, the antibody comprises an HVR-H1 comprising the amino acid sequence of SEQ ID NO: 18, an HVR-H2 comprising the amino acid sequence of SEQ ID NO: 38, an HVR-H3 comprising the amino acid sequence of SEQ ID NO: 51, an HVR-L1 comprising the amino acid sequence of SEQ ID NO: 64, an HVR-L2 comprising the amino acid sequence of SEQ ID NO: 67, and an HVR-L3 comprising the amino acid sequence of SEQ ID NO: 81. In some embodiments, the antibody comprises an HVR-H1 comprising the amino acid sequence of SEQ ID NO: 29, an HVR-H2 comprising the amino acid sequence of SEQ ID NO: 39, an HVR-H3 comprising the amino acid sequence of SEQ ID NO: 52, an HVR-L1 comprising the amino acid sequence of SEQ ID NO: 65, an HVR-L2 comprising the amino acid sequence of SEQ ID NO: 68, and an HVR-L3 comprising the amino acid sequence of SEQ ID NO: 77.

In some embodiments, the antibody comprises: a) a heavy chain variable region comprising an amino acid sequence selected from SEQ ID NOS: 82-94; and/or b) a light chain variable region comprising an amino acid sequence selected from SEQ ID NOS: 95-107. In some embodiments, the antibody comprises a heavy chain variable region comprising an amino acid sequence having at least 90% (e.g., at least 90%, 91%, 92%, 93%, 94%, 95%, 96%, 97%, 98%, or 99%) sequence identity to a sequence selected from SEQ ID NOS: 82-94, and/or a light chain variable region comprising an amino acid sequence having at least 90% (e.g., at least 90%, 91%, 92%, 93%, 94%, 95%, 96%, 97%, 98%, or 99%) sequence identity to a sequence selected from SEQ ID NOS: 95-107. In some embodiments, the antibody comprises a heavy chain variable region and a light chain variable region of any of the exemplary antibodies described in Table B below. In some embodiments, the antibody comprises one, two, or all three HVRs of the heavy chain variable region, and/or one, two, or all three HVRs of the light chain variable region shown for any of the exemplary antibodies described in Table B below.

TABLE B anti-CTLA4 variable region amino acid sequences

| Ab name: | VH: | VL: |
|---|---|---|
| TY21585 | EVQLVESGGGLVQPGGSLRLSCAASGFTFSDY AIHWVRQAPGKGLEWIGIISPSSGSTNYAQKF QGRVTISRDNSKNTLYLQLNSLRAEDTAVYYC ARDIHSGS SGYYYGFDVWGQGTLVTVSS (SEQ ID NO: 82) | DIQLTQSPSSLSASVGDRVTITCRASESVDFF GISFLAWYQQKPGKAPKLLIYDASNRATGI PSRFSGSGSGTDFTLTISSLQPEDFATYYCQ HYTSSPPVYTFGQGTKVEIKR (SEQ ID NO: 95) |
| TY21586 | EVQLVESGGGLVQPGGSLRLSCAASGYSITSG YYWAWIRQAPGKGLEWVSSISGSGSTTYYAD SVKGRFTISRDNSKNTLYLQLNSLRAEDTAVY YCARDGFGYFDYWGQGTLVTVSS (SEQ ID NO: 83) | DIQLTQSPSSLSASVGDRVTITCSASSSVSYV YWYQQKPGKAPKLLIYDASSLESGVPSRFS GSGSGTDFTLTISSLQPEDFATYYCVQGLQT PWTFGQGTKVEIKR (SEQ ID NO: 96) |
| TY21587 | EVQLVESGGGLVQPGGSLRLSCAASGFTFSDY GIHWVRQAPGKGLEWIGEIYHSGSTYYSPSLK SRVTISRDNSKNTLYLQLNSLRAEDTAVYYCA RDVAPGSSGYYDGFDFWGQGTLVTVSS (SEQ ID NO: 84) | DIQLTQSPSSLSASVGDRVTITCRASQGIGSS LAWYQQKPGKAPKLLIYDASNRATGIPSRF SGSGSGTDFTLTISSLQPEDFATYYCQQYDQ WPPWTFGQGTKVEIKR (SEQ ID NO: 97) |
| TY21588 | EVQLVESGGGLVQPGGSLRLSCAASGYSISSG YHWDWIRQAPGKGLEWVSGISGYYGGSTYYA DSVKGRFTISRDNSKNTLYLQLNSLRAEDTAV YYCARHSYYGSGNFDYWGQGTLVTVSS (SEQ ID NO: 85) | DIQLTQSPSSLSASVGDRVTITCRASESVDFF GKSFLHWYQQKPGKAPKLLIYDASNLETG VPSRFSGSGSGTDFTLTISSLQPEDFATYYC QQSYSWPPTFGQGTKVEIKR (SEQ ID NO: 98) |

TABLE B-continued anti-CTLA4 variable region amino acid sequences

| Ab name: | VH: | VL: |
|---|---|---|
| TY21589 | EVQLVESGGGLVQPGGSLRLSCAASGFTFSDY WIHWVRQAPGKGLEWIGWISPSGGGTKYAQK FQGRVTISRDNSKNTLYLQLNSLRAEDTAVYY CARGAYEFDYWGQGTLVTVSS (SEQ ID NO: 86) | DIQLTQSPSSLSASVGDRVTITCRASQSVSS RFLAWYQQKPGKAPKLLIYDASNRATGIPS RFSGSGSGTDFTLTISSLQPEDFATYYCQQS YPTPLTFGQGTKVEIKR (SEQ ID NO: 99) |
| TY21580 | EVQLVESGGGLVQPGGSLRLSCAASGYSISSG YHWSWIRQAPGKGLEWLARIDWDDDKYYST SLKSRLTISRDNSKNTLYLQLNSLRAEDTAVYY CARSYVYFDYWGQGTLVTVSS (SEQ ID NO: 87) | DIQLTQSPSSLSASVGDRVTITCRASQSVRG RFLAWYQQKPGKAPKLLIYDASNRATGIPS RFSGSGSGTDFTLTISSLQPEDFATYYCQQS SSWPPTFGQGTKVEIKR (SEQ ID NO: 100) |
| TY21591 | EVQLVESGGGLVQPGGSLRLSCAASGFSLSTG GVAVSWIRQAPGKGLEWIGEIYHSGSTYYSPS LKSRVTISRDNSKNTLYLQLNSLRAEDTAVYY CARRIATATYFDYWGQGTLVTVSS (SEQ ID NO: 88) | DIQLTQSPSSLSASVGDRVTITCRASQTVFS RYLAWYQQKPGKAPKLLIYDASNRATGIPS RFSGSGSGTDFTLTISSLQPEDFATYYCQQS YYWPPWTFGQGTKVEIKR (SEQ ID NO: 101) |
| TY21686 | EVQLVESGGGLVQPGGSLRLSCAASGFSLSTG GVAVGWIRQAPGKGLEWVSAISGYGSTTYYA DSVKGRFTISRDNSKNTLYLQLNSLRAEDTAV YYCARLPYSAYAFDYWGQGTLVTVSS (SEQ ID NO: 89) | DIQLTQSPSSLSASVGDRVTITCRASQGVSS YLAWYQQKPGKAPKLLIYAASTLQSGVPSR FSGSGSGTDFTLTISSLQPEDFATYYCQHHY GTPLTFGQGTKVEIKR (SEQ ID NO: 102) |
| TY21687 | EVQLVESGGGLVQPGGSLRLSCAASGFTFSGY AIHWVRQAPGKGLEWIGIISPSGGGTKYAQKF QGRVTISRDNSKNTLYLQLNSLRAEDTAVYYC ARHPFAYWGQGTLVTVSS (SEQ ID NO: 90) | DIQLTQSPSSLSASVGDRVTITCRASQSVDF YGISFLDWYQQKPGKAPKLLIYDASNRATG IPSRFSGSGSGTDFTLTISSLQPEDFATYYCQ QYVSSPPEYTFGQGTKVEIKR (SEQ ID NO: 103) |
| TY21689 | EVQLVESGGGLVQPGGSLRLSCAASGYTFSGY GIHWVRQAPGKGLEWIGEIYHSGSTYYSPSLK SRVTISRDNSKNTLYLQLNSLRAEDTAVYYCA RRIDAFDIWGQGTLVTVSS (SEQ ID NO: 91) | DIQLTQSPSSLSASVGDRVTITCRASQSVDF DGFSFLHWYQQKPGKAPKLLIYDASSLESG VPSRFSGSGSGTDFTLTISSLQPEDFATYYC QQRD S WPYTFGQGTKVEIKR (SEQ ID NO: 104) |
| TY21680 | EVQLVESGGGLVQPGGSLRLSCAASGYTFSGY AIHWVRQAPGKGLEWIGIISPSGGGTKYAQKF QGRVTISRDNSKNTLYLQLNSLRAEDTAVYYC ARLYDVAYWGQGTLVTVSS (SEQ ID NO: 92) | DIQLTQSPSSLSASVGDRVTITCRASQSVDF HGKSFLHWYQQKPGKAPKLLIYDASSLES GVPSRFSGSGSGTDFTLTISSLQPEDFATYY CEQSLEVPFTFGQGTKVEIKR (SEQ ID NO: 105) |
| TY21691 | EVQLVESGGGLVQPGGSLRLSCAASGFTFSDY AIHWVRQAPGKGLEWIGIISPSGGSTKYAQKF QGRVTISRDNSKNTLYLQLNSLRAEDTAVYYC ARLGYGYFDVWGQGTLVTVSS (SEQ ID NO: 93) | DIQLTQSPSSLSASVGDRVTITCRASQSVDF YGISFLHWYQQKPGKAPKLLIYDASSLESG VPSRFSGSGSGTDFTLTISSLQPEDFATYYC VQALQLPLTFGQGTKVEIKR (SEQ ID NO: 106) |
| TY21692 | EVQLVESGGGLVQPGGSLRLSCAASGYSITSG HYWSWIRQAPGKGLEWIGDISHSGSTYYSQSL KSRVTISRDNSKNTLYLQLNSLRAEDTAVYYC ARGSRTGYFDYWGQGTLVTVSS (SEQ ID NO: 94) | DIQLTQSPSSLSASVGDRVTITCRASQSISSY LNWYQQKPGKAPKLLIYDASNLETGVPSR FSGSGSGTDFTLTISSLQPEDFATYYCQHHY GTPLTFGQGTKVEIKR (SEQ ID NO: 107) |

In some embodiments, the antibody comprises a heavy chain variable region comprising the amino acid sequence of SEQ ID NO: 82, and a light chain variable region comprising the amino acid sequence of SEQ ID NO: 95. In some embodiments, the antibody comprises a heavy chain variable region comprising the amino acid sequence of SEQ ID NO: 83, and a light chain variable region comprising the amino acid sequence of SEQ ID NO: 96. In some embodiments, the antibody comprises a heavy chain variable region comprising the amino acid sequence of SEQ ID NO: 84, and a light chain variable region comprising the amino acid sequence of SEQ ID NO: 97. In some embodiments, the antibody comprises a heavy chain variable region comprising the amino acid sequence of SEQ ID NO: 85, and a light chain variable region comprising the amino acid sequence of SEQ ID NO: 98. In some embodiments, the antibody comprises a heavy chain variable region comprising the amino acid sequence of SEQ ID NO: 86, and a light chain variable region comprising the amino acid sequence of SEQ ID NO: 99. In some embodiments, the antibody comprises a heavy chain variable region comprising the amino acid sequence of SEQ ID NO: 87, and a light chain variable region comprising the amino acid sequence of SEQ ID NO: 100. In some embodiments, the antibody comprises a heavy chain variable region comprising the amino acid sequence of SEQ ID NO: 88, and a light chain variable region comprising the amino acid sequence of SEQ ID NO: 101. In some embodiments, the antibody comprises a heavy chain variable region comprising the amino acid sequence of SEQ ID NO: 89, and a light chain variable region comprising the amino acid sequence of SEQ ID NO: 102. In some embodiments, the antibody comprises a heavy chain variable region comprising the amino acid sequence of SEQ ID NO: 90, and a light chain variable region comprising the amino acid sequence of SEQ ID NO: 103. In some embodiments, the antibody comprises a heavy chain variable region comprising the amino acid sequence of SEQ ID NO: 91, and a light chain variable region comprising the amino acid sequence of SEQ ID NO: 104. In some embodiments, the antibody comprises a heavy chain variable region comprising the amino acid sequence of SEQ ID NO: 92, and a light chain variable region comprising the amino acid sequence of SEQ ID NO: 105. In some embodiments, the antibody comprises a heavy chain variable region comprising the amino acid sequence of SEQ ID NO: 93, and a light chain variable region comprising the amino acid sequence of SEQ ID NO: 106. In some embodiments, the antibody comprises a heavy chain variable region comprising the amino acid sequence of SEQ ID NO: 94, and a light chain variable region comprising the amino acid sequence of SEQ ID NO: 107.

In some embodiments, an antibody of the present disclosure cross-competes for binding to human CTLA4 with an antibody comprising: a) an HVR-H1 comprising an amino acid sequence selected from SEQ ID NOS: 18-29; an HVR-H2 comprising an amino acid sequence selected from SEQ ID NOS: 30-39; and an HVR-H3 comprising an amino acid sequence selected from SEQ ID NOS: 40-52; and/or b) an HVR-L1 comprising an amino acid sequence selected from SEQ ID NOS: 53-65; an HVR-L2 comprising an amino acid sequence selected from SEQ ID NOS: 66-69; and an HVR-L3 comprising an amino acid sequence selected from SEQ ID NOS: 70-81. In some embodiments, an antibody of the present disclosure cross-competes for binding to human CTLA4 with an antibody comprising one, two, three, four, five, or all six of the HVRs shown for any of the exemplary antibodies described in Table A. In some embodiments, an antibody of the present disclosure cross-competes for binding to human CTLA4 with an antibody comprising: a) a heavy chain variable region comprising an amino acid sequence selected from SEQ ID NOS: 82-94; and/or b) a light chain variable region comprising an amino acid sequence selected from SEQ ID NOS: 95-107. In some embodiments, an antibody of the present disclosure cross-competes for binding to human CTLA4 with an antibody comprising a VH and/or VL shown for any of the exemplary antibodies described in Table B.

The CTLA4 antibodies described herein may be in any class, such as IgG, IgM, IgE, IgA, or IgD. In some embodiments, the CTLA4 antibodies are in the IgG class, such as IgG1, IgG2, IgG3, or IgG4 subclass. A CTLA4 antibody can be converted from one class or subclass to another class or subclass using methods known in the art. An exemplary method for producing an antibody in a desired class or subclass comprises the steps of isolating a nucleic acid encoding a heavy chain of a CTLA4 antibody and a nucleic acid encoding a light chain of a CTLA4 antibody, isolating the sequence encoding the $V_H$ region, ligating the $V_H$ sequence to a sequence encoding a heavy chain constant region of the desired class or subclass, expressing the light chain gene and the heavy chain construct in a cell, and collecting the CTLA4 antibody. Antibodies of the present disclosure may be monoclonal antibodies or polyclonal antibodies. Antibodies of the present disclosure may be monospecific antibodies or multispecific (e.g., bispecific, trispecific, etc.) antibodies. In some embodiments, the CTLA4 antibodies described herein may include one or more Fc mutations (e.g., that modulate (increase or decrease) ADCC or CDC activities). Any suitable Fc mutations known in the art may be used in the CTLA4 antibodies of the present disclosure.

In some embodiments, an antibody of the present disclosure is a bispecific antibody that binds to a first and second target, where the first target is human CTLA4. In some embodiments, the bispecific antibody binds to a first and second target, where the first target is human CTLA4, and where the bispecific antibody comprises a) an HVR-H1 comprising an amino acid sequence selected from SEQ ID NOS: 18-29; an HVR-H2 comprising an amino acid sequence selected from SEQ ID NOS: 30-39; and an HVR-H3 comprising an amino acid sequence selected from SEQ ID NOS: 40-52; and/or b) an HVR-L1 comprising an amino acid sequence selected from SEQ ID NOS: 53-65; an HVR-L2 comprising an amino acid sequence selected from SEQ ID NOS: 66-69; and an HVR-L3 comprising an amino acid sequence selected from SEQ ID NOS: 70-81. In some embodiments, the bispecific antibody binds to a first and second target, where the first target is human CTLA4, and where the bispecific antibody comprises one, two, three, four, five, or all six of the HVRs shown for any of the exemplary antibodies described in Table A. In some embodiments, the bispecific antibody binds to a first and second target, where the first target is human CTLA4, and where the bispecific antibody comprises: a) a heavy chain variable region comprising an amino acid sequence selected from SEQ ID NOS: 82-94; and/or b) a light chain variable region comprising an amino acid sequence selected from SEQ ID NOS: 95-107. In some embodiments, the bispecific antibody binds to a first and second target, where the first target is human CTLA4, and where the bispecific antibody comprises a VH and/or VL shown for any of the exemplary antibodies described in Table B. In some embodiments, the second target is PD-1, PD-L1, PD-L2, LAG3, TIM3, B7-H3, CD95, CD120a, OX40, CD40, BTLA, VISTA, ICOS, Her1, Her2, Her3, or B7-H4.

Antibodies of the present disclosure may be produced by any techniques known in the art, including conventional monoclonal antibody methodology e.g., a standard somatic cell hybridization technique (see e.g., Kohler and Milstein, Nature 256:495 (1975)), viral or oncogenic transformation of B lymphocytes, or recombinant antibody technologies as described in detail herein (see e.g., Examples 1 and 2). In some embodiments, antibodies of the present disclosure are produced using any of the libraries and/or methods described in PCT application number PCT/CN2017/098333 (incorporated herein by reference in its entirety) and/or PCT application number PCT/CN2017/098299 (incorporated herein by reference in its entirety).

Hybridoma production is a very well-established procedure. The common animal system for preparing hybridomas is the murine system. Immunization protocols and techniques for isolation of immunized splenocytes for fusion are known in the art. Fusion partners (e.g., murine myeloma cells) and fusion procedures are also known. One well-known method that may be used for making human CTLA4 antibodies provided by the present disclosure involves the use of a XenoMouse™ animal system. XenoMouse™ mice are engineered mouse strains that comprise large fragments of human immunoglobulin heavy chain and light chain loci and are deficient in mouse antibody production (see e.g., Green et al., (1994) Nature Genetics 7:13-21; WO2003/040170). The animal is immunized with a CTLA4 antigen. The CTLA4 antigen is isolated and/or purified CTLA4. It may be a fragment of CTLA4, such as the extracellular domain of CTLA4. Immunization of animals can be carried out by any method known in the art (see e.g., Harlow and Lane, Antibodies: A Laboratory Manual, New York: Cold Spring Harbor Press, 1990). Methods for immunizing non-human animals such as mice, rats, sheep, goats, pigs, cattle and horses are well known in the art (see e.g., Harlow and Lane, supra, and U.S. Pat. No. 5,994,619). The CTLA4 antigen may be administered with an adjuvant to stimulate the immune response. Exemplary adjuvants include complete or incomplete Freund's adjuvant, RIBI (muramyl dipeptides) or ISCOM (immunostimulating complexes). After immunization of an animal with a CTLA4 antigen, antibody-producing immortalized cell lines are prepared from cells isolated from the immunized animal. After immunization, the animal is sacrificed and lymph node and/or splenic B cells are immortalized. Methods of immortalizing cells include, but are not limited to, transferring them with oncogenes, inflecting them with the oncogenic virus cultivating them under conditions that select for immortalized cells, subjecting them to carcinogenic or mutating compounds, fusing them with an immortalized cell, e.g., a myeloma cell, and inactivating a tumor suppressor gene (see e.g., Harlow and Lane, supra). If fusion with myeloma cells is used, the myeloma cells preferably do not secrete immunoglobulin polypeptides (a non-secretory cell line). Immortalized cells are screened using CTLA4, a portion thereof, or a cell expressing CTLA4. CTLA4 antibody-producing cells, e.g., hybridomas, are selected, cloned and further screened for desirable characteristics, including robust growth, high antibody production and desirable antibody characteristics, as discussed further below. Hybridomas can be expanded in vivo in syngeneic animals, in animals that lack an immune system, e.g., nude mice, or in cell culture in vitro. Methods of selecting, cloning and expanding hybridomas are well known to those of ordinary skill in the art.

Antibodies of the present disclosure may also be prepared using phage display or yeast display methods. Such display methods for isolating human antibodies are established in the art (see e.g., Knappik, et al. (2000) J. Mol. Biol. 296, 57-86; Feldhaus et al. (2003) Nat Biotechnol 21:163-170; see also the methods of Examples 1 and 2 below).

Antigen Binding Fragments

In some other aspects, the present disclosure provides antigen-binding fragments of any of the CTLA4 antibodies described herein.

The antigen-binding fragment may comprise any sequences of any of the antibodies described herein. In some embodiments, the antigen-binding fragment comprises the amino acid sequence of: (1) a light chain of a CTLA4 antibody; (2) a heavy chain of a CTLA4 antibody; (3) a variable region from the light chain of a CTLA4 antibody; (4) a variable region from the heavy chain of a CTLA4 antibody; (5) one or more HVRs (e.g., one, two, three, four, five, or six HVRs) of a CTLA4 antibody; or (6) three HVRs from the light chain and three HVRs from the heavy chain of a CTLA4 antibody.

In some embodiments, the present disclosure provides an antigen-binding fragment of an antibody selected from those listed in Tables A and B.

In some embodiments, the antigen-binding fragments of a CTLA4 antibody include: (i) a Fab fragment, which is a monovalent fragment consisting of the $V_L$, $V_H$, $C_L$ and $C_H1$ domains; (ii) a F(ab')$_2$ fragment, which is a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody; (v) a dAb fragment (Ward et al., (1989) Nature 341:544-546), which consists of a $V_H$ domain; (vi) an isolated CDR, and (vii) single chain antibody (scFv), which is a polypeptide comprising a $V_L$ region of an antibody linked to a $V_H$ region of an antibody (see e.g., Bird et al. (1988) Science 242:423-426; Huston et al. (1988) Proc. Natl. Acad. Sci. USA 85:5879-5883).

Antibody Derivatives

In some further aspects, the present disclosure provides derivatives of any of the CTLA4 antibodies described herein.

In some embodiments, the antibody derivative is derived from modifications of the amino acid sequences of an illustrative antibody (e.g., a "parent antibody") of the present disclosure while conserving the overall molecular structure of the parent antibody amino acid sequence. Amino acid sequences of any regions of the parent antibody chains may be modified, such as framework regions, HVR regions, or constant regions. Types of modifications include substitutions, insertions, deletions, or combinations thereof, of one or more amino acids of the parent antibody.

In some embodiments, the antibody derivative comprises a $V_L$ or $V_H$ region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 82-107 In some embodiments, the antibody derivative comprises an HVR-H1 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 18-29. In some embodiments, the antibody derivative comprises an HVR-H2 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 30-39. In some embodiments, the antibody derivative comprises an HVR-H3 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 40-52. In some embodiments, the antibody derivative comprises an HVR-L1 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 53-65. In some embodiments, the antibody derivative comprises an HVR-L2 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 66-69. In some embodiments, the antibody derivative comprises an HVR-L3 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 70-81.

In some particular embodiments, the derivative comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to an amino acid sequence as set forth in any of SEQ ID NOS: 18-107.

Amino acid substitutions encompass both conservative substitutions and non-conservative substitutions. The term "conservative amino acid substitution" means a replacement of one amino acid with another amino acid where the two amino acids have similarity in certain physico-chemical properties such as polarity, charge, solubility, hydrophobicity, hydrophilicity, and/or the amphipathic nature of the residues involved. For example, substitutions typically may be made within each of the following groups: (a) nonpolar (hydrophobic) amino acids, such as alanine, leucine, isoleucine, valine, proline, phenylalanine, tryptophan, and methionine; (b) polar neutral amino acids, such as glycine, serine, threonine, cysteine, tyrosine, asparagine, and glutamine; (c) positively charged (basic) amino acids, such as arginine, lysine, and histidine; and (d) negatively charged (acidic) amino acids, such as aspartic acid and glutamic acid.

The modifications may be made in any positions of the amino acid sequences of the antibody, including the HVRs, framework regions, or constant regions. In one embodiment, the present disclosure provides an antibody derivative that contains the $V_H$ and $V_L$ HVR sequences of an illustrative antibody of this disclosure, yet contains framework sequences different from those of the illustrative antibody. Such framework sequences can be obtained from public DNA databases or published references that include germline antibody gene sequences. For example, germline DNA sequences for human heavy and light chain variable region genes can be found in the Genbank database or in the "VBase" human germline sequence database (Kaba et al., Sequences of Proteins of Immunological Interest, Fifth Edition, U.S. Department of Health and Human Services, NIH Publication No. 91-3242 (1991); Tomlinson et al., J. Mol. Biol. 227:776-798 (1992); and Cox et al., Eur. J. Immunol. 24:827-836 (1994)). Framework sequences that may be used in constructing an antibody derivative include those that are structurally similar to the framework sequences used by illustrative antibodies of the disclosure For example, the HVR-H1, HVR-H2, and HVR-H3 sequences, and the HVR-L1, HVR-L2, and HVR-L3 sequences of an illustrative antibody can be grafted onto framework regions that have the identical sequence as that found in the germline immunoglobulin gene from which the framework sequence derive, or the HVR sequences can be grafted onto framework regions that contain one or more mutations as compared to the germline sequences.

In some embodiments, the antibody derivative is a chimeric antibody which comprises an amino acid sequence of an illustrative antibody of the disclosure. In one example, one or more HVRs from one or more illustrative antibodies are combined with HVRs from an antibody from a non-human animal, such as mouse or rat. In another example, all of the HVRs of the chimeric antibody are derived from one or more illustrative antibodies. In some particular embodiments, the chimeric antibody comprises one, two, or three HVRs from the heavy chain variable region and/or one, two, or three HVRs from the light chain variable region of an illustrative antibody. Chimeric antibodies can be generated using conventional methods known in the art.

Another type of modification is to mutate amino acid residues within the HVR regions of the $V_H$ and/or $V_L$ chain. Site-directed mutagenesis or PCR-mediated mutagenesis can be performed to introduce the mutation(s) and the effect on antibody binding, or other functional property of interest, can be evaluated in in vitro or in vivo assays known in the art. Typically, conservative substitutions are introduced. The mutations may be amino acid additions and/or deletions. Moreover, typically no more than one, two, three, four or five residues within an HVR region are altered. In some embodiments, the antibody derivative comprises 1, 2, 3, or 4 amino acid substitutions in the heavy chain HVRs and/or in the light chain HVRs. In another embodiment, the amino acid substitution is to change one or more cysteines in an antibody to another residue, such as, without limitation, alanine or serine. The cysteine may be a canonical or non-canonical cysteine. In one embodiment, the antibody derivative has 1, 2, 3, or 4 conservative amino acid substitutions in the heavy chain HVR regions relative to the amino acid sequences of an illustrative antibody.

Modifications may also be made to the framework residues within the $V_H$ and/or $V_L$ regions. Typically, such framework variants are made to decrease the immunogenicity of the antibody. One approach is to "back mutate" one or more framework residues to the corresponding germline sequence. An antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back mutated" to the germline sequence by, for example, site-directed mutagenesis or PCR-mediated mutagenesis.

In addition, modifications may also be made within the Fc region of an illustrative antibody, typically to alter one or more functional properties of the antibody, such as serum half-life, complement fixation, Fc receptor binding, and/or antigen-dependent cellular cytotoxicity. In one example, the hinge region of CH1 is modified such that the number of cysteine residues in the hinge region is altered, e.g., increased or decreased. This approach is described further in U.S. Pat. No. 5,677,425. The number of cysteine residues in the hinge region of CH1 is altered to, for example, facilitate assembly of the light and heavy chains or to increase or decrease the stability of the antibody. In another case, the Fc hinge region of an antibody is mutated to decrease the biological half-life of the antibody.

Furthermore, an antibody of the present disclosure may be modified to alter its potential glycosylation site or pattern in accordance with routine experimentation known in the art. In another aspect, the present disclosure provides a derivative of a CTLA4 antibody that contains at least one mutation in a variable region of a light chain or heavy chain that changes the pattern of glycosylation in the variable region. Such an antibody derivative may have an increased affinity and/or a modified specificity for binding an antigen. The mutations may add a novel glycosylation site in the V region, change the location of one or more V region glycosylation site(s), or remove a pre-existing V region glycosylation site. In one embodiment, the present disclosure provides a derivative of a CTLA4 antibody having a potential N-linked glycosylation site at asparagine in the heavy chain variable region, wherein the potential N-linked glycosylation site in one heavy chain variable region is removed. In another embodiment, the present disclosure provides a derivative of a CTLA4 antibody having a potential N-linked glycosylation site at asparagine in the heavy chain variable region, wherein the potential N-linked glycosylation site in both heavy chain variable regions is removed. Method of altering the glycosylation pattern of an antibody is known in the art, such as those described in U.S. Pat. No. 6,933,368, the disclosure of which incorporated herein by reference.

In another aspect, the present disclosure provides an antibody derivative that comprises a CTLA4 antibody, or antigen-binding fragment thereof, as described herein, linked to an additional molecular entity. Examples of additional molecular entities include pharmaceutical agents, peptides or proteins, detection agent or labels, and antibodies.

In some embodiments, the antibody derivative comprises an antibody of the disclosure linked to a pharmaceutical agent. Examples of pharmaceutical agents include cytotoxic agents or other cancer therapeutic agents, and radioactive isotopes. Specific examples of cytotoxic agents include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Examples of radioactive isotopes that can be conjugated to antibodies for use diagnostically or therapeutically include, but are not limited to, iodine$^{131}$, indium$^{111}$, yttrium$^{90}$ and lutetium$^{177}$. Methods for linking an antibody to a pharmaceutical agent are known in the art, such as using various linker technologies. Examples of linker types include hydrazones, thioethers, esters, disulfides and peptide-containing linkers. For further discussion of linkers and methods for linking therapeutic agents to antibodies see e.g., Saito et al., *Adv. Drug Deliv. Rev.* 55:199-215 (2003); Trail, et al., *Cancer Immunol. Immunother.* 52:328-337 (2003); Payne, *Cancer Cell* 3:207-212 (2003); Allen, *Nat. Rev. Cancer* 2:750-763 (2002); Pastan and Kreitman, *Curr. Opin. Investig. Drugs* 3:1089-1091 (2002); Senter and Springer (2001) *Adv. Drug Deliv. Rev.* 53:247-264.

In some embodiments, the antibody derivative is a CTLA4 antibody multimer, which is a multimeric form of a CTLA4 antibody, such as antibody dimers, trimers, or higher-order oligomers of monomeric antibodies. Individual monomers within an antibody multimer may be identical or different. In addition, individual antibodies within a multimer may have the same or different binding specificities. Multimerization of antibodies may be accomplished through natural aggregation of antibodies. For example, some percentage of purified antibody preparations (e.g., purified IgG4 molecules) spontaneously form protein aggregates containing antibody homodimers, and other higher-order antibody multimers. Alternatively, antibody homodimers may be formed through chemical linkage techniques known in the art, such as through using crosslinking agents. Suitable crosslinkers include those that are heterobifunctional, having two distinctly reactive groups separated by an appropriate spacer (such as m-maleimidobenzoyl-N-hydroxysuccinimide ester, succinimidyl 4-(maleimidomethyl)cyclohexane-1-carboxylate, and N-succinimidyl S-acetylthioacetate) or homobifunctional (such as disuccinimidyl suberate). Such linkers are commercially available from, for example, Pierce Chemical Company, Rockford, Ill. Antibodies can also be made to multimerize through recombinant DNA techniques known in the art.

Examples of other antibody derivatives provided by the present disclosure include single chain antibodies, diabodies, domain antibodies, nanobodies, and unibodies. A "single-chain antibody" (scFv) consists of a single polypeptide chain comprising a $V_L$ domain linked to a $V_H$ domain wherein $V_L$ domain and $V_H$ domain are paired to form a monovalent molecule. Single chain antibody can be prepared according to method known in the art (see e.g., Bird et al., (1988) Science 242:423-426 and Huston et al., (1988) Proc. Natl. Acad. Sci. USA 85:5879-5883). A "diabody" consists of two chains, each chain comprising a heavy chain variable region connected to a light chain variable region on the same polypeptide chain connected by a short peptide linker, wherein the two regions on the same chain do not pair with each other but with complementary domains on the other chain to form a bispecific molecule. Methods of preparing diabodies are known in the art (see e.g., Holliger P. et al., (1993) Proc. Natl. Acad. Sci. USA 90:6444-6448, and Poljak R. J. et al., (1994) Structure 2:1121-1123). Domain antibodies (dAbs) are small functional binding units of antibodies, corresponding to the variable regions of either the heavy or light chains of antibodies. Domain antibodies are well expressed in bacterial, yeast, and mammalian cell systems. Further details of domain antibodies and methods of production thereof are known in the art (see e.g., U.S. Pat. Nos. 6,291,158; 6,582,915; 6,593,081; 6,172,197; 6,696,245; European Patents 0368684 & 0616640; WO05/035572, WO04/101790, WO04/081026, WO04/058821, WO04/003019 and WO03/002609). Nanobodies are derived from the heavy chains of an antibody. A nanobody typically comprises a single variable domain and two constant domains (CH2 and CH3) and retains antigen-binding capacity of the original antibody. Nanobodies can be prepared by methods known in the art (see e.g., U.S. Pat. Nos. 6,765,087, 6,838,254, WO 06/079372). Unibodies consist of one light chain and one heavy chain of an IgG4 antibody. Unibodies may be made by the removal of the hinge region of IgG4 antibodies. Further details of unibodies and methods of preparing them may be found in WO2007/059782.

IV. Activatable Binding Polypeptides Targeting CTLA4

Figure 48A:
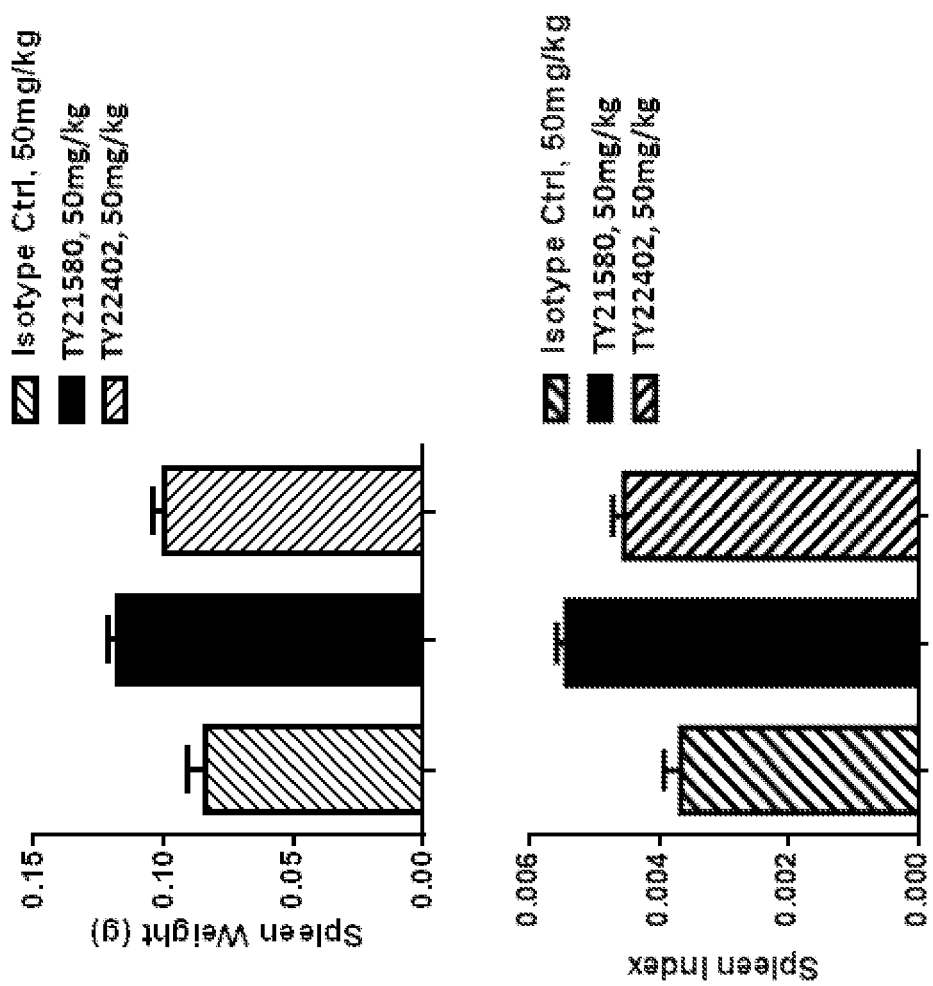
FIGS. 48A-C show the average spleen weight of BALB/c mice after repeat intraperitoneal administration of the indicated activatable antibodies.
Figure 48B:
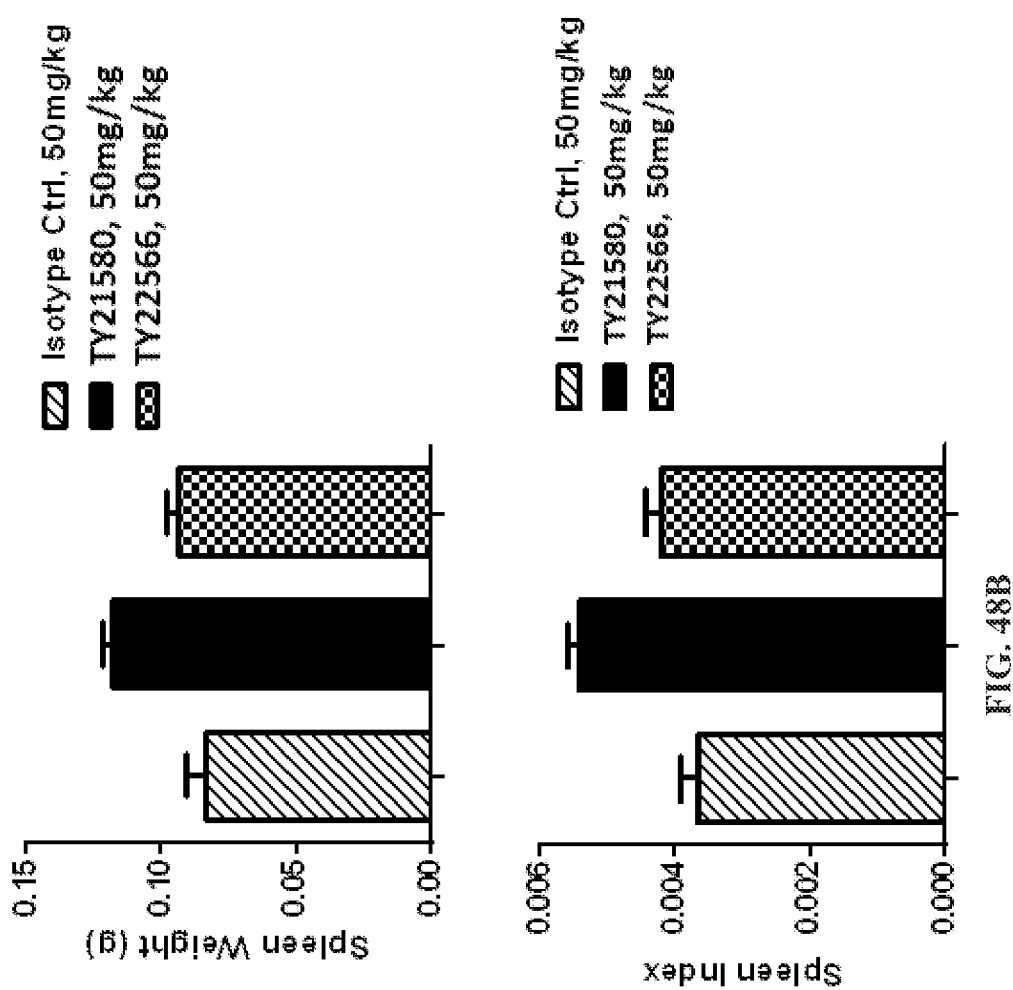

The present disclosure also relates, in part, to precision/context-dependent activatable binding polypeptides (i.e., activatable antibodies) that bind to human CTLA4, including activatable antibodies comprising any of the anti-CTLA4 antibodies described herein (e.g., anti-CTLA4 antibodies, anti-CTLA4 antibody binding fragments, and/or anti-CTLA4 antibody derivatives), antigen binding fragments of the activatable anti-CTLA4 antibodies, and/or derivatives of the activatable anti-CTLA4 antibodies. In some embodiments, the activatable anti-CTLA4 antibodies described herein may have improved safety profiles. For example, the anti-CTLA4 antibodies described herein may have better safety margin as assessed by spleen weight change. The change in spleen size with the increase in drug dose administered is used as a benchmark to assess the safety margin of the drug candidate used. As shown in FIG. 48A-B, the activatable anti-CTLA4 antibodies described herein have a better safety margin relative to the parental antibody (the antibody without the masking moiety).

In some embodiments, an activatable antibody of the present disclosure comprises: (a) a masking moiety (MM); (b) a cleavable moiety (CM); and (c) a target binding moiety (TBM). In some embodiments, the MM is any of the masking moieties described herein. In some embodiments, the CM is any of the cleavable moieties described herein. In some embodiments, the TBM is any of the target binding moieties described herein (e.g., a target binding moiety (TBM) comprising an antibody light chain variable region and/or an antibody heavy chain variable region, such as a VH and/or VL of any of the anti-CTLA4 antibodies described herein). In some embodiments, the MM interferes with and/or inhibits the binding of the activatable antibody to its target (e.g., human CTLA4 or human CD137) when the CM is not cleaved. In some embodiments, the activatable antibody is capable of binding to its target (e.g., human CTLA4 or human CD137) when the CM is cleaved.

In some embodiments, the activatable antibody comprises: (a) a polypeptide comprising, from N-terminus to C-terminus, a masking moiety (MM), a cleavable moiety (CM), and a target binding moiety (TBM), where the MM is any of the masking moieties described herein, the CM is any of the cleavable moieties described herein, and where the TBM comprises an antibody light chain variable region (VL); and (b) an antibody heavy chain variable region (VH).

In some embodiments, the activatable antibody comprises: (a) a polypeptide comprising, from N-terminus to C-terminus, a masking moiety (MM), a cleavable moiety (CM), and a target binding moiety (TBM), where the MM is any of the masking moieties described herein, the CM is any of the cleavable moieties described herein, and where the TBM comprises an antibody heavy chain variable region (VH); and (b) an antibody light chain variable region (VL).

In some embodiments, the activatable antibody comprises: a polypeptide comprising, from N-terminus to C-terminus, a masking moiety (MM), a cleavable moiety (CM), and a target binding moiety (TBM), where the MM is any of the masking moieties described herein, the CM is any of the cleavable moieties described herein, and where the TBM comprises an antibody heavy chain variable region (VH) and an antibody light chain variable region (VL).

The term "activatable binding polypeptide", "ABP", or "activatable antibody" includes a polypeptide that comprises a target binding moiety (TBM), a cleavable moiety (CM), and a masking moiety (MM). In some embodiments, the TBM comprises an amino acid sequence that binds to a target. In some embodiments, the TBM comprises an antigen binding domain (ABD) of an antibody or antibody fragment thereof (e.g., any of the antibodies or antigen binding fragments described herein). In some embodiments, the antigen binding domain comprises a heavy chain variable region comprising one, two, or three of the heavy chain variable region HVRs described herein, and a light chain variable region comprising one, two, or three of the light chain variable region HVRs described herein (e.g., one, two, or three of the heavy chain variable region HVR sequences, and/or one, two, or three of the light chain variable region HVR sequences as shown in Table A, including all six HVRs of any of the exemplary antibodies as shown in Table A). In some embodiments, the antigen binding domain comprises a heavy chain variable region comprising any of the heavy chain variable region sequences described herein, and a light chain variable region comprising any of the light chain variable region sequences described herein (e.g., a heavy chain variable region sequence and/or a light chain variable region sequence as shown in Table B). In some embodiments, the TBM (e.g., comprising an ABD) comprises an antibody light chain variable region (VL) and an antibody heavy chain variable region (VH), wherein the VH and VL forms a binding domain that binds to the target in the absence of the MM. In some embodiments, the VH and VL are covalently linked, e.g., in an scFv. In some embodiments, the VH and VL are not covalently linked. In some embodiments, the VH and VL form a Fab fragment. In some embodiments, the VH is linked to an antibody heavy chain constant region, and the VL is linked to an antibody light chain constant region.

In some embodiments, the activatable antibody comprises a polypeptide comprising the structure, from N-terminus to C-terminus, of: masking moiety (MM)-cleavable moiety (CM)-VL, and the activatable antibody further comprises a second polypeptide comprising a VH (e.g., a Fab fragment). In some embodiments, the activatable antibody comprises a polypeptide comprising the structure, from N-terminus to C-terminus, of: masking moiety (MM)-cleavable moiety (CM)-VL-VH (e.g., an scFv). In some embodiments, the activatable antibody comprises a polypeptide comprising the structure, from N-terminus to C-terminus, of: masking moiety (MM)-cleavable moiety (CM)-VH, and the activatable antibody further comprises a second polypeptide comprising a VL (e.g., a Fab fragment). In some embodiments, the activatable antibody comprises a polypeptide comprising the structure, from N-terminus to C-terminus, of: masking moiety (MM)-cleavable moiety (CM)-VH-VL (e.g., an scFv).

The CM generally includes an amino acid sequence that is cleavable, for example, serves as the substrate for an enzyme and/or a cysteine-cysteine pair capable of forming a reducible disulfide bond. As such, when the terms "cleavage," "cleavable," "cleaved" and the like are used in connection with a CM, the terms encompass enzymatic cleavage, e.g., by a protease, as well as disruption of a disulfide bond between a cysteine-cysteine pair via reduction of the disulfide bond that can result from exposure to a reducing agent.

The MM refers to an amino acid sequence that, when the CM of the activatable antibody is intact (e.g., uncleaved by a corresponding enzyme, and/or containing an unreduced cysteine-cysteine disulfide bond), the MM interferes with or inhibits binding of the TBM to its target. In some embodiments, the MM interferes with or inhibits binding of the TBM to its target so efficiently that binding of the TBM to its target is extremely low and/or below the limit of detection (e.g., binding cannot be detected in an ELISA or flow cytometry assay). The amino acid sequence of the CM may overlap with or be included within the MM. It should be noted that for sake of convenience "ABP" or "activatable antibody" are used herein to refer to an ABP or activatable antibody in both their uncleaved (or "native") state, as well as in their cleaved state. It will be apparent to the ordinarily skilled artisan that in some embodiments a cleaved ABP may lack an MM due to cleavage of the CM, e.g., by a protease, resulting in release of at least the MM (e.g., where the MM is not joined to the ABP by a covalent bond (e.g., a disulfide bond between cysteine residues)). Exemplary ABPs are described in more detail below.

In some embodiments, the masking moiety (MM) interferes with, obstructs, reduces the ability of, prevents, inhibits, or competes with the target binding moiety for binding to its target (e.g., an "inactive activatable antibody). In some embodiments, the masking moiety (MM) interferes with, obstructs, reduces, prevents, inhibits, or competes with the target binding moiety for binding to its target only when the polypeptide has not been activated (e.g., activated by a change in pH (increased or decreased), activated by a temperature shift (increased or decreased), activated after being contacted with a second molecule (such as a small molecule or a protein ligand), etc.). In some embodiments, activation induces cleavage of the polypeptide within the cleavage moiety. In some embodiments, activation induces conformation changes in the polypeptide (e.g., displacement of the masking moiety (MM)), leading to the masking moiety no longer preventing the activatable antibody from binding to its target. In some embodiments, the masking moiety (MM) interferes with, obstructs, reduces the ability of, prevents, inhibits, or competes with the target binding moiety for binding to its target only when the cleavable moiety (CM) has not been cleaved by one or more proteases that cleave within the cleavable moiety (CM). In some embodiments, the masking moiety (MM) has a masking efficiency of at least about 2.0 (e.g., at least about 2.0, at least about 3.0, at least about 4.0, at least about 5.0, at least about 6.0, at least about 7.0, at least about 8.0, at least about 9.0, at least about 10, at least about 25, at least about 50, at least about 75, at least about 100, at least about 150, at least about 200, at least about 300, at least about 400, at least about 500, etc.) prior to activation. In some embodiments, masking efficiency is measured as the difference in affinity of an activatable antibody comprising the masking moiety (MM) for binding its target (before activation) relative to the affinity of a polypeptide lacking the masking moiety for binding its target (e.g., the difference in affinity for a target antigen (such as CTLA4) of an activatable antibody comprising a masking moiety (MM) (before activation) relative to a parental antibody lacking the masking moiety (MM), or the difference in affinity for a target antigen (such as CTLA4) of an activatable antibody comprising a masking moiety (MM) (before activation) relative to the affinity for the target antigen of the activatable antibody after activation). In some embodiments, the masking efficiency is measured by dividing the $EC_{50}$ for binding of an activatable antibody comprising a masking moiety (MM) (before activation) by the $EC_{50}$ of the parental antibody (e.g., by measuring $EC_{50}$ by ELISA; see e.g., the methods of Example 8). In some embodiments, masking efficiency is measured as the difference in affinity of an activatable antibody comprising the masking moiety (MM) for binding its target before activation relative to the affinity of the activatable antibody comprising the masking moiety (MM) for binding its target after activation (e.g., the difference in affinity for a target antigen (such as CTLA4) of an activatable antibody before activation relative to the activatable antibody after activation). In some embodiments, the masking moiety (MM) binds to the target binding moiety (TBM), and prevents the activatable antibody from binding to its target (e.g., an "inactive" activatable antibody). In some embodiments, the masking moiety (MM) has a dissociation constant for binding to the target binding moiety (TBM) that is greater than the dissociation constant of the target binding moiety (TBM) for its target.

In some embodiments, the masking moiety (MM) does not interfere with, obstruct, reduce the ability of, prevent, inhibit, or compete with the target binding moiety (TBM) for binding to its target after the activatable antibody has been activated (e.g., activated by treatment with one or more proteases that cleave within the cleavable moiety (CM), activated by a change in pH (increased or decreased), activated by a temperature shift (increased or decreased), activated after being contacted with a second molecule (such as an enzyme or a protein ligand), etc.). In some embodiments, the masking moiety (MM) does not interfere with, obstruct, reduce the ability of, prevent, inhibit, or compete with the target binding moiety (TBM) for binding its target after the cleavable moiety (CM) has been cleaved by one or more proteases that cleave within the cleavable moiety (CM). In some embodiments, the masking moiety (MM) has a masking efficiency of at most about 1.75 (e.g., at most about 1.75, at most about 1.5, at most about 1.4, at most about 1.3, at most about 1.2, at most about 1.1, at most about 1.0, at most about 0.9, at most about 0.8, at most about 0.7, at most about 0.6, or at most about 0.5, etc.) after activation (e.g., the relative affinity of the activatable antibody after activation as compared to the affinity of a parental antibody).

In some embodiments, an activatable antibody of the present disclosure: contains a masking moiety (MM) comprising a pair of cysteine residues at fixed positions to ensure that the activatable antibodies have constrained conformations, and/or harbor few or no chemically labile residues (such as methionine or tryptophan). Advantageously, the inclusion of a pair of cysteine residues at fixed positions ensured that the activatable antibodies had constrained conformations, tending to exhibit increased binding affinity and/or specificity. Furthermore, activatable antibodies of the present disclosure included masking moieties with few to no unfavorable residues for manufacturing processes, such as methionine or tryptophan.

In some embodiments, activatable antibodies of the present disclosure are context-dependent (e.g., are activated (are only capable of binding their targets) in certain contexts (such as in the protease-rich tumor microenvironment)). In some embodiments, the activatable antibodies of the present disclosure provide improved safety over more traditional, non-activatable antibodies (e.g., show reduced toxicity, do not induce significant alterations to the weights of many organs, do not alter liver histopathology, hematology, and/or blood biochemistry, etc.). In some embodiments, activatable antibodies of the present disclosure have improved pharmacokinetic properties as compared to more traditional, non-activatable antibodies (e.g., have longer in vivo half-lives).

Anti-CTLA4 Activatable Antibody Activities

In some embodiments, the present disclosure relates to activatable antibodies that bind to human CTLA4 when in active form (e.g., the activatable antibodies are active after cleavage in the cleavable moiety (e.g., with one or more proteases), but inactive prior to cleavage in the cleavable moiety (e.g., with one or more proteases)). In some embodiments, the activatable antibodies when in active form have at least one (e.g., at least one, at least two, at least three, at least four, at least five, at least six, at least seven, at least eight, or all nine) of the following functional properties: (a) bind to human, cynomolgus monkey, mouse, rat, and/or dog CTLA4 with a $K_D$ of 500 nM or less, e.g., about 10 nM or less; (b) have antagonist activity on human CTLA4; (c) do not bind to human PD-1, PD-L1, PD-L2, LAG3, TIM3, B7-H3, CD95, CD120a, OX40, CD40, BTLA, VISTA, ICOS, and/or B7-H4 at concentration up to 100 nM; (d) are cross-reactive with monkey, mouse, rat, and/or dog CTLA4; (e) induces ADCC effects (e.g., on Tregs); (f) activates human PBMCs (e.g., stimulates secretion of IL-2 and/or IFNγ); (g) are capable of inhibiting tumor cell growth; (h) have therapeutic effect on a cancer; and (i) inhibit binding of human CTLA4 to human CD80 and/or human CD86. Also provided herein are one or more activatable antibodies that compete or cross-compete for binding to human CTLA4 with one or more of the CTLA4-targeting activatable antibodies and/or anti-CTLA4 antibodies described herein.

In some embodiments, the activatable antibodies bind to human, cynomolgus monkey, mouse, rat, and/or dog CTLA4 with a $K_D$ of about 500 nM or more when in inactive form.

In some embodiments, the activatable antibodies bind to human, cynomolgus monkey, mouse, rat, and/or dog CTLA4 with a $K_D$ of about 500 nM or less when in active form (e.g., about 500 nM or less, about 450 nM or less, about 400 nM or less, about 350 nM or less, about 300 nM or less, about 250 nM or less, about 200 nM or less, about 150 nM or less, about 100 nM or less, about 90 nM or less, about 80 nM or less, about 70 nM or less, about 60 nM or less, about 50 nM or less, about 40 nM or less, about 30 nM or less, about 25 nM or less, about 20 nM or less, about 10 nM or less, about 1 nM or less, about 0.1 nM or less, etc.) In some embodiments, the activatable antibodies bind to human, cynomolgus monkey, mouse, rat, and/or dog CTLA4 with a $K_D$ of about 350 nM or less when in active form. In some embodiments, the activatable antibodies bind to human CTLA4 with a $K_D$ of about 100 nM or less when in active form. In some embodiments, the activatable antibodies bind to human CTLA4 with a $K_D$ of about 50 nM or less when in active form. In some embodiments, the activatable antibodies bind to human CTLA4 with a $K_D$ of about 10 nM or less when in active form. Methods of measuring the $K_D$ of an activatable antibody may be carried out using any method known in the art, including for example, by surface plasmon resonance, an ELISA, isothermal titration calorimetry, a filter binding assay, an EMSA, etc. In some embodiments, the $K_D$ is measured by an ELISA (see e.g., the Examples below).

In some embodiments, the activatable antibodies do not have antagonist activity on human CTLA4 when in inactive form. In some embodiments, the activatable antibodies have antagonist activity on human CTLA4 when in active form (e.g., induces ADCC effects (such as against Tregs), activates PBMCs (such as by activating, inducing, and/or stimulating IL-2 and/or IFNγ secretion), bocks binding of human CTLA4 to human CD80 and/or human CD86, etc.). In some embodiments, the activatable antibodies repress one or more activities of human CTLA4 when in active form (e.g., repress one or more activities of human CTLA4 when a cell (such as a human cell) expressing human CTLA4 is contacted by an activatable antibody).

In some embodiments, when in inactive form, the activatable antibodies are not cross-reactive with monkey (e.g., cynomolgus monkey), mouse, rat, and/or dog CTLA4. In some embodiments, when in active form, the activatable antibodies are cross-reactive with monkey (e.g., cynomolgus monkey), mouse, rat, and/or dog CTLA4. In some embodiments, when in active form, the activatable antibodies are cross-reactive with monkey CTLA4. In some embodiments, when in active form, the activatable antibodies are cross-reactive with mouse CTLA4. In some embodiments, when in active form, the activatable antibodies are cross-reactive with rat CTLA4. In some embodiments, when in active form, the activatable antibodies are cross-reactive with dog CTLA4. In some embodiments, when in active form, the activatable antibodies are cross reactive with monkey and mouse CTLA4; monkey and rat CTLA4; monkey and dog CTLA4; mouse and rat CTLA4; mouse and dog CTLA4; rat and dog CTLA4; monkey, mouse, and rat CTLA4; monkey, mouse, and dog CTLA4; monkey, rat, and dog CTLA4; mouse, rat, and dog CTLA4; or monkey, mouse, rat, and dog CTLA4. In some embodiments, when in active form, the activatable binding polypeptides are cross-reactive at about 350 nM (e.g., at about 1 nM, at about 10 nM, at about 25 nM, at about 50 nM, at about 75 nM, at about 100 nM, at about 150 nM, at about 200 nM, at about 250 nM, at about 300 nM, at about 350 nM). Methods of measuring cross-reactivity are known in the art, including, without limitation, surface plasmon resonance, an ELISA, isothermal titration calorimetry, a filter binding assay, an EMSA, etc.

In some embodiments, the activatable antibodies do not induce ADCC effects (e.g., against CTLA4-expressing human cells such as Tregs) when in inactive form. In some embodiments, the activatable antibodies have reduced ADCC effects (e.g., against CTLA4-expressing human cells such as Tregs) when in inactive form as compared to a control binding polypeptide (e.g., a parental antibody). In some embodiments, the activatable antibodies induce ADCC effects (e.g., against CTLA4-expressing such as Tregs) when in active form. Methods of measuring ADCC effects (e.g., in vitro methods) are known in the art, including, without limitation, via the methods described in the Examples below. In some embodiments, when in inactive form, the activatable antibodies induce ADCC effects by less than about 10% (e.g., induce ADCC by less than about 10%, less than about 5%, less than about 1%, etc.) relative to a control (e.g., a parental antibody). In some embodiments, when in active form, the activatable antibodies induce ADCC effects by more than about 10% (e.g., induce ADCC by more than about 10%, more than about 15%, more than about 20%, more than about 25%, more than about 30%, more than about 35%, more than about 40%, etc.) relative to a control (e.g., an isotype control).

In some embodiments, the activatable antibodies are capable of inhibiting tumor cell growth and/or proliferation. In some embodiments, the tumor cell growth and/or proliferation is inhibited by at least about 5% (e.g., at least about 5%, at least about 10%, at least about 20%, at least about 30%, at least about 40%, at least about 50%, at least about 60%, at least about 70%, at least about 80%, at least about 90%, or at least about 99%) when contacted with the activatable antibodies relative to corresponding tumor cells not contacted with the activatable antibodies (or relative to corresponding tumor cells contacted with an isotype control antibody). In some embodiments, the activatable antibodies are capable of reducing tumor volume in a subject when the subject is administered the activatable antibodies. In some embodiments, the activatable antibodies are capable of reducing tumor volume in a subject by at least about 5% (e.g., at least about 5%, at least about 10%, at least about 20%, at least about 30%, at least about 40%, at least about 50%, at least about 60%, at least about 70%, at least about 80%, at least about 90%, or at least about 99%) relative to the initial tumor volume in the subject (e.g., prior to administration of the activatable antibodies; as compared to a corresponding tumor in a subject administered an isotype control antibody). Methods of monitoring tumor cell growth/proliferation, tumor volume, and/or tumor inhibition are known in the art, including, for example, via the methods described in the Examples below.

In some embodiments, the activatable antibodies have therapeutic effect on a cancer. In some embodiments, the activatable antibodies reduce one or more signs or symptoms of a cancer. In some embodiments, a subject suffering from a cancer goes into partial or complete remission when administered the activatable antibodies.

In some embodiments, the present disclosure provides isolated activatable antibodies that, when in active form, compete or cross-compete for binding to human CTLA4 with an antibody comprising: a) an HVR-H1 comprising the amino acid sequence of SEQ ID NO: 23; an HVR-H2 comprising the amino acid sequence of SEQ ID NO: 35; and an HVR-H3 comprising the amino acid sequence of SEQ ID NO: 45; and/or b) an HVR-L1 comprising the amino acid sequence of SEQ ID NO: 58; an HVR-L2 comprising the amino acid sequence of SEQ ID NO: 66; and an HVR-L3 comprising the amino acid sequence of SEQ ID NO: 75. In some embodiments, the present disclosure provides isolated activatable antibodies that, when in active form, compete or cross-compete for binding to human CTLA4 with an antibody comprising: a) a heavy chain variable region comprising the amino acid sequence of SEQ ID NO: 87; and/or b) a light chain variable region comprising the amino acid sequence of SEQ ID NO: 100. The ability of an activatable antibody to compete or cross-compete for binding with an antibody can be determined using standard binding assays known in the art, such as BIAcore analysis, ELISA assays, or flow cytometry. For example, one can allow an antibody (e.g., as described above) to bind to human CTLA4 under saturating conditions and then measure the ability of the test activatable antibody (when in active form) to bind to the CTLA4. If the test activatable antibody is able to bind to the CTLA4 at the same time as the antibody, then the test activatable antibody binds to a different epitope then the antibody. However, if the test activatable antibody is not able to bind to the CTLA4 at the same time, then the test activatable antibody binds to the same epitope, an overlapping epitope, or an epitope that is in close proximity to the epitope bound by the antibody. This experiment can be performed using various methods, such as ELISA, RIA, FACS or surface plasmon resonance.

In some embodiments, the activatable antibodies (when in inactive form) do not inhibit the binding between CTLA4 and one or more of its binding partners (e.g., human CTLA4 and human CD80, human CTLA4 and human CD86). In some embodiments, the activatable antibodies (when in active form) inhibit the binding between CTLA4 and one or more of its binding partners (e.g., human CTLA4 and human CD80, human CTLA4 and human CD86). In some embodiments, the activatable antibodies inhibit the binding between CTLA4 and its ligand in vitro. In some embodiments, the activatable antibodies have a half maximal inhibitory concentration ($IC_{50}$) of about 500 nM or less (e.g., about 500 nM or less, about 400 nM or less, about 300 nM or less, about 200 nM or less, about 100 nM or less, about 50 nM or less, about 25 nM or less, about 10 nM or less, about 1 nM or less, etc.) for inhibiting binding of CTLA4 to CD80 and/or CD86. In some embodiments, the activatable antibodies have a half maximal inhibitory concentration ($IC_{50}$) of about 100 nM or less for inhibiting binding of CTLA4 to CD80 and/or CD86. In some embodiments, the activatable antibodies completely inhibit binding of human CTLA4 to CD80 and/or CD86 when provided at a concentration of about 100 nM or greater (e.g., about 100 nM or greater, about 500 nM or greater, about 1 µM or greater, about 10 µM or greater, etc.). As used herein, the term "complete inhibiting" or "completely inhibits" refers to the activatable antibody's ability to reduce binding between a first protein and a second protein by at least about 80% (e.g., at least about 80%, at least about 85%, at least about 90%, at least about 95%, at least about 99%, etc.). Methods of measuring the ability of an a polypeptide to inhibit binding of a first protein (e.g., human CTLA4) and a second protein (e.g., human CD80 or human CD86) are known in the art, including, without limitation, via BIAcore analysis, ELISA assays, and flow cytometry.

Masking Moieties (MMs)

In some embodiments, the present disclosure relates to activatable antibodies comprising a masking moiety (MM). In some embodiments, the masking moiety (MM) comprises an amino acid sequence according to Formula (XVIII): $X_mCX_nCZ_o$ (SEQ ID NO: 134), where m is from 2-10, n is from 3-10, and o is from 1-10, where each X is independently an amino acid selected from the group consisting of A, C, D, E, F, G, H, I, K, L, M, N, P, Q, R, S, T, V, W, and Y, and where each Z is independently an amino acid selected from the group consisting of D, A, Y, S, T, N, I, L, F, V, H, and P. In some embodiments, X is not W, M, and/or C. In some embodiments, each X in $X_m$ of formula (XVIII) is independently an amino acid selected from the group consisting of D, A, Y, S, T, N, I, L, F, V, H, and P and/or each X in $X_n$ of formula (XVIII) is independently an amino acid selected from the group consisting of D, A, Y, S, T, N, I, L, F, V, H, and P. In some embodiments, the MM comprises a polypeptide encoded by a polynucleotide sequence according to Formula (XX): $(NNK)_mTGY(NNK)_nTGY(NHC)_o$ (SEQ ID NO: 136), wherein each N is independently A, G, T, or C, wherein each K is independently T or G, wherein each Y is independently T or C, and wherein each H is independently A, T, or C.

In some embodiments, the masking moiety (MM) comprises an amino acid sequence according to Formula (XIX): $Z_mCZ_nCZ_o$ (SEQ ID NO: 135), where m is from 2-10, n is from 3-10, and o is from 1-10, and each Z is independently an amino acid selected from the group consisting of D, A, Y, S, T, N, I, L, F, V, H, and P.

In some embodiments, m is from 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10. In some embodiments, m is from 6-8. In some embodiments, m is 3, 4, 5, 6, 7, 8, 9, or 10. In some embodiments, m is 6.

In some embodiments, n is from 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10. In some embodiments, n is from 6-8. In some embodiments, n is 3, 4, 5, 6, 7, 8, 9, or 10. In some embodiments, n is 6. In some embodiments, n is 8.

In some embodiments, o is from 1-10, 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10. In some embodiments, o is from 1-2. In some embodiments, o is 1, 2, 3, 4, 5, 6, 7, 8, 9, or 10. In some embodiments, o is 2.

In some embodiments, the masking moiety (MM) comprises an amino acid sequence according to Formula (XXI): $Z_6CX_6CZ_2$ (SEQ ID NO: 137), where each X is independently an amino acid selected from the group consisting of A, C, D, E, F, G, H, I, K, L, M, N, P, Q, R, S, T, V, W, and Y, and where each Z is independently an amino acid selected from the group consisting of D, A, Y, S, T, N, I, L, F, V, H, and P.

In some embodiments, the masking moiety (MM) comprises an amino acid sequence according to Formula (XXII): $Z_6CX_8CZ_2$ (SEQ ID NO: 138), where each X is independently an amino acid selected from the group consisting of A, C, D, E, F, G, H, I, K, L, M, N, P, Q, R, S, T, V, W, and Y, and where each Z is independently an amino acid selected from the group consisting of D, A, Y, S, T, N, I, L, F, V, H, and P.

In some embodiments, the first peptide (FP) comprises an amino acid sequence according to Formula (XXIII): $(Z_6)C(Z_6)C(Z_2)$ (SEQ ID NO: 139), where each Z is independently an amino acid selected from the group consisting of D, A, Y, S, T, N, I, L, F, V, H, and P.

In some embodiments, the masking moiety (MM) comprises an amino acid sequence according to Formula (XXIV): $(Z_6)C(Z_8)C(Z_2)$ (SEQ ID NO: 140), where each Z is independently an amino acid selected from the group consisting of D, A, Y, S, T, N, I, L, F, V, H, and P. In some embodiments, an activatable antibody comprises a masking moiety (MM) comprising a sequence selected from the group consisting of $X_m$CPDHPYPCXX (SEQ ID NO:181), $X_m$CDAFYPYCXX (SEQ ID NO:182), $X_m$CDSHYPYCXX (SEQ ID NO:183), and $X_m$CVPYYYACXX (SEQ ID NO:184), where m is from 2-10, and where each X is independently an amino acid selected from the group consisting of A, C, D, E, F, G, H, I, K, L, M, N, P, Q, R, S, T, V, W, and Y. In some embodiments, an activatable antibody comprises a masking moiety (MM) comprising the sequence EVGSYNFVADSCPDHPYPCSA (SEQ ID NO:189), EVGSYIVHHSDCDAFYPYCDS (SEQ ID NO:190), EVGSYYSAYPACDSHYPYCNS (SEQ ID NO:191), EVGSYPNPSSDCVPYYYACAY (SEQ ID NO:192), EVGSYYSAYPACDSHYPYCQS (SEQ ID NO:193), EVGSYPQPSSDCVPYYYACAY (SEQ ID NO:195), or EVGSYPNPASDCVPYYYACAY (SEQ ID NO:196). In some embodiments, the MM comprises the sequence of EDCVPYYYACAY (SEQ ID NO:213), EVGSSDCVPYYYACAY (SEQ ID NO:214), EDCDAFYPYCDS (SEQ ID NO:215), or EVGHSDCDAFYPYCDS (SEQ ID NO:216).

In some embodiments, the masking moiety (MM) comprises an amino acid sequence selected from NFVADSCPDHPYPCSA (SEQ ID NO: 141), IVHHSDCDAFYPYCDS (SEQ ID NO: 142), YSAYPACDSHYPYCNS (SEQ ID NO: 143), PNPSSDCVPYYYACAY (SEQ ID NO: 144), YSAYPACDSHYPYCQS (SEQ ID NO: 145), PQPSSDCVPYYYACAY (SEQ ID NO: 146), and PNPASDCVPYYYACAY (SEQ ID NO: 147).

In some embodiments, any of the masking moieties (MMs) described herein may further comprise one or more additional amino acid sequences (e.g., one or more polypeptide tags). Examples of suitable additional amino acid sequence may include, without limitation, purification tags (such as his-tags, flag-tags, maltose binding protein and glutathione-S-transferase tags), detection tags (such as tags that may be detected photometrically (e.g., red or green fluorescent protein, etc.)), tags that have a detectable enzymatic activity (e.g., alkaline phosphatase, etc.), tags containing secretory sequences, leader sequences, and/or stabilizing sequences, protease cleavage sites (e.g., furin cleavage sites, TEV cleavage sites, Thrombin cleavage sites), and the like. In some embodiments, the one or more additional amino acid sequences are at the N-terminus of the masking moiety (MM). In some embodiments, the additional amino acid sequence comprises or consists of the sequence EVGSY (SEQ ID NO: 148).

In some embodiments, the masking moiety binds to the target binding moiety (TBM) and inhibits the activatable antibody from binding to its target before activation (e.g., before treatment with one or more proteases that cleave within the cleavable moiety (CM), before undergoing a (local) change in pH (increased or decreased), before a temperature shift (increased or decreased), before being contacted with a second molecule (such as a small molecule or a protein ligand), etc.), but does not bind to the TBM and/or inhibit the activatable antibody from binding to its target after activation (e.g., after treatment with one or more proteases that cleave within the cleavable moiety (CM), after undergoing a (local) change in pH (increased or decreased), after a temperature shift (increased or decreased), after being contacted with a second molecule (such as a small molecule or a protein ligand), etc.). In some embodiments, the masking moiety (MM) inhibits binding of an activatable antibody to its target when the CM is not cleaved, but does not inhibit binding of the activatable antibody to its target when the CM is cleaved. In some embodiments, the masking moiety (MM) has a dissociation constant for binding to the TBM that is greater (e.g., at least about 1.5-fold greater, at least about 2-fold greater, at least about 2.5-fold greater, at least about 3-fold greater, at least about 3.5-fold greater, at least about 4-fold greater, at least about 4.5-fold greater, at least about 5-fold greater, at least about 10-fold greater, at least about 100-fold greater, at least about 500-fold greater, etc.) than the dissociation constant of the activatable antibody for its target (when in active form).

Cleavable Moieties (CMs)

In some embodiments, the present disclosure relates to activatable antibodies comprising a cleavable moiety (CM). In some embodiments, the cleavable moiety (CM) is cleaved and/or disrupted by treatment with one or more proteases that cleave within the cleavable moiety (CM), by a change in pH (increased or decreased), by a temperature shift (increased or decreased), and/or by contact with a second molecule (such as a small molecule or a protein ligand), etc.)

In some embodiments, the cleavable moiety (CM) comprises at least a first cleavage site ($CS_1$) (e.g., a first protease cleavage site). In some embodiments, the first cleavage site is a first protease cleavage site. Any suitable protease cleavage site recognized and/or cleaved by any protease (e.g., a protease that is known to be co-localized with a target of an activatable antibody comprising the CM) known in the art may be used, including, for example, a protease cleavage site recognized and/or cleaved by urokinase-type plasminogen activator (uPA); matrix metalloproteinases (e.g., MMP-1, MMP-2, MMP-3, MMP-7, MMP-8, MMP-9, MMP-10, MMP-11, MMP-12, MMP-13, MMP-14, MMP-15, MMP-16, MMP-17, MMP-19, MMP-20, MMP-23, MMP-24, MMP-26, and/or MMP-27); Tobacco Etch Virus (TEV) protease; plasmin; Thrombin; PSA; PSMA; ADAMS/ADAMTS (e.g., ADAM 8, ADAM 9, ADAM10, ADAM12, ADAM15, ADAM17/TACE, ADAMDEC1, ADAMTS1, ADAMTS4, and/or ADAMTS5); caspases (e.g., Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, and/or Caspase-14); aspartate proteases (e.g., RACE and/or Renin); aspartic cathepsins (e.g., Cathepsin D and/or Cathepsin E); cysteine cathepsins (e.g., Cathepsin B, Cathepsin C, Cathepsin K, Cathepsin L, Cathepsin S, Cathepsin V/L2, and/or Cathepsin X/Z/P); cysteine proteinases (e.g., Cruzipain, Legumain, and/or Otubain-2); KLKs (e.g., KLK4, KLK5, KLK6, KLK7, KLK8, KLK10, KLK11, KLK13, and/or KLK14); metallo proteainases (e.g., Meprin, Neprilysin, PSMA, and/or BMP-1); serine proteases (e.g., activated protein C, Cathepsin A, Cathepsin G, Chymase, and/or coagulation factor proteases (such as FVIIa, FIXa, FXa, FXIa, FXIIa)); elastase; granzyme B; guanidinobenzoatase; HtrAl; human neutrophil elastase; lactoferrin; marapsin; NS3/4A; PACE4; tPA; tryptase; type II transmembrane serine proteases (TTSPs) (e.g., DESC1, DPP-4, FAP, Hepsin, Matriptase-2, MT-SP1/Matriptase, TMPRSS2, TMPRSS3 and/or TMPRSS4); etc. In some embodiments, the first protease cleavage site is a cleavage site for a protease selected from uPA, MMP-1, MMP-2, MMP-3, MMP-8, MMP-9, MMP-14, TEV protease, plasmin, Thrombin, Factor X, PSA, PSMA, Cathepsin D, Cathepsin K, Cathepsin S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE. In some embodiments, the first protease cleavage site is a cleavage site for a protease selected from uPA, MMP-2, MMP-9, and/or TEV protease. In some embodiments, the protease cleavage comprises an amino acid sequence selected from SGRSA (SEQ ID NO: 149), PLGLAG (SEQ ID NO: 150), and ENLYFQG (SEQ ID NO: 151).

In some embodiments, an activatable antibody comprises a masking moiety (MM) and a cleavable moiety (CM) comprising an amino acid sequence according to Formula (XXV): EVGSY($Z_6$)C($Z_6$)C($Z_2$)SGRSA (SEQ ID NO: 152), where each Z is independently an amino acid selected from D, A, Y, S, T, N, I, L, F, V, H, and P.

In some embodiments, an activatable antibody comprises a masking moiety (MM) and a cleavable moiety (CM) comprising an amino acid sequence according to Formula (XXVI): EVGSY($Z_6$)C($X_6$)C($Z_2$)SGRSA (SEQ ID NO: 153), where each X is independently an amino acid selected from A, C, D, E, F, G, H, I, K, L, M, N, P, Q, R, S, T, V, W, and Y, and where each Z is independently an amino acid selected from the group consisting of D, A, Y, S, T, N, I, L, F, V, H, and P.

In some embodiments, an activatable antibody comprises a masking moiety (MM) and a cleavable moiety (CM) comprising an amino acid sequence according to Formula (XXVII): EVGSY($Z_6$)C($Z_8$)C($Z_2$)SGRSA (SEQ ID NO: 154), where each Z is independently an amino acid selected from D, A, Y, S, T, N, I, L, F, V, H, and P.

In some embodiments, an activatable antibody comprises a masking moiety (MM) and a cleavable moiety (CM) comprising an amino acid sequence according to Formula (XXVIII): EVGSY($Z_6$)C($X_8$)C($Z_2$)SGRSA (SEQ ID NO: 155), where each X is independently an amino acid selected from the group consisting of A, C, D, E, F, G, H, I, K, L, M, N, P, Q, R, S, T, V, W, and Y, and wherein each Z is independently an amino acid selected from the group consisting of D, A, Y, S, T, N, I, L, F, V, H, and P.

In some embodiments, the cleavable moiety (CM) further comprises a first linker ($L_1$). In some embodiments, the first linker ($L_1$) is C-terminal to the first cleavage site ($CS_1$) (e.g., a first protease cleavage site). In some embodiments, the cleavable moiety (CM) comprises a structure, from N-terminus to C-terminus, of: ($CS_1$)-$L_1$.

Any suitable linker (e.g., a flexible linker) known in the art may be used, including, for example: glycine polymers (G)n, where n is an integer of at least 1 (e.g., at least one, at least 2, at least 3, at least 4, at least 5, at least 6, at least 7, at least 8, at least 9, at least 10, etc.); glycine-serine polymers (GS)n, where n is an integer of at least 1 (e.g., at least one, at least 2, at least 3, at least 4, at least 5, at least 6, at least 7, at least 8, at least 9, at least 10, etc.) such as GGGGS (SEQ ID NO: 156), SGGS (SEQ ID NO: 157), GGSG (SEQ ID NO: 158), GGSGG (SEQ ID NO: 159), GSGSG (SEQ ID NO: 160), GSGGG (SEQ ID NO: 161), GGGSG (SEQ ID NO: 162), and/or GSSSG (SEQ ID NO: 163)); glycine-alanine polymers; alanine-serine polymers; and the like. Linker sequences may be of any length, such as from about 1 amino acid (e.g., glycine or serine) to about 20 amino acids (e.g., 20 amino acid glycine polymers or glycine-serine polymers), about 1 amino acid to about 15 amino acids, about 3 amino acids to about 12 amino acids, about 4 amino acids to about 10 amino acids, about 5 amino acids to about 9 amino acids, about 6 amino acids to about 8 amino acids, etc. In some embodiments, the linker is any of about 1, 2, 3, 4, 5, 6, 7, 8, 9, 10, 11, 12, 13, 14, 15, 16, 17, 18, 19, or 20 amino acids in length. In some embodiments, the linker comprises an amino acid sequence selected from SEQ ID NOS: 159-163. In some embodiments, the linker comprises an amino acid sequence of SEQ ID NO: 156 or 157.

In some embodiments, the cleavable moiety (CM) further comprises at least a second cleavage site (e.g., at least a second, at least a third, at least a fourth, at least a fifth, etc.). In some embodiments, the cleavable moiety (CM) further comprises a second cleavage site ($CS_2$). In some embodiments, the second cleavage site is a second protease cleavage site. The second protease cleavage site may be any suitable protease cleavage site recognized and/or cleaved by any of the proteases described above. In some embodiments, the first ($CS_1$) and second ($CS_2$) cleavage sites are protease cleavage sites recognized and/or cleaved by the same protease. In some embodiments, the first ($CS_1$) and second ($CS_2$) cleavage sites are protease cleavage sites recognized and/or cleaved by different proteases (e.g., the first protease cleavage site is recognized and/or cleaved by uPA, and the second protease cleavage site is recognized and/or cleaved by MMP-2; the first protease cleavage site is recognized and/or cleaved by uPA, and the second protease cleavage site is recognized and/or cleaved by MMP-9; the first protease cleavage site is recognized and/or cleaved by uPA, and the second protease cleavage site is recognized and/or cleaved by TEV protease; etc.). In some embodiments, the at least second cleavage site ($CS_2$) is C-terminal to the first linker ($L_1$). In some embodiments, the cleavable moiety (CM) comprises a structure, from N-terminus to C-terminus, of: ($CS_1$)-$L_1$-($CS_2$).

In some embodiments, the cleavable moiety (CM) further comprises at least a second linker (e.g., at least a second, at least a third, at least a fourth, at least a fifth, etc.). In some embodiments, the cleavable moiety (CM) further comprises a second linker ($L_2$). The second linker ($L_2$) may be any suitable linker described above. In some embodiments, the second linker comprises an amino acid sequence selected from SEQ ID NO: 156-163. In some embodiments, the first ($L_1$) and second ($L_2$) linkers are the same (e.g., both linkers comprise the sequence of SEQ ID NO: 156 or 157). In some embodiments, the first ($L_1$) and second ($L_2$) linkers are different (e.g., the first linker ($L_1$) comprises the amino acid sequence of SEQ ID NO: 156, and the second linker ($L_2$) comprises the amino acid sequence of SEQ ID NO: 157, etc.). In some embodiments, the at least second linker ($L_2$) is C-terminal to the second cleavage site ($CS_2$). In some embodiments, the cleavable moiety (CM) comprises a structure, from N-terminus to C-terminus, of: ($CS_1$)-$L_1$-($CS_2$)-$L_2$.

Exemplary MM-CM Sequences

In some embodiments, an activatable antibody of the present disclosure comprises the structure, from N-terminus to C-terminus, of: (FP)-($PCS_1$)-$L_1$-($PCS_2$)-$L_2$. In some embodiments, an activatable antibody comprises an amino acid sequence according to Formula (XXIX), EVGSY$X_1$$X_2$$X_3$$X_4$$X_5$$X_6$C$X_7$$X_8$$X_9$$X_{10}$$X_{11}$$X_{12}$C$X_{13}$$X_{14}$SGRSAGGGGT-ENLYFQGSGGS (SEQ ID NO: 164), where X1 is A, D, I, N, P, or Y, X2 is A, F, N, S, or V, X3 is A, H, L, P, S, V, or Y, X4 is A, H, S, or Y, X5 is A, D, P, S, V, or Y, X6 is A, D, L, S, or Y, X7 is D, P, or V, X8 is A, D, H, P, S, or T, X9 is A, D, F, H, P, or Y, X10 is L, P, or Y, X11 is F, P, or Y, X12 is A, P, S, or Y, X13 is A, D, N, S, T, or Y, and X14 is A, S, or Y. In some embodiments, an activatable antibody of the present disclosure comprises the amino acid sequence of: EVGSYDALHYACPPDYYACYYSGRSAGGGGTEN-LYFQGSGGS (SEQ ID NO: 165); EVGSYNSY-HAYCPHPLYPCTASGRSAGGGGTENLYFQGSGGS (SEQ ID NO: 166); EVGSYASSAVLCVTAYFSCNSSGR-SAGGGGTENLYFQGSGGS (SEQ ID NO: 167);

EVGSYNFVADSCPDHPYPCSASGRSAGGGGSPLG-LAGSGGS (SEQ ID NO: 168); EVGSYNFVADSCPDHPYPCSASGRSAGGGGTENLYFQGSGGS (SEQ ID NO: 169); EVGSYIVHHSDCDAFYPYCDSSGRSAGGGGSPLGLAGSGGS (SEQ ID NO: 170); EVGSYIVHHSDCDAFYPYCDSSGRSAGGGGTENLYFQGSGGS (SEQ ID NO: 171); EVGSYYSAYPACDSHYPYCNSSGRSAGGGGSPLGLAGSGGS (SEQ ID NO: 172); EVGSYYSAYPACDSHYPYCNSSGRSAGGGGTENLYFQGSGGS (SEQ ID NO: 173); EVGSYPNPSSDCVPYYYACAYSGRSAGGGGSPLGLAGSGGS (SEQ ID NO: 174); EVGSYPNPSSDCVPYYYACAYSGRSAGGGGTENLYFQGSGGS (SEQ ID NO: 175); EVGSYYSAYPACDSHYPYCQSSGRSAGGGGSPLGLAGSGGS (SEQ ID NO: 176); EVGSYYSAYPACDSHYPYCNSAGRSAGGGGSPLGLAGSGGS (SEQ ID NO: 177); EVGSYPQPSSDCVPYYYACAYSGRSAGGGGSPLGLAGSGGS (SEQ ID NO: 178); and/or EVGSYPNPASDCVPYYYACAYSGRSAGGGGSPLGLAGSGGS (SEQ ID NO: 179). In some embodiments, a polypeptide of the present disclosure comprises the structure, from N-terminus to C-terminus, of: (FP)-(PCS$_1$)-L$_1$-(PCS$_2$)-L$_2$-(TBM).

In some embodiments, an activatable antibody comprises an amino acid sequence SGRSAGGGGTENLYFQGSGGS (SEQ ID NO:220), SGRSAGGGGTPLGLAGSGGS (SEQ ID NO:221), or SGRSAPLGLA (SEQ ID NO:222). In some embodiments, an activatable antibody comprises the sequence of EV(Zn)C(X$_8$)C(Z$_2$)SGRSA (SEQ ID NO:217), EDC(Z$_6$)C(Z$_2$)SGRSA (SEQ ID NO:218), or EDC(Z$_6$)C(Z$_2$)PLGLA (SEQ ID NO:219), where each X is independently an amino acid selected from the group consisting of A, C, D, E, F, G, H, I, K, L, M, N, P, Q, R, S, T, V, W, and Y, wherein n is 1-11 and wherein each Z is independently an amino acid selected from the group consisting of D, A, Y, S, T, N, I, L, F, V, H, and P.

Target Binding Moieties (TBMs)

In some embodiments, the present disclosure relates to activatable antibodies comprising a target binding moiety (TBM). In some embodiments, the target binding moiety (TBM) comprises an antibody light chain variable region and/or an antibody heavy chain variable region. In some embodiments, the target binding moiety (TBM) comprises an antibody light chain variable region. In some embodiments, the target binding moiety (TBM) comprises an antibody heavy chain variable region. In some embodiments, the target binding moiety (TBM) comprises an antibody light chain variable region and an antibody heavy chain variable region.

In some embodiments, the target binding moiety (TBM) comprises a full length antibody light chain and/or a full length antibody heavy chain. The antibody light chain may be a kappa or lambda light chain. The antibody heavy chain may be in any class, such as IgG, IgM, IgE, IgA, or IgD. In some embodiments, the antibody heavy chain is in the IgG class, such as IgG1, IgG2, IgG3, or IgG4 subclass. An antibody heavy chain described herein may be converted from one class or subclass to another class or subclass using methods known in the art.

Any one or more of the target binding moieties (TBMs) described herein may incorporate: any of the HVR sequences described herein (e.g., one, two, or three of the heavy chain variable region HVR sequences, and/or one, two, or three of the light chain variable region HVR sequences as shown in Table A above); any of the heavy chain variable region sequences and/or light chain variable region sequences described herein (e.g., a heavy chain variable region sequence and/or a light chain variable region sequence as shown in Table B above); and/or any of any of the antibodies described herein.

In some embodiments, the target binding moiety (TBM) comprises a sequence of one or more of the anti-CTLA4 antibodies described herein, including antibodies described with reference to specific amino acid sequences of HVRs, variable regions (VL, VH), and/or light and heavy chains (e.g., IgG1, IgG2, IgG4). In some embodiments, the target binding moiety (TBM) comprises an antibody light chain variable region comprising an HVR-L1 comprising the amino acid sequence RASQSVRGRFLA (SEQ ID NO: 58), an HVR-L2 comprising the amino acid sequence DASNRATGI (SEQ ID NO: 66), and/or an HVR-L3 comprising the amino acid sequence YCQQSSSWPPT (SEQ ID NO: 75). In some embodiments, the target binding moiety (TBM) comprises an antibody light chain variable region comprising the amino acid sequence of SEQ ID NO: 100 or a sequence having at least 90% (e.g., 95%, 96%, 97%, 98% or 99%) sequence identity to the sequence of SEQ ID NO:100. In some embodiments, the target binding moiety (TBM) comprises an antibody heavy chain variable region comprising an HVR-H1 comprising the amino acid sequence YSISSGYHWSWI (SEQ ID NO: 23), an HVR-H2 comprising the amino acid sequence LARIDWDDDKYYSTSLKSRL (SEQ ID NO: 35), and/or an HVR-H3 comprising the amino acid sequence ARSYVYFDY (SEQ ID NO: 45). In some embodiments, the target binding moiety (TBM) comprises an antibody heavy chain variable region comprising the amino acid sequence of SEQ ID NO: 87 or a sequence having at least 90% (e.g., 95%, 96%, 97%, 98% or 99%) sequence identity to the sequence of SEQ ID NO:87. In some embodiments, the target binding moiety (TBM) comprises: a) an antibody light chain variable region comprising an HVR-L1 comprising the amino acid sequence RASQSVRGRFLA (SEQ ID NO: 58), an HVR-L2 comprising the amino acid sequence DASNRATGI (SEQ ID NO: 66), and/or an HVR-L3 comprising the amino acid sequence YCQQSSSWPPT (SEQ ID NO: 75); and b) an antibody heavy chain variable region comprising an HVR-H1 comprising the amino acid sequence YSISSGYHWSWI (SEQ ID NO: 23), an HVR-H2 comprising the amino acid sequence LARIDWDDDKYYSTSLKSRL (SEQ ID NO: 35), and/or an HVR-H3 comprising the amino acid sequence ARSYVYFDY (SEQ ID NO: 45). In some embodiments, the target binding moiety (TBM) comprises an antibody light chain variable region comprising the amino acid sequence of SEQ ID NO: 100, and an antibody heavy chain variable region comprising the amino acid sequence of SEQ ID NO: 87.

Activatable Binding Polypeptide Properties

In some embodiments, an activatable binding polypeptide (i.e., activatable antibody) of the present disclosure comprises: (a) a masking moiety (MM), (b) a cleavable moiety, and (c) a target binding moiety. In some embodiments, the masking moiety (MM) binds to the target binding moiety (TBM) of the activatable antibody and reduces or inhibits binding of the activatable binding moiety to CTLA4 (e.g., human CTLA4), as compared to the binding of a corresponding binding polypeptide lacking the masking moiety to CTLA4 (e.g., human CTLA4) and/or as compared to the binding of a parental antibody to CTLA4 (e.g., human CTLA4).

In some embodiments, an "activatable" binding polypeptides refers to a binding polypeptide that exhibits a first level of binding to CTLA4 when in an inhibited, masked, and/or uncleaved state, and exhibits a second level of binding to CTLA4 in an uninhibited, unmasked, and/or cleaved state, where the second level of CTLA4 binding is greater than the first level of CTLA4 binding. In some embodiments, access to CTLA4 by the activatable binding polypeptide is greater after cleavage within the cleavable moiety (e.g., by one or more proteases).

In some embodiments, an activatable antibody of the present disclosure is generally considered to be an "activatable" binding polypeptide when binding affinity of the polypeptide to CTLA4 (e.g., human CTLA4) increases by at least about 2-fold (e.g., at least about 2-fold, at least about 2.5-fold, at least about 3, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 25-fold, at least about 50-fold, at least about 75-fold, at least about 100-fold, at least about 250-fold, at least about 500-fold, at least about 750-fold, or at least about 1000-fold, or more) after activation of the activatable antibody as compared to prior to activation of the activatable antibody (e.g., after activation by treatment with one or more proteases that cleave within the cleavable moiety (CM), after activation by a change in pH (increased or decreased), after activation by a temperature shift (increased or decreased), after activation by being contacted with a second molecule (such as a small molecule), etc.). In some embodiments, an activatable antibody of the present disclosure is generally considered "activatable" if the $EC_{50}$ of the activatable antibody decreases by at least about 2-fold (e.g., at least about 2-fold, at least about 2.5-fold, at least about 3, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 25-fold, at least about 50-fold, at least about 75-fold, at least about 100-fold, at least about 250-fold, at least about 500-fold, at least about 750-fold, or at least about 1000-fold, or more) after "activation" (e.g., as measured by an ELISA or FACS assay; see the examples below). In some embodiments, an activatable antibody of the present disclosure is generally considered "activatable" if the $EC_{50}$ of the polypeptide decreases by at least about 2-fold after treatment with a protease that cleaves within the cleavable moiety (CM) (e.g., as measured by an ELISA or FACS assay; see the examples below).

In some embodiments, when the masking moiety (MM) is bound to the target binding moiety (TBM) of the activatable antibody, the $K_D$ of the activatable antibody for CTLA4 is about 2 (e.g., about 2, about 2.5, about 3, about 3.5 about 4, about 4.5, about 5, about 5.5, about 6, about 6.5, about 7, about 7.5, about 8, about 8.5, about 9, about 9.5, about 10, about 25, about 50, about 75, about 100, about 250, about 500, about 750, or about 1000 or more) times greater than when the masking moiety (MM) is not bound to the target binding moiety (TBM) (e.g., after "activation" of the activatable antibody (such as after protease treatment to cleave within the cleavable moiety (CM))) and/or than the $K_D$ of the parental antibody for CTLA4. Methods of measuring affinity are known in the art, including, for example, by the methods described in the Examples below).

In some embodiments, when the masking moiety is bound to the target binding moiety of the activatable antibody, the $K_D$ of the activatable antibody for CTLA4 is reduced by at least about 25% (e.g., at least about 25%, at least about 30%, at least about 40%, at least about 50%, at least about 60%, at least about 70%, at least about 80%, at least about 90%, at least about 95%, at least about 99%) relative to when the masking moiety is not bound to the target binding moiety (e.g., after "activation" of the activatable antibody (such as after protease treatment to cleave within the cleavable moiety (CM))) and/or relative to the $K_D$ of the parental antibody for CTLA4. Methods of measuring affinity are known in the art, including, for example, by the methods described in the Examples below).

In some embodiments, the masking moiety sterically hinders binding of the activatable antibody to CTLA4 and/or allosterically hinders binding of the activatable antibody to CTLA4. In some embodiments, the masking moiety does not comprise an amino acid sequence of a natural binding partner of the activatable antibody and/or parental antibody.

In some embodiments, the dissociation constant of the masking moiety for the target binding moiety is greater than the dissociation constant for the activatable antibody for CTLA4 (when activated). In some embodiments, the dissociation constant of the masking moiety for the target binding moiety is about 2 (e.g., about 2, about 2.5, about 3, about 3.5 about 4, about 4.5, about 5, about 5.5, about 6, about 6.5, about 7, about 7.5, about 8, about 8.5, about 9, about 9.5, about 10, about 25, about 50, about 75, about 100, about 250, about 500, about 750, or about 1000 or more) times greater than the dissociation constant for the activatable antibody for CTLA4 (when activated). In some embodiments, the dissociation constant of the masking moiety for the target binding moiety is about equal to the dissociation constant for the activatable antibody for CTLA4 (when activated).

The activatable antibodies described herein may be further modified. In some embodiments, the activatable antibodies are linked to an additional molecular entity. Examples of additional molecular entities include pharmaceutical agents, peptides or proteins, detection agent or labels, and antibodies.

In some embodiments, an activatable antibody of the present disclosure is linked to a pharmaceutical agent. Examples of pharmaceutical agents include cytotoxic agents or other cancer therapeutic agents, and radioactive isotopes. Specific examples of cytotoxic agents include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Examples of radioactive isotopes that can be conjugated to antibodies for use diagnostically or therapeutically include, but are not limited to, iodine$^{131}$, indium$^{111}$, ytnium$^{90}$ and lutetium$^{177}$. Methods for linking a polypeptide to a pharmaceutical agent are known in the art, such as using various linker technologies.

Examples of linker types include hydrazones, thioethers, esters, disulfides and peptide-containing linkers. For further discussion of linkers and methods for linking therapeutic agents to antibodies see e.g., Saito et al., *Adv. Drug Deliv. Rev.* 55:199-215 (2003); Trail, et al., *Cancer Immunol. Immunother.* 52:328-337 (2003); Payne, *Cancer Cell* 3:207-212 (2003); Allen, *Nat. Rev. Cancer* 2:750-763 (2002); Pastan and Kreitman, *Curr. Opin. Investig. Drugs* 3:1089-1091 (2002); Senter and Springer (2001) *Adv. Drug Deliv. Rev.* 53:247-264.

V. Nucleic Acids, Vectors, Host Cells, and Recombinant Methods of Producing CTLA4 Antibodies and/or Precision/Context-Dependent Activatable Antibodies Another aspect of the disclosure provides an isolated nucleic acid molecule that comprises a nucleotide sequence encoding an amino acid sequence of a binding molecule (e.g., an antibody or activatable antibody) provided herein. The amino acid sequence encoded by the nucleotide sequence may be any portion of an antibody, such as an HVR, a sequence comprising one, two, or three HVRs, a variable region of a heavy chain, variable region of a light chain, or may be a full-length heavy chain or full length light chain. A nucleic acid of the disclosure can be, for example, DNA or RNA, and may or may not contain intronic sequences. Typically, the nucleic acid is a cDNA molecule.

In some embodiments, the disclosure provides an isolated nucleic acid molecule that comprises or consists of a nucleotide sequence encoding an amino acid sequence selected from the group consisting of: (1) amino acid sequence of an HVR-H1, HVR-H2, HVR-H3, HVR-L1, HVR-L2 and/or and HVR-L3 of an illustrative antibody described herein; (2) a variable region of a heavy chain and/or variable region of a light chain of an illustrative antibody described herein; or (3) a full length heavy chain or full length light chain of an illustrative antibody.

In some embodiments, the nucleic acid molecule comprises or consists of a nucleotide sequence that encodes an amino acid sequence as set forth in any one of SEQ ID NOS: 18-107.

In some embodiments, the nucleic acid molecule comprises or consists of a nucleotide sequence described in Table C below.

TABLE C

| anti-CTLA4 variable region polynucleotide sequences | | |
|---|---|---|
| Ab name: | VH: | VL: |
| TY21585 | GAGGTTCAGCTGGTGGAGTCTGGCGGTGG CCTGGTGCAGCCAGGGGGCTCACTCCGTTT GTCCTGTGCAGCTTCCGGATTCACCTTCTCC GACTACGCTATTCACTGGGTGCGTCAGGCC CCGGGTAAGGGACTCGAGTGGATCGGTATC ATCTCCCCATCTAGCGGTTCTACTAACTACG CCCAGAAGTTCCAGGGTCGTGTGACTATAA GTCGCGACAATTCGAAAAACACACTGTACC TACAACTGAACAGCTTAAGAGCTGAGGAC ACTGCCGTCTATTATTGCGCCAGAGACATTC ACTCTGGTTCTTCTGGTTACTACTACGGTTT CGACGTCTGGGGTCAAGGAACACTAGTCA CCGTCTCCTCG (SEQ ID NO: 108) | GATATCCAGTTGACCCAGTCCCCGAGTTC CCTGTCCGCCTCTGTGGGCGATCGGGTCA CCATCACCTGCCGTGCCTCTGAGTCTGTG GACTTCTTCGGTATCTCTTTCCTGGCCTGG TATCAACAGAAACCAGGAAAAGCTCCGA AGCTTCTGATCTACGACGCCTCTAACCGT GCCACCGGTATCCCATCTCGCTTCTCTGGA TCCGGTTCCGGGACGGATTTCACTCTGAC CATCAGCAGTCTGCAGCCGGAAGACTTC GCAACTTATTACTGCCAGCACTACACCTC TTCGCCACCAGTGTACACCTTCGGACAGG GTACCAAGGTGGAGATCAAACGA (SEQ ID NO: 121) |
| TY21586 | GAGGTTCAGCTGGTGGAGTCTGGCGGTGG CCTGGTGCAGCCAGGGGGCTCACTCCGTTT GTCCTGTGCAGCTTCCGGATACTCTATCACC TCTGGTTACTACTGGGCCTGGATTCGTCAG GCCCCGGGTAAGGGCCTCGAGTGGGTGTCT TCCATCTCTGGTTCCGGTTCTACTACCTACT ACGCCGACTCTGTCAAGGGCCGTTTCACTA TAAGTCGCGACAATTCGAAAAACACACTGT ACCTACAACTGAACAGCTTAAGAGCTGAG GACACTGCCGTCTATTATTGCGCCAGAGAT GGTTTCGGCTACTTCGACTACTGGGGTCAA GGAACACTAGTCACCGTCTCCTCG (SEQ ID NO: 109) | GATATCCAGTTGACCCAGTCCCCGAGTTC CCTGTCCGCCTCTGTGGGCGATCGGGTCA CCATCACCTGCTCTGCCTCTTCTAGCGTG AGCTACGTGTACTGGTATCAACAGAAACC AGGAAAAGCTCCGAAGCTTCTGATCTACG ACGCCTCTTCTCTGGAATCTGGTGTGCCA TCTCGCTTCTCTGGATCCGGTTCCGGGAC GGATTTCACTCTGACCATCAGCAGTCTGC AGCCGGAAGACTTCGCAACTTATTACTGC GTGCAGGGTCTTCAGACCCCTTGGACCTT CGGACAGGGTACCAAGGTGGAGATCAAA CGA (SEQ ID NO: 122) |
| TY21587 | GAGGTTCAGCTGGTGGAGTCTGGCGGTGG CCTGGTGCAGCCAGGGGGCTCACTCCGTTT GTCCTGTGCAGCTTCCGGATTCACCTTCTCC GACTACGGTATTCACTGGGTGCGTCAGGCC CCGGGTAAGGGCCTCGAGTGGATCGGTGA AATCTACCACTCTGGTTCTACCTACTACTCT CCATCTCTGAAGTCTCGTGTGACTATAAGTC GCGACAATTCGAAAAACACACTGTACCTAC AACTGAACAGCTTAAGAGCTGAGGACACT GCCGTCTATTATTGCGCCAGAGACGTTGCC CCTGGTTCTTCTGGTTACTACGACGGTTTCG ACTTCTGGGGTCAAGGAACACTAGTCACCG TCTCCTCG (SEQ ID NO: 110) | GATATCCAGTTGACCCAGTCCCCGAGTTC CCTGTCCGCCTCTGTGGGCGATCGGGTCA CCATCACCTGCCGTGCCTCTCAGGGTATT GGCTCTTCCCTGGCTTGGTATCAACAGAA ACCAGGAAAAGCTCCGAAGCTTCTGATCT ACGACGCCTCTAACCGTGCCACCGGTATC CCATCTCGCTTCTCTGGATCCGGTTCCGG GACGGATTTCACTCTGACCATCAGCAGTC TGCAGCCGGAAGACTTCGCAACTTATTAC TGCCAGCAGTACGACCAATGGCCACCTTG GACCTTCGGACAGGGTACCAAGGTGGAG ATCAAACGA (SEQ ID NO: 123) |

TABLE C-continued anti-CTLA4 variable region polynucleotide sequences

| Ab name: | VH: | VL: |
| --- | --- | --- |
| TY21588 | GAGGTTCAGCTGGTGGAGTCTGGCGGTGG<br>CCTGGTGCAGCCAGGGGGCTCACTCCGTTT<br>GTCCTGTGCAGCTTCCGGATACTCTATCTCC<br>TCTGGTTACCACTGGGACTGGATTCGTCAG<br>GCCCCGGGTAAGGGCCTCGAGTGGGTGTCT<br>GGTATCTCTGGTTACGGTGGTTCTACCTACT<br>ACGCCGACTCTGTCAAGGGCCGTTTCACTA<br>TAAGTCGCGACAATTCGAAAAACACACTGT<br>ACCTACAACTGAACAGCTTAAGAGCTGAG<br>GACACTGCCGTCTATTATTGCGCCAGACAC<br>AGTTATTACGGTTCCGGTAATTTCGACTACT<br>GGGGTCAAGGAACACTAGTCACCGTCTCCT<br>CG<br>(SEQ ID NO: 111) | GATATCCAGTTGACCCAGTCCCCGAGTTC<br>CCTGTCCGCCTCTGTGGGCGATCGGGTCA<br>CCATCACCTGCCGTGCCTCTGAGTCTGTG<br>GACTTCTTCGGTAAGTCTTTCCTGCACTG<br>GTATCAACAGAAACCAGGAAAAGCTCCG<br>AAGCTTCTGATCTACGACGCCTCTAACCT<br>GGAAACCGGTGTGCCATCTCGCTTCTCTG<br>GATCCGGTTCCGGGACGGATTTCACTCTG<br>ACCATCAGCAGTCTGCAGCCGGAAGACT<br>TCGCAACTTATTACTGCCAGCAGTCCTAC<br>TCCTGGCCTCCGACCTTCGGACAGGGTAC<br>CAAGGTGGAGATCAAACGA<br>(SEQ ID NO: 124) |
| TY21589 | GAGGTTCAGCTGGTGGAGTCTGGCGGTGG<br>CCTGGTGCAGCCAGGGGGCTCACTCCGTTT<br>GTCCTGTGCAGCTTCCGGATTCACCTTCTCC<br>GACTACTGGATTCACTGGGTGCGTCAGGCC<br>CCGGGTAAGGGCCTCGAGTGGATCGGTTGG<br>ATCTCCCCATCTGGCGGTGGTACTAAGTAC<br>GCCCAGAAGTTCCAGGGTCGTGTGACTATA<br>AGTCGCGACAATTCGAAAAACACACTGTAC<br>CTACAACTGAACAGCTTAAGAGCTGAGGA<br>CACTGCCGTCTATTATTGCGCCAGAGGGGC<br>TTACGAATTTGACTACTGGGGTCAAGGAAC<br>ACTAGTCACCGTCTCCTCG<br>(SEQ ID NO: 112) | GATATCCAGTTGACCCAGTCCCCGAGTTC<br>CCTGTCCGCCTCTGTGGGCGATCGGGTCA<br>CCATCACCTGCCGTGCCTCTGAGTCTGTG<br>AGCAGCCGTTTCCTGGCCTGGTATCAACA<br>GAAACCAGGAAAAGCTCCGAAGCTTCTG<br>ATCTACGACGCCTCTAACCGTGCCACCGG<br>TATCCCATCTCGCTTCTCTGGATCCGGTTC<br>CGGGACGGATTTCACTCTGACCATCAGCA<br>GTCTGCAGCCGGAAGACTTCGCAACTTAT<br>TACTGCCAGCAGTCCTACCCCACCCCTCT<br>TACCTTCGGACAGGGTACCAAGGTGGAG<br>ATCAAACGA<br>(SEQ ID NO: 125) |
| TY21580 | GAGGTTCAGCTGGTGGAGTCTGGCGGTGG<br>CCTGGTGCAGCCAGGGGGCTCACTCCGTTT<br>GTCCTGTGCAGCTTCCGGATACTCTATCTCC<br>TCTGGTTACCACTGGAGCTGGATTCGTCAG<br>GCCCCGGGTAAGGGCCTCGAGTGGCTGGC<br>CCGGATCGACTGGGACGATGACAAGTACTA<br>CTCTACCTCTCTGAAGTCTCGTCTGACTATA<br>AGTCGCGACAATTCGAAAAACACACTGTAC<br>CTACAACTGAACAGCTTAAGAGCTGAGGA<br>CACTGCCGTCTATTATTGCGCCAGATCGTAC<br>GTGTACTTCGACTACTGGGGTCAAGGAACA<br>CTAGTCACCGTCTCCTCG<br>(SEQ ID NO: 113) | GATATCCAGTTGACCCAGTCCCCGAGTTC<br>CCTGTCCGCCTCTGTGGGCGATCGGGTCA<br>CCATCACCTGCCGTGCCTCTGAGTCTGTG<br>CGCGGCCGTTTCCTGGCCTGGTATCAACA<br>GAAACCAGGAAAAGCTCCGAAGCTTCTG<br>ATCTACGACGCCTCTAACCGTGCCACCGG<br>TATCCCATCTCGCTTCTCTGGATCCGGTTC<br>CGGGACGGATTTCACTCTGACCATCAGCA<br>GTCTGCAGCCGGAAGACTTCGCAACTTAT<br>TACTGCCAGCAGTCCTCCTCCTGGCCTCC<br>GACCTTCGGACAGGGTACCAAGGTGGAG<br>ATCAAACGA<br>(SEQ ID NO: 126) |
| TY21591 | GAGGTTCAGCTGGTGGAGTCTGGCGGTGG<br>CCTGGTGCAGCCAGGGGGCTCACTCCGTTT<br>GTCCTGTGCAGCTTCCGGATTCTCTCTGTCT<br>ACCGGCGGTGTGGCTGTGAGCTGGATTCGT<br>CAGGCCCCGGGTAAGGGCCTCGAGTGGAT<br>CGGTGAAATCTACCACTCTGGTTCTACCTAC<br>TACTCTCCATCTCTGAAGTCTCGTGTGACTA<br>TAAGTCGCGACAATTCGAAAAACACACTGT<br>ACCTACAACTGAACAGCTTAAGAGCTGAG<br>GACACTGCCGTCTATTATTGCGCCCGTCGTA<br>TCGCCACCGCTACTTACTTCGACTACTGGG<br>GTCAAGGAACACTAGTCACCGTCTCCTCG<br>(SEQ ID NO: 114) | GATATCCAGTTGACCCAGTCCCCGAGTTC<br>CCTGTCCGCCTCTGTGGGCGATCGGGTCA<br>CCATCACCTGCCGTGCCTCTCAGACCGTG<br>TTCTCTCGTTACCTGGCTTGGTATCAACA<br>GAAACCAGGAAAAGCTCCGAAGCTTCTG<br>ATCTACGACGCCTCTAACCGTGCCACCGG<br>TATCCCATCTCGCTTCTCTGGATCCGGTTC<br>CGGGACGGATTTCACTCTGACCATCAGCA<br>GTCTGCAGCCGGAAGACTTCGCAACTTAT<br>TACTGCCAGCAGTCCTACTACTGGCCACC<br>TTGGACCTTCGGACAGGGTACCAAGGTG<br>GAGATCAAACGA<br>(SEQ ID NO: 127) |
| TY21686 | GAGGTTCAGCTGGTGGAGTCTGGCGGTGG<br>CCTGGTGCAGCCAGGGGGCTCACTCCGTTT<br>GTCCTGTGCAGCTTCCGGATTCTCTCTGTCT<br>ACCGGCGGTGTGGCTGTGGGCTGGATTCGT<br>CAGGCCCCGGGTAAGGGCCTCGAGTGGGT<br>GTCTGCTATCTCTGGTTACGGTTCTACTACC<br>TACTACGCCGACTCTGTCAAGGGCCGTTTC<br>ACTATAAGTCGCGACAATTCGAAAAACACA<br>CTGTACCTACAACTGAACAGCTTAAGAGCT<br>GAGGACACTGCCGTCTATTATTGCGCCAGA<br>TTGCCATACTCCGCCTACGCTTTCGACTACT<br>GGGGTCAAGGAACACTAGTCACCGTCTCCT<br>CG<br>(SEQ ID NO: 115) | GATATCCAGTTGACCCAGTCCCCGAGTTC<br>CCTGTCCGCCTCTGTGGGCGATCGGGTCA<br>CCATCACCTGCCGTGCCTCTCAGGGTGTG<br>TCTTCTTACCTGGCCTGGTATCAACAGAA<br>ACCAGGAAAAGCTCCGAAGCTTCTGATCT<br>ACGCCGCCTCTACCTTGCAGTCTGGTGTG<br>CCATCTCGCTTCTCTGGATCCGGTTCCGG<br>GACGGATTTCACTCTGACCATCAGCAGTC<br>TGCAGCCGGAAGACTTCGCAACTTACTAC<br>TGCCAGCACCACTACGGCACCCCCACTGA<br>CCTTCGGTCAGGGTACCAAGGTGGAGATC<br>AAACGA<br>(SEQ ID NO: 128) |
| TY21687 | GAGGTTCAGCTGGTGGAGTCTGGCGGTGG<br>CCTGGTGCAGCCAGGGGGCTCACTCCGTTT<br>GTCCTGTGCAGCTTCCGGATTCACCTTCTCC<br>GGCTACGCTATTCACTGGGTGCGTCAGGCC | GATATCCAGTTGACCCAGTCCCCGAGTTC<br>CCTGTCCGCCTCTGTGGGCGATCGGGTCA<br>CCATCACCTGCCGTGCCTCTCAGTCTGTG<br>GACTTCTACGGTATCTCTTTCCTGGACTG |

TABLE C-continued anti-CTLA4 variable region polynucleotide sequences

| Ab name: | VH: | VL: |
|---|---|---|
| | CCGGGTAAGGGCCTCGAGTGGATCGGTATC<br>ATCTCCCCATCTGGCGGTGGTACTAAGTAC<br>GCCCAGAAGTTCCAGGGTCGTGTGACTATA<br>AGTCGCGACAATTCGAAAAACACACTGTAC<br>CTACAACTGAACAGCTTAAGAGCTGAGGA<br>CACTGCCGTCTATTATTGCGCCAGACACCCA<br>TTCGCCTACTGGGGTCAAGGAACACTAGTC<br>ACCGTCTCCTCG<br>(SEQ ID NO: 116) | GTATCAACAGAAACCAGGAAAAGCTCCG<br>AAGCTTCTGATCTACGACGCCTCTAACCG<br>TGCCACCGGTATCCCCATCTCGCTTCTCTGG<br>ATCCGGTTCCGGGACGGATTTCACTCTGA<br>CCATCAGCAGTCTGCAGCCGGAAGACTT<br>CGCAACTTATTACTGCCAGCAGTACGTCT<br>CTTCGCCACCAGAGTACACCTTCGGACAG<br>GGTACCAAGGTGGAGATCAAACGA<br>(SEQ ID NO: 129) |
| TY21689 | GAGGTTCAGCTGGTGGAGTCTGGCGGTGG<br>CCTGGTGCAGCCAGGGGGCTCACTCCGTTT<br>GTCCTGTGCAGCTTCCGGATACACCTTCTC<br>CGGCTACGGTATTCACTGGGTGCGTCAGGC<br>CCCGGGTAAGGGCCTCGAGTGGATCGGTG<br>AAATCTACCACTCTGGTTCTACCTACTACTC<br>TCCATCTCTGAAGTCTCGTGTGACTATAAGT<br>CGCGACAATTCGAAAAACACACTGTACCTA<br>CAACTGAACAGCTTAAGAGCTGAGGACAC<br>TGCCGTCTATTATTGCGCCAGAAGAATTGAC<br>GCCTTCGACATCTGGGGTCAAGGAACACTA<br>GTCACCGTCTCCTCG<br>(SEQ ID NO: 117) | GATATCCAGTTGACCCAGTCCCCGAGTTC<br>CCTGTCCGCCTCTGTGGGCGATCGGGTCA<br>CCATCACCTGCCGTGCCTCTCAGTCTGTG<br>GACTTCGACGGTTTCTCTTTCCTGCACTG<br>GTATCAACAGAAACCAGGAAAAGCTCCG<br>AAGCTTCTGATCTACGACGCCTCTTCTCT<br>GGAATCTGGTGTGCCATCTCGCTTCTCTG<br>GATCCGGTTCCGGGACGGATTTCACTCTG<br>ACCATCAGCAGTCTGCAGCCGGAAGACT<br>TCGAACTTATTACTGCCAGCAGCGTGAC<br>TCCTGGCCTTACACCTTCGGACAGGGTAC<br>CAAGGTGGAGATCAAACGA<br>(SEQ ID NO: 130) |
| TY21680 | GAGGTTCAGCTGGTGGAGTCTGGCGGTGG<br>CCTGGTGCAGCCAGGGGGCTCACTCCGTTT<br>GTCCTGTGCAGCTTCCGGATACACCTTCTC<br>CGGCTACGCTATTCACTGGGTGCGTCAGGC<br>CCCGGGTAAGGGCCTCGAGTGGATCGGTAT<br>CATCTCCCCATCTGGCGGTGGTACTAAGTAC<br>GCCCAGAAGTTCCAGGGTCGTGTGACTATA<br>AGTCGCGACAATTCGAAAAACACACTGTAC<br>CTACAACTGAACAGCTTAAGAGCTGAGGA<br>CACTGCCGTCTATTATTGCGCCAGACTCTAT<br>GACGTTGCCTACTGGGGTCAAGGAACACTA<br>GTCACCGTCTCCTCG<br>(SEQ ID NO: 118) | GATATCCAGTTGACCCAGTCCCCGAGTTC<br>CCTGTCCGCCTCTGTGGGCGATCGGGTCA<br>CCATCACCTGCCGTGCCTCTCAGTCTGTG<br>GACTTCCACGGTAAGTCTTTCCTGCACTG<br>GTATCAACAGAAACCAGGAAAAGCTCCG<br>AAGCTTCTGATCTACGACGCCTCTTCTCT<br>GGAATCTGGTGTGCCATCTCGCTTCTCTG<br>GATCCGGTTCCGGGACGGATTTCACTCTG<br>ACCATCAGCAGTCTGCAGCCGGAAGACT<br>TCGAACTTATTACTGCGAGCAATCCCTG<br>GAAGTCCCATTCACCTTCGGACAGGGTAC<br>CAAGGTGGAGATCAAACGA<br>(SEQ ID NO: 131) |
| TY21691 | GAGGTTCAGCTGGTGGAGTCTGGCGGTGG<br>CCTGGTGCAGCCAGGGGGCTCACTCCGTTT<br>GTCCTGTGCAGCTTCCGGATTCACCTTCTCC<br>GACTACGCTATTCACTGGGTGCGTCAGGCC<br>CCGGGTAAGGGCCTCGAGTGGATCGGTATC<br>ATCTCCCCATCTGGCGGTTCTACTAAGTACG<br>CCCAGAAGTTCCAGGGTCGTGTGACTATAA<br>GTCGCGACAATTCGAAAAACACACTGTACC<br>TACAACTGAACAGCTTAAGAGCTGAGGAC<br>ACTGCCGTCTATTATTGCGCCAGACTCGGTT<br>ACGGGTACTTCGACGTCTGGGGTCAAGGA<br>ACACTAGTCACCGTCTCCTCG<br>(SEQ ID NO: 119) | GATATCCAGTTGACCCAGTCCCCGAGTTC<br>CCTGTCCGCCTCTGTGGGCGATCGGGTCA<br>CCATCACCTGCCGTGCCTCTCAGTCTGTG<br>GACTTCTACGGTATCTCTTTCCTGCACTGG<br>TATCAACAGAAACCAGGAAAAGCTCCGA<br>AGCTTCTGATCTACGACGCCTCTTCTCTG<br>GAATCTGGTGTGCCATCTCGCTTCTCTGG<br>ATCCGGTTCCGGGACGGATTTCACTCTGA<br>CCATCAGCAGTCTGCAGCCGGAAGACTT<br>CGCAACTTATTACTGCGTGCAGGCTCTTC<br>AGTTGCCTCTTACCTTCGGACAGGGTACC<br>AAGGTGGAGATCAAACGA<br>(SEQ ID NO: 132) |
| TY21692 | GAGGTTCAGCTGGTGGAGTCTGGCGGTGG<br>CCTGGTGCAGCCAGGGGGCTCACTCCGTTT<br>GTCCTGTGCAGCTTCCGGATACTCTATCACC<br>TCTGGTCACTACTGGAGCTGGATTCGTCAG<br>GCCCCGGGTAAGGGCCTCGAGTGGATCGGT<br>GACATCTCCCACTCTGGTTCTACCTACTACT<br>CTCAATCTCTGAAGTCTCGTGTGACTATAAG<br>TCGCGACAATTCGAAAAACACACTGTACCT<br>ACAACTGAACAGCTTAAGAGCTGAGGACA<br>CTGCCGTCTATTATTGCGCGCGTGGTAGTAG<br>GACCGGCTACTTCGACTATTGGGGTCAAGG<br>AACACTAGTCACCGTCTCCTCG<br>(SEQ ID NO: 120) | GATATCCAGTTGACCCAGTCCCCGAGTTC<br>CCTGTCCGCCTCTGTGGGCGATCGGGTCA<br>CCATCACCTGCCGTGCCTCTCAGTCTATCT<br>CTTCTTACCTGAACTGGTATCAACAGAAA<br>CCAGGAAAAGCTCCGAAGCTTCTGATCTA<br>CGACGCCTCTAACCTGGAAACCGGTGTG<br>CCATCTCGCTTCTCTGGATCCGGTTCCGG<br>GACGGATTTCACTCTGACCATCAGCAGTC<br>TGCAGCCGGAAGACTTCGCAACTTACTAC<br>TGCCAGCACCACTACGCACCCCACTGA<br>CCTTCGGTCAGGGTACCAAGGTGGAGATC<br>AAACGA<br>(SEQ ID NO: 133) |

Nucleic acids of the present disclosure may be obtained using any suitable molecular biology techniques. For antibodies expressed by hybridomas, cDNAs encoding the light and heavy chains of the antibody made by the hybridoma can be obtained by PCR amplification or cDNA cloning techniques. For antibodies obtained from an immunoglobulin gene library (e.g., using phage display techniques), the nucleic acid encoding the antibody can be recovered from the library.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat et al. (1991) NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (see e.g., Kabat et al. (1991) NIH Publication No. 91-3242) and DNA fragments encompassing these regions can be obtained by standard PCR amplification. The light chain constant region can be a kappa or lambda constant region.

To create an scFv gene, the $V_H$- and $V_L$-encoding DNA fragments are operatively linked to another fragment encoding a flexible linker, e.g., encoding the amino acid sequence $(Gly_4-Ser)_3$, such that the $V_H$ and $V_L$ sequences can be expressed as a contiguous single-chain protein, with the $V_L$ and $V_H$ regions joined by the flexible linker (see e.g., Bird et al., Science 242:423-426 (1988); Huston et al., *Proc. Natl. Acad. Sci. USA* 85:5879-5883 (1988); and McCafferty et al., *Nature* 348:552-554 (1990)).

The present disclosure further provides a vector that comprises a nucleic acid molecule described herein. In some embodiments, the vector is an expression vector or a display vector (e.g., a viral display vector, a bacterial display vector, a yeast display vector, an insect display vector, a mammalian display vector, etc.). The nucleic acid molecule may encode a portion of a light chain or heavy chain (such as a CDR or a HVR; a light or heavy chain variable region), a full-length light or heavy chain, polypeptide that comprises a portion or full-length of a heavy or light chain, or an amino acid sequence of an antibody derivative or antigen-binding fragment. In some embodiments, the vector is an expression vector useful for the expression of a binding molecule, such as an antibody or an antigen binding fragment thereof. In some embodiments, provided herein are vectors, wherein a first vector comprises a polynucleotide sequence encoding a heavy chain variable region as described herein, and a second vector comprises a polynucleotide sequence encoding a light chain variable region as described herein. In some embodiments, a single vector comprises polynucleotides encoding a heavy chain variable region as described herein and a light chain variable region as described herein.

To express a binding molecule of the disclosure, DNAs encoding partial or full-length light and heavy chains are inserted into expression vectors such that the DNA molecules are operatively linked to transcriptional and translational control sequences. In this context, the term "operatively linked" means that an antibody gene is ligated into a vector such that transcriptional and translational control sequences within the vector serve their intended function of regulating the transcription and translation of the DNA molecule. The expression vector and expression control sequences are chosen to be compatible with the expression host cell used. The antibody light chain gene and the antibody heavy chain gene can be inserted into separate vectors, or both genes can be inserted into the same expression vector. The antibody genes are inserted into the expression vector by any suitable methods (e.g., ligation of complementary restriction sites on the antibody gene fragment and vector, or homologous recombination-based DNA ligation). The light and heavy chain variable regions of the antibodies described herein can be used to create full-length antibody genes of any antibody isotype and subclass by inserting them into expression vectors already encoding heavy chain constant and light chain constant regions of the desired isotype and subclass such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody sequences, the expression vectors of the disclosure typically carry regulatory sequences that control the expression of the antibody sequences in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Examples of regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SR promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the expression vectors may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by any suitable techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the disclosure in either prokaryotic or eukaryotic host cells, expression of antibodies in eukaryotic cells, and typically mammalian host cells, is most typical.

The present disclosure further provides a host cell containing a nucleic acid molecule provided by the present disclosure. The host cell can be virtually any cell for which expression vectors are available. It may be, for example, a higher eukaryotic host cell, such as a mammalian cell, a lower eukaryotic host cell, such as a yeast cell, and may be a prokaryotic cell, such as a bacterial cell. Methods of introducing a recombinant nucleic acid into a host cell are known in the art, including, for example, by calcium phosphate transfection, DEAE, dextran mediated transfection, electroporation or phage infection.

Suitable prokaryotic hosts for transformation include *E. coli, Bacillus subtilis, Salmonella typhimurium* and various species within the genera *Pseudomonas, Streptomyces*, and *Staphylococcus*.

Suitable eukaryotic hosts for transformation include yeast, insect (e.g., S2 cells), and mammalian cells. Mammalian host cells for expressing a binding molecule of the disclosure include, for example, Chinese Hamster Ovary (CHO) cells (including dhfr-CHO cells, described in Urlaub and Chasin, *Proc. Natl. Acad. Sci. USA* 77:4216-4220 (1980); Sharp, *J. Mol. Biol.* 159:601-621 (1982)), NSO myeloma cells, COS cells, HEK293F cells, HEK293Tcells, and Sp2 cells. In particular, for use with NSO myeloma or CHO cells, another expression system is the GS (glutamine synthetase) gene expression system disclosed in WO 87/04462, WO 89/01036 and EP 338,841. In some embodiments, antibodies of the present disclosure are produced in CHO cells. In some embodiments, antibodies of the present disclosure are modified, and do not include a C-terminal lysine residue (e.g., the C-terminal lysine residue of an antibody heavy chain described herein is removed (such as before or during antibody production)). When expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using any suitable protein purification methods known in the art (e.g., protein A chromatography and/or ion exchange chromatography).

VI. Compositions

In other aspects, the present disclosure provides a composition containing a binding molecule (e.g., an antibody or activatable antibody) provided by the disclosure. In one aspect, the composition is a pharmaceutical composition comprising a binding molecule (e.g., an antibody or activatable antibody) and a pharmaceutically acceptable carrier. The compositions can be prepared by conventional methods known in the art.

In some embodiments, present disclosure provides a composition comprising a binding molecule (e.g., an antibody or activatable antibody) provided by the present disclosure and a pharmaceutically acceptable carrier, wherein said binding molecule comprises a variable domain comprising the HVR amino acid sequence disclosed herein, and wherein said composition comprises not more than about 11%, 10%, 8%, 5%, 3%, or 2% of said binding molecule (e.g., an antibody or activatable antibody) that is glycosylated at the asparagine of said amino acid sequence compared with the total amount of binding molecule (e.g., an antibody or activatable antibody) present in said composition. In another embodiment, the composition comprises at least about 2% of said binding molecule (e.g., an antibody or activatable antibody) that is glycosylated at the asparagine of said amino acid sequence compared with the total amount of binding molecule (e.g., an antibody or activatable antibody) present in said composition.

The term "pharmaceutically acceptable carrier" refers to any inactive substance that is suitable for use in a formulation for the delivery of a binding molecule. A carrier may be an anti-adherent, binder, coating, disintegrant, filler or diluent, preservative (such as antioxidant, antibacterial, or antifungal agent), sweetener, absorption delaying agent, wetting agent, emulsifying agent, buffer, and the like. Examples of suitable pharmaceutically acceptable carriers include water, ethanol, polyols (such as glycerol, propylene glycol, polyethylene glycol, and the like) dextrose, vegetable oils (such as olive oil), saline, buffer, buffered saline, and isotonic agents such as sugars, polyalcohols, sorbitol, and sodium chloride.

The compositions may be in any suitable forms, such as liquid, semi-solid, and solid dosage forms. Examples of liquid dosage forms include solution (e.g., injectable and infusible solutions), microemulsion, liposome, dispersion, or suspension. Examples of solid dosage forms include tablet, pill, capsule, microcapsule, and powder. A particular form of the composition suitable for delivering a binding molecule (e.g., an antibody or activatable antibody) is a sterile liquid, such as a solution, suspension, or dispersion, for injection or infusion. Sterile solutions can be prepared by incorporating the antibody in the required amount in an appropriate carrier, followed by sterilization microfiltration. Generally, dispersions are prepared by incorporating the binding molecule (e.g., an antibody or activatable antibody) into a sterile vehicle that contains a basic dispersion medium and other carriers. In the case of sterile powders for the preparation of sterile liquid, methods of preparation include vacuum drying and freeze-drying (lyophilization) to yield a powder of the active ingredient plus any additional desired ingredient from a previously sterile-filtered solution thereof. The various dosage forms of the compositions can be prepared by conventional techniques known in the art.

The relative amount of a binding molecule (e.g., an antibody or activatable antibody) included in the composition will vary depending upon a number of factors, such as the specific binding molecule and carriers used, dosage form, and desired release and pharmacodynamic characteristics. The amount of a binding molecule (e.g., an antibody or activatable antibody) in a single dosage form will generally be that amount which produces a therapeutic effect, but may also be a lesser amount. Generally, this amount will range from about 0.01 percent to about 99 percent, from about 0.1 percent to about 70 percent, or from about 1 percent to about 30 percent relative to the total weight of the dosage form.

In addition to the binding molecule (e.g., an antibody or activatable antibody), one or more additional therapeutic agents may be included in the composition. Examples of additional therapeutic agents are described herein below. The suitable amount of the additional therapeutic agent to be included in the composition can be readily selected by a person skilled in the art, and will vary depending on a number of factors, such as the particular agent and carriers used, dosage form, and desired release and pharmacodynamic characteristics. The amount of the additional therapeutic agent included in a single dosage form will generally be that amount of the agent which produces a therapeutic effect, but may be a lesser amount as well.

Any of the binding molecules (e.g., antibodies or activatable antibodies) and/or compositions (e.g., pharmaceutical compositions) described herein may be used in the preparation of a medicament (e.g., a medicament for use in treating or delaying progression of cancer in a subject in need thereof).

VII. Use of the Binding Molecules and Pharmaceutical Compositions

Binding molecules (e.g., antibodies or activatable antibodies) and pharmaceutical compositions provided by the present disclosure are useful for therapeutic, diagnostic, or other purposes, such as modulating an immune response, treating cancer, enhancing efficacy of other cancer therapy, enhancing vaccine efficacy, or treating autoimmune diseases. Thus, in other aspects, the present disclosure provides methods of using the binding molecules (e.g., antibodies or activatable antibodies) or pharmaceutical compositions. In one aspect, the present disclosure provides a method of treating a disorder in a mammal, which comprises administering to the mammal in need of treatment an effective amount of a binding molecule (e.g., an antibody or activatable antibody) or composition provided by the present disclosure. The binding molecule (e.g., an antibody or activatable antibody) may be a CTLA4 antibody (e.g., a human anti-human CTLA4 antibody) or a CTLA4 activatable antibody. In some embodiments, the mammal is a human.

In some embodiments, the disorder is a cancer. A variety of cancers may be treated or prevented with a method, use, composition, or medicament provided by the present disclosure. Examples of such cancers include lung cancers such as bronchogenic carcinoma (e.g., squamous cell carcinoma, small cell carcinoma, large cell carcinoma, and adenocarcinoma), alveolar cell carcinoma, bronchial adenoma, chondromatous hamartoma (noncancerous), and sarcoma (cancerous); heart cancer such as myxoma, fibromas, and rhabdomyomas; bone cancers such as osteochondromas, condromas, chondroblastomas, chondromyxoid fibromas, osteoid osteomas, giant cell tumors, chondrosarcoma, multiple myeloma, osteosarcoma, fibrosarcomas, malignant fibrous histiocytomas, Ewing's tumor (Ewing's sarcoma), and reticulum cell sarcoma; brain cancer such as gliomas (e.g., glioblastoma multiforme), anaplastic astrocytomas, astrocytomas, oligodendrogliomas, medulloblastomas, chordoma, Schwannomas, ependymomas, meningiomas, pituitary adenoma, pinealoma, osteomas, hemangioblastomas, craniopharyngiomas, chordomas, germinomas, teratomas, dermoid cysts, and angiomas; cancers in digestive system such as leiomyoma, epidermoid carcinoma, adenocarcinoma, leiomyosarcoma, stomach adenocarcinomas, intestinal lipomas, intestinal neurofibromas, intestinal fibromas, polyps in large intestine, and colorectal cancers; liver cancers such as hepatocellular adenomas, hemangioma, hepatocellular carcinoma, fibrolamellar carcinoma, cholangiocarcinoma, hepatoblastoma, and angiosarcoma; kidney cancers such as kidney adenocarcinoma, renal cell carcinoma, hypernephroma, and transitional cell carcinoma of the renal pelvis; bladder cancers; hematological cancers such as acute lymphocytic (lymphoblastic) leukemia, acute myeloid (myelocytic, myelogenous, myeloblastic, myelomonocytic) leukemia, chronic lymphocytic leukemia (e.g., Sezary syndrome and hairy cell leukemia), chronic myelocytic (myeloid, myelogenous, granulocytic) leukemia, Hodgkin's lymphoma, non-Hodgkin's lymphoma, B cell lymphoma, mycosis fungoides, and myeloproliferative disorders (including myeloproliferative disorders such as polycythemia vera, myelofibrosis, thrombocythemia, and chronic myelocytic leukemia); skin cancers such as basal cell carcinoma, squamous cell carcinoma, melanoma, Kaposi's sarcoma, and Paget's disease; head and neck cancers; eye-related cancers such as retinoblastoma and intraoccular melanocarcinoma; male reproductive system cancers such as benign prostatic hyperplasia, prostate cancer, and testicular cancers (e.g., seminoma, teratoma, embryonal carcinoma, and choriocarcinoma); breast cancer; female reproductive system cancers such as uterine cancer (endometrial carcinoma), cervical cancer (cervical carcinoma), cancer of the ovaries (ovarian carcinoma), vulvar carcinoma, vaginal carcinoma, fallopian tube cancer, and hydatidiform mole; thyroid cancer (including papillary, follicular, anaplastic, or medullary cancer); pheochromocytomas (adrenal gland); noncancerous growths of the parathyroid glands; pancreatic cancers; and hematological cancers such as leukemias, myelomas, non-Hodgkin's lymphomas, and Hodgkin's lymphomas.

In another aspect, the present disclosure provides a method of enhancing an immune response in a mammal, which comprises administering to the mammal an effective amount of a binding molecule (e.g., an antibody or activatable antibody) or composition provided by the present disclosure. In some embodiments, the binding molecule is a CTLA4 antibody or antigen-binding fragment thereof and the mammal is a human. In some embodiments, the binding molecule is a CTLA4 activatable antibody and the mammal is a human. The term "enhancing immune response" or its grammatical variations, means stimulating, evoking, increasing, improving, or augmenting any response of a mammal's immune system. The immune response may be a cellular response (i.e. cell-mediated, such as cytotoxic T lymphocyte mediated) or a humoral response (i.e. antibody mediated), and may be a primary or secondary immune response. Examples of enhancement of immune response include activation of PBMCs and/or T cells (including increasing secretion of one or more cytokines such as IL-2 and/or IFNγ). The enhancement of immune response can be assessed using a number of in vitro or in vivo measurements known to those skilled in the art, including, but not limited to, cytotoxic T lymphocyte assays, release of cytokines, regression of tumors, survival of tumor bearing animals, antibody production, immune cell proliferation, expression of cell surface markers, and cytotoxicity. Typically, methods of the present disclosure enhance the immune response by a mammal when compared to the immune response by an untreated mammal or a mammal not treated using the recited methods.

In practicing the therapeutic methods, the binding molecules (e.g., antibodies or activatable antibodies) may be administered alone as monotherapy, or administered in combination with one or more additional therapeutic agents or therapies. Thus, in another aspect, the present disclosure provides a combination therapy, which comprises a binding molecule (e.g., an antibody or activatable antibody) in combination with one or more additional therapies or therapeutic agents for separate, sequential or simultaneous administration. The term "additional therapeutic agent" may refer to any therapeutic agent other than a binding molecule (e.g., an antibody or activatable antibody) provided by the disclosure. In one particular aspect, the present disclosure provides a combination therapy for treating cancer in a mammal, which comprises administering to the mammal an effective amount of a binding molecule (e.g., an antibody or activatable antibody) provided herein in combination with one or more additional therapeutic agents. In a further embodiment, the mammal is a human.

A wide variety of cancer therapeutic agents may be used in combination with a binding molecule (e.g., an antibody or activatable antibody) provided by the present disclosure. One of ordinary skill in the art will recognize the presence and development of other cancer therapies which can be used in combination with the methods and binding molecules e.g., antibodies or activatable antibodies) of the present disclosure, and will not be restricted to those forms of therapy set forth herein. Examples of categories of additional therapeutic agents that may be used in the combination therapy for treating cancer include (1) chemotherapeutic agents, (2) immunotherapeutic agents, and (3) hormone therapeutic agents. In some embodiments, the additional therapeutic is a viral gene therapy, an immune checkpoint inhibitor, a target therapy, a radiation therapies, vaccination therapies, and/or a chemotherapeutic.

The term "chemotherapeutic agent" refers to a chemical or biological substance that can cause death of cancer cells, or interfere with growth, division, repair, and/or function of cancer cells. Examples of chemotherapeutic agents include those that are disclosed in WO 2006/129163, and US 20060153808, the disclosures of which are incorporated herein by reference. Examples of particular chemotherapeutic agents include: (1) alkylating agents, such as chlorambucil (LEUKERAN), mcyclophosphamide (CYTOXAN), ifosfamide (IFEX), mechlorethamine hydrochloride (MUSTARGEN), thiotepa (THIOPLEX), streptozotocin (ZANOSAR), carmustine (BICNU, GLIADEL WAFER), lomustine (CEENU), and dacarbazine (DTIC-DOME); (2) alkaloids or plant vinca alkaloids, including cytotoxic antibiotics, such as doxorubicin (ADRIAMYCIN), epirubicin (ELLENCE, PHARMORUBICIN), daunorubicin (CERUBIDINE, DAUNOXOME), nemorubicin, idarubicin (IDAMYCIN PFS, ZAVEDOS), mitoxantrone (DHAD, NOVANTRONE). dactinomycin (actinomycin D, COSMEGEN), plicamycin (MITHRACIN), mitomycin (MUTAMYCIN), and bleomycin (BLENOXANE), vinorelbine tartrate (NAVELBINE)), vinblastine (VELBAN), vincristine (ONCOVIN), and vindesine (ELDISINE); (3) antimetabolites, such as capecitabine (XELODA), cytarabine (CYTOSAR-U), fludarabine (FLUDARA), gemcitabine (GEMZAR), hydroxyurea (HYDRA), methotrexate (FOLEX, MEXATE, TREXALL), nelarabine (ARRANON), trimetrexate (NEUTREXIN), and pemetrexed (ALIMTA); (4) Pyrimidine antagonists, such as 5-fluorouracil (5-FU); capecitabine (XELODA), raltitrexed (TOMUDEX), tegafur-uracil (UFTORAL) and gemcitabine (GEMZAR); (5) taxanes, such as docetaxel (TAXOTERE), paclitaxel (TAXOL); (6) platinum drugs, such as cisplatin (PLATINOL) and carboplatin (PARAPLATIN), and oxaliplatin (ELOXATIN); (7) topoisomerase inhibitors, such as irinotecan (CAMPTOSAR), topotecan (HYCAMTIN), etoposide (ETOPOPHOS, VEPESSID, TOPOSAR), and teniposide (VUMON); (8) epipodophyllotoxins (podophyllotoxin derivatives), such as etoposide (ETOPOPHOS, VEPESSID, TOPOSAR); (9) folic acid derivatives, such as leucovorin (WELLCOVORIN); (10) nitrosoureas, such as carmustine (BiCNU), lomustine (CeeNU); (11) inhibitors of receptor tyrosine kinase, including epidermal growth factor receptor (EGFR), vascular endothelial growth factor (VEGF), insulin receptor, insulin-like growth factor receptor (IGFR), hepatocyte growth factor receptor (HGFR), and platelet-derived growth factor receptor (PDGFR), such as gefitinib (IRESSA), erlotinib (TARCEVA), bortezomib (VELCADE), imatinib mesylate (GLEEVEC), genefitinib, lapatinib, sorafenib, thalidomide, sunitinib (SUTENT), axitinib, rituximab (RITUXAN, MABTHERA), trastuzumab (HERCEPTIN), cetuximab (ERBITUX), bevacizumab (AVASTIN), and ranibizumab (LUCENTIS), lym-1 (ONCOLYM), antibodies to insulin-like growth factor-1 receptor (IGF-1R) that are disclosed in WO2002/053596); (12) angiogenesis inhibitors, such as bevacizumab (AVASTIN), suramin (GERMANIN), angiostatin, SU5416, thalidomide, and matrix metalloproteinase inhibitors (such as batimastat and marimastat), and those that are disclosed in WO2002055106; and (13) proteasome inhibitors, such as bortezomib (VELCADE).

The term "immunotherapeutic agents" refers to a chemical or biological substance that can enhance an immune response of a mammal. Examples of immunotherapeutic agents include: *bacillus* Calmette-Guerin (BCG); cytokines such as interferons; vaccines such as MyVax personalized immunotherapy, Onyvax-P, Oncophage, GRNVAC1, Favld, Provenge, GVAX, Lovaxin C, BiovaxID, GMXX, and NeuVax; and antibodies such as alemtuzumab (CAMPATH), bevacizumab (AVASTIN), cetuximab (ERBITUX), gemtuzunab ozogamicin (MYLOTARG), ibritumomab tiuxetan (ZEVALIN), panitumumab (VECTIBIX), rituximab (RITUXAN, MABTHERA), trastuzumab (HERCEPTIN), tositumomab (BEXXAR), ipilimumab (YERVOY) tremelimumab, CAT-3888, agonist antibodies to OX40 receptor (such as those disclosed in WO2009/079335), agonist antibodies to CD40 receptor (such as those disclosed in WO2003/040170, and TLR-9 agonists (such as those disclosed in WO2003/015711, WO2004/016805, and WO2009/022215).

The term "hormone therapeutic agent" refers to a chemical or biological substance that inhibits or eliminates the production of a hormone, or inhibits or counteracts the effect of a hormone on the growth and/or survival of cancerous cells. Examples of such agents suitable for the methods herein include those that are disclosed in US20070117809. Examples of particular hormone therapeutic agents include tamoxifen (NOLVADEX), toremifene (Fareston), fulvestrant (FASLODEX), anastrozole (ARIMIDEX), exemestane (AROMASIN), letrozole (FEMARA), megestrol acetate (MEGACE), goserelin (ZOLADEX), and leuprolide (LUPRON). The binding molecules of this disclosure may also be used in combination with non-drug hormone therapies such as (1) surgical methods that remove all or part of the organs or glands which participate in the production of the hormone, such as the ovaries, the testicles, the adrenal gland, and the pituitary gland, and (2) radiation treatment, in which the organs or glands of the patient are subjected to radiation in an amount sufficient to inhibit or eliminate the production of the targeted hormone.

In some embodiments, the additional therapeutic agent is one or more of pomalyst, revlimid, lenalidomide, pomalidomide, thalidomide, a DNA-alkylating platinum-containing derivative, cisplatin, 5-fluorouracil, cyclophosphamide, an anti-CD137 antibody, an anti-PD-1 antibody, an anti-PD-L1 antibody, an anti-CD20 antibody, an anti-CD40 antibody, an anti-DR5 antibody, an anti-CD1d antibody, an anti-TIM3 antibody, an anti-SLAMF7 antibody, an anti-KIR receptor antibody, an anti-OX40 antibody, an anti-HER2 antibody, an anti-ErbB-2 antibody, an anti-EGFR antibody, cetuximab, rituximab, trastuzumab, pembrolizumab, radiotherapy, single dose radiation, fractionated radiation, focal radiation, whole organ radiation, IL-12, IFNα, GM-CSF, a chimeric antigen receptor, adoptively transferred T cells, an anticancer vaccine, and an oncolytic virus.

The combination therapy for treating cancer also encompasses the combination of a binding molecule (e.g., an antibody or activatable antibody) with surgery to remove a tumor. The binding molecule (e.g., an antibody or activatable antibody) may be administered to the mammal before, during, or after the surgery.

The combination therapy for treating cancer also encompasses combination of a binding molecule (e.g., an antibody or activatable antibody) with radiation therapy, such as ionizing (electromagnetic) radiotherapy (e.g., X-rays or gamma rays) and particle beam radiation therapy (e.g., high linear energy radiation). The source of radiation can be external or internal to the mammal. The binding molecule (e.g., an antibody or activatable antibody) may be administered to the mammal before, during, or after the radiation therapy.

The binding molecules (e.g., antibodies or activatable antibodies) and compositions provided by the present disclosure can be administered via any suitable enteral route or parenteral route of administration. The term "enteral route" of administration refers to the administration via any part of the gastrointestinal tract. Examples of enteral routes include oral, mucosal, buccal, and rectal route, or intragastric route. "Parenteral route" of administration refers to a route of administration other than enteral route. Examples of parenteral routes of administration include intravenous, intramuscular, intradermal, intraperitoneal, intratumor, intravesical, intraarterial, intrathecal, intracapsular, intraorbital, intracardiac, transtracheal, intraarticular, subcapsular, subarachnoid, intraspinal, epidural and intrasternal, subcutaneous, or topical administration. The binding molecules (e.g., antibodies or activatable antibodies) and compositions of the present disclosure can be administered using any suitable method, such as by oral ingestion, nasogastric tube, gastrostomy tube, injection, infusion, implantable infusion pump, and osmotic pump. The suitable route and method of administration may vary depending on a number of factors such as the specific binding molecule (e.g., an antibody or activatable antibody) being used, the rate of absorption desired, specific formulation or dosage form used, type or severity of the disorder being treated, the specific site of action, and conditions of the patient, and can be readily selected by a person skilled in the art.

The term "effective amount" of a binding molecule (e.g., an antibody or activatable antibody) may refer to an amount that is effective for an intended therapeutic purpose. For example, in the context of enhancing an immune response, an "effective amount" may be any amount that is effective in stimulating, evoking, increasing, improving, or augmenting any response of a mammal's immune system. In the context of treating a disease, an "effective amount" may be any amount that is sufficient to cause any desirable or beneficial effect in the mammal being treated. Specifically, in the treatment of cancer, examples of desirable or beneficial effects include inhibition of further growth or spread of cancer cells, death of cancer cells, inhibition of reoccurrence of cancer, reduction of pain associated with the cancer, or improved survival of the mammal. The therapeutically effective amount of a binding molecule (e.g., an antibody or activatable antibody) usually ranges from about 0.001 to about 500 mg/kg, and more usually about 0.01 to about 100 mg/kg, of the body weight of the mammal. For example, the amount can be about 0.3 mg/kg, 1 mg/kg, 3 mg/kg, 5 mg/kg, 10 mg/kg, 50 mg/kg, or 100 mg/kg of body weight of the mammal. In some embodiments, the therapeutically effective amount of a binding molecule (e.g., an antibody or activatable antibody) is in the range of about 0.01-30 mg/kg of body weight of the mammal. In some other embodiments, the therapeutically effective amount of a binding molecule (e.g., an antibody or activatable antibody) is in the range of about 0.05-15 mg/kg of body weight of the mammal. The precise dosage level to be administered can be readily determined by a person skilled in the art and will depend on a number of factors, such as the type, and severity of the disorder to be treated, the particular binding molecule (e.g., an antibody or activatable antibody) employed, the route of administration, the time of administration, the duration of the treatment, the particular additional therapy employed, the age, sex, weight, condition, general health and prior medical history of the patient being treated, and like factors well known in the medical arts.

A binding molecule (e.g., an antibody or activatable antibody) or composition is usually administered on multiple occasions. Intervals between single doses can be, for example, daily, weekly, monthly, every three months or yearly. An exemplary treatment regimen entails administration once per week, once every two weeks, once every three weeks, once every four weeks, once a month, once every three months or once every three to six months. Typical dosage regimens for a binding molecule (e.g., an antibody or activatable antibody) include 1 mg/kg body weight or 3 mg/kg body weight via intravenous administration, using one of the following dosing schedules: (i) every four weeks for six dosages, then every three months; (ii) every three weeks; (iii) 3 mg/kg body weight once followed by 1 mg/kg body weight every three weeks.

VIII. Kits

In another aspect, provided herein is a kit comprising a binding molecule (e.g., an antibody or activatable antibody) and/or composition of the present disclosure. In some embodiments, the kit further comprises a package insert comprising instructions for use of the binding molecule (e.g., an antibody or activatable antibody) and/or composition. In some embodiments, the kit further comprises one or more buffers, e.g., for storing, transferring, administering, or otherwise using the binding molecule (e.g., an antibody or activatable antibody) and/or composition. In some embodiments, the kit further comprises one or more containers for storing the binding molecule (e.g., an antibody or activatable antibody) and/or composition.

The foregoing written description is considered to be sufficient to enable one skilled in the art to practice the present disclosure. The following Examples are offered for illustrative purposes only, and are not intended to limit the scope of the present disclosure in any way. Indeed, various modifications of the present disclosure in addition to those shown and described herein will become apparent to those

EXAMPLES

Example 1: Generation of Primary Fabs that Specifically Bind to Human CTLA4

Proprietary phagemid libraries (see PCT application number PCT/CN2017/098333, incorporated herein by reference in its entirety; see also PCT application number PCT/CN2017/098299, incorporated herein by reference in its entirety) were employed to pan against human CTLA4 antigens. A total of 3-5 rounds of panning were conducted. After the final round of panning, single-colony supernatant ELISA was performed to identify the primary hits that specifically recognized human CTLA4 (see e.g., UniProt Accession Number P16410). The primary hits were defined as those whose ELISA signals were at least twice that of background. The hits were then sequenced, and the unique clones were expressed in *E. coli* and purified. Their affinities against human CTLA4 were measured by ForteBio Octet RED96 Systems. Briefly, AHC sensors (Anti-Human IgG Fc Capture Dip and Read Biosensors) were used to capture recombinant human CTLA4-Fc (Sino Biological, 11159-H03H), and dipped into wells containing purified Fabs that were diluted to 10 μg/mL in kinetic buffer (0.02% Tween20, 0.1% BSA in PBS buffer). The acquired ForteBio data were processed with Data Acquisition software 7.1, and kinetic data were fitted to a 1:1 Langmuir binding model. The list of candidates was refined to 234 Fab hits with both ELISA positive hits and unique sequences. Following the criteria of $K_D$ response signal R>0.1, $R^2$>0.9, the list was further refined to 43 hits of interest. The affinity and kinetic parameters (with background subtracted) of these hits are shown in Table 1 below.

TABLE 1 affinities of selected Fabs for human CTLA4

| Hit ID: | $K_D$ (M): | kon(1/Ms): | koff(1/s): |
|---|---|---|---|
| B18153 | 5.96E−09 | 8.93E+04 | 5.32E−04 |
| B15719 | 6.93E−09 | 3.21E+05 | 2.22E−03 |
| B15746 | 7.15E−09 | 3.07E+05 | 2.20E−03 |
| B15734 | 7.63E−09 | 3.05E+05 | 2.33E−03 |
| B15710 | 8.01E−09 | 3.51E+05 | 2.81E−03 |
| B13874 | 1.06E−08 | 1.19E+05 | 1.26E−03 |
| B13898 | 1.07E−08 | 1.09E+05 | 1.16E−03 |
| B15728 | 1.18E−08 | 4.24E+05 | 4.99E−03 |
| B15705 | 1.20E−08 | 1.94E+05 | 2.33E−03 |
| B15716 | 1.21E−08 | 3.91E+04 | 4.71E−04 |
| B15672 | 1.23E−08 | 6.83E+04 | 8.39E−04 |
| B15738 | 1.24E−08 | 3.76E+05 | 4.67E−03 |
| B15694 | 1.28E−08 | 1.52E+05 | 1.94E−03 |
| B15754 | 1.35E−08 | 2.76E+05 | 3.71E−03 |
| B15749 | 1.38E−08 | 2.69E+05 | 3.72E−03 |
| B15740 | 1.45E−08 | 1.78E+05 | 2.58E−03 |
| B15489 | 1.46E−08 | 6.08E+04 | 8.87E−04 |
| B13880 | 1.59E−08 | 1.04E+05 | 1.66E−03 |
| B15699 | 1.66E−08 | 4.42E+05 | 7.35E−03 |
| B15745 | 1.73E−08 | 2.58E+05 | 4.47E−03 |
| B18174 | 1.82E−08 | 5.16E+04 | 9.38E−04 |
| B15739 | 1.86E−08 | 4.24E+05 | 7.86E−03 |
| B15721 | 2.21E−08 | 5.31E+05 | 1.17E−02 |
| B15673 | 2.44E−08 | 6.95E+04 | 1.70E−03 |
| B15737 | 2.75E−08 | 4.77E+05 | 1.31E−02 |
| B15696 | 2.79E−08 | 1.44E+05 | 4.03E−03 |
| B15491 | 2.98E−08 | 6.24E+04 | 1.86E−03 |
| B15724 | 3.01E−08 | 5.52E+05 | 1.66E−02 |
| B15741 | 3.08E−08 | 2.09E+05 | 6.44E−03 |
| B15757 | 3.72E−08 | 1.05E+05 | 3.91E−03 |

TABLE 1-continued affinities of selected Fabs for human CTLA4

| Hit ID: | $K_D$ (M): | kon(1/Ms): | koff(1/s): |
|---|---|---|---|
| B15759 | 5.36E−08 | 2.46E+05 | 1.32E−02 |
| B15756 | 5.55E−08 | 1.20E+05 | 6.63E−03 |
| B15722 | 6.12E−08 | 7.09E+04 | 4.34E−03 |
| B15750 | 6.23E−08 | 9.37E+04 | 5.84E−03 |
| B15702 | 6.92E−08 | 3.61E+05 | 2.50E−02 |
| B14242 | 7.58E−08 | 3.36E+05 | 2.55E−02 |
| B13878 | 8.59E−08 | 3.08E+04 | 2.64E−03 |
| B15717 | 1.05E−07 | 1.77E+05 | 1.85E−02 |
| B15187 | 1.37E−07 | 2.73E+04 | 3.75E−03 |
| B15695 | 1.52E−07 | 1.81E+05 | 2.76E−02 |
| B15189 | 1.70E−07 | 2.04E+04 | 3.47E−03 |
| B15762 | 1.85E−07 | 4.60E+04 | 8.49E−03 |
| B15730 | 2.59E−07 | 3.45E+04 | 8.93E−03 |

Next, the species cross-reactivity of various Fab hits was determined by ELISA. Briefly, 100 μL of 1.25 μg/mL anti-human IgG (Fab specific) antibody (Sigma, 15260) was coated on a Maxisorp microplate (Thermo Scientific 446469) at 4° C. overnight. After blocking, 100 μL of the Fab hits (2 μg/mL) were added and incubated for one hour. After washing the wells 3-4 times, serial dilutions of human, cynomolgus monkey, or mouse CTLA4 antigens fused with human FC fragments were added and incubated for one hour. After washing, HRP-labelled goat anti-human FC was diluted 1:2000 with PBS, and added to each well for a one hour incubation. Plates were washed three times and incubated with TMB substrate for 3-5 minutes at room temperature. Absorbance at 450 nm was measured after the reaction was stopped. Species cross-reactivity for each of the tested Fabs is summarized in Table 2 below. Interestingly, this analysis identified Fabs with varying cross-reactivities: the results indicated that hits B13873, B15700, B15704, B15706, B15709, B15711, B15712, B15715, B15720, B15725, B15723, B15731, B15732, B15735, B15736, B15744, B15760, B16083, and B15188 bound to human, monkey and mouse CTLA4; hits B15188, B15190, B15701, B15729, B15733, B15742, B15747, B15743, B15751, B15752, B15753 and B18157 bound to human and monkey CTLA4, and weakly bind to mouse CTLA4; hits B13878, B14242, B15189, B15491, B15673, B15694, B15696, B15699, B15702, B15705, B15710, B15716, B15717, B15719, B15721, B15722, B15724, B15728, B15734, B15737, B15738, B15739, B15740, B15745, B15746, B15749, B15750, B15754, B15756, B15757, B15759 and B15762 bound to human CTLA4, but not to mouse CTLA4; hit B15688 bound to human and mouse CTLA4, but not to monkey CTLA4; and hits B13874, B13880, B13898, B15187, B15489, B15672, B15695, B15730, B15741, B18153 and B18174 bound to human CTLA4, but not to monkey or mouse CTLA4.

TABLE 2

Fab cross-reactivities with human, monkey, and mouse CTLA4

| Hit ID: | Binds Human CTLA? | Binds Monkey CTLA4? | Binds Mouse CTLA4? |
|---|---|---|---|
| B13873 | Yes | Yes | Yes |
| B15688 | Yes | No | Yes |
| B15700 | Yes | Yes | Yes |
| B15704 | Yes | Yes | Yes |
| B15706 | Yes | Yes | Yes |
| B15709 | Yes | Yes | Yes |

TABLE 2-continued

Fab cross-reactivities with human, monkey, and mouse CTLA4

| Hit ID: | Binds Human CTLA? | Binds Monkey CTLA4? | Binds Mouse CTLA4? |
|---|---|---|---|
| B15711 | Yes | Yes | Yes |
| B15712 | Yes | Yes | Yes |
| B15715 | Yes | Yes | Yes |
| B15720 | Yes | Yes | Yes |
| B15723 | Yes | Yes | Yes |
| B15725 | Yes | Yes | Yes |
| B15731 | Yes | Yes | Yes |
| B15732 | Yes | Yes | Yes |
| B15735 | Yes | Yes | Yes |
| B15736 | Yes | Yes | Yes |
| B15744 | Yes | Yes | Yes |
| B15760 | Yes | Yes | Yes |
| B16083 | Yes | Yes | Yes |
| B15188 | Yes | Yes | weak |
| B15190 | Yes | Yes | weak |
| B15701 | Yes | Yes | weak |
| B15729 | Yes | Yes | weak |
| B15733 | Yes | Yes | weak |
| B15742 | Yes | Yes | weak |
| B15743 | Yes | Yes | weak |
| B15747 | Yes | Yes | weak |
| B15751 | Yes | Yes | weak |
| B15752 | Yes | Yes | weak |
| B15753 | Yes | Yes | weak |
| B18157 | Yes | Yes | weak |
| B13874 | Yes | No | No |
| B13878 | Yes | Yes | No |
| B13880 | Yes | No | No |
| B13898 | Yes | No | No |
| B14242 | Yes | Yes | No |
| B15187 | Yes | No | No |
| B15189 | Yes | Yes | No |
| B15489 | Yes | No | No |
| B15491 | Yes | Yes | No |
| B15672 | Yes | No | No |
| B15673 | Yes | Yes | No |
| B15694 | Yes | Yes | No |
| B15695 | Yes | No | No |
| B15696 | Yes | Yes | No |
| B15699 | Yes | Yes | No |
| B15702 | Yes | Yes | No |
| B15705 | Yes | Yes | No |
| B15710 | Yes | Yes | No |
| B15716 | Yes | Yes | No |
| B15717 | Yes | Yes | No |
| B15719 | Yes | Yes | No |
| B15721 | Yes | Yes | No |
| B15722 | Yes | Yes | No |
| B15724 | Yes | Yes | No |
| B15728 | Yes | Yes | No |
| B15730 | Yes | No | No |
| B15734 | Yes | Yes | No |
| B15737 | Yes | Yes | No |
| B15738 | Yes | Yes | No |
| B15739 | Yes | Yes | No |
| B15740 | Yes | Yes | No |
| B15741 | Yes | No | No |
| B15745 | Yes | Yes | No |
| B15746 | Yes | Yes | No |
| B15749 | Yes | Yes | No |
| B15750 | Yes | Yes | No |
| B15754 | Yes | Yes | No |
| B15756 | Yes | Yes | No |
| B15757 | Yes | Yes | No |
| B15759 | Yes | Yes | No |
| B15762 | Yes | Yes | No |
| B18153 | Yes | No | No |
| B18174 | Yes | No | No |

Example 2: IgG Conversion and Expression 13 of the refined hits from Example 1 above were then converted into human IgG1 antibodies for detailed biophysical and functional characterization (Table 3). The heavy and light chains of Fab Hits B15709, B15716, B15722, B15732, B15740, B15744, B15756, B15700, B15711, B15717, B15735, B15736 and B16083 were separately cloned into the mammalian expression vector pTT5-SPB. The heavy and light chain of a reference antibody was also cloned into pTT5-SPB.

TABLE 3

Fab hits cloned as IgG1 antibodies

| Antibody (AB) Name: | Fab Hit ID: | Isotype: |
|---|---|---|
| TY21585 | B15709 | hIgG1 |
| TY21586 | B15716 | hIgG1 |
| TY21587 | B15722 | hIgG1 |
| TY21588 | B15732 | hIgG1 |
| TY21589 | B15740 | hIgG1 |
| TY21580 | B15744 | hIgG1 |
| TY21591 | B15756 | hIgG1 |
| TY21687 | B15700 | hIgG1 |
| TY21688 | B15711 | hIgG1 |
| TY21689 | B15717 | hIgG1 |
| TY21680 | B15735 | hIgG1 |
| TY21691 | B15736 | hIgG1 |
| TY21692 | B16083 | hIgG1 |
| TAC2114 | Reference | hIgG1 |

Pairs of plasmids encoding the antibody heavy and lights chains were transiently transfected into 293F cells following the manufacturer's protocol. The supernatants of cells transfected with plasmids encoding antibodies TY21585, TY21586, TY21587, TY21588, TY21589, TY21580, or TY21591 were harvested, cleared by centrifugation and filtration, and the resulting IgGs were purified with standard protein A affinity chromatography (MabSelect SuRe, GE Healthcare). The proteins were eluted and neutralized, and buffer exchanged into 20 mM PB buffer (20 mM NaH2PO4, 150 mM NaCl, pH 7.0). Protein concentrations were determined by UV-spectrophotometry, and IgG purity was analyzed under denaturing, reducing and non-reducing conditions by SDS-PAGE or SEC-HPLC.

The supernatants of cells transfected with plasmids encoding antibodies TY21687, TY21689, TY21680, TY21691, or TY21692 were harvested, cleared by centrifugation and filtration, and the resulting IgGs were purified with standard protein A affinity chromatography (MabSelect SuRe, GE Healthcare). The proteins were eluted and neutralized, and buffer exchanged into 20 mM Histidine buffer (20 mM Histidine, 3.5 mL 6 M HCl, pH5.5). Protein concentrations were determined by UV-spectrophotometry, and IgG purity was analyzed under denaturing, reducing and non-reducing conditions by SDS-PAGE or SEC-HPLC.

Example 3: In Vitro Functional Characterization of IgG-Converted Antibodies

Binding affinity and kinetics of antibodies against human, monkey and mouse CTLA4 were examined (Table 4) by surface plasmon resonance (SPR) analysis using a Biacore™ T200 instrument (Biacore AB, Uppsala, Sweden) according to the manufacturer's guidelines. Anti-Human IgG (Fc) antibody from Human Antibody Capture Kit (GE BR-1008-39) was immobilized on CM5 chips by coupling of its amine groups onto carboxylated surfaces of sensor chips according to the instructions of an Amine Coupling kit (GE Biacore #BR-1000-50). The immobilized Anti-Human IgG (Fc) antibody was used to capture antibodies TY21585, TY21586, TY21580, TY21591, TY21687, TY21689, TY21680, TY21691, TY21692 and TAC2114. TAC2114 has the same amino acid sequence as the commercial antibody Ipilimumab. Binding was measured at six different concentrations (3.13, 6.25, 12.5, 25, 50, and 100 nM diluted in running buffer), and a flow rate of 30 μl/min was used. The running buffer used was HBS-EP (100 mM HEPES, 1.5M sodium chloride, 0.05% sur-factant P20, pH 7.6). The association and dissociation curves were fitted to a 1:1 Langmuir binding model using Biacore T200 Evaluation Software (Biacore AB) according to the manufacturer's guidelines. As shown in Table 4 below, all of the tested antibodies were able to bind human and monkey CTLA4, and all antibodies except for TY21591, TY21689, and TAC2114 were also capable of binding to mouse CTLA4.

TABLE 4 binding affinity of IgG1 antibodies to human, monkey, and mouse CTLA4

| Ab name: | $K_D$ (nM) | | |
|---|---|---|---|
| | Human CTLA4: | Monkey CTLA4: | Mouse CTLA4: |
| TY21585 | 8.15 | 8.26 | 1.71 |
| TY21586 | 7.80 | 15.00 | 303 |
| TY21580 | 2.58 | 0.44 | 0.51 |
| TY21591 | 9.68 | 3.27 | NC |
| TY21687 | 1.82 | 1.52 | 2.76 |
| TY21689 | 0.95 | 0.91 | NC |
| TY21680 | 1.48 | 1.29 | 0.67 |
| TY21691 | 2.08 | 2.44 | 1.46 |
| TY21692 | 3.95 | 2.76 | 1.12 |
| TAC2114 | 6.68 | 1.98 | NC |

NC = not cross-reactive.

Figure 1B:
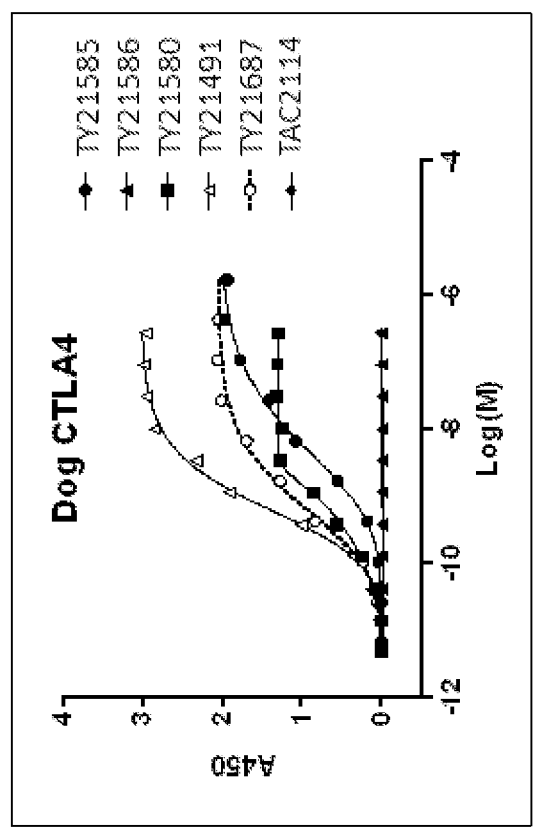

The ability of certain IgG antibodies to bind to soluble human (FIG. 1A, Table 5A) or canine (FIG. 1B, Table 5B) CTLA4 was next tested. 1 μg/mL human CTLA4 fused with human FC fragment, or canine CTLA4 fused with His tag, were prepared and used to coat an ELISA plate at 2-8° C. overnight. After blocking, 100 μL serial diluted IgG antibodies were added and incubated at 37° C. for 1 hour. Plates were washed for four times and then incubated with HRP-anti human IgG (Fab specific) (1:6000 dilution) at 37° C. for 1 hour. Plates were washed again four times and incubated with TMB substrate for 15 minutes at room temperature. Absorbance at 450 nm was measured after the reaction was stopped. The data was analyzed by Graphpad Prism 6 with nonlinear fitting. As shown in FIGS. 1A-B and Tables 5A-B, all tested antibodies bound to human CTLA4, and, with the exception of antibodies TY21586 and TAC2114, also bound to canine CTLA4. Interestingly, TY21580 bound both human and dog CTLA4 with the highest affinity, with $K_D$s of 0.27 and 0.49, respectively.

TABLE 5A

ELISA for human CTLA4

| Ab name: | LogEC$_{50}$: | EC$_{50}$: | | $K_D$ |
|---|---|---|---|---|
| | | M | nM | nM |
| TY21585 | −9.256 | 5.552E−10 | 0.5552 | 0.56 |
| TY21586 | −8.896 | 1.27E−09 | 1.2710 | 1.27 |
| TY21580 | −9.571 | 2.685E−10 | 0.2685 | 0.27 |
| TY21591 | −9.080 | 8.309E−10 | 0.8309 | 0.83 |
| TY21687 | −9.495 | 3.201E−10 | 0.3201 | 0.32 |
| TAC2114 | −9.482 | 3.296E−10 | 0.3296 | 0.33 |

TABLE 5B

ELISA for canine CTLA4

| Ab name: | LogEC$_{50}$: | EC$_{50}$: | | $K_D$ |
|---|---|---|---|---|
| | | M | nM | nM |
| TY21585 | −8.219 | 6.045E−09 | 6.0450 | 6.05 |
| TY21586 | ND | ND | ND | ND |
| TY21580 | −9.313 | 4.86E−10 | 0.4860 | 0.49 |
| TY21591 | −9.151 | 7.066E−10 | 0.7066 | 0.71 |
| TY21687 | −9.128 | 7.451E−10 | 0.7451 | 0.75 |
| TAC2114 | ND | ND | ND | ND |

ND = not determined.

Figure 2:
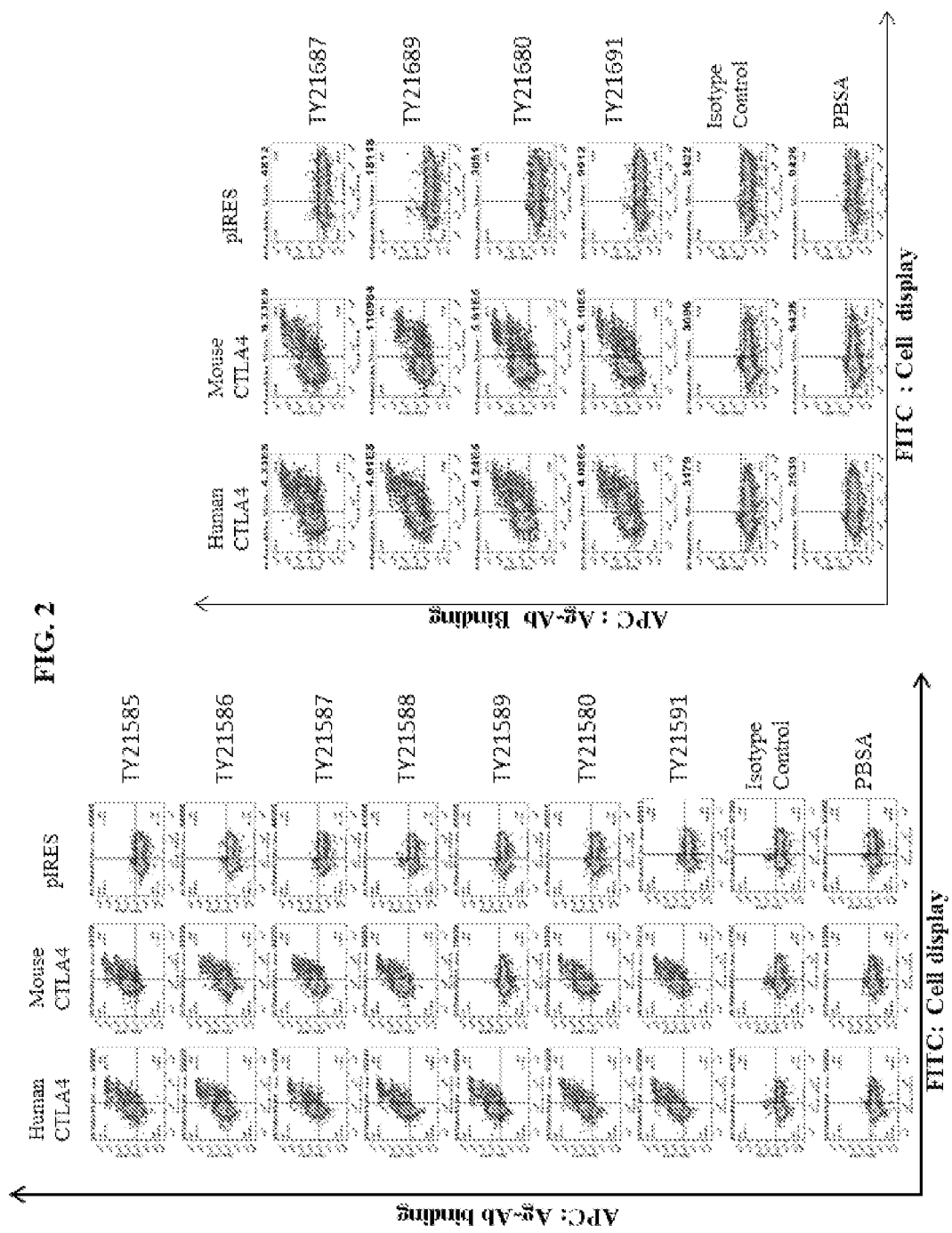
FIG. 2 shows species cross-reactivity of the indicated antibodies, isotype control, or vehicle (PBSA) to HEK293F cells transiently overexpressing empty vector (pIRES), or mouse or human CTLA4, as determined by flow cytometry.

The affinities of the antibodies were also assessed against human and mouse CTLA4 transiently expressed on the surface of HEK293F cells (FIG. 2). Briefly, HEK293F cells were transfected with a plasmid expressing full-length human, monkey or mouse CTLA4 from a bicistronic IRES vector also encoding EGFP, and EGFP expression was used to identify the transfected cells. After 48 hours, the mammalian cell suspension ($2 \times 10^5$/well) was transferred to an Eppendorf tube, centrifuged, the supernatant was discarded, the cells were resuspended with 1 mL PBSA (to a density is $4 \times 10^6$ cells/mL), and added to a 96 well plate. 3-fold serial dilutions of the test antibodies (15 μg/mL, 5 μg/mL, 1.67 μg/mL, 0.55 μg/mL, 0.185 μg/mL, 0.062 μg/mL, and 0.0309 μg/mL, plus a 0 μg/mL blank control) were pipetted into the 96-well plate, incubated on ice for 1 hour (protected from light), the cells were washed with pre-chilled 1×PBSA buffer, and subsequently incubated with an Alexa Fluor® 647 conjugated mouse anti-human FC antibody for 30 minutes on ice. The cells were then washed once prior to analysis by flow cytometry (Beckman® CytoFlex). As shown in FIG. 2, all test antibodies were capable of binding human CTLA4 expressed on the surface of HEK293F cells, and, with the exception of TY21589, all antibodies bound to mouse cell-surface exposed mouse CTLA4. TY21580 bound to human and mouse CTLA4 expressed on the cell surface with low nM affinity, whereas antibodies TY21585 and TY21586 bound to human CTLA4 expressed on the cell surface with high nM affinities.

Binding affinity and kinetics of antibodies TY21580, TY21687, TY21680 and TY21691 against rat CTLA4 protein were also tested using a ForteBio red 96 instrument (Pall, USA). SA sensors (Pall, 185019) were used to immobilize biotinylated rat CTLA4 protein fused with human FC, and the sensors were then contacted with the IgG-converted hits at a concentration of 15 μg/mL (diluted with KB Buffer, PBS buffer supplemented with 0.02% Tween 20 and 0.1% BSA) for 300 seconds, then dissociated in KB buffer for 300 seconds. The association and dissociation curves were fitted to a 1:1 Langmuir binding model using ForteBio Data Analysis 7.1 (Pall, USA) according to the manufacturer's guidelines. As shown in Table 6 below, all of the tested antibodies were able to bind to rat CTLA4.

TABLE 6 binding affinity of test antibodies for rat CTLA4

| Ab name: | $K_D$ (nM): |
|---|---|
| TY21580 | 0.38 |
| TY21687 | 0.78 |
| TY21680 | 0.21 |
| TY21691 | 0.58 |

Binding of IgGs to Activated T Cells

Figure 3:
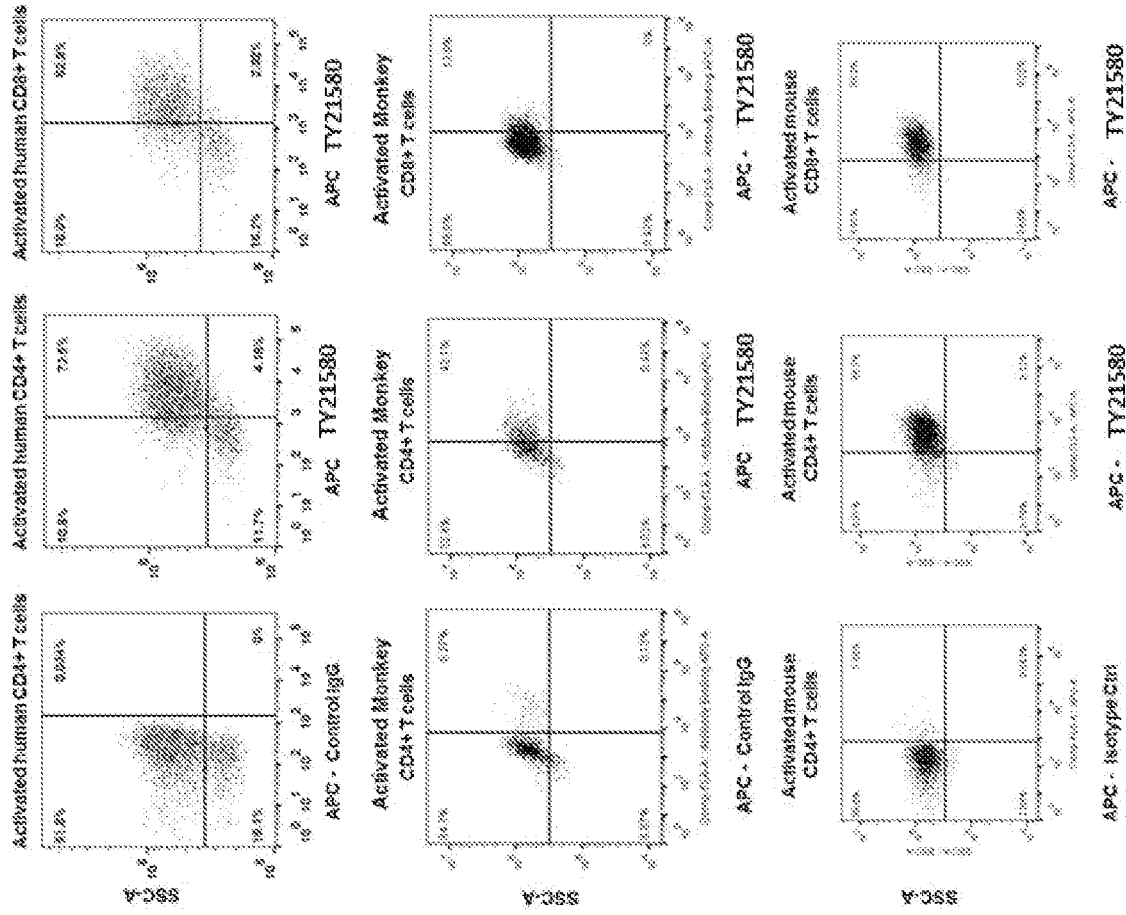
FIG. 3 shows binding of antibody TY21580, or isotype control, to activated human, monkey, and mouse T cells, as determined by flow cytometry.

Next, the ability of the IgGs to bind to activated human, monkey, and mouse T cells was tested. Human PBMCs were freshly isolated from the blood of a healthy donor (#106) by density gradient centrifugation using Histopaque-1077 (Sigma). Human T cells were isolated from PBMCs using the Human T Cell Enrichment Kit (StemCell Technologies), followed by stimulation with anti-CD3 and anti-CD28 antibodies. Briefly, anti-CD3 antibody (Clone: OKT3, BioLegend) was coated at 0.2 µg in 200 µL per well in a 96 well plate at 4° C. overnight. After washing, T cells suspended in RPMI-1640 containing 10% FBS and 1% Penn/Strep were added to the plate. 5×10E5 T cells in 200 µL were added to each well of the 96 well plate. Then 1 µL of anti-human CD28 antibody (Clone: 28.2, BD) was added to a final concentration of 5 µg/mL. T cells were incubated for 96 hours, and then the binding of TY21580 to T cells was determined by flow cytometric analysis (FIG. 3). T cells were stained with APC-labeled TY21580 or human IgG1 (isotype control) for 2 hours at 37° C. After washing, cells were analyzed on the CytoFLEX flow cytometer (Beckman Coulter) and the data was analyzed with FlowJo software. As shown in FIG. 3, TY21580 bound to activated CD4+ and CD8+ human T cells, while control IgG showed no binding. In addition, APC-TY21580 showed no binding to resting T cells (data not shown).

Monkey PBMCs were freshly isolated from the blood of a naïve cynomolgus monkey by density gradient centrifugation using Histopaque-1077 (Sigma). Monkey T cells were isolated from PBMCs using the Pan T cell Isolate Kit Non-human primate (Miltenyi Biotec), followed by stimulation with anti-CD3 and anti-CD28 antibodies. Briefly, anti-CD3 antibody (Clone: SP34, BD) was coated at 0.2 µg in 200 µL per well in a 96 well plate at 4° C. overnight. After washing, T cells suspended in RPMI-1640 containing 10% FBS and 1% Penn/Strep were added to the plate. 2×10E5 T cells in 200 µL were added to each well of the 96 well plate. Then 1 µL of anti-human CD28 antibody (Clone: 28.2, BD) was added to a final concentration of 5 µg/mL. T cells were incubated for 72 h, and binding of TY21580 to the T cells was determined by flow cytometric analysis (FIG. 3). T cells were stained with APC-labeled TY21580 or human IgG1 (isotype control) for 2 h at 37° C. After washing, cells were analyzed on the CytoFLEX flow cytometer (Beckman Coulter) and the data was analyzed with FlowJo software. As shown in FIG. 3, TY21580 bound to activated CD4+ and CD8+ monkey T cells, while control IgG showed no binding. In addition, APC-TY21580 showed no binding to resting T cells (data not shown).

Mouse T cells isolated from adult BALB/c mouse spleens were used to induce CTLA-4 expression. Splenocytes from fresh mouse spleens were used to isolate T cells with the EasySep™ Mouse T Cell Isolation kit (StemCell Technologies), followed by stimulation with anti-mouse CD3 and anti-CD28 antibodies. Briefly, anti-mouse CD3c antibody (Biolegend) was coated at 0.2 µg in 200 µL per well in a 96 well plate at 4° C. overnight. After washing, mouse T cells suspended in RPMI-1640 containing 10% FBS and 1% Penn/Strep were added to each well of the plate at 5×10E5 T cells in 200 µL. Then 1 µL of anti-mouse CD28 antibody (eBioscience) was added to a final concentration of 5 µg/mL. Mouse T cells were incubated for 72 h and then the binding of TY21580 to T cells was determined by flow cytometric analysis (FIG. 3). T cells were stained with APC-labeled TY21580 or human IgG1 (isotype control) for 2 h at 37° C. After washing, cells were analyzed on the CytoFLEX flow cytometer (Beckman Coulter) and the data was analyzed with FlowJo software. As shown in FIG. 3, TY21580 bound to activated mouse CD4+ and CD8+ T cells, while control IgG showed no binding.

Binding Selectivity of Antibodies for Human CTLA4

Figure 4A:
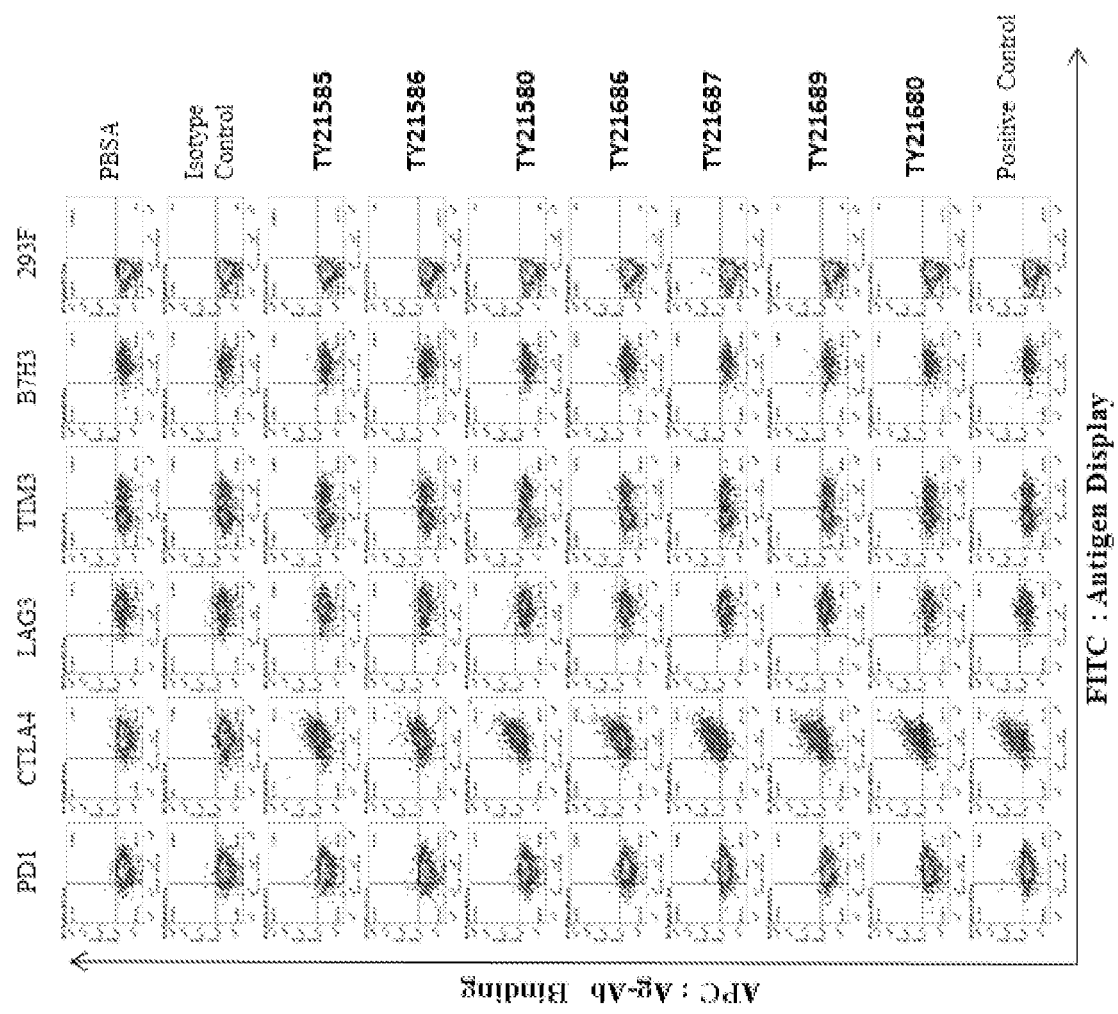
FIGS. 4A-C show antibody specificity for CTLA4, as determined by flow cytometry.
Figure 4B:
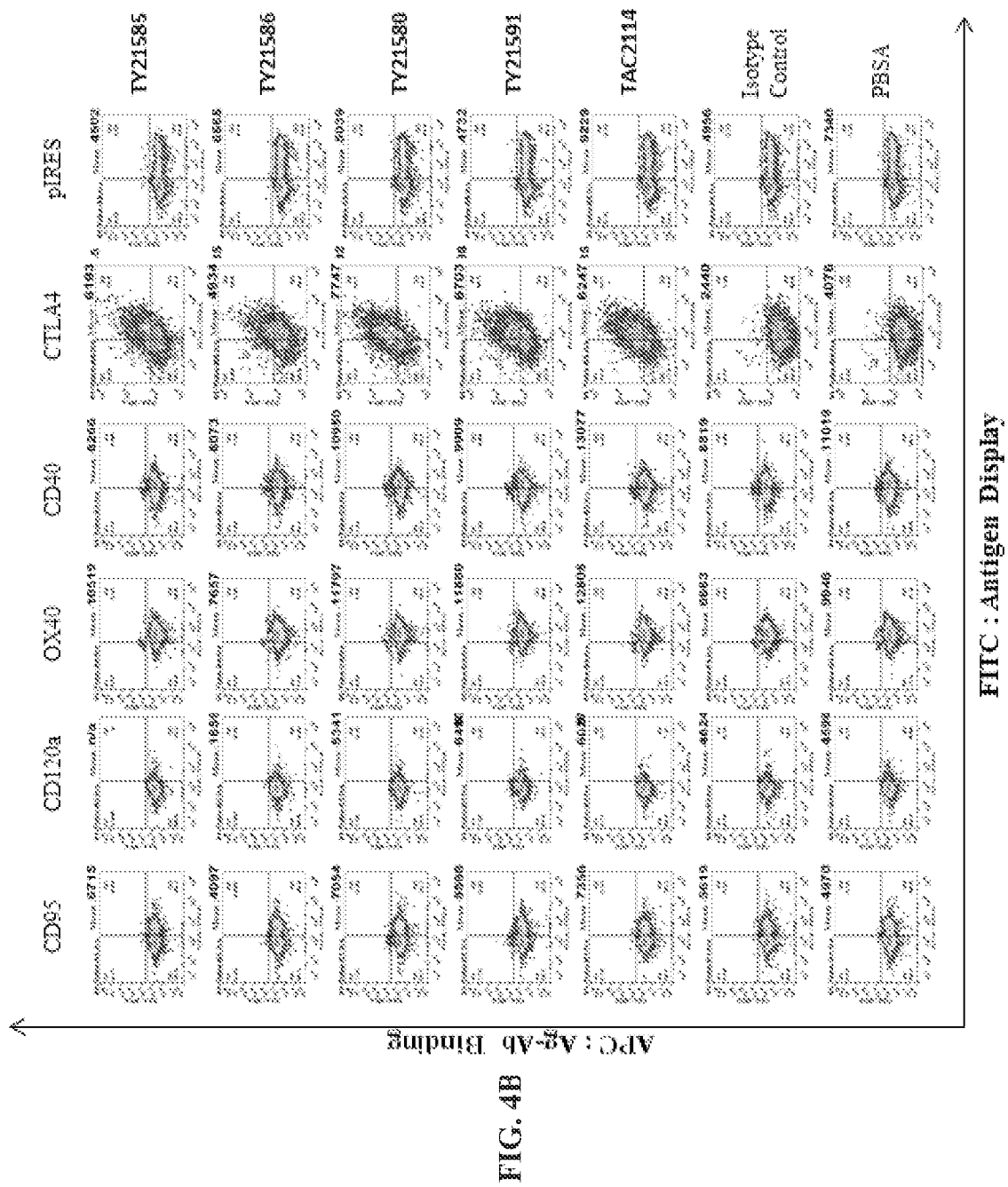
Figure 4C:
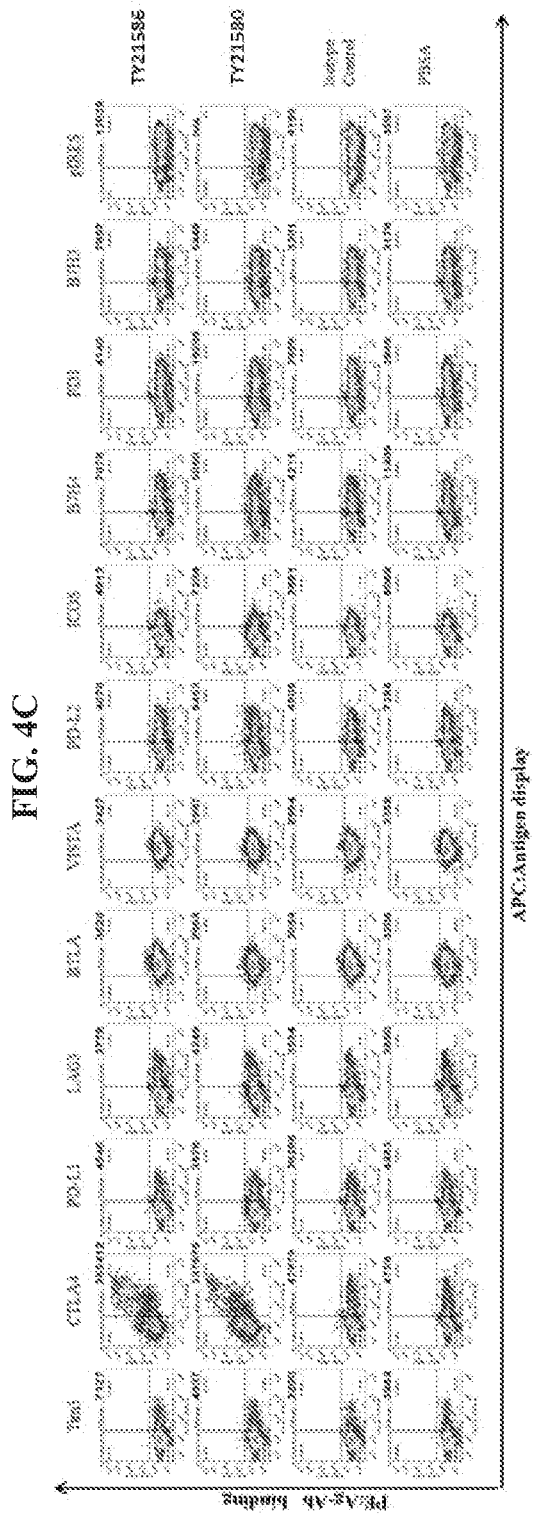

Antibody selectivity was next examined. Human CTLA4, PD1, LAG3, Tim3, B7H3, CD95, TNFR1, OX40, CD40, PD-L1, BLTA, VISTA, PDL2, ICOS and B7H4 were transiently overexpressed on the surface of HEK293F cells. Transfected cells were washed in pre-chilled 1×PBSA buffer (1.76 mM KH2PO4, 10.14 mM Na2HPO4.12H2O, 2.68 mM KCl, 136.89 mM NaCl and 1% BSA), then incubated with 100 nM test antibodies for 1 hour on ice. Cells were washed once with staining buffer, and Alexa Fluor® 647 conjugated mouse anti-human FC antibodies were added and incubated for 30 minutes on ice, protected from light. Samples were washed once with staining buffer prior to analysis by flow cytometry. TY21585 TY21586, TY21580, TY21687, TY21689, TY21680 and TY21691 were tested in human CTLA4, PD1, LAG3, Tim3, and B7-H3 (FIG. 4A); TY21585 TY21586, TY21580 were further tested in human CD95, TNFR1, OX40, and CD40 (FIG. 4B); in addition, TY21586, TY21580 were tested in human PD-L1, BLTA, VISTA, PDL2, ICOS and B7-H4 (FIG. 4C). As shown in FIGS. 4A-C, all tested antibodies bound specially to human CTLA4, and not to any other tested antigen (or parental cells transfected with empty vectors).

Ligand Competition Binding by ELISA

Figure 5A:
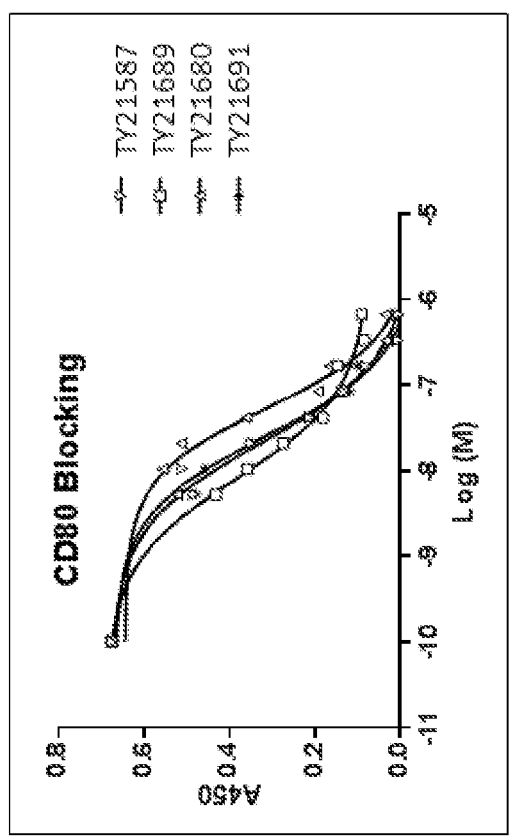
FIGS. 5A-D show the blocking capabilities of the antibodies, as determined by ELISA.
Figure 5B:
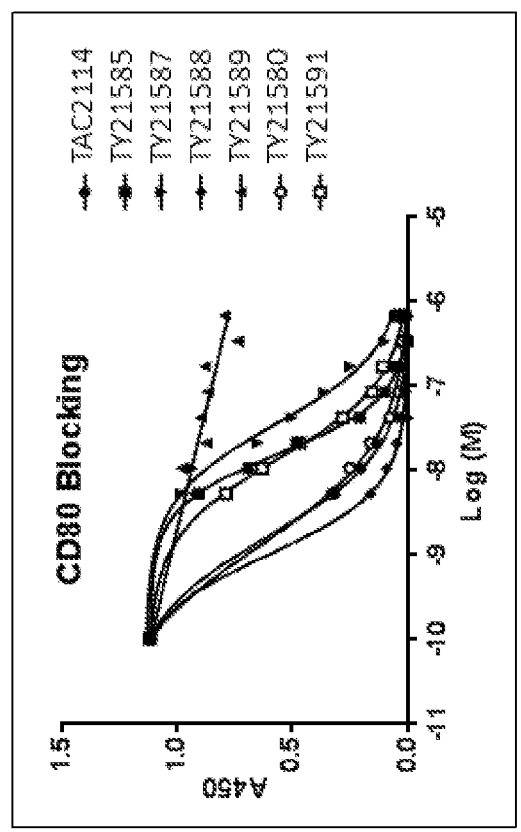

Antibodies were then tested for their ability to block binding of CTLA4 to its cognate ligands CD80 and CD86 by ELISA. Recombinant human CTLA4 (fused with human Fc and His tag) was diluted to 1 µg/mL in carbonate buffer solution, pH 9.4, and coated on a Maxisorp plate at 4° C. overnight. Plates were blocked with PBS supplemented with 2% (w/v) skim milk at 37° C. for 1 hour. After washing, 50 uL biotinylated CD80 (4 µg/mL) and 50 uL of various concentrations of test antibodies (2-fold serial dilutions ranging from 200 µg/mL to 1.56 µg/mL) were added successively to each well and incubated at 37° C. for 1 hour. Plates were washed four times, and 100 µL HRP-neutravidin (1:1000) was added to each well and incubated at 37° C. for 1 hour. Plates were washed as previously described, and 50 µL TMB substrate solution was added and incubated at room temperature for 5 minutes before the reaction was stopped by 50 µL sulfate acid (2M). As shown in FIGS. 5A-B, all tested antibodies blocked binding of CTLA4 to CD80, except for TY21589.

Figure 5C:
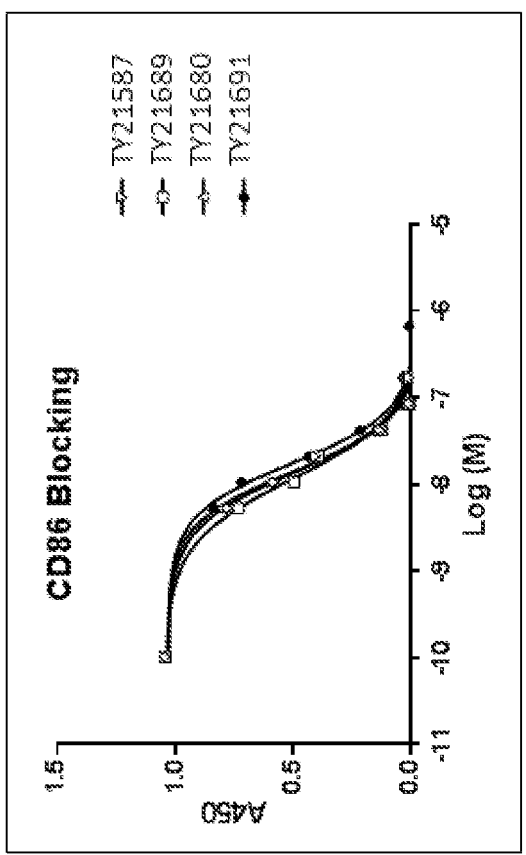
Figure 5D:
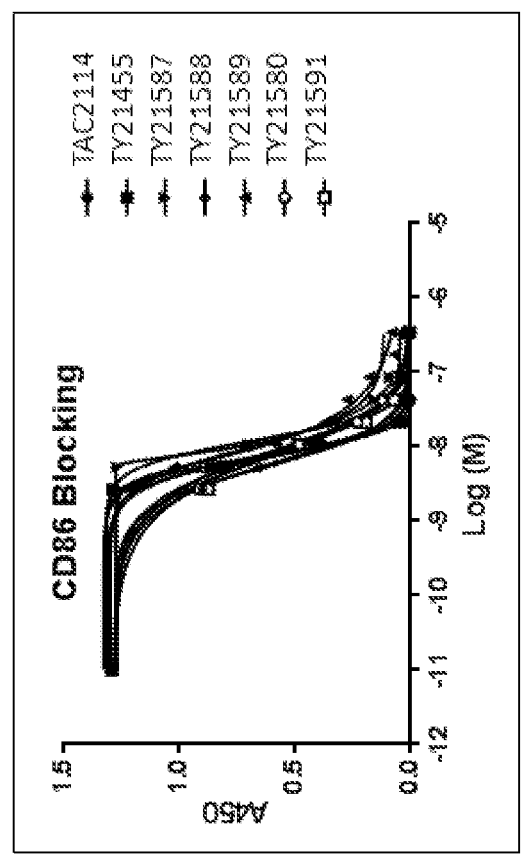

Recombinant human CD86 fused with human Fc was diluted to 1 µg/mL in carbonate buffer solution, pH 9.4, and coated on a Maxisorp plate at 4° C. overnight. Plates were blocked with PBS supplemented with 2% (w/v) skim milk at 37° C. for 1 hour. After washing, 50 uL biotinylated human CTLA4 fused with human FC and His tag (2.8 µg/mL), and 50 uL of various concentrations of test antibodies (2-fold serial dilutions ranging from 100 µg/mL to 0.78 µg/mL) were added successively to each well and incubated at 37° C. for 1 hour. Plates were washed four times, and 100 µL HRP-neutravidin (1:1000) were added to each well and incubated at 37° C. for 1 hr. Plates were washed as previously described, and 50 µL TMB substrate solution was added and incubated at room temperature for 5 minutes before the reaction was stopped by 50 µL sulfate acid (2M). As shown in FIGS. 5C-D, all tested antibodies blocked binding of CTLA4 to CD86.

Ligand Competition Binding by Flow Cytometry

Antibodies were also tested for their ability to block binding of CTLA4 to its cognate ligands CD80 and CD86 by flow cytometry. The plasmid encoding full-length human CTLA4 was transiently expressed in HEK293F cells. Cells were washed with staining buffer (PBSA buffer including 1.76 mM $KH_2PO_4$, 10.14 mM $Na_2HPO_4.12H_2O$, 2.68 mM KCl, 136.89 mM NaCl and 1% BSA), and resuspended in staining buffer containing 100 nM test antibodies. After incubation on ice for 60 minutes, 100 nM biotinylated human CD80-Fc-Bio or CD86-Fc-Bio was added to each well and incubated for another 1 hour on ice. Cells were washed with staining buffer once, and 100 µL staining buffer containing Alexa fluor 633 conjugated streptavidin were added and incubated on ice for 30 minutes, protected from light. Cells were washed once, and analyzed by CytoFlex flow cytometry. As shown in FIG. 6A, all tested antibodies blocked binding of CTLA4 to CD80 in a concentration dependent manner. TY21588 showed the strongest blocking capability, followed by TY21580 and TAC2114 with significant blocking; and TY21585, TY21587, TY21589, TY21591 with less effective blocking. TY21589 showed little to no blocking. As shown in FIG. 6B, all tested antibodies blocked binding of CTLA4 to CD86 in a concentration dependent manner. TY21588, TY21589, TY21580, TY21591 and TAC2114 showed the strongest blocking capability; TY21585 and TY21587 had less effective blocking.

Binding to FcγR

Binding affinity of TY21586, TY21580 and TAC2114 against CD16a (176Phe) (Sino Biological Inc, 10389-H08H), CD16a (176Val, 10389-H08H1), CD32a (Sino Biological Inc, 10374-H08H), CD32b (Sino Biological Inc, 10259-H08H), and CD64 (Sino Biological Inc, 10256-H08H) was next tested. Protein binding was examined by surface plasmon resonance (SPR) analysis using a Biacore™ T200 instrument (Biacore AB, Uppsala, Sweden) according to the manufacturer's guidelines. Protein L (Sino Biological Inc. 11044-H07E) was immobilized on CM5 chips by coupling of its amine groups onto carboxylated surfaces of sensor chips according to the instructions of an Amine Coupling kit (GE Biacore #BR-1000-50). The immobilized Anti-Human IgG (Fc) antibody was used to capture TY21586, TY21580 and TAC2114. Serial concentrations (12.5, 25, 50, 25, 100 and 200 nM) diluted in running buffer of FcγR protein were injected at a flow rate of 30 µl/min. The running buffer used was HBS-EP (100 mM HEPES, 1.5M sodium chloride, 0.05% sur-factant P20, pH 7.6). The association and dissociation curves were fitted to a 1:1 Langmuir binding model using Biacore T200 Evaluation Software (Biacore AB, Uppsala, Sweden) according to the manufacturer's guidelines. As shown in Table 7 below, TY21586 and TY21580 showed similar affinity for binding to FcγR, as compared to the reference antibody (TAC2114).

TABLE 7 antibody binding to FcγR

| | $K_D$ (nM) | | | | |
|---|---|---|---|---|---|
| Ab name | CD16a (176Phe) | CD16a (176Val) | CD32a | CD32b | CD64 |
| TY21586 | 143.000 | 453.000 | 884.000 | 1340.000 | 0.214 |
| TY21580 | 145.000 | 624.000 | 884.000 | 1110.000 | 0.202 |
| TAC2114 | 237.000 | 577.000 | 706.000 | 735.000 | 0.255 |

Binding to FcRn

Figure 7:
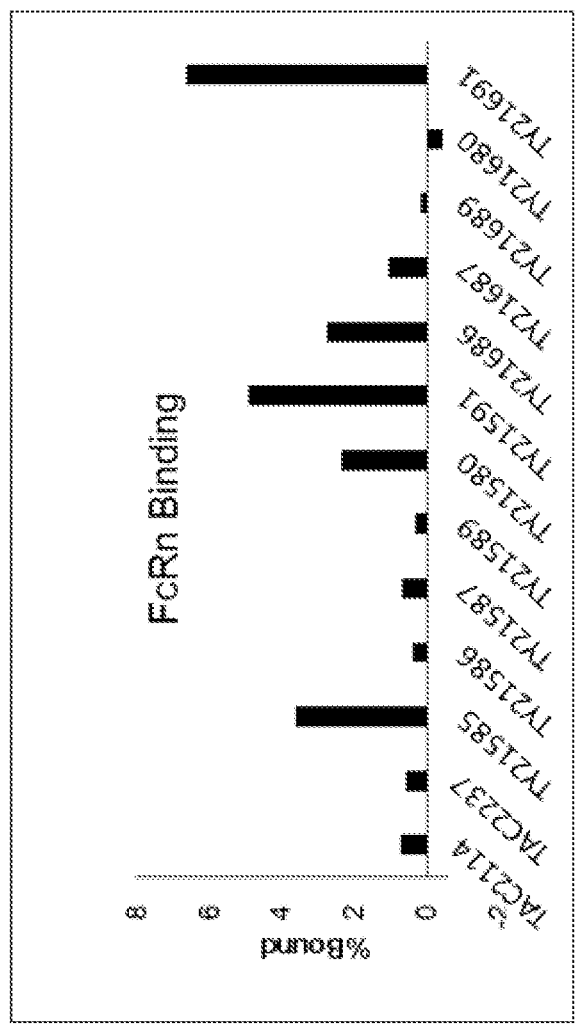
FIG. 7 shows the ability of the indicated antibodies to bind FcRn, as determined by surface plasmon resonance (SPR).

Binding affinity of test antibodies to recombinant human FcRn was examined by surface plasmon resonance (SPR) analysis using a Biacore™ T200 instrument (Biacore AB, Uppsala, Sweden) according to the manufacturer's guidelines. Human FcRn protein (Sino Biological Inc. 11044-H07E) was immobilized on CM5 chips by coupling of its amine groups onto carboxylated surfaces of sensor chips according to the instructions of an Amine Coupling kit (GE Biacore #BR-1000-50). 100 nM of each antibody was diluted in running buffer (50 mM NaPO4, 150 mM NaCl, and 0.05% (v/v) Surfactant 20, pH 6.0), and the samples were injected at a flow rate of 30 µl/min for 120 seconds. As show in FIG. 7, antibodies TY21585, TY21580, TY21591, TY21687, and TY21691 exhibited higher % bound than TAC2114 to FcRn, which indicated that the IgG-FcRn complex on the Biacore chip could undergo conformation change that stabilizes the complex, as compared with the reference antibody (TAC2114). Antibodies TY21586, TY21587, TY21589, TY21689 and TY21680 showed low % bound.

Human PBMC Activation

Figure 8A:
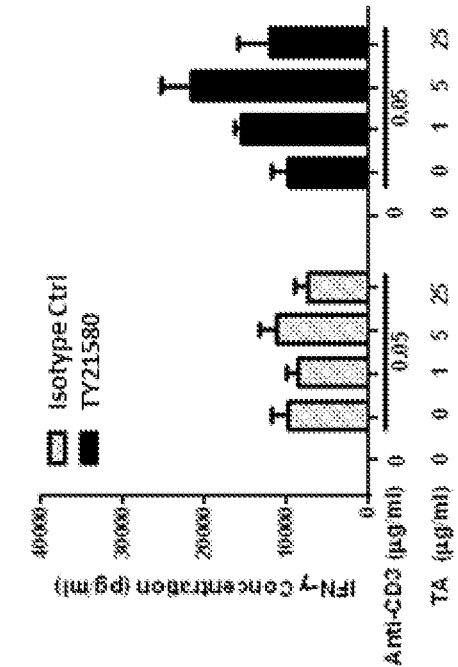
FIG. 8A-B show human peripheral blood mononuclear cell (PBMC) activation by antibody TY21580 or isotype control, as measured by ELISA.
Figure 8B:
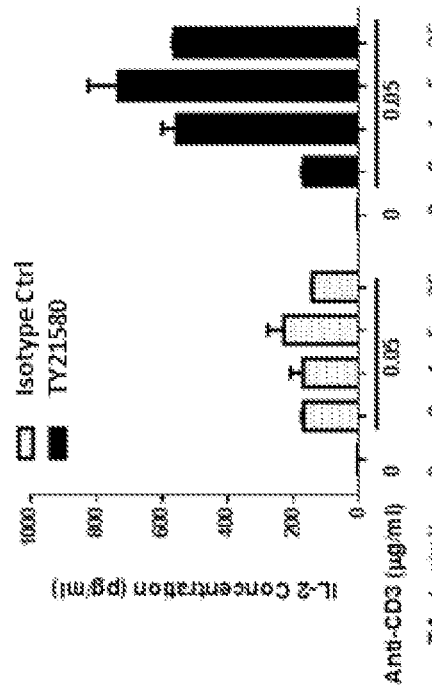
Figure 9:
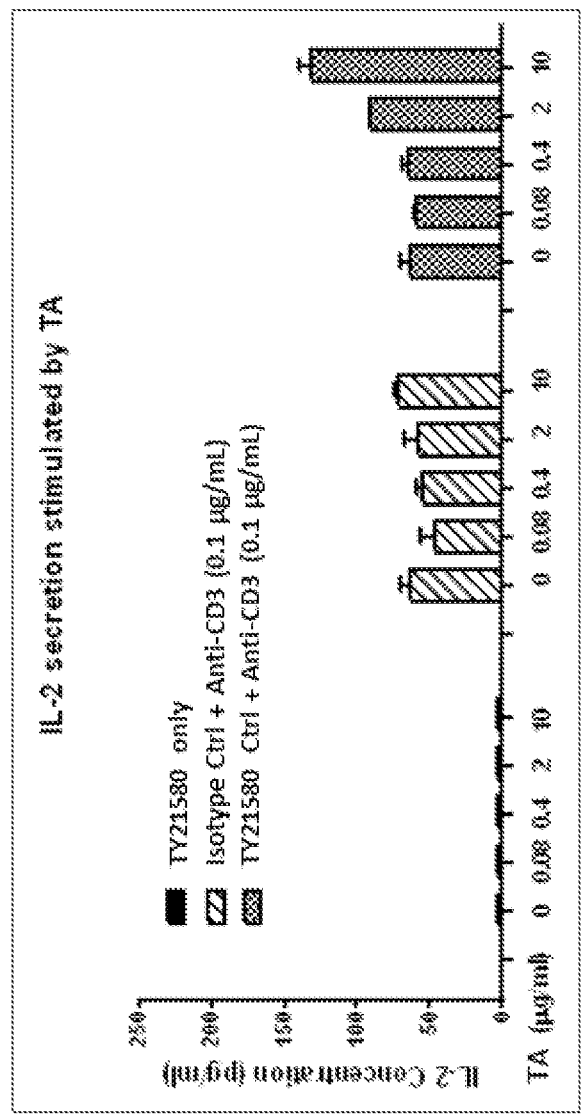
FIG. 9 shows the effect on IL-2 secretion from human PBMCs treated with antibody TY21580 in the presence or absence of an anti-CD3 antibody, as measured by ELISA.

Preliminary studies showed TY21580 did not stimulate human T cell activation or proliferation. Since CTLA4 activity on T cells is related to the first signal (TCR/CD3) and second signals involving B7-CD28/CTLA-4, human PBMCs were chosen, and the activity of TY21580 in the presence of low concentration of anti-CD3 was determined. Anti-CD3 antibody (OKT-3) was coated on a 96 well plate overnight at 4° C. After washing, $1 \times 10^5$ freshly isolated human PBMCs were added to each well, followed by adding the test articles at different concentrations. Induction of IL-2 was measured 48 hours after stimulation using a Human IL-2 ELISA Ready-SET-Go (Invitrogen) kit. IFNγ in the supernatant was measured using a Human IFNγ ELISA Ready-SET-Go (Invitrogen) kit. As shown in FIG. 8A and FIG. 9, antibody TY21580 significantly increased human PBMC activation in the presence of anti-CD3, while TY21580 alone had no activity.

Dendritic Cell MLR Assay

Figure 10:
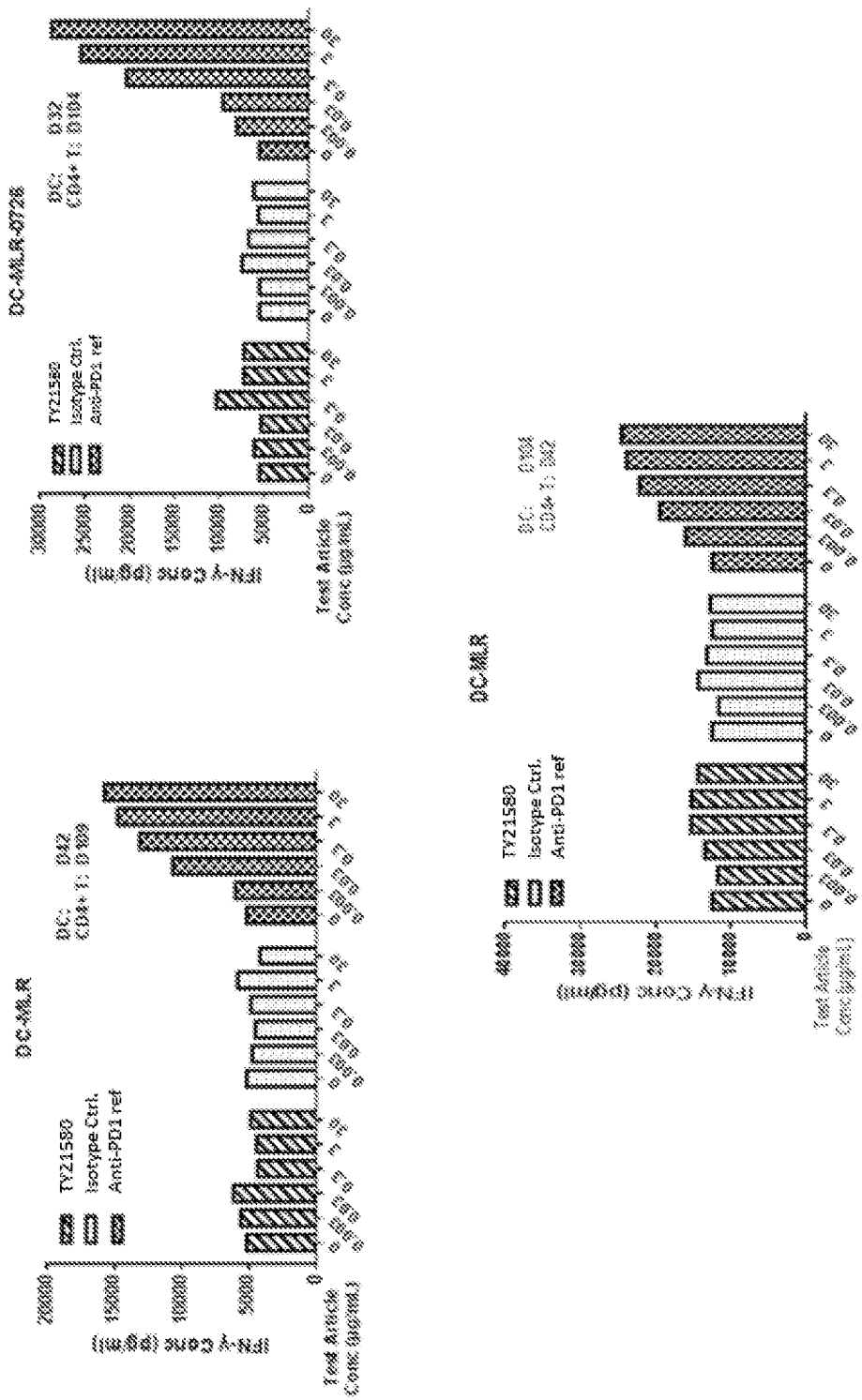
FIG. 10 shows the effect on IFNγ secretion from human dendritic cells (DCs) co-cultured with allogenic CD4+ T cells treated with antibody TY21580, isotype control, or an anti-PD-1 antibody, as measured by ELISA.

DC-MLR assays were conducted using monocyte derived DCs and CD4+T lymphocytes in three donor pairs: D42/D109, D32/D104, and D104/D42 (FIG. 10). To get DC cells, PBMCs were isolated by density gradient centrifugation from a healthy donor, and CD14+ monocytes were purified from PBMCs using a positive selection commercial kit (StemCell). CD14+ monocytes were skewed into DCs by in vitro culturing in RPMI-1640 supplemented with 10% heat-inactivated FBS, 1% penicillin/streptomycin, 20 ng/mL rhGM-CSF and 20 ng/mL rhIL-4 for 6 days. Culture medium was changed with fresh medium on day 3. DC maturation was induced in RPMI-1640 medium supplemented with 10% heat-inactivated FBS, 1% penicillin/streptomycin, and 50 ng/mL rhTNF-α on day 6 for 24 hours. CD4+ T cells were purified by negative isolation from another healthy donor. Test articles were titrated into corresponding concentrations (as shown in FIG. 10). Collected DCs ($1 \times 10^4$) were co-cultured with allogenic CD4+ T cells ($1 \times 10^5$) with or without titrated test articles. Anti-PD1 antibody was used as positive control for DC-MLR assays. On day 5 after co-culture, IFNγ was measured in the supernatant by ELISA using a human IFNγ Ready-SET-Go ELISA kit. As shown in FIG. 10, antibody TY21580 showed weak activity in the DC-MLR assay using human CD4+ T cells and DCs.

ADCC Activity of Antibody TY21580

Figure 11B:
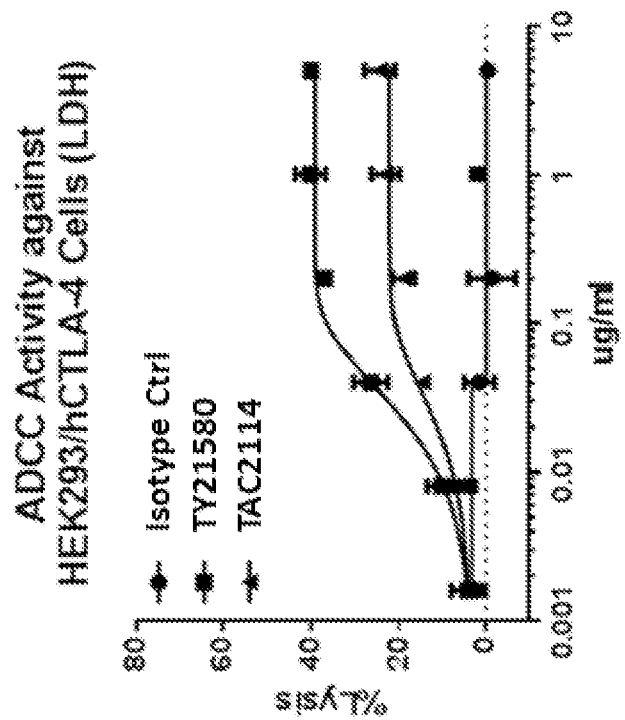
FIGS. 11A-B show the antibody-dependent cell-mediated cytotoxicity (ADCC) activity of exemplary antibodies on HEK293F cells transiently overexpressing human CTLA4, as determined by lactate dehydrogenase (LDH) release assay.
Figure 11A:
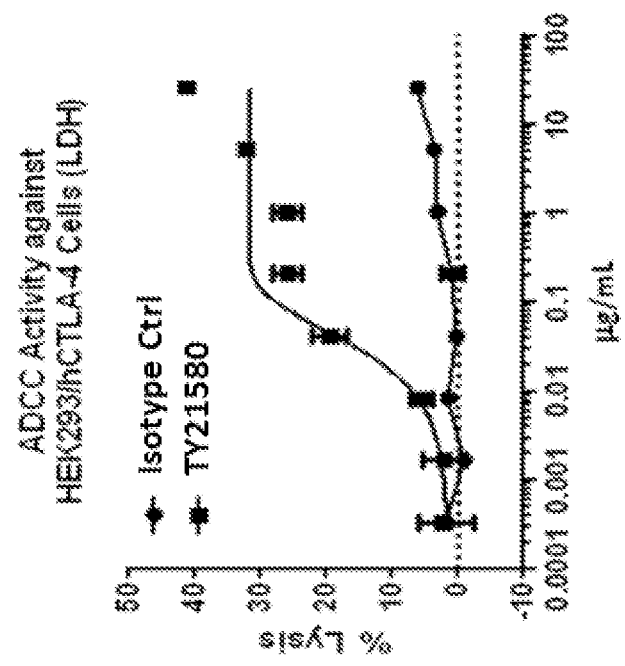

HEK293F cells overexpressing human CTLA-4 were used as target cells to evaluate TY21580-mediated ADCC activity. Human NK cells were freshly isolated from human PBMCs using a human NK isolation kit (StemCell). $1 \times 10^5$ NK cells and $1 \times 10^4$ HEK293F/hCTLA-4 cells (E:T ratio 10:1) were mixed with different concentrations of antibody. After incubation for 4 hours, LDH was measured to determine the ADCC activity. The % lysis was then calculated using the following formula: % Lysis=[(Experimental Release)−Ave (Target+NK)]/[Ave (Target Max)−Ave (Target only)]×100%. As shown in FIGS. 11A-B, TY21580 showed stronger ADCC activity than a reference antibody (TAC2114). Isotype control showed no ADCC activity whatsoever.

Figure 12B:
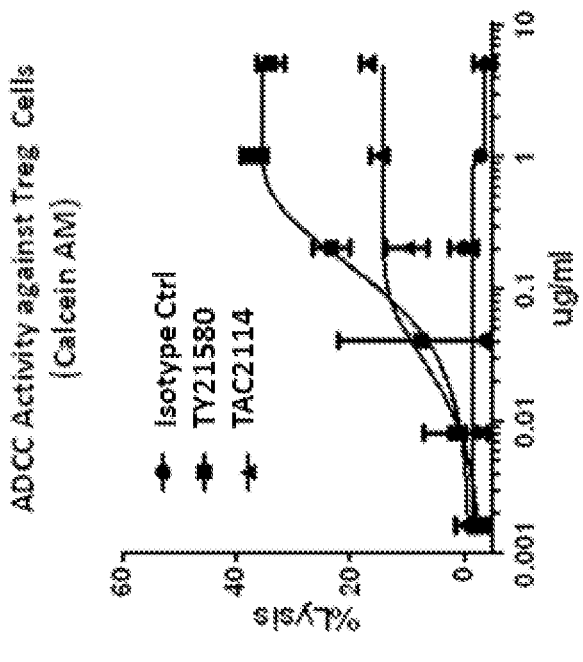
FIGS. 12A-B show the ADCC activity of exemplary antibodies on human Tregs isolated from two donors, as determined by calcein-AM release assay.
Figure 12A:
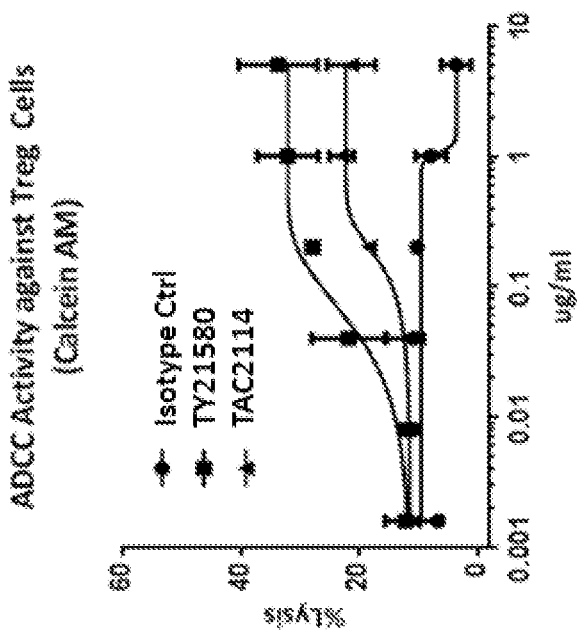

ADCC activity was also evaluated using human Treg cells (A, donor #96; B, donor #12) and NK cells (A, donor #99; .B, donor #05). To get human Treg cells, human PBMCs were freshly isolated from a healthy donor, and Treg cells were negatively selected using an EASYSEP™ Human Regulatory T Cell Enrichment Kit (StemCell Technologies). Enriched human Treg cells were further expanded by CD3/CD28 stimulation in the presence of IL-2, and confirmed by CD25 and FOXP3 staining and FACS analysis. To get human NK cells, human PBMCs were freshly isolated from another healthy donor, and NK cells were isolated using a Human NK isolation kit (StemCell Technologies). Human Treg cells were labeled with 10 μM Calcein-AM (Invitrogen) at 37° C. for 30 min. After washing three times, labeled Treg cells were mixed with different concentration of test articles, followed by the addition of NK cells. $1 \times 10^5$ NK cells and $1 \times 10^4$ of labeled human Treg cells were added to the wells of a 96 well plate, and mixed to make the E:T ratio 10:1. After 4 hours of incubation, calcein-AM concentration in the supernatant was measured to determine the ADCC activity using the following formula: % Lysis=[(Experimental Release)−Ave (Target+NK)]/[Ave (Target Max)−Ave (Target only)]×100%. As shown in FIGS. 12A-B, antibody TY21580 showed stronger ADCC activity than the reference antibody (TAC2114). Isotype control showed no ADCC activity.

CDC Activity of TY21580

Figure 13:
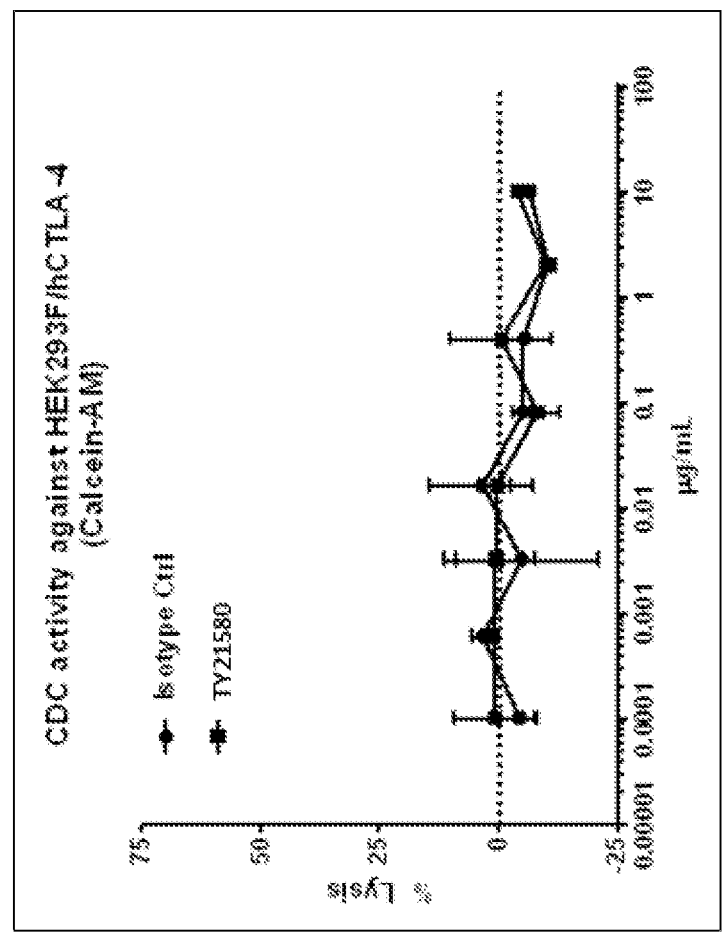
FIG. 13 shows the complement-dependent cytotoxicity (CDC) activity of antibody TY21580, or isotype control, on HEK293F cells transiently overexpressing human CTLA4, as determined by calcein-AM release assay.

HEK293F cells overexpressing human CTLA-4 were labeled with 10 μM Calcein-AM (Invitrogen) at 37° C. for 30 min. To the wells of the 96 well plate, antibodies of different concentrations were mixed with $1 \times 10^4$ labeled cells and 5% normal human serum complement (NHSC, Quidel). After 5 hours of incubation, calcein-AM in the supernatant was measured to determine the CDC activity (FIG. 13).

Figure 14:
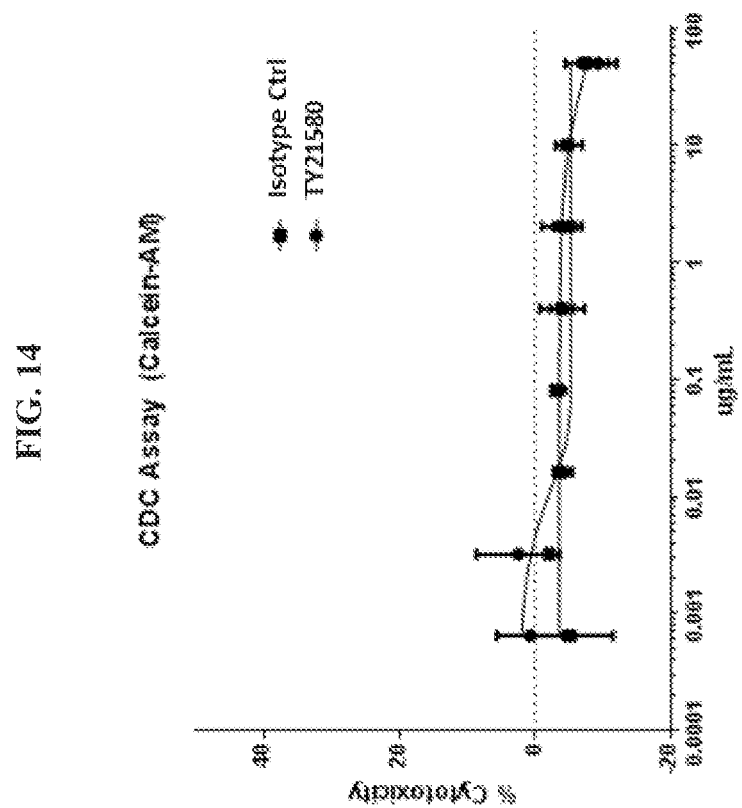
FIG. 14 shows the CDC activity of antibody TY21580, or isotype control, on activated human CD4+ T cells, as determined by calcein-AM release assay.

Human PBMCs were freshly isolated from a healthy donor (donor #57). CD4+ T cells were isolated using an EasySep Human CD4+ T cell enrichment KIT (StemCell), and stimulated with PMA (50 ng/mL)+Ionmycin (1 μM) for 20 hours to induce CTLA-4 expression on the cell surface. Activated human CD4+ T cells were then labeled with 10 μM Calcein-AM (Invitrogen) at 37° C. for 30 minutes. To the wells of the 96 well plate, antibodies of different concentrations were mixed with $1 \times 10^4$ labeled human CD4+ T cells and 5% normal human serum complement (NHSC, Quidel). After 5 hours of incubation, calcein-AM in the supernatant was measured to determine the CDC activity (FIG. 14). TY21580 showed no CDC activity against HEK293F/hCTLA-4 cells or activated human T cells.

Taken together, these results indicate that the antibodies described herein were capable of binding to human CTLA4 with high affinity and specificity, and such antibodies efficiently blocked the interaction of CTLA4 with its cognate ligands CD86 and CD80. The antibodies were also shown to be cross-reactive with CTLA4 from multiple species. Furthermore, binding to CTLA4 could modulate T cell activation and induce ADCC activity against CTLA4-expressing cell such as Tregs.

Example 4: In Vivo Characterization of IgG-Converted Antibodies

As described in the Examples above, the species cross-reactivity (human and mouse) of the antibodies allowed for the determination of the anti-tumor potency of the antibodies in multiple syngeneic tumor models, including MC38 and CT26 colorectal tumor models, an H22 liver tumor model, a PAN02 pancreatic tumor model, and a 3LL lung tumor model.

Anti-Tumor Efficacy in an MC38 Colorectal Tumor Model

C57BL/6 mice (n=8 per group, female, 6-8 weeks old) were inoculated subcutaneously with MC38 (NTCC-MC38) murine colon cancer cells. When tumors were established (80 mm³), treatment began with isotype control antibody and three different dosages of antibody TY21580 by intraperitoneal injection, twice a week for three weeks. Tumor growth was monitored twice a week and reported as the mean tumor volume±s.e.m. over time (FIGS. 15A-C). As shown in FIG. 15A, compared to the isotype control antibody, TY21580 exhibited potent in vivo anti-tumor activity with tumors completely regressing at all three dosages. As shown in FIG. 15B, up to sixty days post-treatment, 8 out of 8 mice in the 10 mg/kg of TY21580 group, 7/8 in the 2.5 mg/kg of TY21580 group, 6/8 in the 0.5 mg/kg of TY21580 group, remained tumor free. The long lasting memory of immunity against MC38 tumor cells was demonstrated when the mice in the 10 mg/kg of TY21580 group were re-challenged, as shown in FIG. 15C.

Anti-Tumor Efficacy in a CT26 Colorectal Tumor Model

Figure 16:
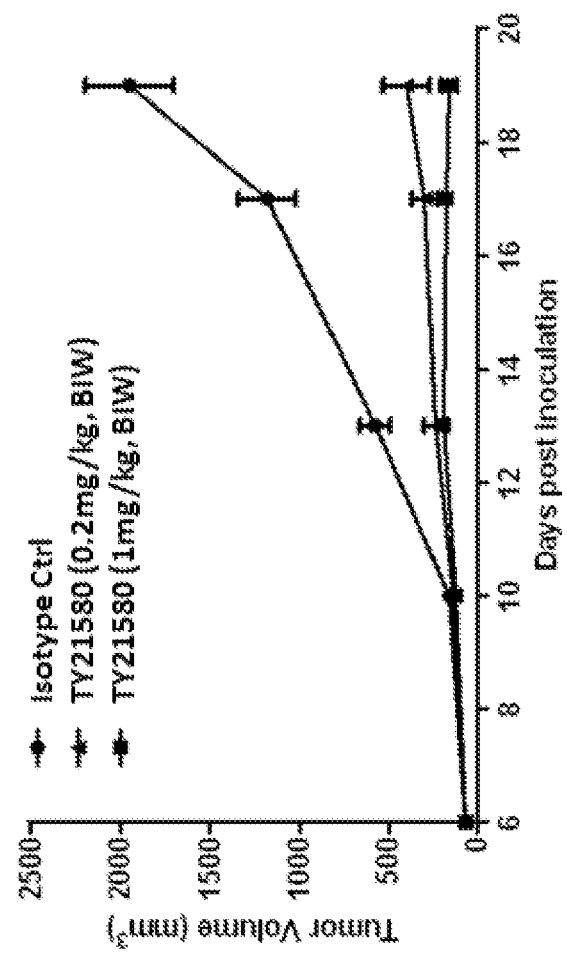
FIG. 16 shows the in vivo anti-tumor efficacy of antibody TY21580, or isotype control, in a CT26 syngeneic mouse colorectal tumor model. Tumor growth curves of different treatment groups of female C57BL/6 mice bearing CT26-established tumors are shown. Data points represent group mean; error bars represent SEM.

BALB/c mice (n=8 per group, female, 7-8 weeks old) were inoculated subcutaneously with CT26 (Shanghai Institutes for Biological Sciences) murine colon cancer cells. When tumors were established (70 mm³), treatment began with isotype control antibody and two different dosages of antibody TY21580 by intraperitoneal injection, twice a week. Tumor growth was monitored twice a week and reported as the mean tumor volume±s.e.m. over time. As shown in FIG. 16, compared to the isotype control antibody, TY21580 exhibited potent in vivo anti-tumor activity with almost 100% inhibition at dosages as low as 0.1-1 mg/kg.

Anti-Tumor Efficacy in an H22 Liver Tumor Model

Figure 17:
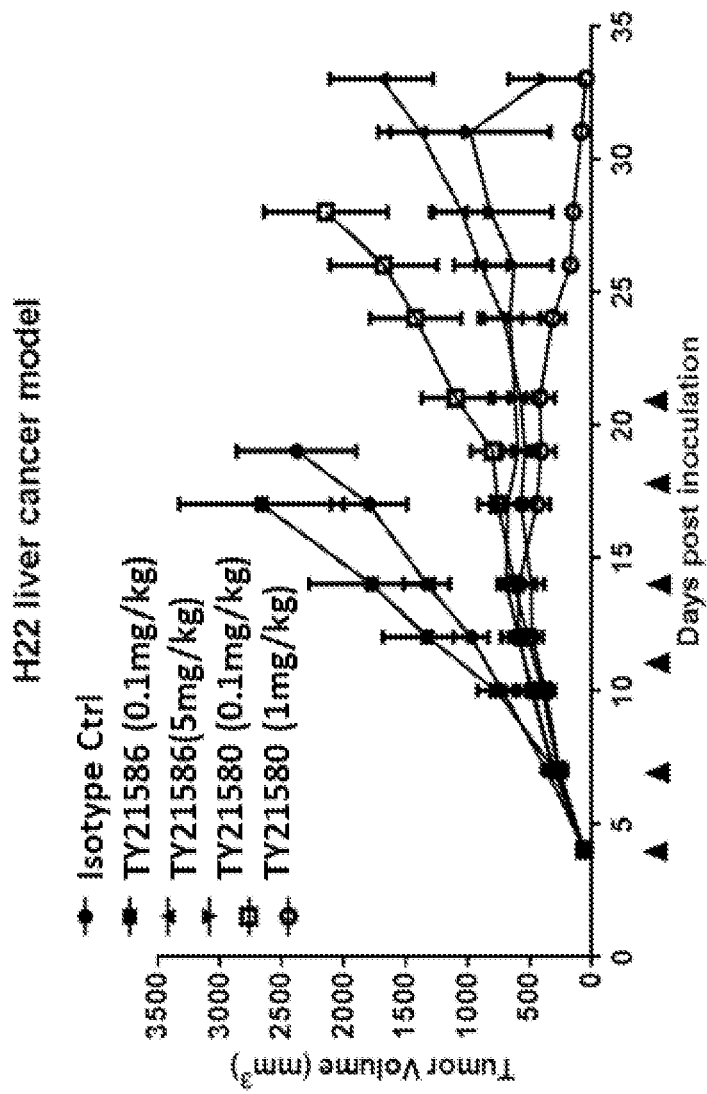
FIG. 17 shows the in vivo anti-tumor efficacy of antibodies TY21586, TY21580, or isotype control in an H22 syngeneic mouse liver tumor model. Tumor growth curves of different treatment groups of female C57BL/6 mice bearing H22-established tumors are shown. Data points represent group mean; error bars represent SEM.

BALB/c mice (n=5 per group, female, 7-8 weeks old) were inoculated subcutaneously with H22 (China Center for Type Culture Collection) murine liver cancer cells. When tumors were established (60 mm³), treatment began with isotype control antibody, antibody TY21586 at three different dosages (0.1 mg/kg, 1 mg/kg, 5 mg/kg), or antibody TY21580 at two different dosages (0.1 mg/kg, 1 mg/kg) by intraperitoneal injection, twice a week. Tumor growth was monitored twice a week and reported as the mean tumor volume±s.e.m. over time. As shown in FIG. 17, compared to the isotype control antibody, both TY21580 and TY21586 exhibited potent in vivo anti-tumor activity in a dose-dependent manner. When compared at the same dosage, TY21580 was more potent than TY21586 in this tumor model. In addition, TY21580 administration at 1 mg/kg led to tumor regression.

Anti-Tumor Efficacy in a Lewis Lung Tumor Model

Figure 18:
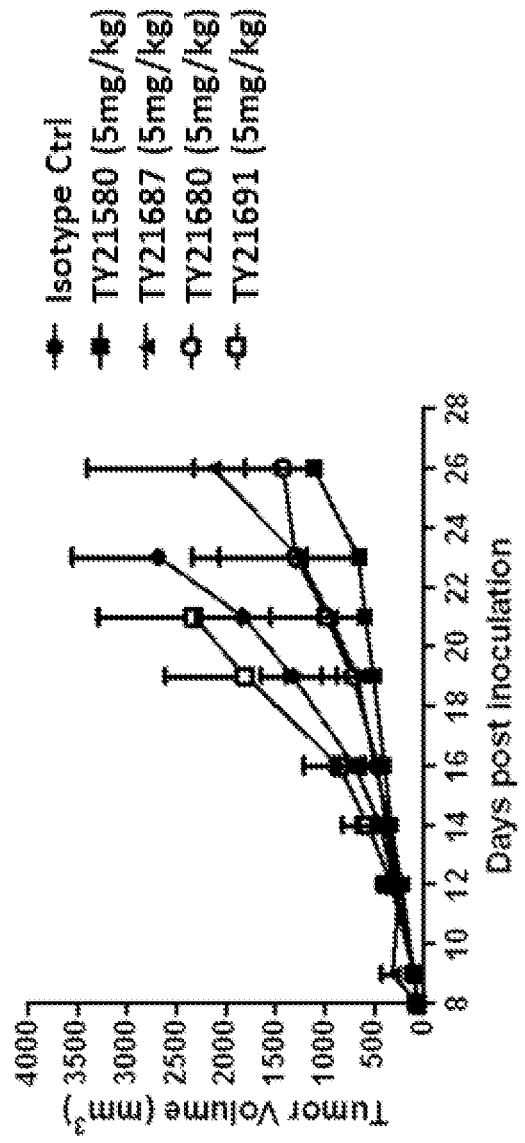
FIG. 18 shows the in vivo anti-tumor efficacy of antibodies TY21580, TY21687, TY21687, TY21691 and TY21580, or isotype control in a Lewis syngeneic mouse lung tumor model. Tumor growth curves of different treatment groups of female C57BL/6 mice bearing Lewis-established tumors are shown. Data points represent group mean; error bars represent SEM.

C57BL/6 mice (n=6 per group, female, 8 weeks old) were inoculated subcutaneously with Lewis (JenNio Bio, Guandong, China) murine lung cancer cells. When tumors were established (70 mm$^3$), treatment began with isotype control antibody, or antibodies TY21580, TY21687, TY21680, or TY21691, all at a dosage of 5 mg/kg by intraperitoneal injection, twice a week. Tumor growth was monitored twice a week and reported as the mean tumor volume±s.e.m. over time. As shown in FIG. 18, compared to the isotype control antibody, antibodies TY21580, TY21687, and TY21680 showed significant inhibition of tumor growth, while antibody TY21691 did not show potent anti-tumor activity.

Anti-Tumor Efficacy in a PAN02 Pancreatic Tumor Model

Figure 19:
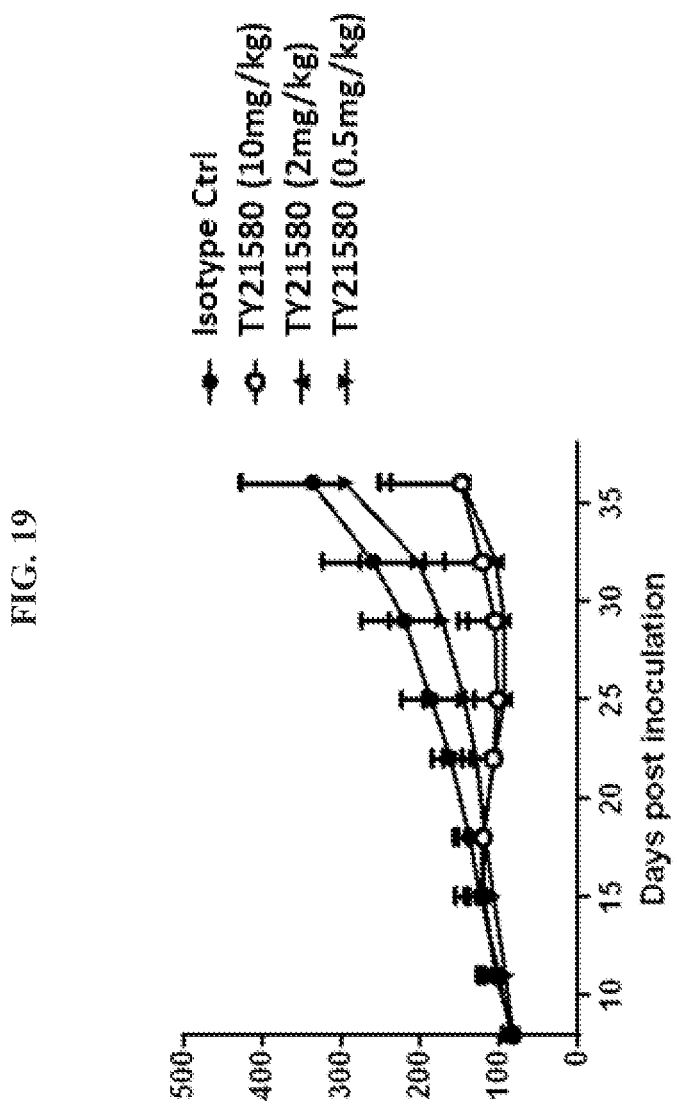
FIG. 19 shows the in vivo anti-tumor efficacy of antibody TY21580, or isotype control, in a PAN02 syngeneic mouse pancreatic tumor model. Tumor growth curves of different treatment groups of female C57BL/6 mice bearing PAN02-established tumors are shown. Data points represent group mean; error bars represent SEM.

C57BL/6 mice (n=8 per group, female, 6 weeks old) were inoculated subcutaneously with PAN-02 (CAMS Cell Culture Center) murine pancreatic cancer cells. When tumors were established (85 mm$^3$), treatment began with isotype control antibody, or antibody TY21580 at three different dosages (0.5 mg/kg, 2 mg/kg, 0.5 mg/kg), by intraperitoneal injection, twice a week. Tumor growth was monitored twice a week and reported as the mean tumor volume±s.e.m. over time. As shown in FIG. 19, compared to the isotype control antibody, TY21580 showed potent anti-tumor activity in a dose-dependent manner.

Figure 20A:
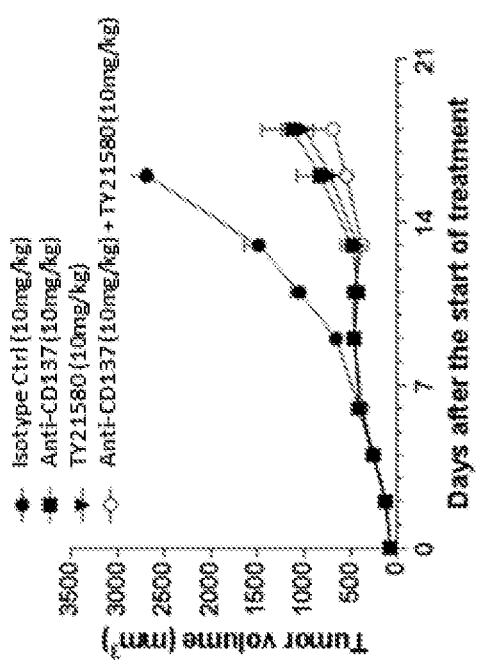
FIGS. 20A-B show the in vivo anti-tumor efficacy of a monotherapy of antibody TY21580, an anti-CD137 antibody, or isotype control, as well as an TY21580+anti-CD137 combination therapy, in a 3LL syngeneic mouse lung tumor model.
Figure 20B:
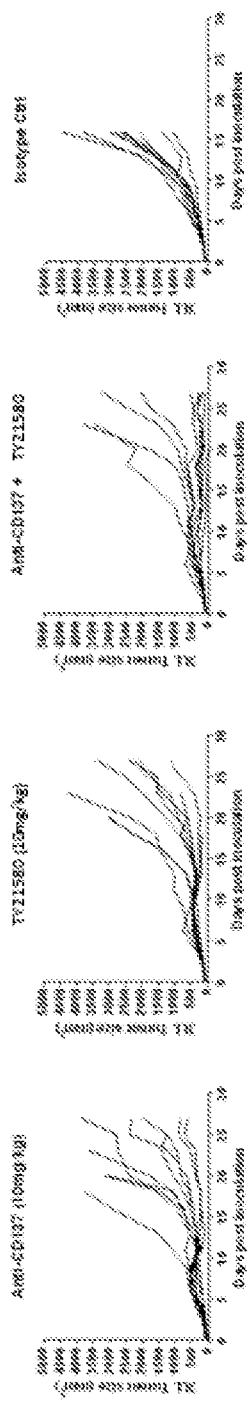

Anti-Tumor Efficacy of Antibody TY21580 Monotherapy, or in Combination with Anti-CD137 Antibody in a 3LL Lung Tumor Model C57BL/6 mice (n=10 per group, female, 6-8 weeks old) were inoculated subcutaneously with 3LL (JCRB) murine lung cancer cells. When tumors were established (75 mm$^3$), treatment began with isotype control antibody, TY21580 (10 mg/kg), anti-CD137 (10 mg/kg), or the combination of TY21580 and anti-CD137 by intraperitoneal injection, twice a week. Anti-CD137 is a proprietary monoclonal antibody developed that possesses the ability to bind both human and murine CD137 (see PCT application number PCT/CN2017/098332, incorporated herein by reference in its entirety). Tumor growth was monitored twice a week and reported as the mean tumor volume±s.e.m. over time. As shown in FIGS. 20A-B, compared to the isotype control antibody, both TY21580 and anti-CD137 showed potent anti-tumor activity, and the combination inhibited tumor growth more than either monotherapy alone.

Re-Challenge of Mice with Complete Response to TY21580

Figure 21:
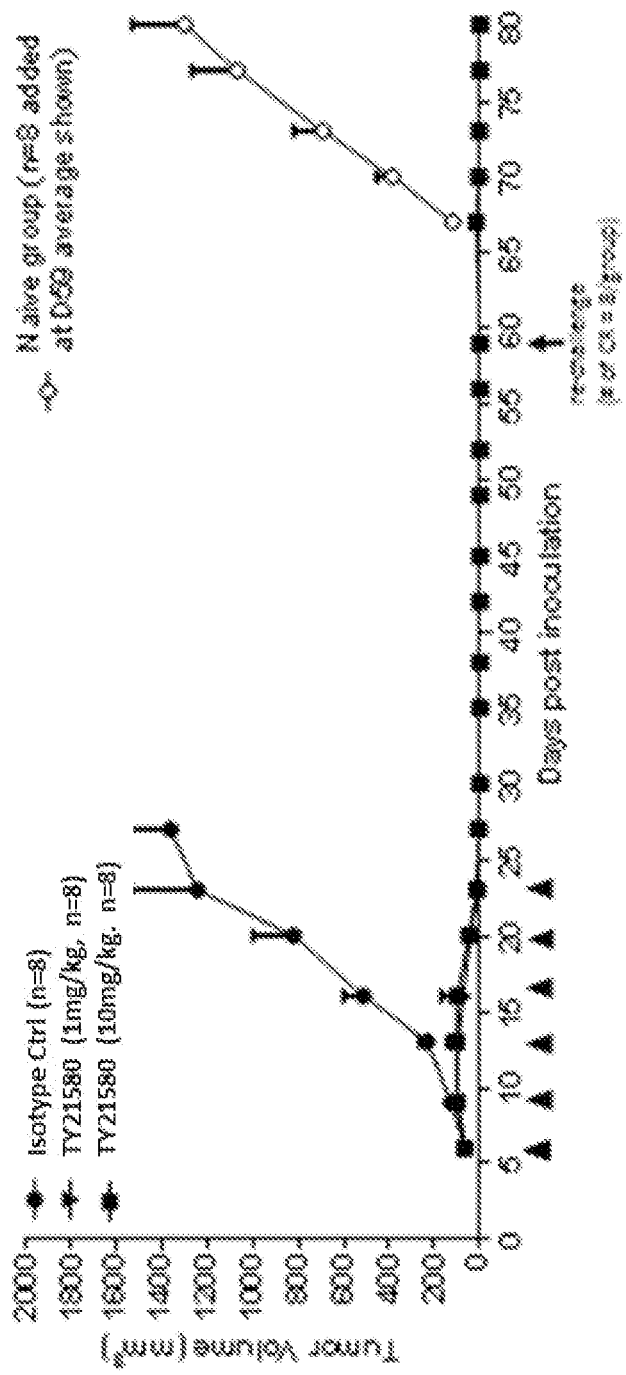
FIG. 21 shows a re-challenge study indicating the long lasting memory of immunity against H22 mouse liver tumor cells. Mice with a complete response in an TY21580 treatment group were subcutaneously re-challenged with H22 tumor cells at the opposite flank on Day 59. Naïve mice were also inoculated with H22 tumor cells at the same time.

BALB/c mice (n=8 per group, female, 7-8 weeks old) were inoculated subcutaneously with H22 (China Center for Type Culture Collection) murine liver cancer cells. When tumors were established (60 mm$^3$), treatment began with isotype control antibody, or antibody TY21580 at two different dosages (1 mg/kg, 10 mg/kg), by intraperitoneal injection twice a week for three weeks. Tumor growth was monitored twice a week and reported as the mean tumor volume±s.e.m. over time. Compared to the isotype control antibody, TY21580 at both dosages lead to complete tumor regression a few days after the last dose, and the mice remained tumor free 60 days post treatment. Mice in the 10 mg/kg of TY21580 treatment group were then re-challenged on Day 60 subcutaneously with H22 tumor cells in the opposite flank, and monitored for tumor growth. As shown in FIG. 21, these mice remained tumor free after re-challenge with the same tumor cells, suggesting that specific anti-tumor memory was developed in these mice. A re-challenge control group was set up at the same time with naïve mice inoculated with the same number of H22 tumor cells, and their tumors grew out rapidly.

Antibody Pharmacokinetics

Figure 22:
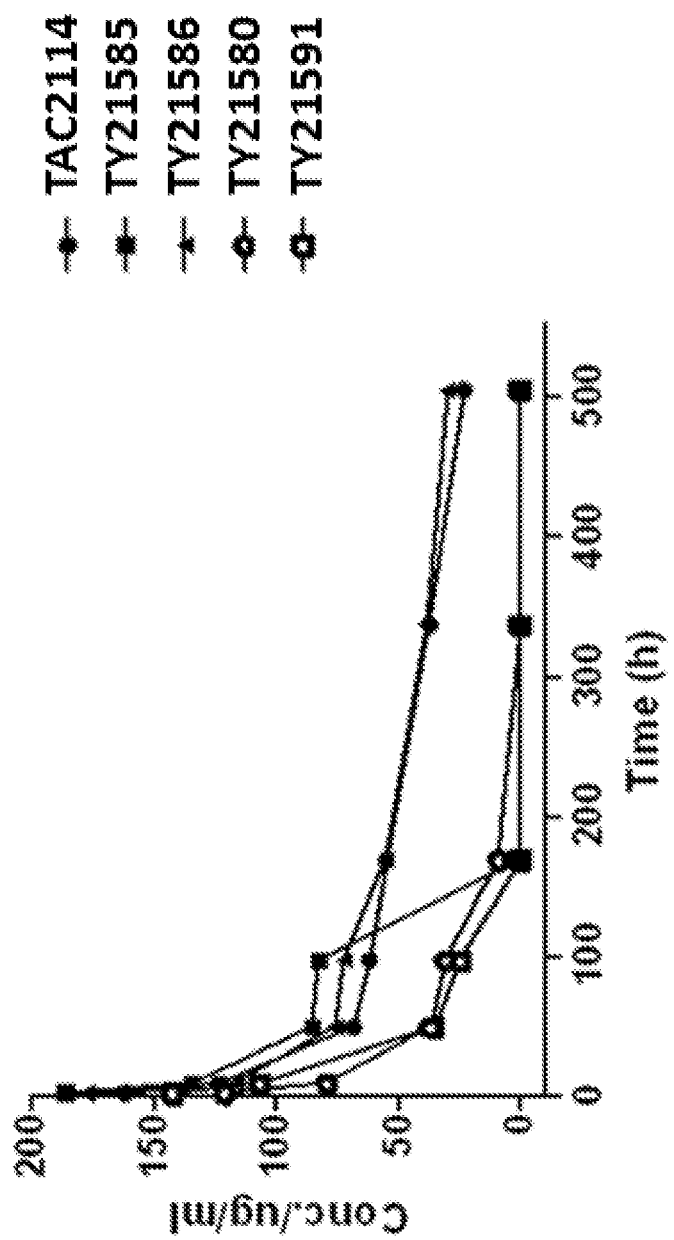
FIG. 22 shows a time course of the blood concentrations of the indicated antibodies intravenously administered at a concentration of 10 mg/kg to female BALB/c mice, as determined by ELISA.

A pharmacokinetic study of antibodies TY21585, TY21586, TY21580 and TY21591 was conducted in BALB/c female mice (at about eight weeks of age). Three mice per group were intravenously injected with the test antibodies at 10 mg/kg by tail vein injection. Blood samples (~2 μL per sample) were collected at 1 hour, 8 hours, 48 hours, 168 hours, 336 hours, and 500 hours post dosing. Blank control blood was collected from three naive female mice without antibody administration. Serum concentrations of each test antibody were determined by ELISA, in which CTLA4-His-Fc was used for capture, and HRP-labeled anti-human IgG (Fab specific) antibody (Sigma) was used for detection. As shown in FIG. 22, TY21586 exhibited comparable pharmacokinetics to TAC2114 in mice, while TY21585, TY21580, and TY21591 were cleared much faster.

Figure 23:
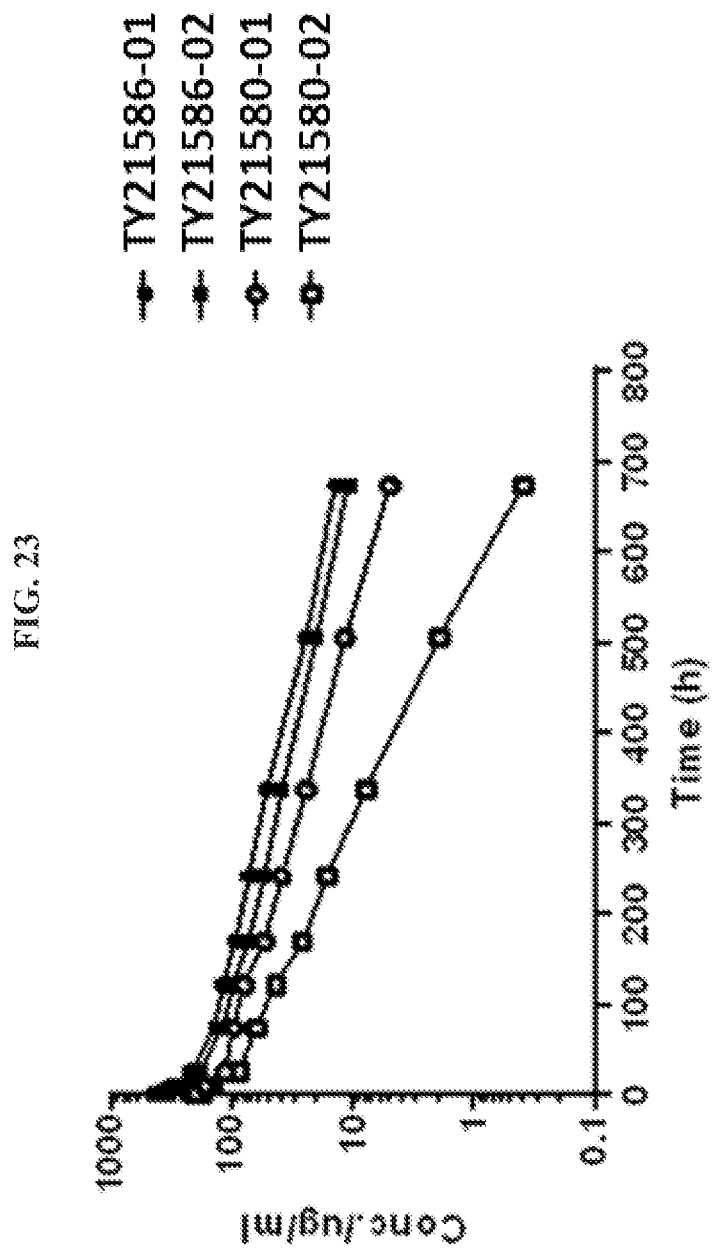
FIG. 23 shows a time course of the blood concentrations of the indicated antibodies intravenously administered at a concentration of 10 mg/kg in cynomolgus monkeys, as determined by ELISA.
Figure 24:
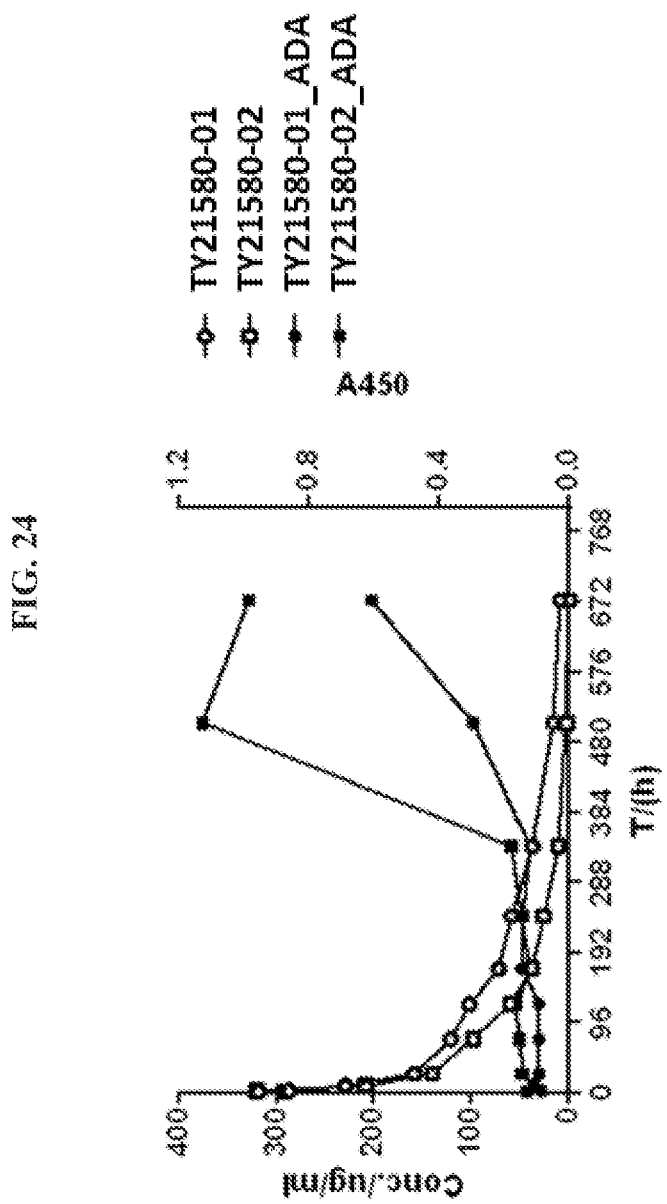
FIG. 24 shows a time course of the blood concentrations of the indicated antibodies intravenously administered at a concentration of 10 mg/kg in cynomolgus monkeys, in comparison to the appearance of anti-drug antibodies (ADAs) in these monkeys, as determined by ELISA.

A pharmacokinetic study of TY21586 and TY21580 was also conducted in naive cynomolgus monkeys. Each antibody was administered by intravenous bolus injection at 10 mg/kg to one female and one male monkey. Serum samples were collected pre-dose (0 h) and 0.25 hours, 1 hour, 8 hours, 24 hours, 72 hours, 120 hours, 168 hours, 240 hours, 336 hours, 504 hours, and 672 hours post dosing. Serum concentrations of TY21586 and TY21580 were determined by ELISA, in which CTLA4-His-Fc was used for capture, and HRP-labeled anti-human IgG (Fab specific) antibody (Sigma) was used for detection. As shown in FIG. 23 and FIG. 24, compared to TY21586, TY21580 was cleared much more quickly in monkeys, potentially due to the rapid increase in anti-drug antibodies observed in these animals.

Repeated Dosing Toxicity Studies

Repeated dosing toxicity of TY21580 was conducted in normal BALB/c mice. Vehicle control or antibody TY21580 (at 25 mg/kg or 50 mg/kg) was administered i.p. (10 mL/kg) on Day 1, Day 4, Day 7, and Day 11. Five female mice and five male mice (five weeks old) were included in each group. Mice were monitored daily for abnormal behaviors and symptoms, and measured daily for food intake and body weight. On day 14, animals were euthanized for post-mortem examination, and other analysis. Blood was collected from each animal, with up to six blood samples collected per group (three male, three female) used for hematology (RBC, platelet, WBC, WBC differential) and/or blood biochemistry (ALT, AST, GLB, ALP, and LDH etc.) analysis. The following organs from each mouse were collected and weighed: heart, lung, thymus, liver, spleen, kidney, testes, and ovaries. The liver samples from 6 animals (three male, three female) per group were fixed in FFPE. FFPE blocks for liver tissues were prepared, sectioned and H&E stained for histopathology analysis.

Figure 25A:
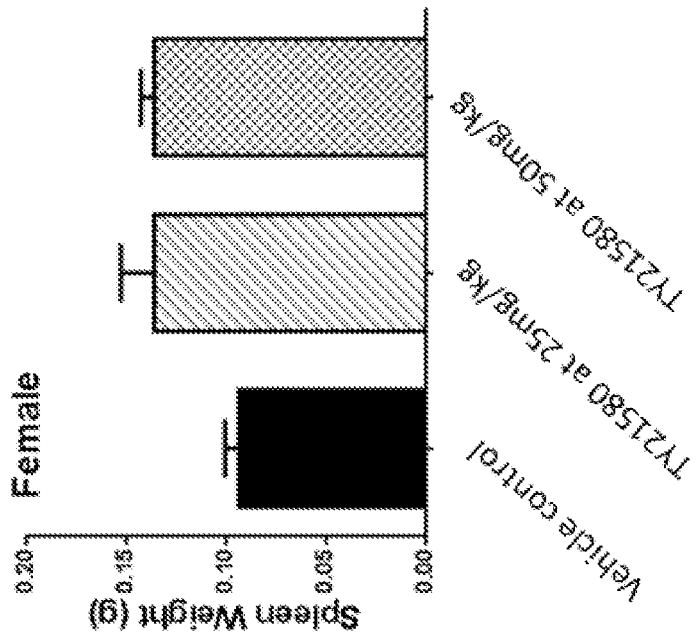
FIGS. 25A-B show the average spleen weight of male and female BALB/c mice after repeat intraperitoneal administration of either antibody TY21580 or vehicle control.
Figure 25B:
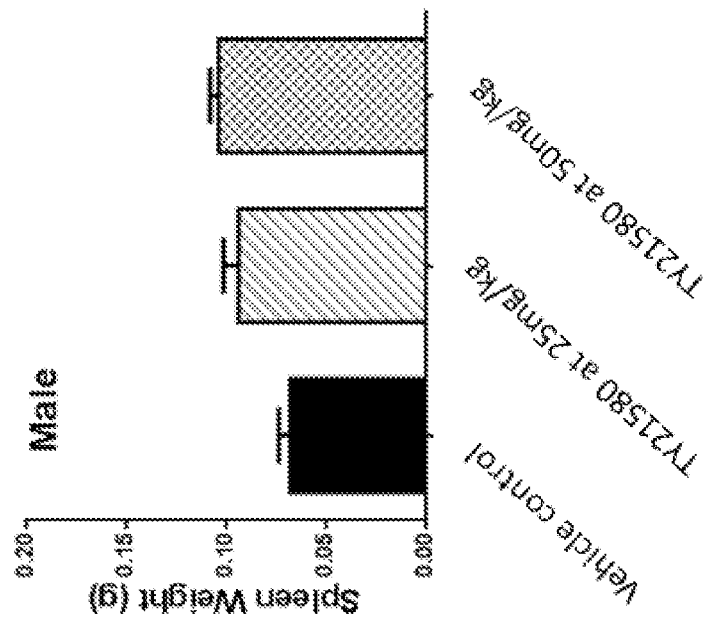
Figure 26:
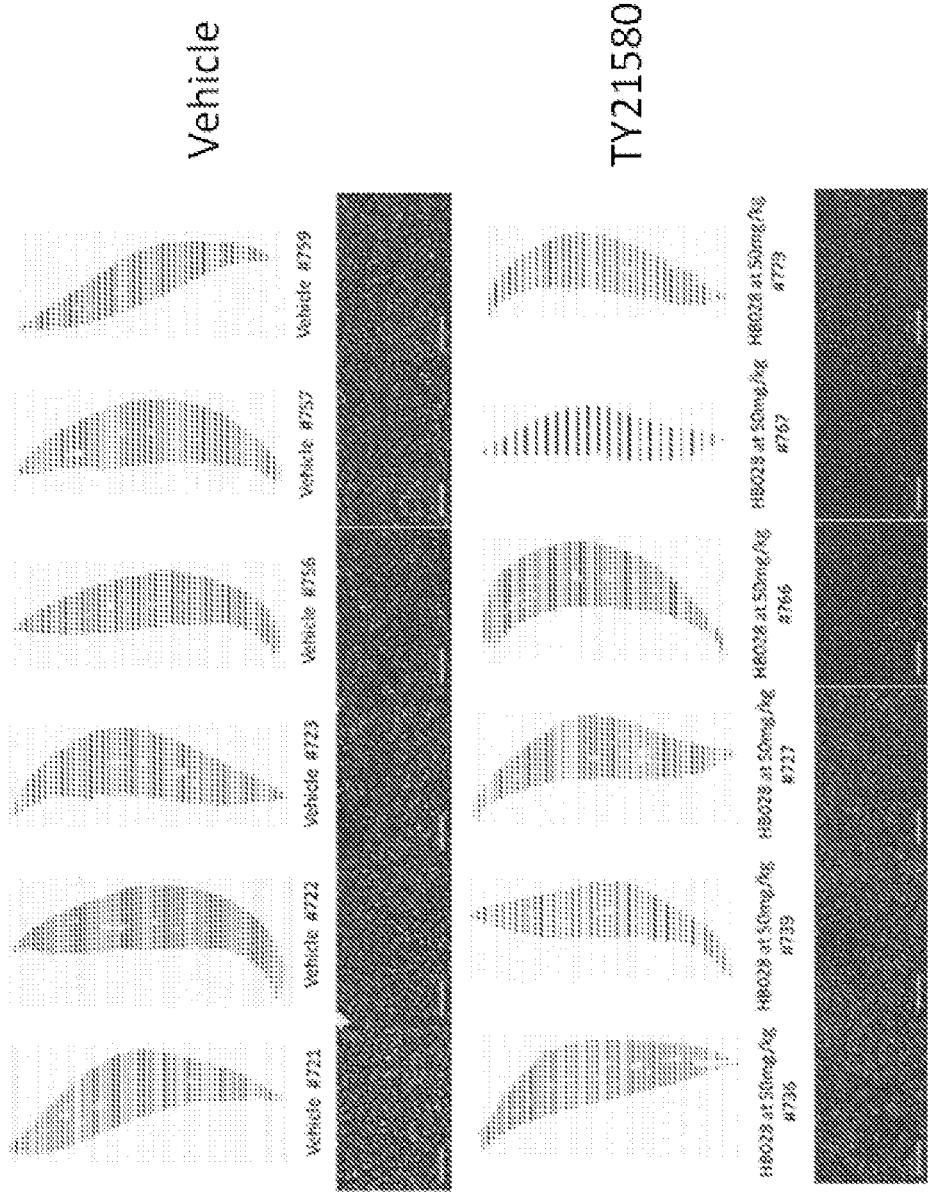
FIG. 26 shows the histopathology of BALB/c mice after repeat intraperitoneal administration of either antibody TY21580 or vehicle control on days 1, 4, 7, and 11.

During the in-life period of the whole study, there was no abnormal behavior observed, or un-scheduled animal death. Compared to the vehicle treatment, TY21580 did not affect the food intake and body weight of the animals. Post-mortem examination also did not show any obvious lesions in mice of the treatment groups at both dosage levels, except that the spleen weight was increased in the TY21580 treated groups (FIG. 25A-B). Hematology analysis did not show any significant changes, as indicated by the blood biochemistry parameters tested in mice treated with TY21580. No obvious abnormalities were found in the histopathology sections of the liver from the mice (FIG. 26). Overall, TY21580 was well tolerated in this study, with no significant toxicity observed in mice.

Taken together, these results indicate that the CTLA4 antibodies described herein were very safe to mice, had potent anti-tumor activity, and could induce long-lasting immune memory against tumor cells.

Example 5: Antibody Developability Profile

For developability assessment, purified TY21586 and TY21580 were exchanged into storage buffer (20 mM histidine, pH 5.5). All experiments, including solubility, stability under accelerated stress conditions, and differential scanning fluorescence (DSF) tests were performed in storage buffer. For all SEC-HPLC analyses, TSKgel columns (Tosoh Bioscience G3000SWx1) were used.

Antibody Solubility

Figure 27:
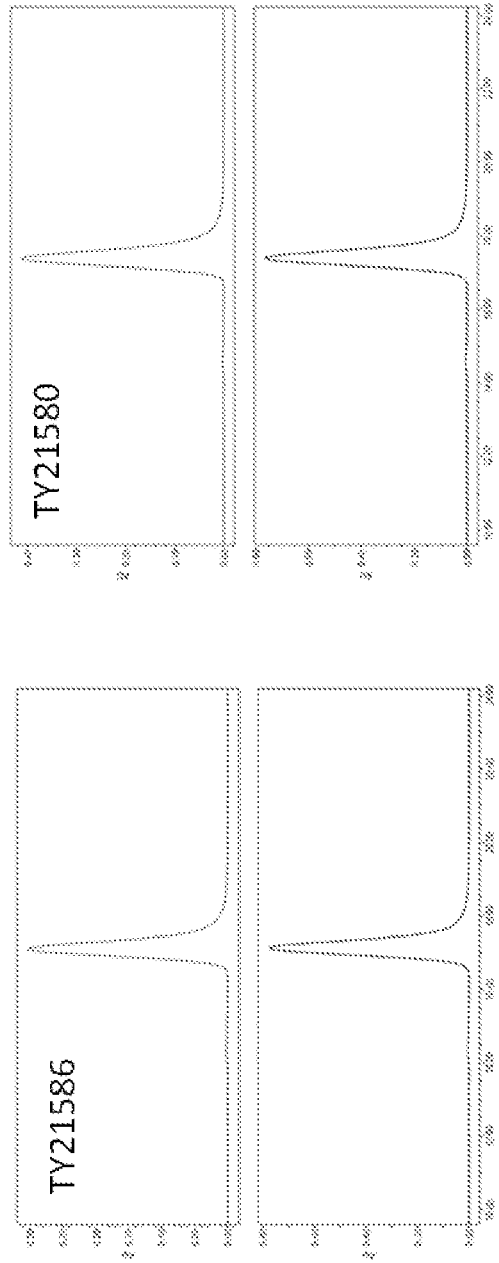
FIGS. 27A-B shows the stability of exemplary antibodies after storage at high concentration.

Samples containing antibodies TY21586 or TY21580 were formulated at a concentration greater than 100 mg/mL in storage buffer, and the amount of high molecular weight (HMW) protein aggregates was tested (Table 8). Antibodies then were adjusted to about 12 mg/mL in storage buffer. Samples (12 μg each) were then assayed through SEC-HPLC for detection of high molecular weight protein aggregates. As shown in FIG. 27, no significant increase of HMW aggregates was observed at antibodies formulated at high concentrations (above 100 mg/mL) for 30 min.

TABLE 8 antibody solubility

| Ab name | Concentration (mg/mL) | Aggregation (HMW %) |
|---|---|---|
| TY21586 | 197.8 | 0 |
| TY21580 | 126.0 | +0.10 |

Antibody Stability Under Accelerated Stress Conditions

Figure 28:
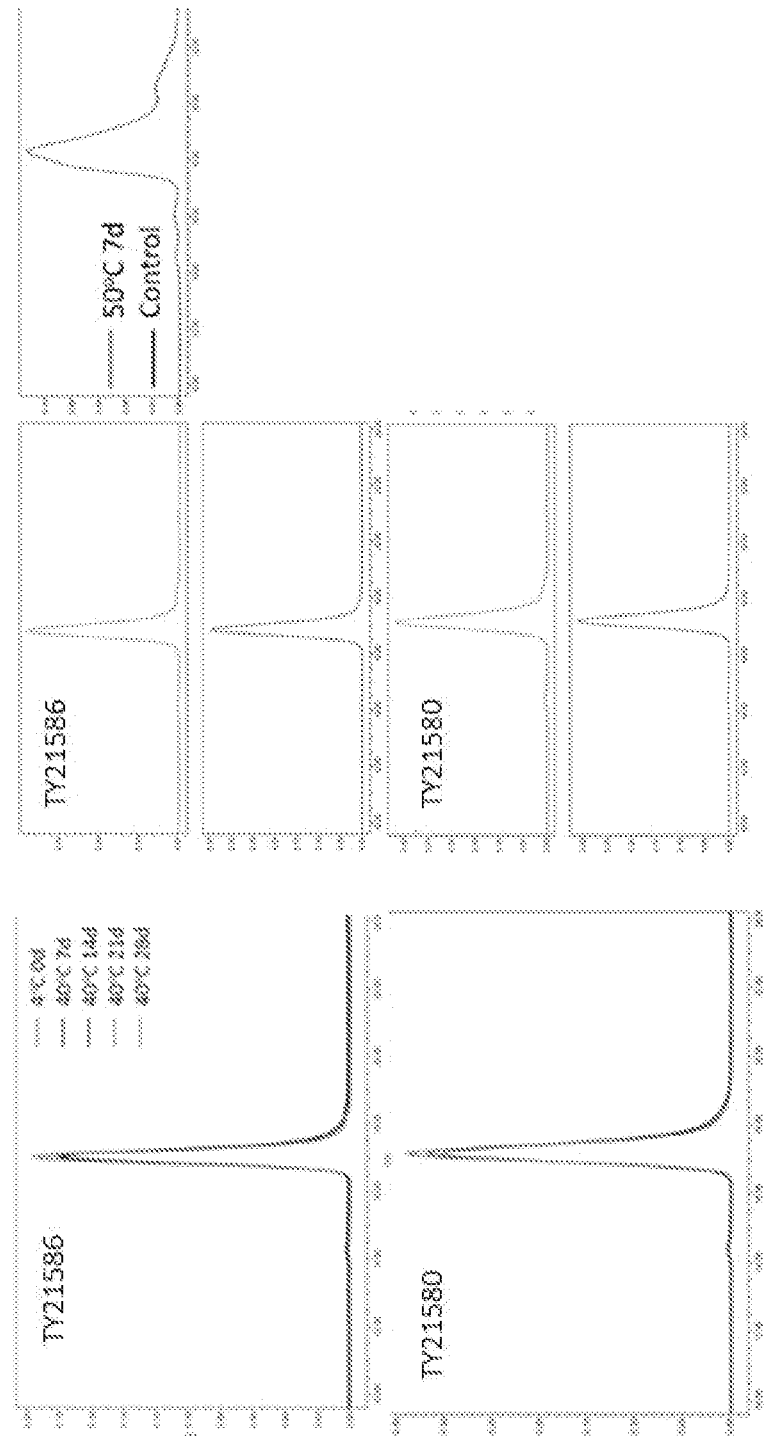
FIG. 28 shows the SEC profiles of exemplary antibodies under accelerated stress conditions.

Antibody stabilities were also examined under accelerated stress conditions. Results of these experiments are summarized in Table 9 and FIG. 28. TY21586 and TY21580 remained stable after 6 cycles of freezing (−80° C.) and thawing (room temperature). After seven days at 50° C., there was little change of HMW aggregate or low molecular weight (LMW) fragments. In longer-term time course experiments (40° C. for up to 28 days), TY21586 and TY21580 remained stable, and there were no significant increases of HMW aggregates or LMW fragments.

TABLE 9 changes of HMX % under accelerated stress conditions

| Ab name | Freeze-thaw 6 cycles | 50° C. 7 d | 50° C. 7 d LMW% | 40° C. 28 d | 40° C. 28 d LMW% |
|---|---|---|---|---|---|
| TY21586 | 5.34 | 0 | 2.14 | −0.22 | 1.37 |
| TY21580 | 0.49 | 0 | 2.02 | 0.02 | 0.43 |

Furthermore, thermostability (as measured by differential scanning fluorescence (DSF)) showed that both TY21586 and TY21580 were stable up to at least about 55° C. The transition midpoint (Tm), the characteristic temperature at which the unfolding transition for almost all protein domains occur, is shown Table 10 below.

TABLE 10 thermostability by DSF

| Ab name | Tm onset (° C.) | Tm1 (° C.) | Tm2 (° C.) |
|---|---|---|---|
| TY21586-16Z01 | 55 | 67.26 | 76.40 |
| TY21580-16Z01 | 55 | 67.64 | 76.50 |

Finally, it was found that the highest achievable concentration of antibodies TY21586 and TY21580 was over 197.8 mg/mL and 126.0 mg/mL, respectively, after centrifugation.

Taken together, these results indicate that even without formulation optimization, the CTLA4 antibodies TY21586 and TY21580 had excellent developability profile.

Figure 29:
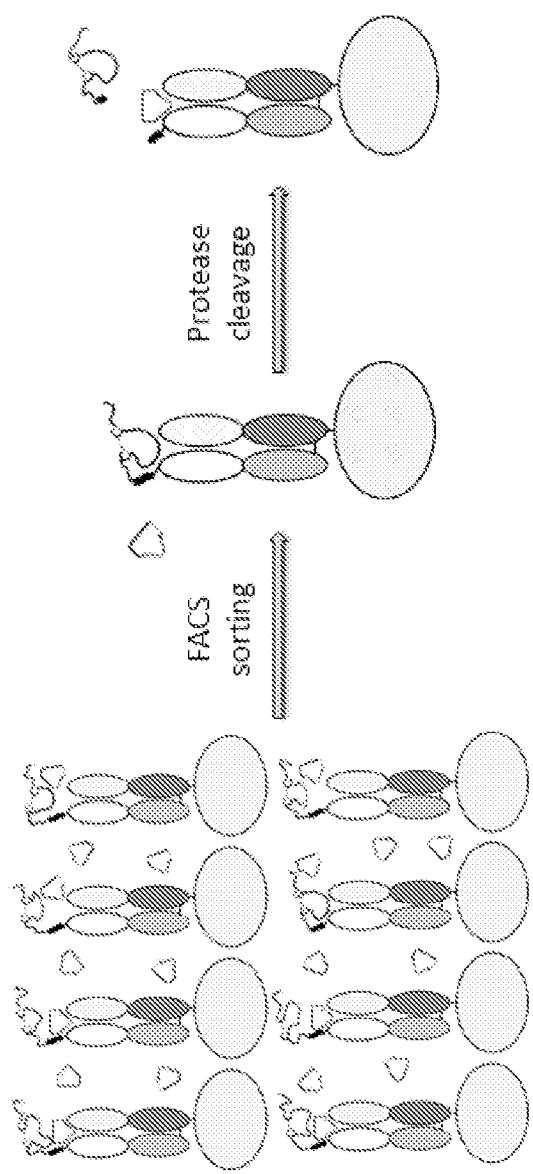
FIG. 29 shows a schematic of the selection process for self-blocking peptides using the Fab fragment of the anti-CTLA4 antibody displayed on yeast surface.
Figure 30:
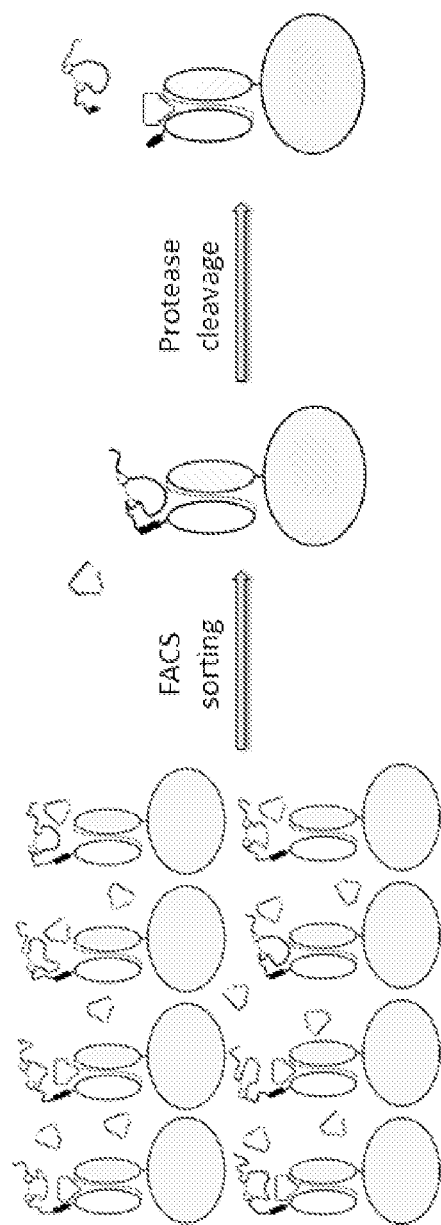
FIG. 30 shows a schematic of the selection process for self-blocking peptides using the scFv fragment of the anti-CTLA4 antibody displayed on yeast surface.

Example 6: Methods of Identifying Self-Blocking Peptides for TY21580-Derived CTLA4 Activatable Antibodies Described herein is a new system that has been designed and executed for efficient discovery of masking moieties with good developability. In this system, the target antibody fragments, either Fab (FIG. 29) or scFv (FIG. 30), were first displayed on the yeast surface, and were confirmed to be functional in binding to its antigen. Then the improved peptide libraries were directly fused to the N-terminus of the light chain of a CTLA4 antibody (TY21580), and a yeast library was constructed that displayed the fusion protein on the yeast surface. The yeast library then underwent several rounds of FACS-based screening: first the yeast clones that had low binding to antigen were enriched, then the enriched yeast clones were treated with a protease to remove the N-terminal peptide, and the clones with high binding to antigen were selected (FIGS. 29 and 30). After 4-5 rounds of sorting, the plasmids were extracted from these clones and the masking peptide sequences were confirmed through DNA sequencing.

Example 7: Design of Constrained Peptide Libraries (CPLs) for CTLA4 Activatable Antibodies Four exemplary constrained peptide libraries (CPLs) were designed (Table 11).

TABLE 11

Designed CPLs

| CPL name: | Amino Acid Sequence: |
|---|---|
| CPL010 | EVGSY($Z_6$)C($Z_6$)C($Z_2$)SGRSA (SEQ ID NO: 152) |
| CPL011 | EVGSY($Z_6$)C($X_6$)C($Z_2$)SGRSA (SEQ ID NO: 153) |
| CPL012 | EVGSY($Z_6$)C($Z_8$)C($Z_2$)SGRSA (SEQ ID NO: 154) |
| CPL013 | EVGSY($Z_6$)C($X_8$)C($Z_2$)SGRSA (SEQ ID NO: 155) |

Each X is independently an amino acid selected from the group consisting of A, C, D, E, F, G, H, I, K, L, M, N, P, Q, R, S, T, V, W, and Y; each Z is independently an amino acid selected from the group consisting of D, A, Y, S, T, N, I, L, F, V, H, and P At their cores were the sequences $Z_6CX_6CZ_2$ (SEQ ID NO: 137) or Z6CX8CZ2 (SEQ ID NO: 138), and the two fixed cysteine residues formed a disulfide bond to constrain the peptide conformations. In the synthesized oligonucleotides, the degenerate codon NHC was adopted in all places except inside the loop, where an NNK codon was also employed in CPL011 and CPL013. In contrast to the NNK or NNS codon, NHC codon encodes 12 residues (Table 12), encompassing significant diversity, but lacking the chemically labile residues methionine, tryptophan, and cysteine. In addition, the reduced theoretical diversity compared with the NNK or NNS codon enabled the construction of libraries with better coverage.

TABLE 12

| NHC codons | | | | | | | | | | | | |
|---|---|---|---|---|---|---|---|---|---|---|---|---|
| NHC: | AAC | ACC | ATC | TAC | TCC | TTC | GAC | GCC | GTC | CAC | CCC | CTC |
| Amino acid: | N | T | I | Y | S | F | D | A | V | H | P | L |

Following these masking peptide sequences was an invariant cleavage peptide sequence (SGR-SAGGGGSPLGLAGSGGS, SEQ ID NO: 180) containing two protease recognition sites: SGRSA (SEQ ID NO: 149) for the protease urokinase-type plasminogen activator (uPA), and PLGLAG (SEQ ID NO: 150) for the proteases matrix metalloproteinase-2 (MMP-2) and matrix metalloproteinase-9 (MMP-9). These recognition sites have been used by many group in in vivo tumor cell-specific activation of targeting agents (see e.g., Ke et al. (1997) J Biol Chem 272(33):20456-62; Gerspach et al. (2006) Cancer Immunol Immunother 55(12):1590-600; and Jiang et al. (2004) Proc Natl Acad Sci USA 101(51):17867-72). During yeast-based screening, the MMP-9 recognition sequence was replaced with the Tobacco Etch Virus (TEV) protease recognition sequence (ENLYFQG, SEQ ID NO: 151) due to the availability and specificity of the TEV protease.

The CPLs and the invariant cleavage peptide were fused to the N-terminus of light chain of the target antibody (TY21580), in the form of either scFv or Fab, that is connected to the yeast surface displayed Aga2 protein. The inclusion of the surrogate TEV protease recognition site was important in identifying the right type of masking peptide sequences, i.e, the antigen binding is blocked before protease cleavage, and antigen binding is enabled after protease cleavage. The examples described below demonstrated that the cleavage-activation mechanism of activatable antibodies initially shown in yeast was replicated in full IgG molecules expressed in mammalian cells.

Example 8: Construction and Validation of TY21580-Derived Activatable Antibodies Targeting CTLA4

Display of the Functional Target Antibody on the Yeast Surface

A low copy number, CEN/ARS-based vector was used to express the target antibody (antibody TY21580, targeting human CTLA4) under the control of the inducible GAL1-10 promoter in the yeast S. cerevisiae. The surface display of scFvs was achieved through the Aga2 protein fused at its C-terminus under the control of the GAL1 promoter, similar to previously published arrangements (Boder and Wittrup (1997) Nat Biotechnol 15(6):553-7). For Fabs, their surface display was achieved through the Aga2 protein fused to the N-terminus of the heavy chain (fusion of VH and CH1), under the control of the GAL1 promoter, while the light chain (fusion of VL and CL) was under the control of the GAL10 promoter. The Fabs were displayed on the yeast surface through its association with the membrane anchored heavy chain.

Figures 31A, 31B:
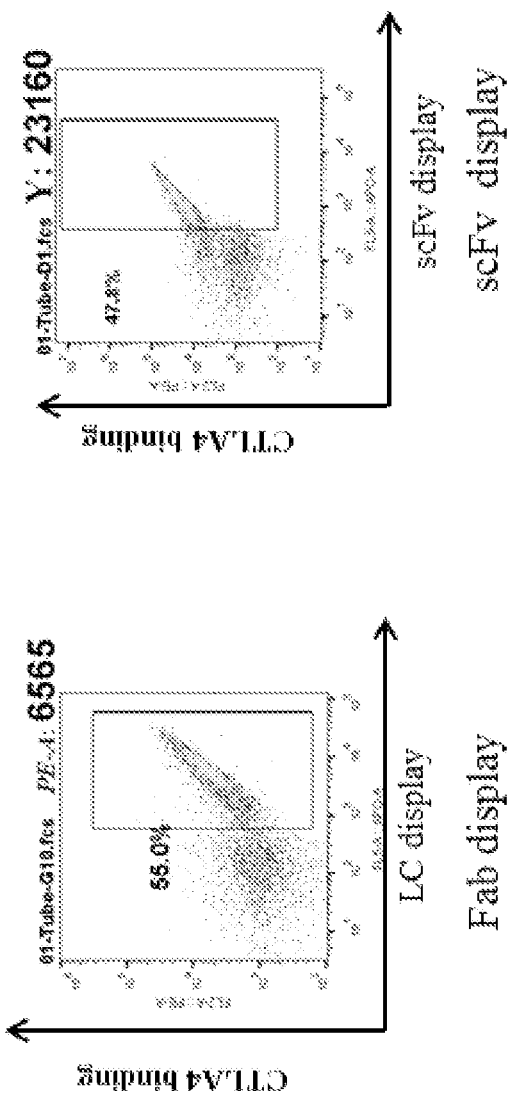
FIGS. 31A-B show functional display of Fabs and scFvs targeting CTLA4 on yeast, as determined by flow cytometry.

The surface display of the Fab or scFv was verified by staining with antibodies recognizing the fused affinity tag, and the functionality of the Fabs or scFvs displayed on yeast was examined using biotinylated human CTLA4. Briefly, 48 hours after induction in galactose medium, yeast cells (1×10^6) were harvested, washed once with PBSA buffer, and then incubated with 10 nM of biotinylated antigen for 1 hour at room temperature. The yeast cells were then washed twice with PBSA buffer, and incubated with PE conjugated streptavidin (1:500 dilution) (eBioscience #2-4317-87) for 30 minutes at 4° C. The yeast cells were then analyzed by flow cytometry. As shown in FIGS. 31A-B, both Fabs (FIG. 31A) and scFvs (FIG. 31B) targeting CTLA4 were successfully displayed on the yeast surface, and were both capable of binding strongly to their antigens.

Construction of Yeast Libraries Containing CPLs

Synthesized oligonucleotides encoding the CPLs were fused with the oligonucleotides encoding the cleavage peptides through 5 cycles of PCR. The compositions of PCR reactions were: 1× PrimeSTAR buffer, 2.5 mM dNTP, 100 µM of F-primer and R-primer each, and 100 µM each of template 1 (CPL oligonucleotide) and template 2 (oligonucleotide encoding the cleavage peptide), and 2.5 U of PrimeSTAR HS DNA Polymerase. The PCR program used was: a) 1 cycle of 96° C. for 5 minutes; 2) 5 cycles of 96° C. (15 sec), 60° C. (15 sec), 72° C. (6 sec); and 3) 1 cycle of 72° C. for 3 minutes. Exonuclease I was used to digest the single-stranded DNA before purification of the PCR product through gel electrophoresis. The purified PCR product was then digested with BamHI and KpnI, and cloned into a bacterial filter vector digested with the same two restriction enzymes. In the filter vector, the CPL and the cleavage peptides were placed downstream of a bacterial secretion signal peptide, and upstream of a beta-lactamase lacking signal sequence. The functional beta-lactamase, selected on ampicillin plates, indicated in-frame fusions of CPLs and the cleavage peptides, thereby eliminating any out-of-frame errors (N-1 or N-2) introduced into the synthesized degenerate oligonucleotides. In addition, some poorly folded sequences were also reduced from the pool. The ligation product was transformed into electro-competent bacterial cells, and the diversity of CPL libraries was generally between 5×10^9 and 1×10^10. Sequencing of individual clones indicated that very high in-frame rate (in many cases, almost 100%) were achieved through this approach.

To make yeast libraries containing CPLs, the plasmids were extracted from the bacterial libraries, and used as templates for PCR amplification of the DNA fragments encoding the CPLs and cleavage peptide. The amplified PCR fragments were purified through gel-electrophoresis, and together with a linearized plasmid that expressed the target antibody fused to Aga2, were transformed into electro-competent yeast cells. The homologous sequences on both ends of the PCR fragments and the plasmids ensured efficient homologous recombination inside yeast cells. The diversity of the constructed yeast libraries was generally between 1×10^9 to 2×10^9.

FACS-Based Screening of Masking Peptides Against a CTLA4 Antibody

Figure 32:
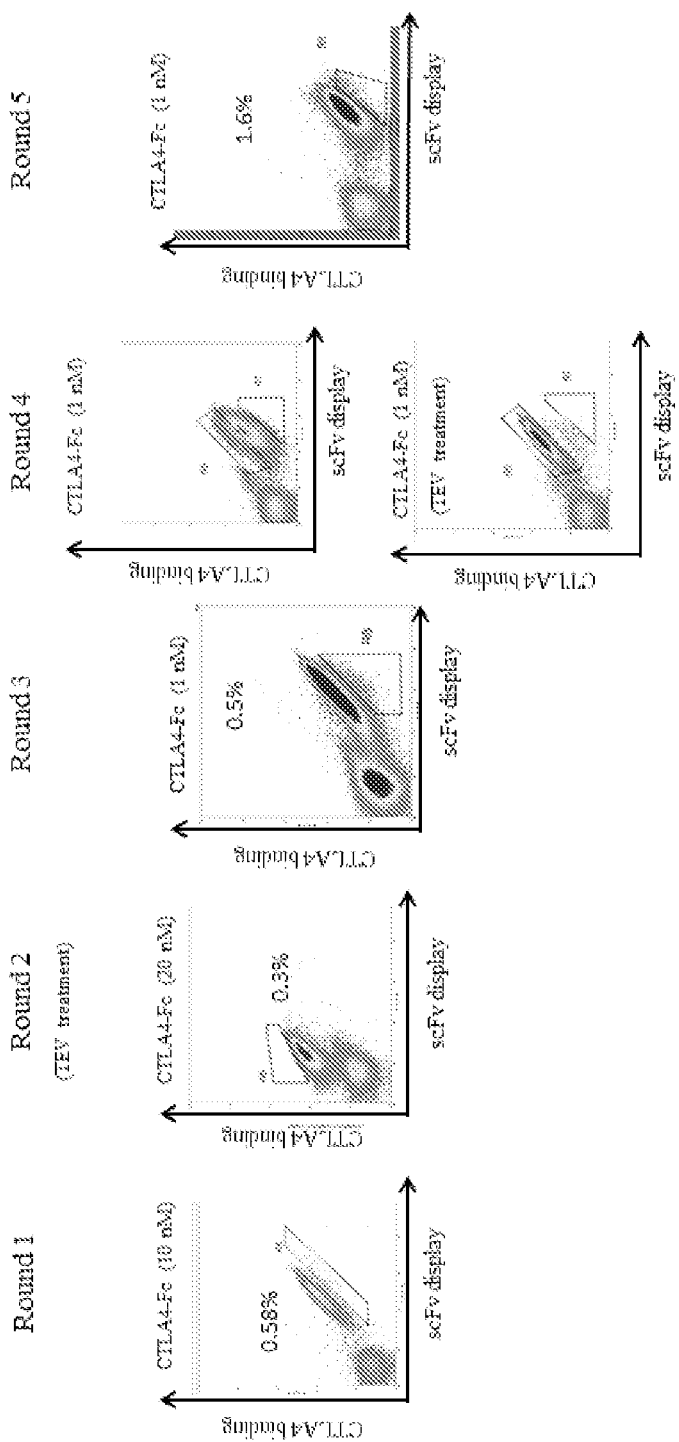
FIG. 32 shows an exemplary selection process for activatable antibodies targeting human CTLA4. A yeast library displaying fusion proteins were subjected to several rounds of FACS-based screening.

A total of 1×10^8 yeast cells from a CPL yeast library were used to screen for masking peptides against the target antibody. For each round of sorting through MoFlo XDP, yeast cells induced in galactose medium were harvested, washed once with PBSA buffer, and then incubated with 10 nM (decreased to 1 nM in the later rounds) of biotinylated antigen for 1 hour at room temperature. The yeast cells were then washed twice with PBSA buffer, and incubated with PE conjugated streptavidin (1:500 dilution) (eBioscience #2-4317-87) for 30 minutes at 4° C. After two more washes with PBSA buffer, the yeast cells were adjusted to 2-3 OD/mL, and subject to sorting. As shown in FIG. 32, in round 1, 10 nM of biotinylated CTLA4-Fc was used, and the weak binders were enriched. The yeast cells from round 1, after growth in glucose medium, were induced in galactose medium and treated with AcTEV protease (6U/OD cell) (Thermo Fisher Scientific #12575015) for 2 hours at 30° C., and the strong binders were purified. Starting from the 3rd round of sorting, the concentration of the biotinylated CTLA4-Fc was reduced to 1 nM, and the weak binders were collected. At the 4th round, fractions of the yeast cells were also treated with AcTEV in parallel, to verify the protease cleavage mediated activation of the target antibody. As shown in FIG. 32, it was apparent that AcTEV cleavage resulted in a dramatic increase of the population of cells that bound strongly to antigen, suggesting that the screening strategy was effective. The single clones from the 5th round of sorting were plated on selective media, and grown individually for further confirmation of cleavage mediated activated antigen binding.

Figures 33A, 33B:
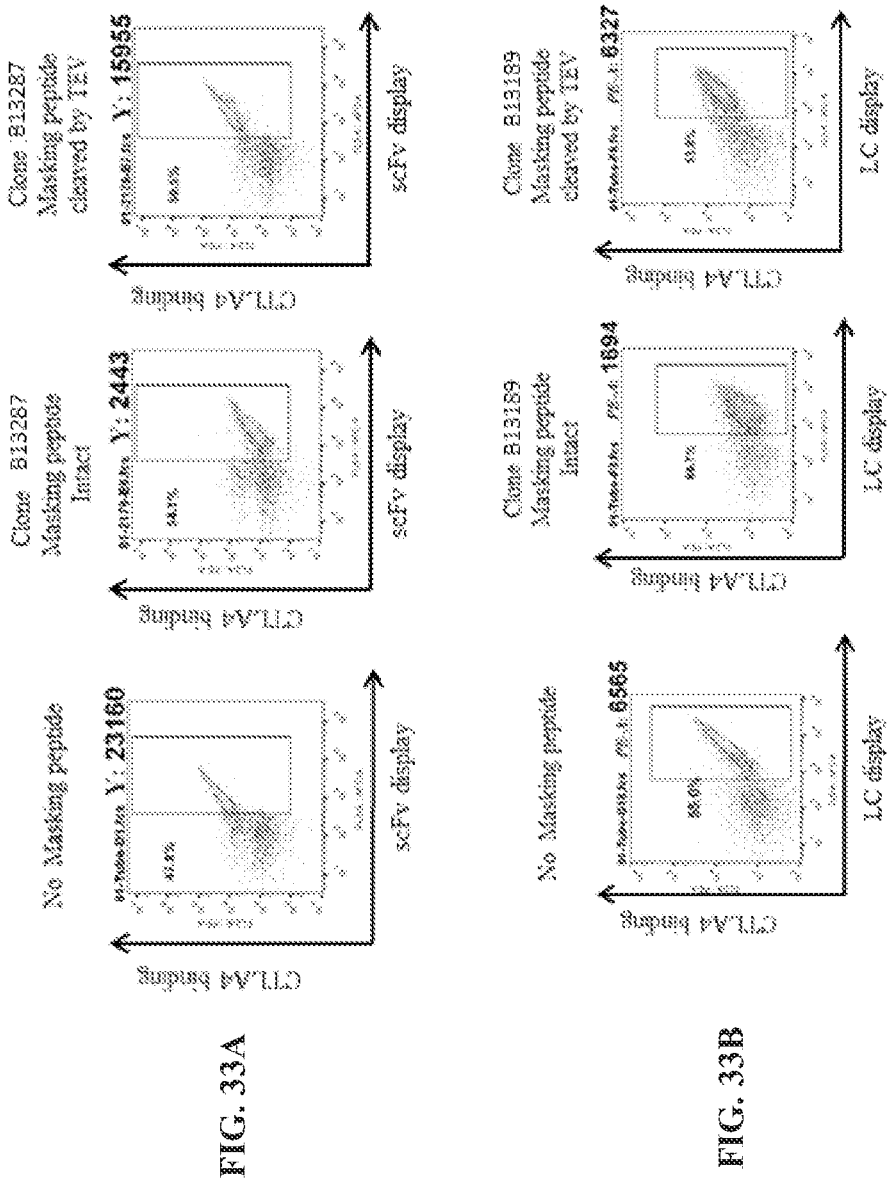
FIGS. 33A-B show CTLA4 binding affinity of exemplary CTLA4 activatable antibody clones, as determined by flow cytometry.

As shown in FIGS. 33A-B, the selected CTLA4 activatable antibody clones, either in scFv (FIG. 33A) or Fab (FIG. 33B) format, exhibited little binding to antigen in the presence of masking peptide. However, binding to antigen was dramatically increased when the yeast cells were treated with TEV protease to remove the masking peptide. The incorporation of the TEV recognition site in the cleavage peptide, combined with the application of TEV protease to verify the selected clones, significantly increased the success rate of masking peptide selection.

To identify the masking peptide sequences, the shuttle plasmids were extracted from the selected yeast clones (Generay #GK2002-200), and transformed into competent *E. coli* cells. The plasmids were prepared, and the regions encoding the masking peptides were sequenced and aligned. As anticipated, these sequences could be separated into several groups, indicating clear enrichment through rounds of sorting. Four groups of masking peptide sequences, together with the invariant cleavage peptide sequences, are listed in Table 13.

TABLE 13

Masking peptide sequences

| Sample ID: | Peptide name: | Masking + cleavage peptide sequences: |
|---|---|---|
| TY22401 | B13189 | EVGSYNFVADSCPDHPYPCSASGRSAGGGGSPLGLAGSGGS (SEQ ID NO: 168) |
| TY22402 | B13180 | EVGSYIVHHSDCDAFYPYCDSSGRSAGGGGSPLGLAGSGGS (SEQ ID NO: 170) |
| TY22403 | B13192 | EVGSYYSAYPACDSHYPYCNSSGRSAGGGGSPLGLAGSGGS (SEQ ID NO: 172) |
| TY22404 | B13197 | EVGSYPNPSSDCVPYYYACAYSGRSAGGGGSPLGLAGSGGS (SEQ ID NO: 174) |

IgG Conversion and Expression

The four groups of masking peptides listed in Table 13, as well as additional four masking peptide sequences (Table 14) derived from two of them (B13192 and B13197) to eliminate a potential glycosylation site, were converted into IgG1s.

TABLE 14 additional masking peptide sequences

| Sample ID: | Masking + cleavage peptide sequences: |
|---|---|
| TY22563 | EVGSYYSAYPACDSHYPYCQSSGRSAGGGGSPLGLAGSGGS (SEQ ID NO: 177) |
| TY22564 | EVGSYYSAYPACDSHYPYCNSAGRSAGGGGSPLGLAGSGGS (SEQ ID NO: 178) |
| TY22565 | EVGSYPQPSSDCVPYYYACAYSGRSAGGGGSPLGLAGSGGS (SEQ ID NO: 179) |
| TY22566 | EVGSYPNPASDCVPYYYACAYSGRSAGGGGSPLGLAGSGGS (SEQ ID NO: 180) |

The heavy and light chains were cloned into the mammalian expression vector pCDNA3.3 (Thermo Fisher Scientific, cat #K830001) separately, and the masking peptides and the invariant cleavage peptide were fused to the N-terminus of the light chain in the same manner as displayed on yeast surface. The VH and VL sequences for the parental CTLA4 antibody (TY21580) are listed below:

Anti-CTLA4 heavy chain variable region (SEQ ID NO: 87):
EVQLVESGGGLVQPGGSLRLSCAASGYSISSGYHWSWIRQAPGKGLEWL
ARIDWDDDKYYSTSLKSRLTISRDNSKNTLYLQLNSLRAEDTAVYYCAR
SYVYFDYWGQGTLVTVSS -continued Anti-CTLA4 light chain variable region (SEQ ID
NO: 100):
DIQLTQSPSSLSASVGDRVTITCRASQSVRGRFLAWYQQKPGKAPKLLI
YDASNRATGIPSRFSGSGSGTDFTLTISSLQPEDFATYYCQQSSSWPPT
FGQGTKVEIKR.

Pairs of plasmids were transiently transfected into HEK293F cells. After six days, the supernatants were harvested, cleared by centrifugation and filtration, and IgGs were purified with standard protein A affinity chromatography (MabSelect SuRe, GE Healthcare). The IgGs were eluted and neutralized, and buffer exchanged into PB buffer (20 mM sodium phosphate, 150 mM NaCl, pH 7.0). Protein concentrations were determined by UV-spectrophotometry, and IgG purity was analyzed under denaturing, reducing and non-reducing conditions by SDS-PAGE or SEC-HPLC. Importantly, the expression levels of the activatable antibodies in HEK293 cells were similar to their parental antibody, and their purification yields after protein A resin were also similar, suggesting that the presence of the masking and cleavage peptides do not have a negative impact on antibody expression in mammalian cells.

Measurement of Masking Efficiency

Figure 34A:
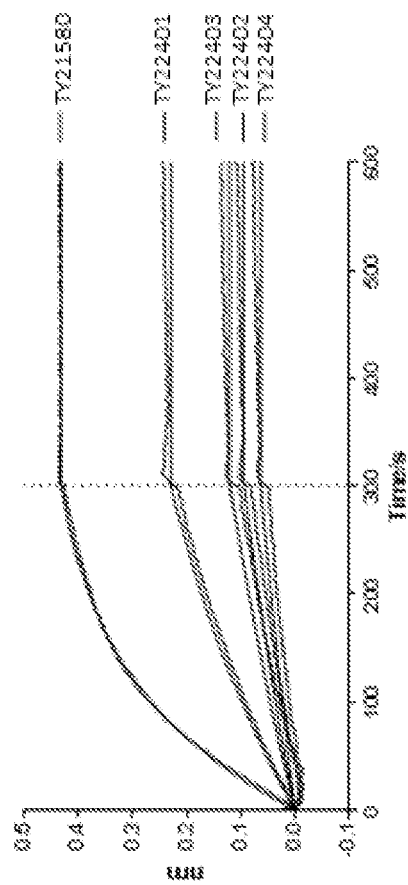
FIGS. 34A-B show the masking efficiency of exemplary CTLA4 activatable antibodies TY22401, TY22403, TY22402, and TY22404, as compared to the parental antibody TY21580.
Figure 34B:
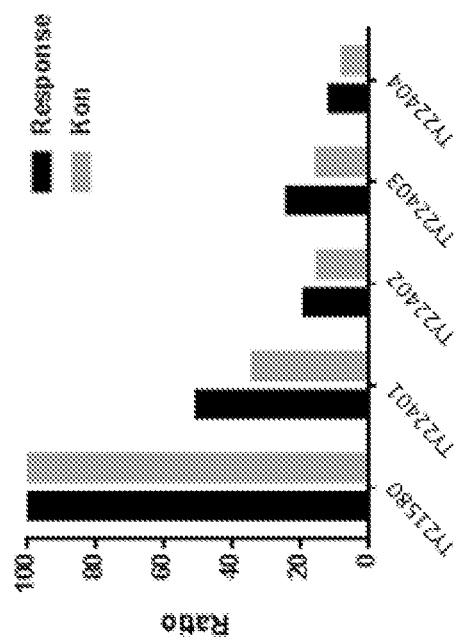

The ForteBio Octet RED96 system (Pall, USA) was used to quickly assess the efficiency of the masking peptides. Briefly, activatable antibodies (and their parent antibody, TY21580) were diluted to 30 ng/mL in KB buffer (PBS buffer supplemented with 0.02% Tween 20 and 0.1% BSA), and captured by anti-Human IgG Capture (AHC) Biosensors (Pall, USA) in parallel. The sensors were then allowed to associate with His-tagged CTLA4 protein (25 nM) for 300 seconds, and then dissociate in KB buffer for another 300 seconds. The association and dissociation curves were fitted to a 1:1 Langmuir binding model using ForteBio Data Analysis 7.1 (Pall, USA) according to the manufacturer's guidelines. As shown in FIGS. 34A-B, the responses achieved with the activatable antibodies were significantly lower than that for the parent antibody, suggesting that masking peptides effectively blocked the binding of the antibody to its antigen. Among the four activatable antibodies, however, TY22401 was less effective, consistent with the results from the ELISA assay discussed below.

Figure 35A:
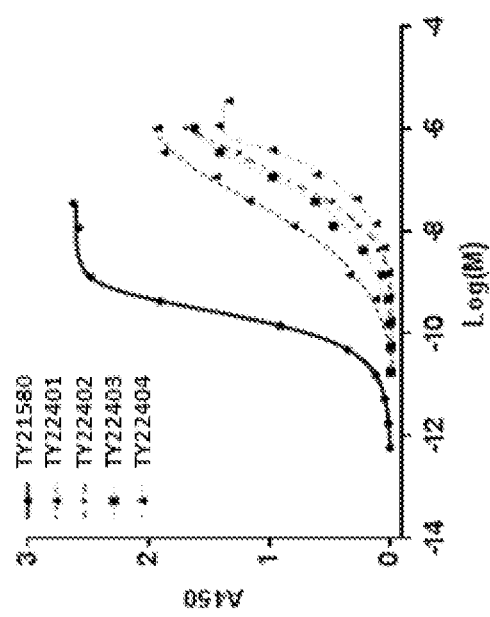
FIGS. 35A-B show the masking efficiency of exemplary CTLA4 activatable antibodies against recombinant human CTLA4-Fc, as determined by ELISA.
Figure 35B:
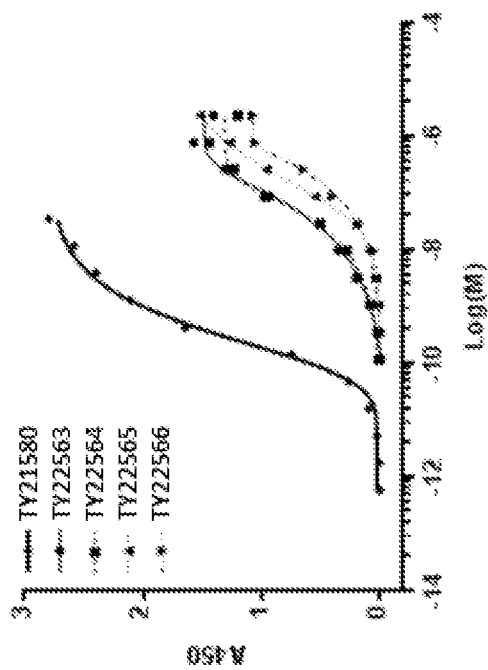

Recombinant human CTLA4-Fc was diluted to 1 µg/mL in PBS and coated on a Maxisorp plate at 4° C. overnight. Plates were blocked with PBS supplemented with 3% nonfat milk at 37° C. for 1 hour. After washing, 100 µL of 3-fold serial dilutions of antibodies were added to each well. After incubation at 37° C. for 1 hour, plates were washed four times, and 100 HRP conjugated anti-human IgG (Fab specific) (1:6000 dilution) was added to each well. Plates were incubated at 37° C. for 1 hour, washed four times, and then 50 µL TMB substrate solution was added to each well, and the plate was incubated at room temperature. Absorbance at 450 nm was measured after the reactions were stopped with 50 µL $H_2SO_4$ per well. The $EC_{50}$ was evaluated by fitting the ELISA data using the asymmetrical sigmoidal (five-parameter logistic equation) model of GraphPad Prism 6 software. Experiments for activatable antibodies TY22401, TY22402, and TY22404 were performed twice, leading to two calculated masking efficiencies being obtained for each of these activatable antibodies. Masking efficiencies for each activatable antibody were calculated by dividing the $EC_{50}$ for binding of the activatable antibody by the $EC_{50}$ of the parental antibody (TY21580). As shown in FIGS. 35A-B and Table 15, compared with the parental antibody, all of the activatable antibodies showed dramatically reduced binding to its antigen, and the calculated masking efficiency ranged from 48 to 2213. Differences in masking efficiency likely resulted from variation in measurement and data fitting for the $EC_{50}$ values, and the masking efficiency for each activatable antibody likely falls within the calculated ranges (e.g., the masking efficiency for activatable antibody TY22402 is between 377 and 2213). These results indicated that multiple masking peptides identified from the CPLs maintained their masking efficiency when expressed in mammalian cells, and as part of a full IgG molecule.

TABLE 15

Activatable antibody ELISAs prior to protease cleavage

| Sample ID: | LogEC$_{50}$: | EC$_{50}$ M: | nM: | R$^2$: | Masking efficiency: |
|---|---|---|---|---|---|
| Data Batch 1 | | | | | |
| TY21580 | −9.665 | 2.161E−10 | 0.216 | 0.999 | 1.0 |
| TY22401 | −7.623 | 2.382E−08 | 23.82 | 0.997 | 110 |
| TY22402 | −6.321 | 4.779E−07 | 477.9 | 0.997 | 2213 |
| TY22404 | −6.749 | 178.4E−07 | 178.4 | 0.998 | 826 |
| Data Batch 2 | | | | | |
| TY21580 | −9.478 | 3.324E−10 | 0.3324 | 0.998 | 1.0 |
| TY22401 | −7.800 | 1.586E−08 | 15.86 | 0.994 | 48 |
| TY22402 | −6.902 | 1.254E−07 | 125.4 | 0.998 | 377 |
| TY22404 | −6.892 | 1.281E−07 | 128.1 | 0.998 | 385 |
| TY21580 | −9.48 | 3.3E−10 | 0.33 | | 1.0 |
| TY22563 | −7.32 | 4.771E−08 | 47.71 | | 143.5 |
| TY22564 | −7.41 | 3.898E−08 | 38.98 | | 117.3 |
| TY22565 | −6.68 | 2.099E−07 | 209.9 | | 631.5 |
| TY22566 | −6.79 | 1.6264E−07 | 162.6 | | 489.2 |

Removal of the Masking Peptide Restores Antibody Activity

Figure 36A:
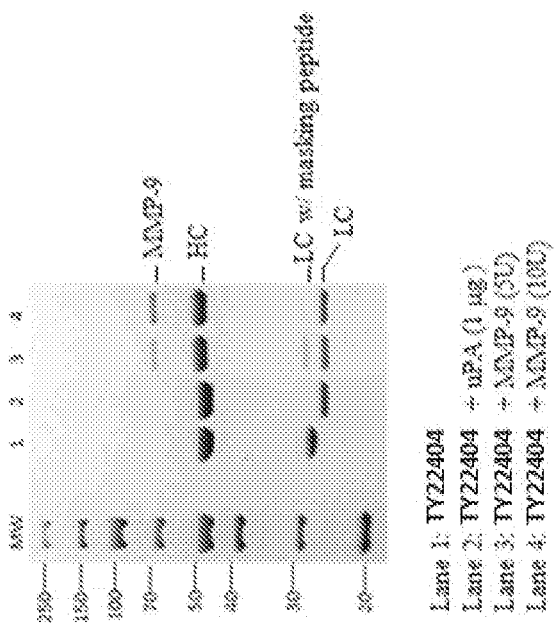
FIGS. 36A-B show activity of CTLA4 activatable antibody TY22404 upon removal of the masking peptide.
Figure 36B:
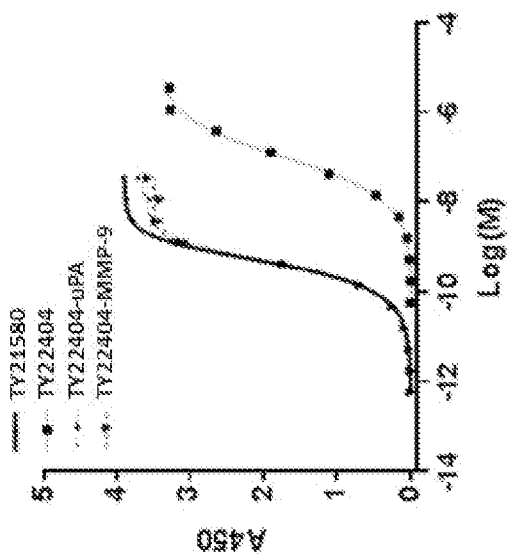

The purified activatable antibodies were treated with the proteases which recognize the cleavage sequences, and were then tested to determine whether removal of the masking peptide restored their activity. As an example, 20 µg of TY22404 (0.5 mg/mL) was treated with 1 µg of recombinant human uPA (Acrobiosystems, #PLU-H5229) in reaction buffer (50 mM Tris-HCl, 0.01% Tween 20, pH 8.5); or TY22404 was treated with 5 or 10 units of recombinant human MMP-9 (BioVision, #7867-500) in reaction buffer (50 mM Tris, 150 mM NaCl, 5 mM $CaCl_2$, 20 µM $ZnCl_2$, pH 7.5). The reactions were carried out at 37° C. for 21 hours. The masking peptides were confirmed to be removed from the light chain by SDS-PAGE analysis FIG. 36A. The masking efficiency was then measured by ELISA as described above. As shown in FIG. 36B and Table 16, after removal of masking peptide, the activatable antibody became indistinguishable from the parent antibody in its binding to the antigen.

TABLE 16

Activatable antibody ELISAs after protease cleavage

| Sample ID: | LogEC$_{50}$: | EC$_{50}$ nM: | Masking efficiency: |
|---|---|---|---|
| TY21580 | −9.35 | 0.447 | 1.0 |
| TY22404 | −7.01 | 96.8 | 216 |
| TY22404-uPA | −9.40 | 0.402 | 0.9 |
| TY22404-MMP-9 | −9.39 | 0.412 | 0.9 |

Activatable Antibody Developability Profiles

For manufacturing purpose, it is critical that the discovered activatable antibodies have a good developability profile. Several different tests were performed with purified activatable antibodies that were expressed in mammalian cells. The activatable antibodies were adjusted to 1 mg/mL in 20 mM Histidine, pH 5.5, and antibody quality analysis was performed using analytical size-exclusion chromatography using a Waters 2695 with a Waters 2996 UV detector and aTSKgel g3000 SWXL column (300 mm×7.8 mm) (Tosoh Bioscience). For each assay, 10 µg of antibody was injected, and fractionation was performed at a flow rate of 0.5 mL/min in buffer (200 mM sodium phosphate at pH 7.0).

Three accelerated stress tests were conducted: incubation of the activatable antibodies at 50° C. for 7 days, incubation of the activatable antibodies at 40° C. for 28 days, and six cycles of freeze-thaw. The freeze-thaw tests were conducted by freezing 100 µL sample (1 mg/mL in 20 mM histidine, pH 5.5) at −80° C. for 30 minutes, followed by thawing at room temperature for 60 min. As shown in FIGS. 37A-C, all activatable antibodies remained stable, and exhibited little aggregation after storage at 50° C. for 7 days or 40° C. for 28 days. After six cycles of freeze-thaw, they showed slight deterioration; however, the main monomer peak remained around 95%, indicating that these activatable antibodies were very stable under these accelerated stress tests. Without wishing to be bound by theory, it is worth noting that the activatable antibodies had not yet gone through an extensive buffer optimization process, and therefore, the stability of the activatable antibodies may be further improved with optimized buffer and excipient.

Figure 38:
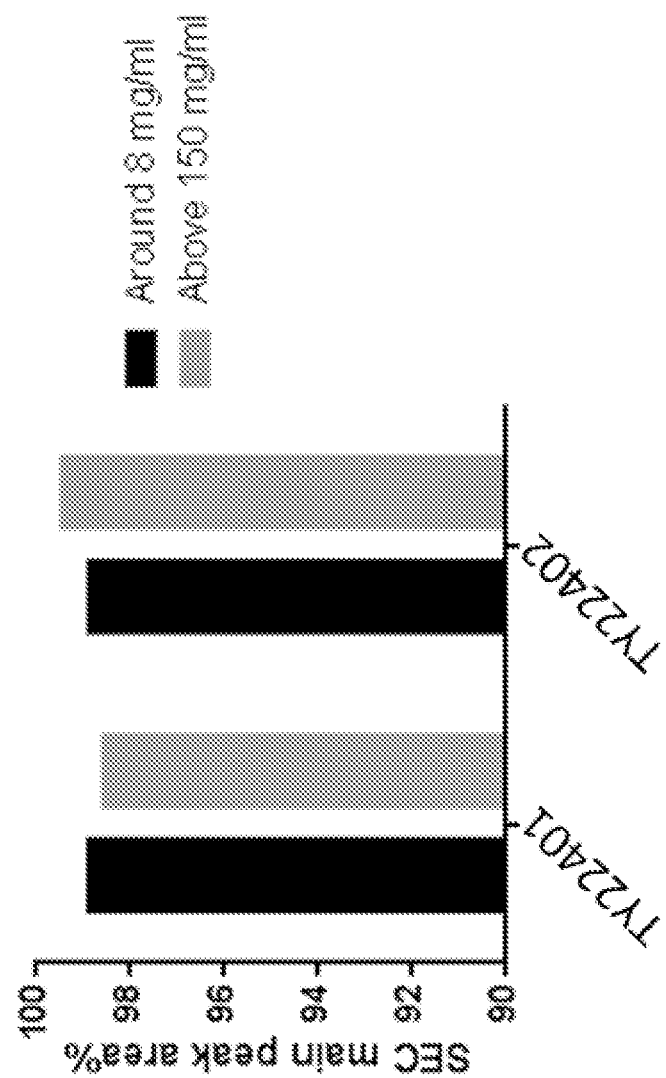
FIG. 38 shows the percentages of SEC main peak area of activatable antibodies TY22401 and TY22402 after storage at approximately 8 mg/mL or at >150 mg/mL.

Next, activatable antibodies were concentrated to more than 150 mg/mL in 20 mM histidine, pH 5.5 (Table 17). No activatable antibody precipitation was observed, and viscosity of the samples was quite manageable. The concentrated activatable antibodies were then diluted to either 20 mg/mL or 1 mg/mL for analysis of high molecular weight (HMW) species. As shown in FIG. 38 and Table 17, no apparent increase of the HMW species was observed, suggesting that these activatable antibodies were very soluble and stable in the buffer tested, up to high concentrations.

TABLE 17

Concentration of activatable antibodies >150 mg/mL

| Sample ID: | Starting conc. (mg/mL): | High conc. (mg/mL): |
|---|---|---|
| TY22401 | 10.9 | 187.2 |
| TY22402 | 8.4 | 160.0 |

Figure 39:
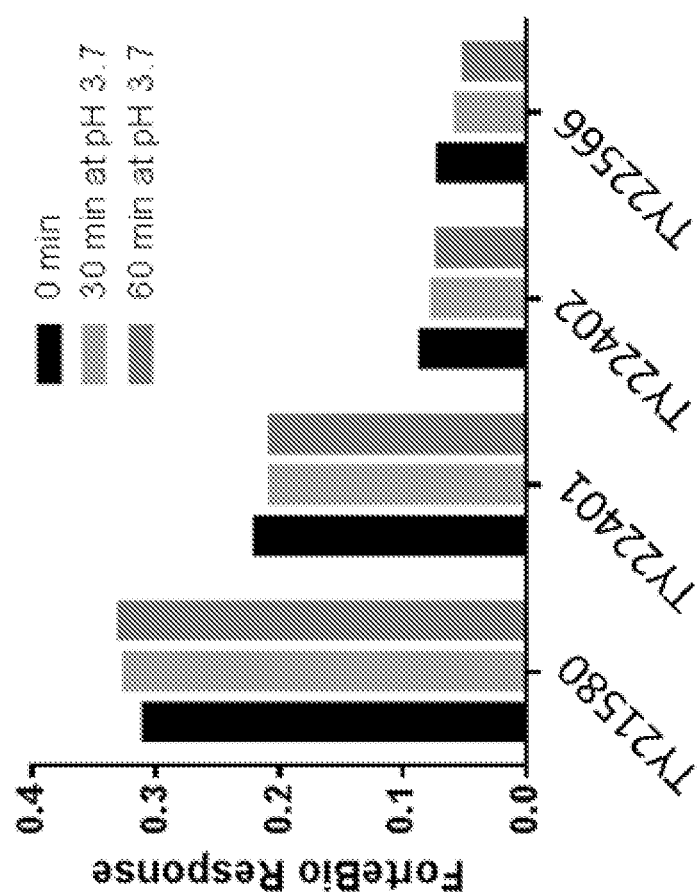
FIG. 39 shows the masking efficiency of untreated activatable antibodies TY21580, TY22401, TY22402 and TY22566 incubated at pH 3.7 for 30 minutes, or incubated at pH 3.7 for an hour, as determined by the ForteBio System.

To study the stability of the activatable antibodies at low pH, the purified activatable antibodies (at 10 mg/mL in 20 mM histidine, pH 5.5) were titrated to 1 mg/mL with citric acid, and the pH was adjusted to 3.7 and held at room temperature for 30 and 60 minutes. Afterwards, the samples were neutralized to pH 7.0 with 1 M Tris-base. The masking efficiency of the activatable antibodies was measured with ForteBio, as described above. As shown in FIG. 39, masking efficiency remained unchanged after low pH incubation for 30 or 60 minutes, suggesting that the masking peptides retained their blocking efficacy after low pH incubation.

Taken together, the data indicates that the discovered activatable antibodies remained stable under various stress conditions, and therefore, they have good developability profile.

Example 9: In Vitro and In Vivo Characterization of Activatable Antibodies Targeting CTLA4

It is known that CTLA-4 activity on T cells is related to the first (TCR/CD3) and second signals involving B7-CD28/CTLA-4.

In Vitro Functional Characterization

Figure 40A:
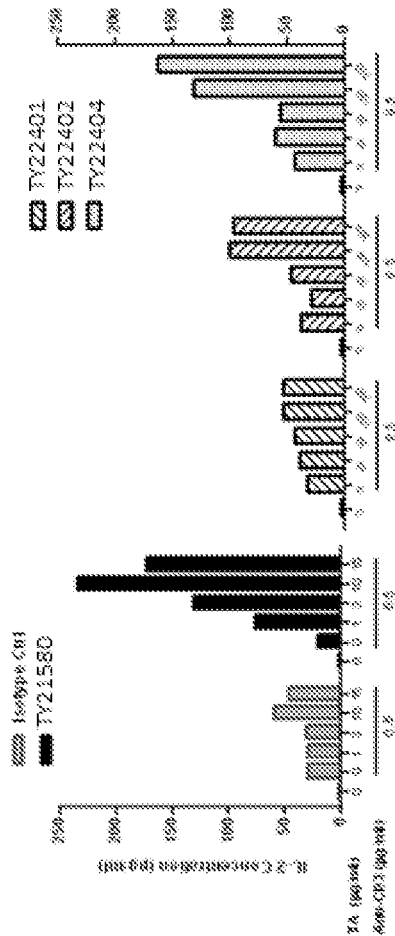
FIGS. 40A-B show human peripheral blood mononuclear cell (PBMC) activation by isotype control antibody, parental antibody TY21580, or exemplary CTLA4 activatable antibodies TY22401, TY22402, or TY22404, as measured by ELISA.
Figure 40B:
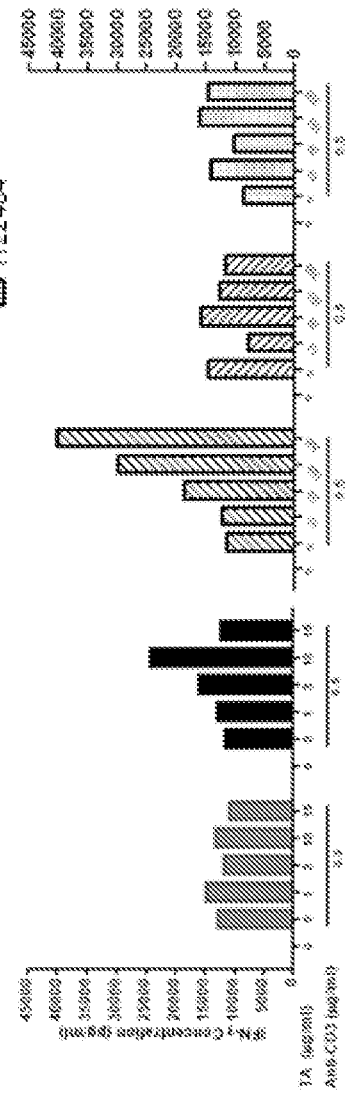

Here the activities of the activatable antibodies targeting CTLA4 were evaluated in the presence of a low concentration of anti-CD3 antibody on human PMBC activation. Human PBMCs were freshly isolated from the blood of a healthy donor (#44) by density gradient centrifugation using Histopaque-1077 (Sigma). Anti-CD3 (OKT-3) antibody was coated on a 96 well plate overnight at 4° C. After washing, 1×10^5 freshly isolated human PBMCs were added to each well, followed by the addition of the test articles at different concentrations. Induction of IL-2 was measured 48 hours after stimulation using a Human IL-2 ELISA Ready-SET-Go (Invitrogen) kit. IFN-γ in the supernatant was measured using a Human IFN-γ ELISA Ready-SET-Go (Invitrogen) kit. As demonstrated in FIGS. 40A-B, at high concentrations, TY22404 induced IL-2 production, and TY22401 induced IFN-γ production. Nevertheless, the activities of the activatable antibodies were significantly lower than that of the parental TY21580 antibody.

Figure 41:
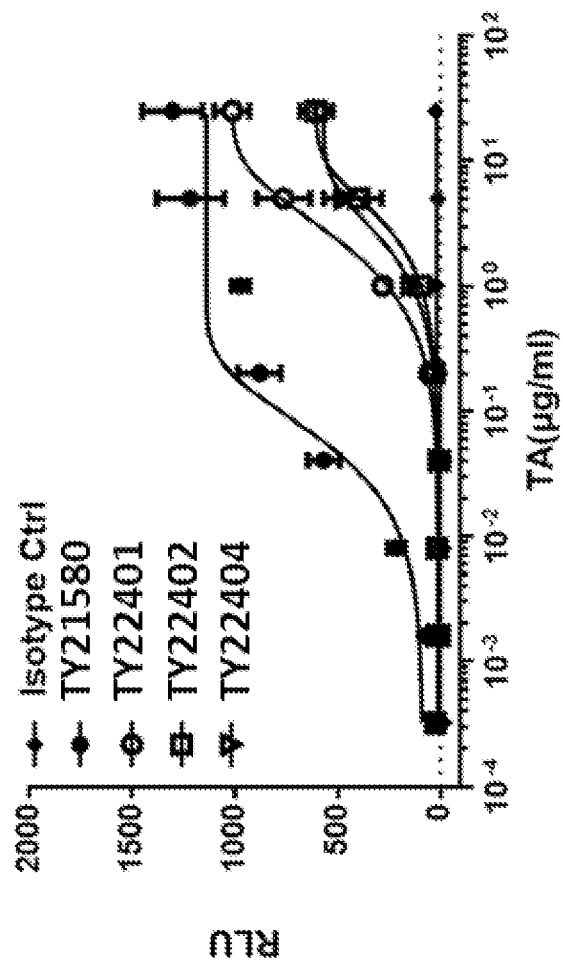
FIG. 41 shows the antibody-dependent cell-mediated cytotoxicity (ADCC) activity of isotype control antibody, the parental antibody TY21580, or exemplary activatable antibodies TY22401, TY21580, or TY22404 on HEK293F cells transiently overexpressing human CTLA4, as determined by an ADCC reporter gene assay.

Next, the antibody-dependent cell cytotoxicity activities of the activatable antibodies were tested and compared with that of the parental antibody TY21580. An ADCC reporter gene assay was used to evaluate the ADCC activities of the activatable antibodies. HEK293F cells overexpressing human CTLA4 (HEK293F/hCTLA-4 cells) were used as target cells; a Jurkat cell line overexpressing CD16a and NFAT-Luc (Jurkat/CD16a cells) was used as effector cells. 1×10^5 Jurkat/CD16a cells and 1×10^4 HEK293F/hCTLA-4 cells (E:T ratio 10:1) were mixed with different concentrations of antibody. After incubation for 6 hours, 100 µL of One-Glo reagent was added to the cells, and the cells were lysed for 10 min. Supernatants were removed for luminescence measurements using a SpectraMax i3x plate reader. As shown in FIG. 41, the activatable antibodies showed several log lower ADCC activities than the parental antibody TY21580. The ADCC activity of TY22401 was higher than that of TY22402 and TY22404. Taken together, the in vitro data indicates that the better masked activatable antibodies had less ADCC activity.

The anti-tumor activities of the activatable antibodies were next evaluated and compared with the anti-tumor activity of the parental antibody TY21580 in multiple syngeneic mouse tumor models, including an MC38 colorectal tumor model, a CT26 colorectal tumor models, an H22 liver tumor model, and a 3LL lung tumor model.

Anti-Tumor Efficacy in an MC38 Colorectal Tumor Model

Figure 42A:
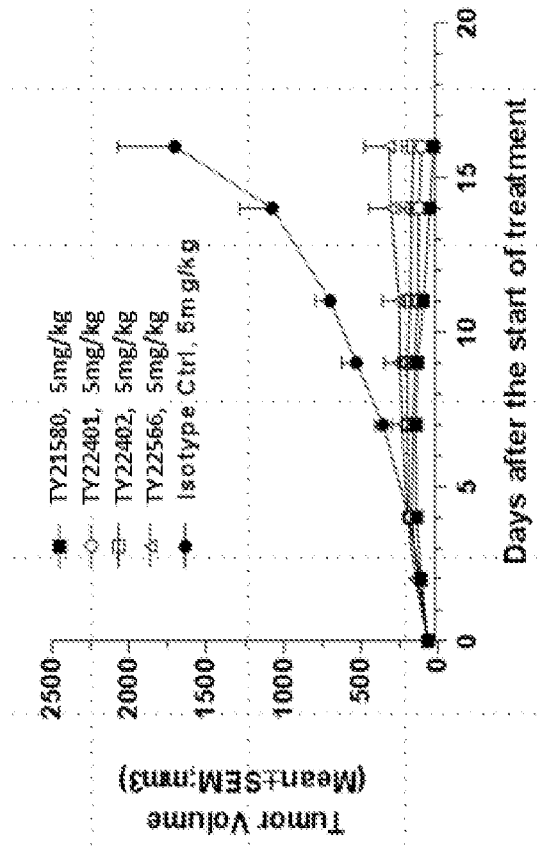
FIGS. 42A-B show the in vivo anti-tumor efficacy of parental antibody TY21580, isotype control antibody, or exemplary CTLA4 activatable antibodies TY22401, TY22402, or TY22566 in an MC38 syngeneic mouse colorectal tumor model.
Figure 42B:
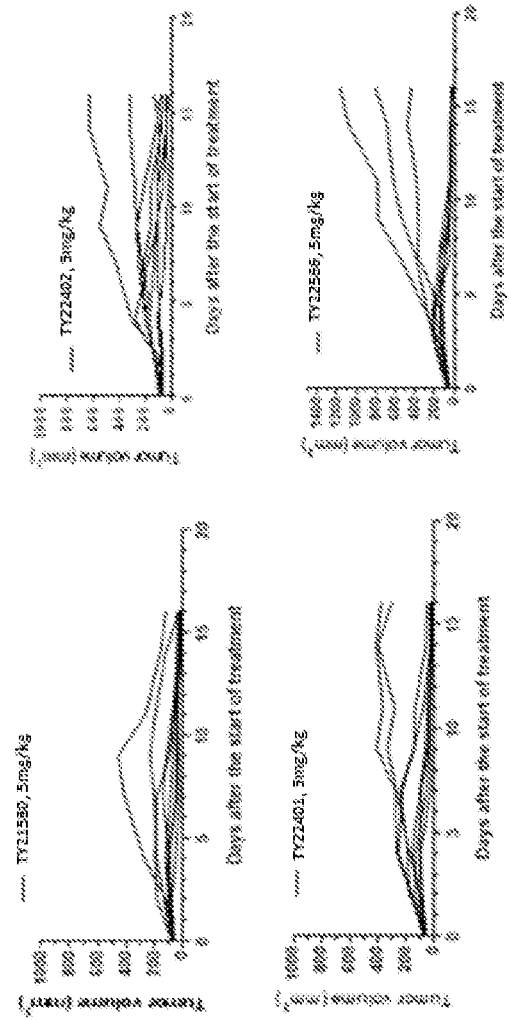

C57BL/6 mice (n=8 per group, female, 6-8 weeks old) were inoculated subcutaneously with MC38 (NTCC-MC38) murine colon cancer cells. When tumors were established (70 mm3), treatment began with isotype control antibody, parental antibody TY21580, or one of three activatable antibodies by intraperitoneal injection, twice a week. Tumor growth was monitored twice a week, the mean tumor volume±s.e.m. over time (FIG. 42A) and individual tumor growth curves (FIG. 42B) were assessed. As shown in FIGS. 42A-B, all three activatable antibodies showed potent anti-tumor activities, comparable to the parental antibody TY21580 in the MC38 syngeneic mouse tumor model.

Anti-Tumor Efficacy in a CT26 Colorectal Tumor Model

Figure 43:
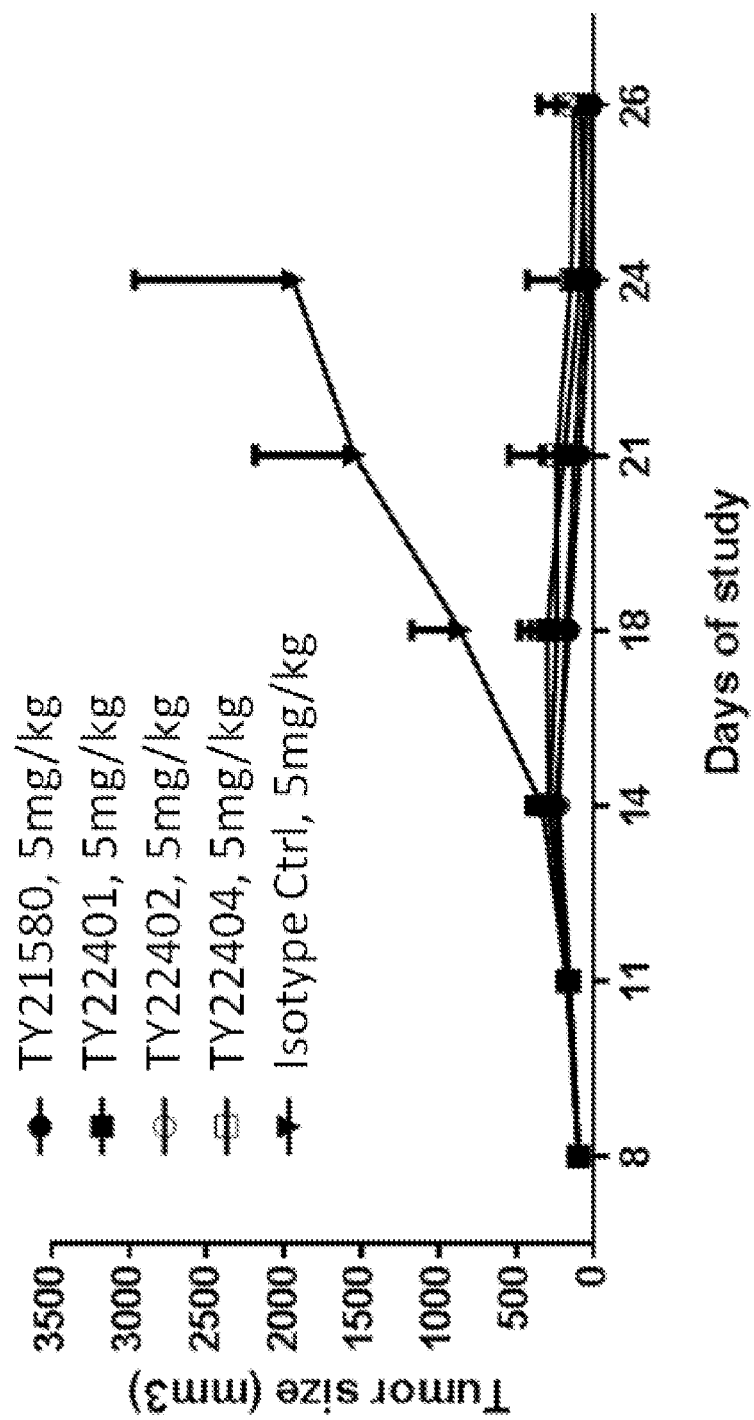
FIG. 43 shows the in vivo anti-tumor efficacy of isotype control antibody, parental antibody TY21580, or one of three activatable antibodies, in a CT26 syngeneic mouse colorectal tumor model. Tumor growth curves of different treatment groups of female C57BL/6 mice bearing CT26-established tumors are shown. Data points represent group mean; error bars represent SEM.

BALB/c mice (n=8 per group, female, 7-8 weeks old) were inoculated subcutaneously with CT26 (Shanghai Institutes for Biological Sciences) murine colon cancer cells. When tumors were established (100 mm3), treatment began with isotype control antibody, parental antibody TY21580, or one of three activatable antibodies at 5 mg/kg by intraperitoneal injection, twice a week. Tumor growth was monitored twice a week and reported as the mean tumor volume±s.e.m. over time. As shown in FIG. 43, all three activatable antibodies showed potent anti-tumor activities, comparable to the parental antibody TY21580 in CT26 syngeneic mouse tumor model.

Anti-Tumor Efficacy in an H22 Liver Tumor Model

Figure 44:
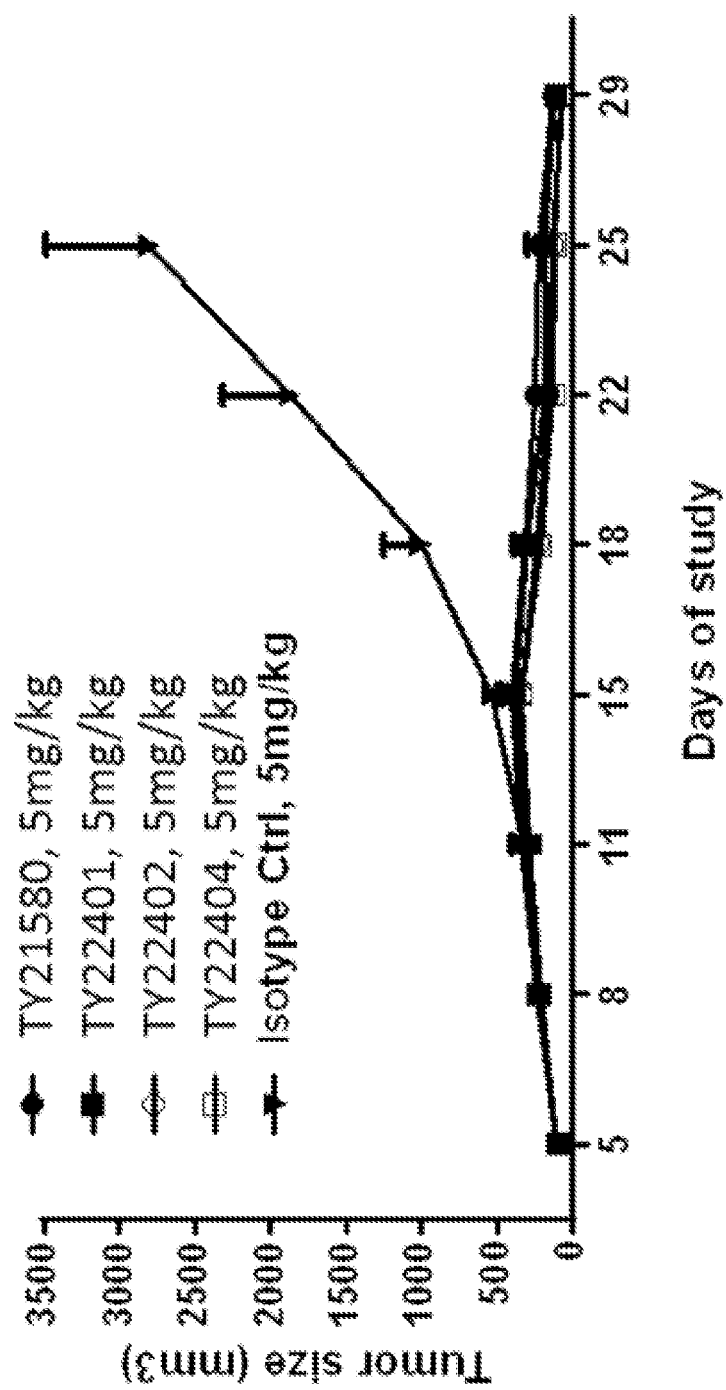
FIG. 44 shows the in vivo anti-tumor efficacy of isotype control antibody, parental antibody TY21580, or one of three activatable antibodies, in an H22 syngeneic mouse liver tumor model. Tumor growth curves of different treatment groups of female C57BL/6 mice bearing H22-established tumors are shown. Data points represent group mean; error bars represent SEM.

BALB/c mice (n=8 per group, female, 7-8 weeks old) were inoculated subcutaneously with H22 (China Center for Type Culture Collection) murine liver cancer cells. When tumors were established (100 mm3), treatment began with isotype control antibody, parental antibody TY21580, or one of three activatable antibodies at 5 mg/kg by intraperitoneal injection, twice a week. Tumor growth was monitored twice a week and reported as the mean tumor volume±s.e.m. over time. As shown in FIG. 44, all three Activatable antibodies showed potent anti-tumor activities, comparable to the parental antibody TY21580 in H22 syngeneic mouse tumor model.

Anti-Tumor Efficacy in a 3LL Lung Cancer Model

Figure 45A:
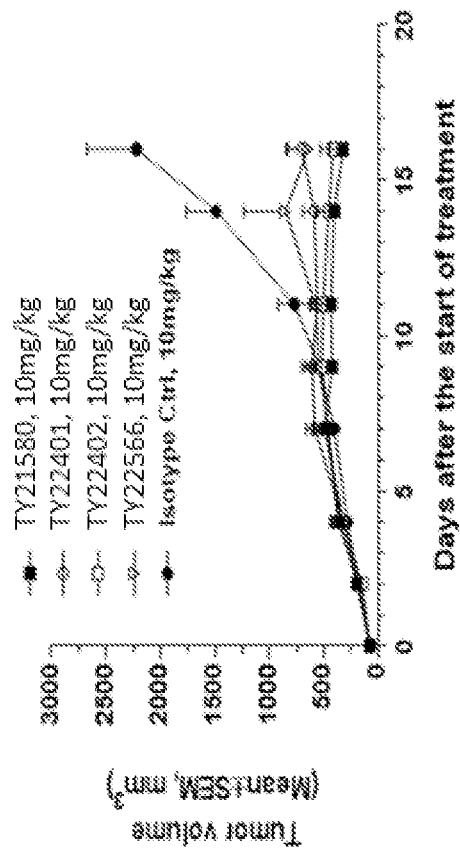
FIGS. 45A-B show the in vivo anti-tumor efficacy of parental antibody TY21580, isotype control antibody, and exemplary activatable antibodies TY22401, TY22402, or TY22566 in a 3LL syngeneic mouse lung tumor model.
Figure 45B:
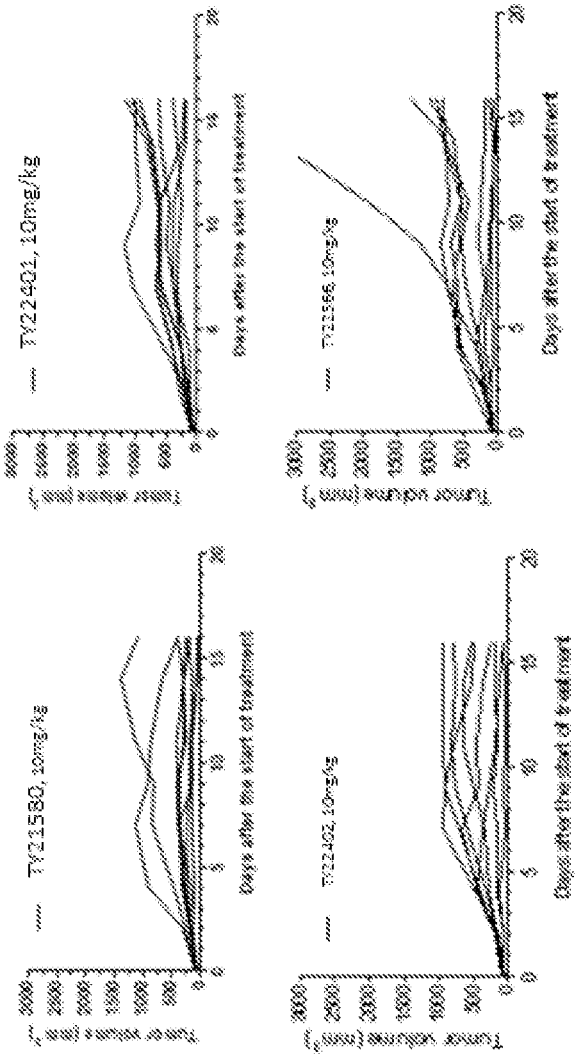

C57BL/6 mice (n=10 per group, female, 6-8 weeks old) were inoculated subcutaneously with 3LL (JCRB) murine lung cancer cells. When tumors were established (75 mm3), treatment began with isotype control antibody, parental antibody TY21580, or one of three activatable antibodies by intraperitoneal injection, twice a week. Tumor growth was monitored twice a week, the mean tumor volume±s.e.m. over time (FIG. 45A) and individual tumor growth curves (FIG. 45B) were assessed. As shown in FIGS. 45A-B, all three activatable antibodies showed potent anti-tumor activities, comparable to the parental antibody TY21580 in 3LL syngeneic mouse tumor model.

Pharmacokinetic Analysis

Figure 46B:
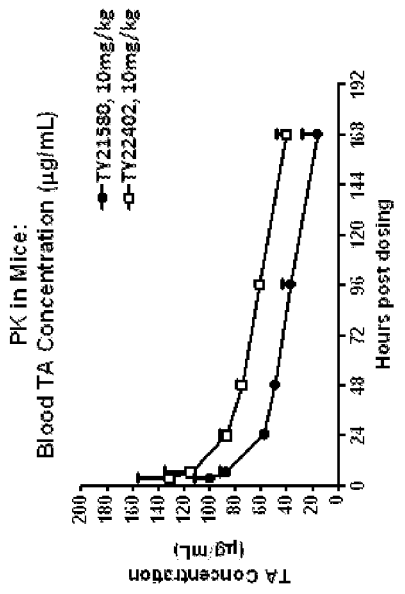
FIGS. 46A-C show time courses of the blood concentrations of the test articles (TAs) intravenously administered at a concentration of 10 mg/kg to female BALB/c mice, as determined by ELISA.
Figure 46A:
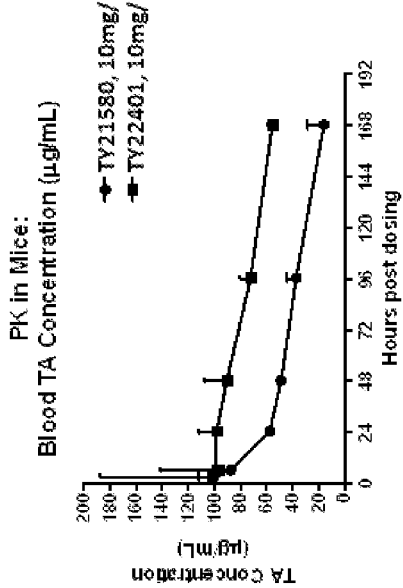
Figure 46C:
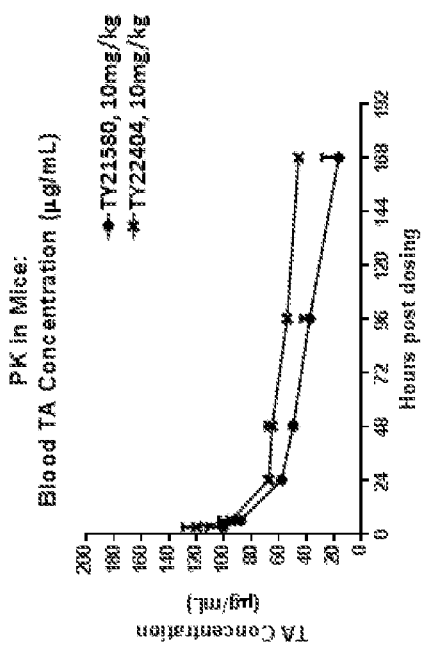

A pharmacokinetics study was conducted in BALB/c female mice at about eight weeks of age. Three mice per group were intraperitoneally injected with the test article at 10 mg/kg. Blood samples (~50 ul per sample) were collected at 3, 6, 24, 48, 96, and 168 hours post-dosing. Blank control blood was collected from three naïve female mice without antibody administration. Serum concentrations of each test antibody were determined by ELISA, in which anti-human IgG Fc was used for capture, and HRP-labeled anti-human IgG (Fab specific) antibody (Sigma) was used for detection (FIGS. 46A-C). As compared to the previous data collected for parental antibody TY21580, activatable antibodies TY22401 (FIG. 46A), TY22402 (FIG. 46B), and TY22404 (FIG. 46C) had a much slower clearance time and longer half-life. TY22401 has a half-life of 196 hours, and the drug concentration at 168 hours was about 55 µg/mL. TY22402 had a half-life of 134 hours, and the drug concentration at 168 hours was about 40 µg/mL. TY22404 had a half-life of 254 hours, and the drug concentration at 168 hours was about 45 µg/mL. In comparison, the parental antibody TY21580 had a half-life of 107 hours, and the drug concentration at 168 hours was about 17 µg/mL.

Repeated Dosing Toxicity Studies

Figure 47:
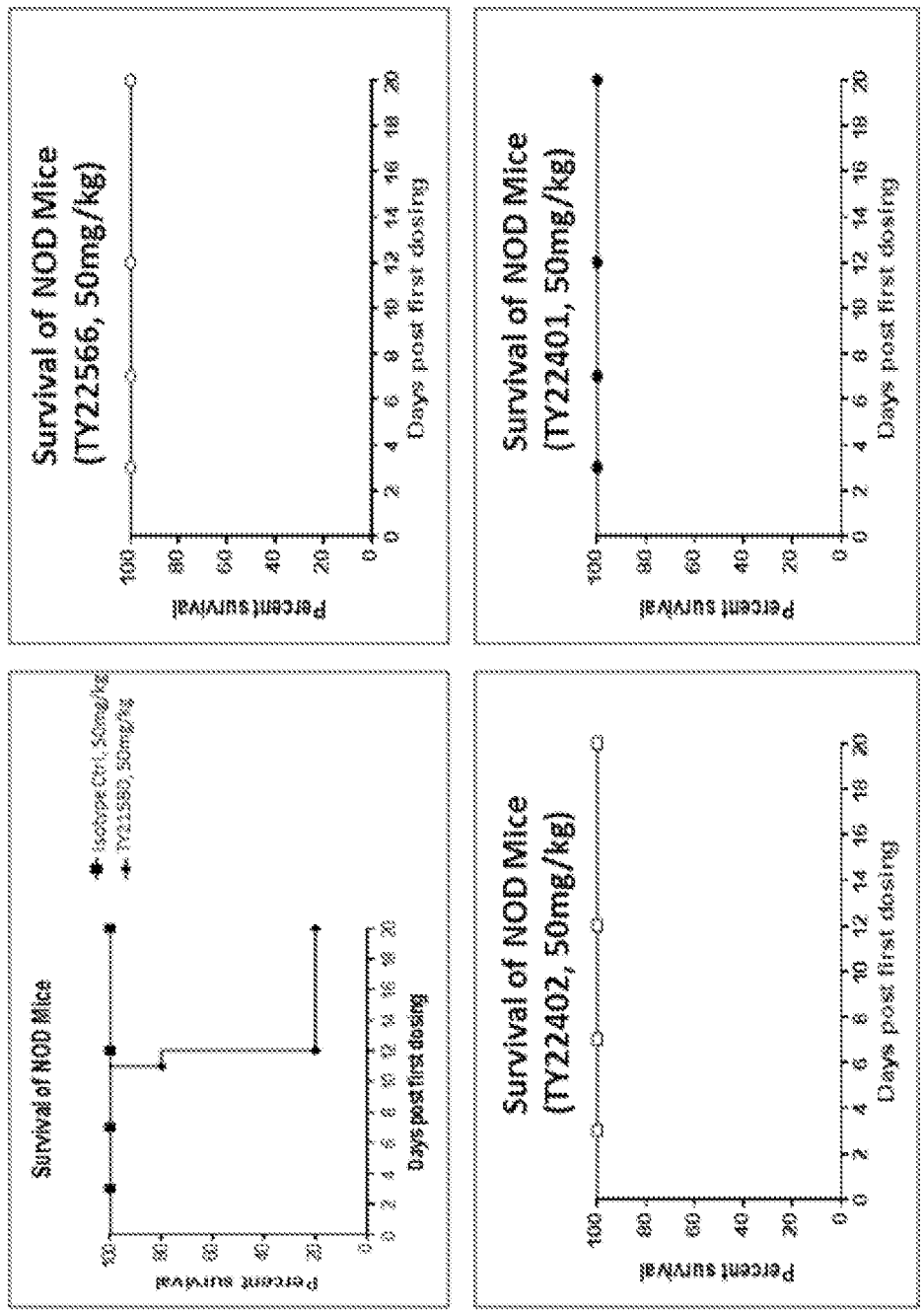
FIG. 47 shows the repeated dosing toxicity of isotype control antibody, parental antibody TY21580, and exemplary activatable antibodies TY22566, TY22401, and TY22402 using the NOD mouse model. Percent survival rate over 20 days were shown for each treatment group.

While evaluating the effect of TY21580 on diabetes onset age in NOD mice, it was found that high dosages of TY21580 could lead to animal death of NOD but not normal BALB/c mice. Here the NOD mouse model was used to evaluate the safety of the activatable antibodies, as compared to that of TY21580. NOD mice (n=5 per group, female, 6 weeks old) were treated with isotype control antibody, parental antibody TY21580, or one of three activatable antibodies by intraperitoneal injection at 50 mg/kg on days 0, 3, 7, and 12. In the TY21580 treatment group, 1 animal died after the third dosing, and 3 animals died after the fourth dosing. As shown in FIG. 47, all animals treated with the isotype control or any of the three activatable antibodies were alive and in good health at the termination of the study. These data indicated that the activatable antibodies have acceptable safety/toxicity profiles in mice, and, in NOD mice, the activatable antibodies are much safer than the parental antibody TY21580.

Example 10: Additional In Vivo Characterizations of Activatable Antibodies Targeting CTLA4

In the previous studies of the parental antibody TY21580, it was found that repeated dosing of TY21580 lead to increased spleen size in both female and male normal BALB/c mice. Other than that, TY21580 did not show any significant side effects on other evaluated parameters, including the weights of many organs, liver histopathology, hematology, and blood biochemistry. Therefore, the effect of several activatable antibodies on spleen size was evaluated and compared with that of the parental antibody TY21580.

Figure 48C:
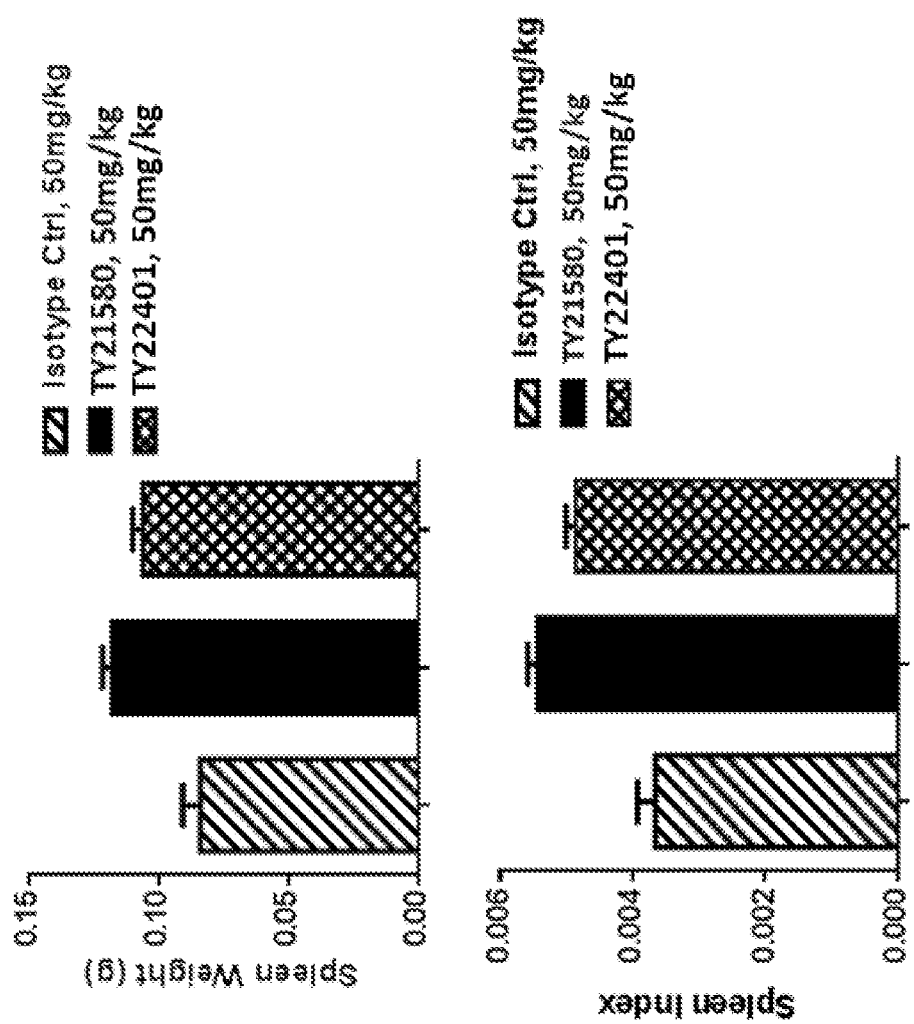

Repeated dosing toxicity of the activatable antibodies was conducted in normal BALB/c mice as follows: 50 mg/kg of isotype control antibody, TY21580 parental antibody, or activatable antibody TY22402, TY22566, or TY22401 was administered intraperitoneally (10 mL/kg) on days 1, 4, 7, and 11. Five female mice (five weeks old) were included in each group. Mice were monitored daily for abnormal behaviors and symptoms, and measured daily for food intake and body weight. On day 14, animals were euthanized for post-mortem examination and other analyses. Interestingly, while administration of activatable antibodies TY22402 (FIG. 48A) or TY22566 (FIG. 48B) slightly increased the spleen size in mice as compared to the isotype control, these activatable antibodies showed significantly less effect on spleen size as compared to administration of the parental antibody TY21580. Administration of activatable antibody TY22401 significantly increased the spleen size as compared to isotype control, but still to a lesser extent than was observed using the parental antibody TY21580 (FIG. 48C).

As CTLA4 is constitutively expressed on Treg cells, the effects of activatable antibodies TY22402, TY22566, or TY22401 on Treg cells, CD4$^+$ T cells, and CD8$^+$ T cells in both whole blood and the spleen were evaluated and compared to parental antibody TY21580. Monocytes from whole blood or splenocytes were stained and gated using the following antibodies: anti-CD45-BV421, anti-CD3-AF488, anti-CD4-BV510, anti-CD8a-PerCP-cy5.5, anti-CD25-APC, and antiFoxP3-PE. Treg cells were defined as CD45$^+$CD3$^+$CD4$^+$CD25$^+$Foxp3$^+$. As shown in Table 18, compared to isotype control, parental antibody TY21580 increased the percentage of Treg cells in the spleen; however, activatable antibodies TY22402 and TY22566 did not affect the percentage of splenic Tregs. In whole blood, TY21580, TY22402, and TY22566 slightly increased the percentage of Treg cells when compared to isotype control. Activatable antibody TY22401 increased the percentage of Treg cells in the spleen and whole blood. The percentages of CD4$^+$ and CD8$^+$ T cells were not significantly altered by TY21580, TY22402, TY22566, or TY22401 (data not shown).

TABLE 18

FACS analysis showing effect of activatable antibodies on spleen Treg and blood Treg cells

| Group: | Sample: | Spleen: Treg % in CD4+ T cells | Blood: Treg % in CD4+ T cells |
|---|---|---|---|
| Isotype control (50 mg/kg, BIW) | 6-1 | 10.50 | 1.71 |
| | 6-2 | 8.25 | 0.70 |
| | 6-3 | 8.04 | 0.67 |
| | 6-4 | 6.81 | 0.90 |
| | Mean | 8.40 | 1.00 |
| | SD | 1.54 | 0.49 |
| TY21580 (50 mg/kg, BIW) | 5-1 | 11.55 | 2.14 |
| | 5-2 | 8.52 | 1.56 |
| | 5-3 | 10.64 | 1.84 |
| | 5-4 | 11.69 | 1.40 |
| | Mean | 10.60 | 1.74 |
| | SD | 1.47 | 0.32 |
| TY22402 (50 mg/kg, BIW) | 3-1 | 7.10 | 1.42 |
| | 3-2 | 7.08 | 1.00 |
| | 3-3 | 10.77 | 1.70 |
| | 3-4 | 10.25 | 1.98 |
| | Mean | 8.80 | 1.53 |
| | SD | 1.99 | 0.42 |
| TY22566 (50 mg/kg, BIW) | 4-1 | 11.31 | 3.07 |
| | 4-2 | 6.42 | 1.04 |
| | 4-3 | 11.31 | 2.70 |
| | 4-4 | 5.26 | 1.48 |
| | Mean | 8.58 | 2.07 |
| | SD | 3.19 | 0.97 |
| TY22401 (50 mg/kg, BIW) | 2-1 | 10.39 | 2.23 |
| | 2-2 | 11.12 | 4.09 |
| | 2-3 | 10.63 | 1.71 |
| | 2-4 | 11.96 | 2.76 |
| | Mean | 11.03 | 2.70 |
| | SD | 0.69 | 1.02 |

Example 11: Additional Activatable Antibody Developability Assays

Figure 49:
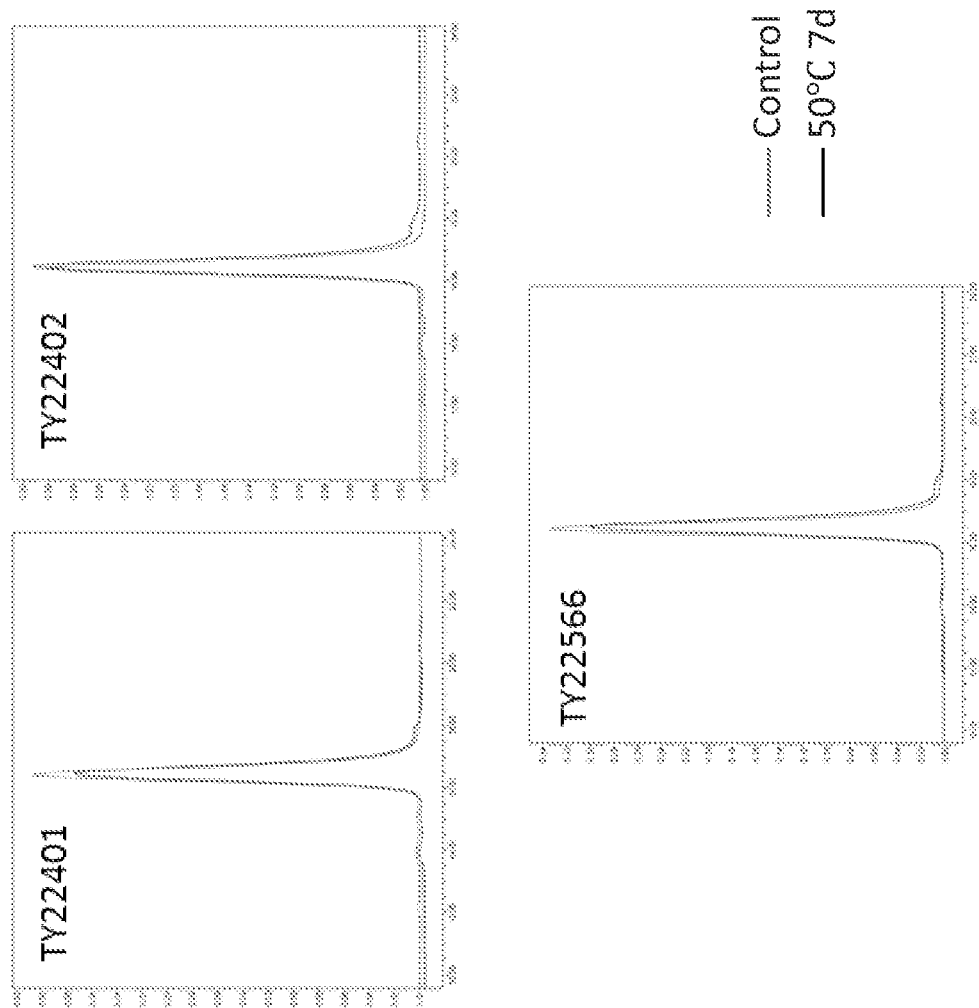
FIG. 49 shows the size-exclusion chromatography (SEC) profiles of the indicated activatable antibodies after seven days at 50° C., as compared to the control condition.

Several different tests were performed with purified activatable antibodies that were expressed in mammalian cells to determine their developability profiles. Three accelerated stress tests were conducted. First, activatable antibodies TY22401, TY22402, or TY22566 were incubated at 50° C. for 7 days, and their stabilities were determined by SEC and compared to isotype control (FIG. 49). Only slight increases, if any, in high molecular weight (HMW) aggregates or low molecular weight (LMW) fragments were observed for the activatable antibodies after incubation for 7 days at 50° C. (Table 19).

TABLE 19

Activatable antibody stability at 50° C. for 7 days

| Sample: | HMW % (control) | LMW % (control) | HMW % (50° C., 7 days) | LMW % (50° C., 7 days) |
|---|---|---|---|---|
| TY22566 | 1.35 | 0.33 | 1.24 | 2.78 |
| TY22401 | 2.15 | 0.20 | 2.13 | 1.97 |
| TY22402 | 2.46 | 0 | 0.45 | 2.57 |

Figure 50:
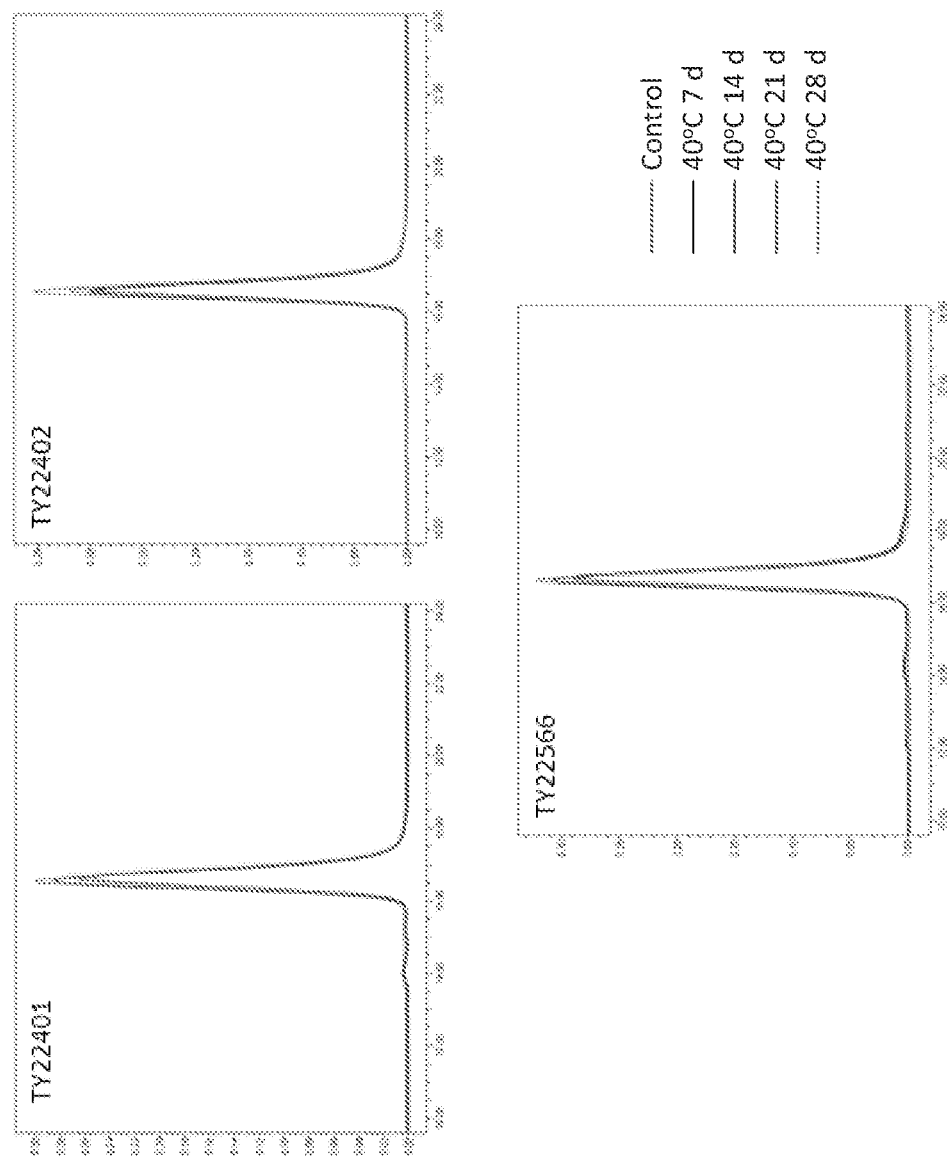
FIG. 50 shows the size-exclusion chromatography (SEC) profiles of the indicated activatable antibodies after storage at 40° C. for 7, 14, 21, or 28 days, as compared to the control condition.

Nest, activatable antibodies TY22401, TY22402, or TY22566 were incubated at 40° C. for 7, 14, 21, or 28 days, and their stabilites were determined by SEC and compared to isotype control (FIG. 50). Only slight increases, if any, in high molecular weight (HMW) aggregates or low molecular weight (LMW) fragments were observed for the activatable antibodies after incubation for at 40° C. at the various time points (Table 20).

TABLE 20

Activatable antibody stability at 40° C. for 28 days

| Sample: | HMW % (control) | LMW % (control) | HMW % (40° C., 28 days) | LMW % (40° C., 28 days) |
|---|---|---|---|---|
| TY22566 | 1.02 | 0.00 | 1.86 | 1.64 |
| TY22401 | 1.57 | 0.00 | 2.03 | 1.19 |
| TY22402 | 1.02 | 0.00 | 1.86 | 1.64 |

Figure 51:
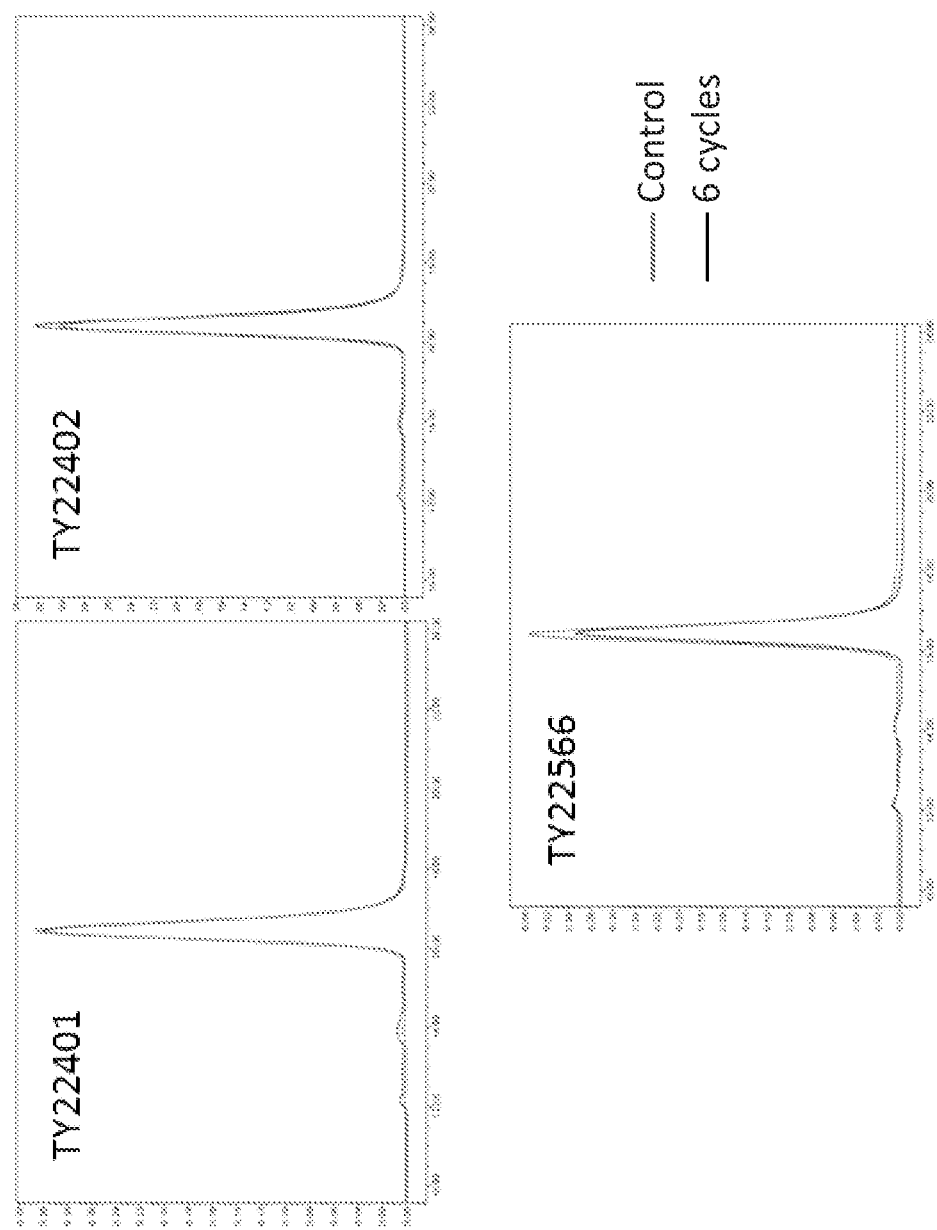
FIG. 51 shows the size-exclusion chromatography (SEC) profiles of the indicated activatable antibodies after six cycles of freezing and thawing, as compared to the control condition.

In addition, activatable antibodies TY22401, TY22402, or TY22566 were subjected to six cycles of freeze-thaw. The freeze-thaw tests were conducted by freezing 100 μL sample (1 mg/mL in 20 mM histidine, pH 5.5) at −80° C. for 30 minutes, followed by thawing at room temperature for 60 min, and stability was measured by SEC and compared to isotype control (FIG. 51). Only slight increases, if any, in high molecular weight (HMW) aggregates were observed for the activatable antibodies after these freeze-thaw cycles (Table 21).

TABLE 21

Activatable antibody stability after 6 freeze-thaw cycles

| Sample: | HMW % (control) | HMW % (6 cycles) |
|---|---|---|
| TY22566 | 1.35 | 4.36 |
| TY22401 | 2.15 | 4.96 |
| TY22402 | 2.46 | 3.48 |

Figure 52:
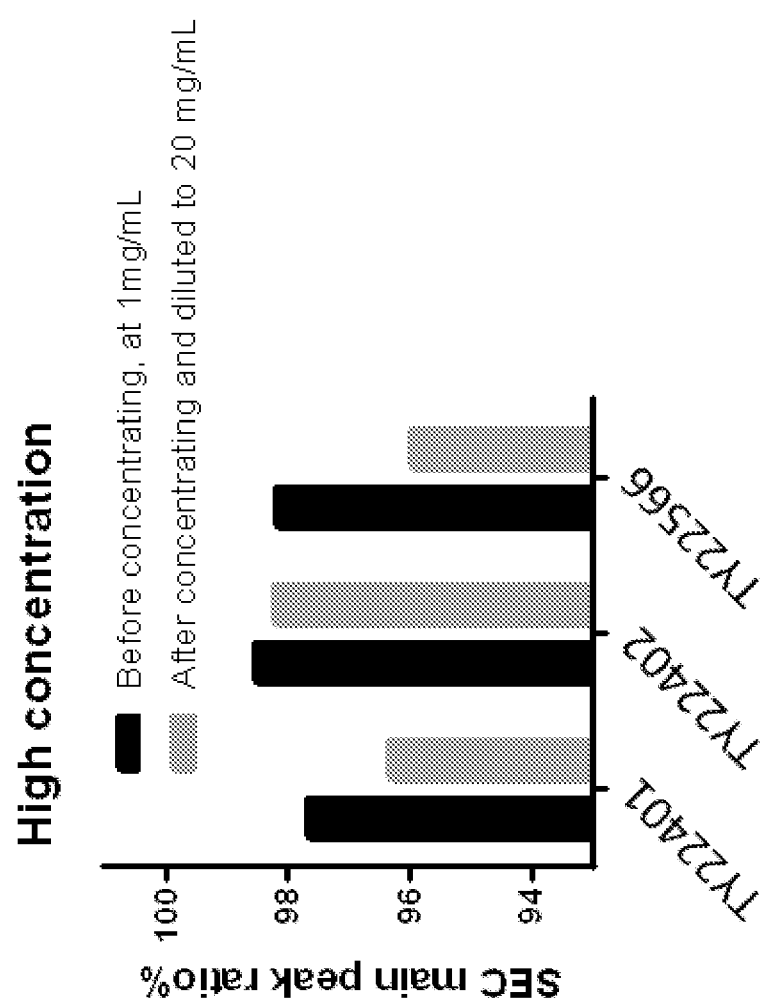
FIG. 52 shows the percentages of SEC main peak ratios of the indicated activatable antibodies after storage at >115 mg/mL.

Next, activatable antibodies were concentrated to more than 115 mg/mL in 20 mM histidine, pH 5.5. The concentrated activatable antibodies were then diluted to 20 mg/mL for analysis of high molecular weight (HMW) species. As shown in FIG. 52 and Table 22, no apparent increase of the HMW species was observed, suggesting that these activatable antibodies were very soluble and stable in the buffer tested, up to high concentrations.

TABLE 22

Concentration of activatable antibodies >150 mg/mL

| Sample: | Concentrated (mg/mL) | HMW % (control) | HMW % (concentrated) |
|---|---|---|---|
| TY22566 | 125.73 | 2.35 | 3.69 |
| TY22401 | 115.98 | 1.47 | 1.80 |
| TY22402 | 128.87 | 1.82 | 4.04 |

Figure 53:
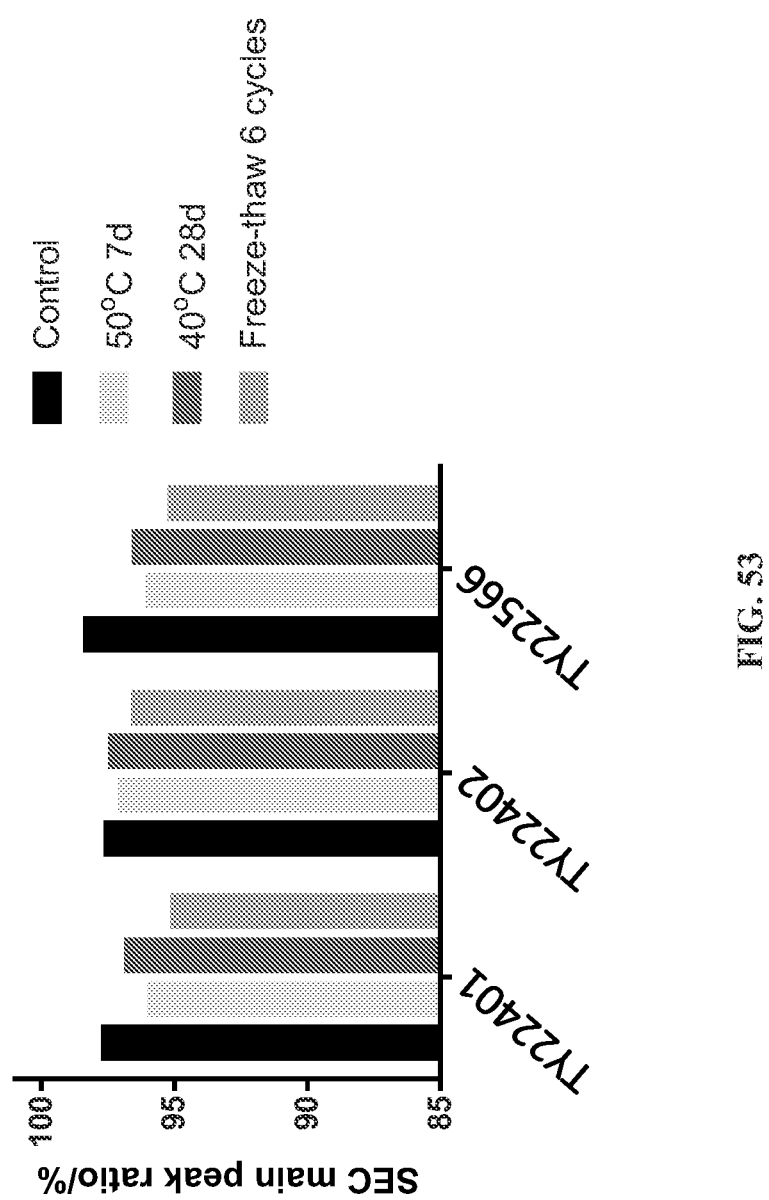
FIG. 53 shows a summary of the stability data.

Taken together, the data indicates that the discovered activatable antibodies remained stable under various stress conditions, and therefore, even without formulation optimization, they have good developability profiles (FIG. 53).

Example 12: Epitope Binding and Cross-Reactivity of TY21580 and Ipilimumab to CTLA4

Figure 54:
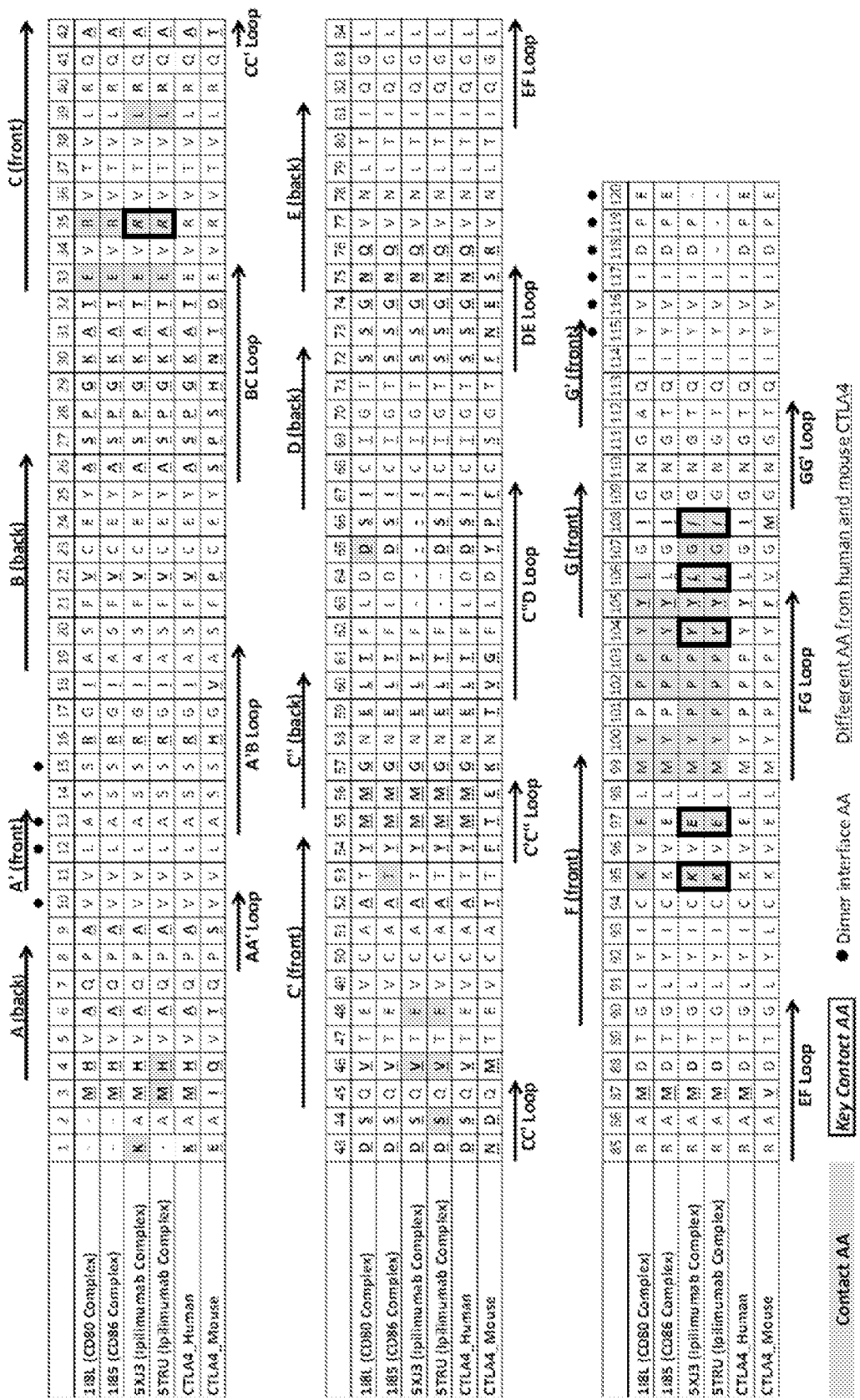
FIG. 54 depicts a multiple sequence alignment of a portion of human and mouse CTLA4, with contact residues between human CTLA4 and one of CD80, CD86, or Ipilimumab (based on two crystal structures) mapped. Contact amino acids are shaded in gray, key contact amino acids are in boxes, dimer interface amino acids are indicated with a dot, and amino acids that are different between mouse and human CTLA4 are underlined and bolded. Sequences shown are represented by SEQ ID NOs: 203-208, from top to bottom.
Figure 55A:
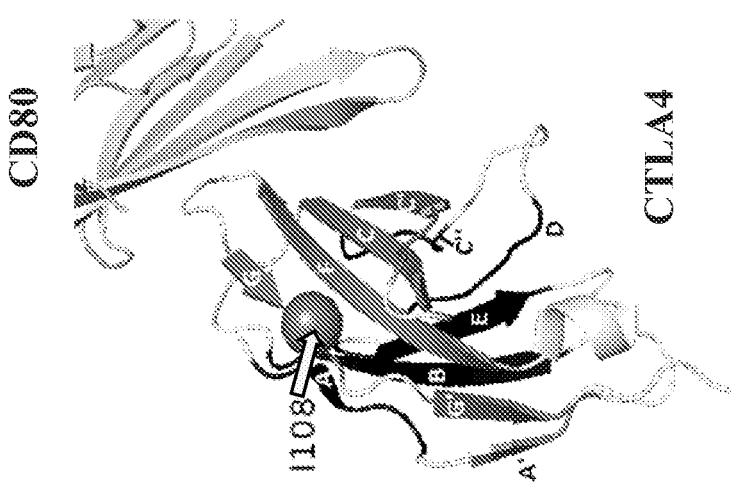
FIG. 55A depicts the interaction between human CTLA4 and its ligand CD80.
Figure 55B:
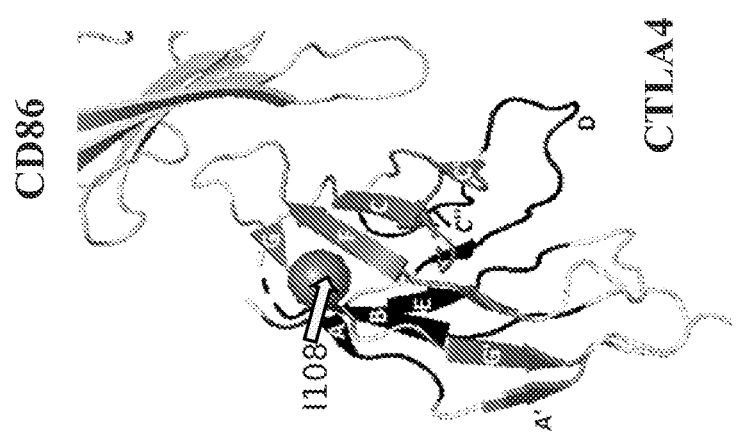
FIG. 55B depicts the interaction between human CTLA4 and its ligand CD86.
Figure 55C:
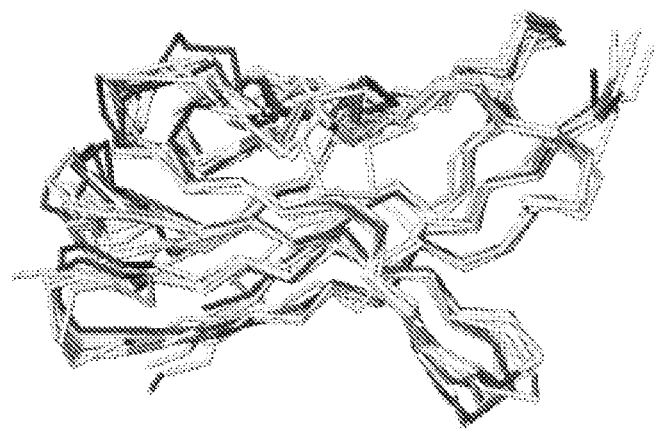
FIG. 55C depicts the structure alignment between human and mouse CTLA4. Human CTLA4 is colored in black, mouse CTLA4 is colored in white.
Figures 56A, 56B:
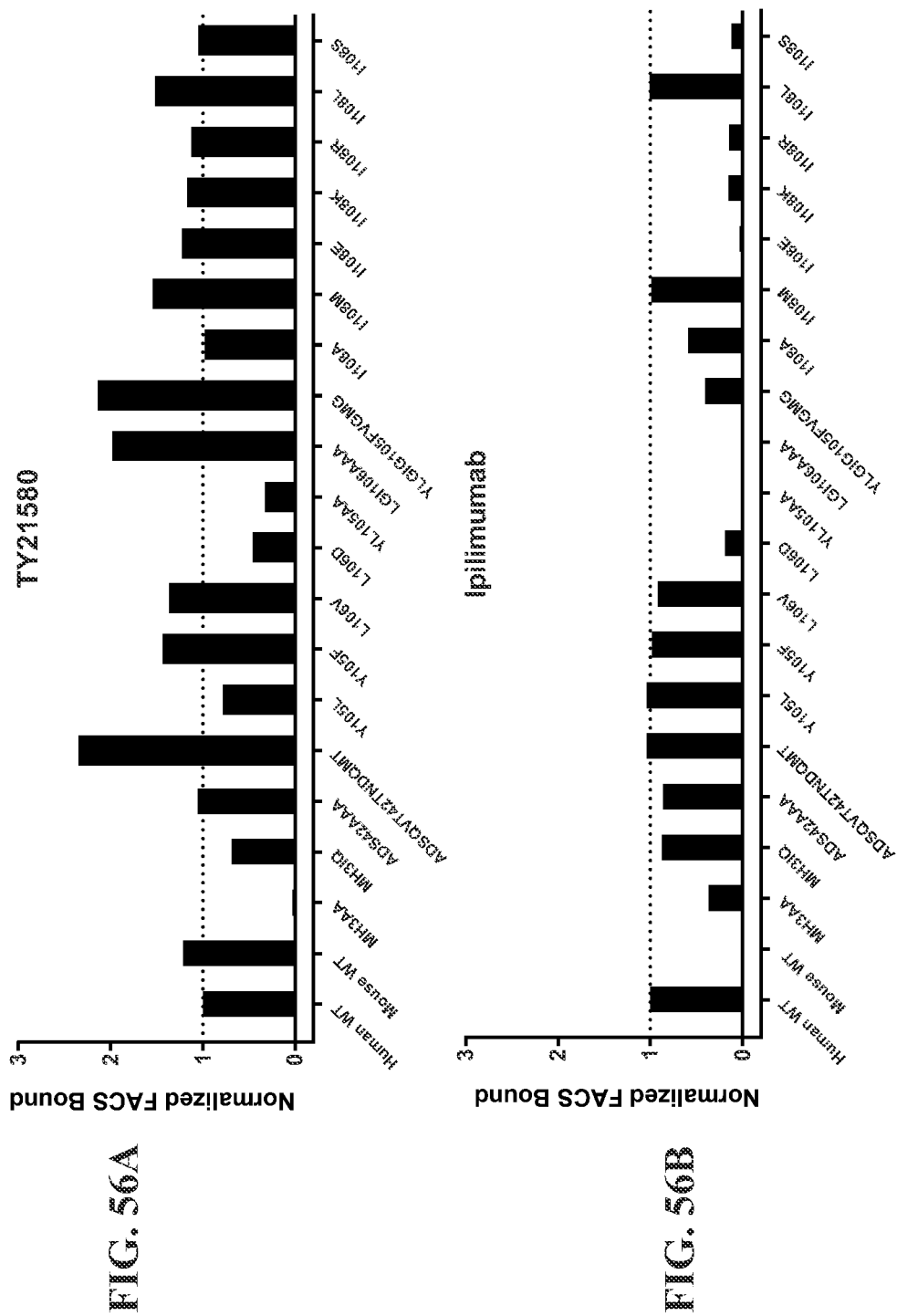

The F sheet, FG loop, and G sheet of human CTLA4 contain most of the contact residues important for CTLA4 interaction with its ligands CD80 and CD86 (FIG. 54; FIGS. 55A and 55B). For example, the human CTLA-4/CD86 interface is formed by residues E33, R35, T53, E97, M99, Y100, P101, P102, P103, Y104, Y105, L106 on the front β-sheet of CTLA4 (Schwartz et al. (2001) Nature 410 (6828): 604-608) and alanine substitutions of residues in the FG loop of CTLA4 (99MYPPPYY105) reduce or abolish binding to CD80 (Stamper et al. (2001) Nature 410(6828): 608-611).

Ipilimumab, an anti-CTLA4 antibody, also interfaces with CTLA4 on the front β-sheet of CTLA4 at the F and G strands (residues 193, K95, E97, L106, and I108), the FG loop (residues 99MYPPPY104) and the CC' loop (residues L39, V46, and 193; located opposite the FG loop). A pervious study showed that mutation of residues S20, R35, R40, Q76, D88, K95, E97, Y104, L106, and I108 of human CTLA4 resulted in significant loss of Ipilimumab binding, with mutations in residues R35, K95, E97, Y104, and I108 showing a severe loss in CTLA4 binding. In addition, Ipilimumab was shown to directly contact residues R35, K95, E97, Y104, L106, and I108 of CTLA4 in a Ipilimumab-CTLA4 crystal structure (Ramagopal et al. (2017) Proc Natl Acad Sci USA 114(21): 4223-4232). In addition, crystal structures have revealed that the Ipilimumab epitope partially occupies the CD80/CD86 binding site of CTLA4, with a larger interface area (1,880 Å2 for CTLA4/Ipilimumab) than the receptor-ligand interfaces (1,255 Å2 for CTLA-4/CD80 and 1,212 Å2 for CTLA-4/CD86) (Ramagopal et al. (2017) Proc Natl Acad Sci USA 114(21): 4223-4232; Lee et al. (2016) Nat Commun 7(13354); He et al. (2017) Oncotarget 8:67129-67139).

The epitope binding characteristics of the anti-CTLA4 antibodies TY21580 and Ipilimumab were investigated. A systematic approach was taken to narrow in on the important CTLA4 epitope motifs and residues for TY21580 and Ipilimumab binding to CTLA4. First, a low copy number, CEN/ARS-based vector was used to express mouse CTLA4, human CTLA4, or various human CTLA4 mutant proteins under the control of the inducible GAL1-10 promoter for cell surface display in the yeast *S. cerevisiae* (Boder and Wittrup (1997) Nat Biotechnol 15(6):553-7). In mutant CTLA4 vectors, particular motifs or residues of human CTLA4 were mutated to alanine or to the corresponding residues of the mouse CTLA4. TY21580 or Ipilimumab was added to the cells displaying CTLA4 and antibody binding was assessed through flow cytometry.

For comparison, the contact residues on CTLA4 from CTLA4-CD80 (PDBID:1I8L), CTLA4-CD86 (PDBID: 1185), and CTLA4-Ipilimumab (PDBID: 5XJ3, 5TRU) crystal structures (within 4 A of C-alpha atoms from the inter-molecular interface) are shown in FIG. 54. The contact residues defined by their interacting C-alpha atoms are marked as the gray-colored residues in their human sequences derived from their corresponding X-ray structures.

As shown in FIGS. 56A and 56B, the difference in the cross-reactivity of TY21580 and Ipilimumab are striking, with TY21580 binding to both human and mouse CTLA4 and Ipilimumab binding to human CTLA4 but not mouse CTLA4. For comparison, human CD80 (FIG. 56C), human CD86 (FIG. 56D), and mouse CD86 (FIG. 56E) interact with both human and mouse CTLA4.

To further investigate the epitope binding profiles of Ipilimumab and TY21580 to CTLA4, various motifs of human CTLA4 were mutated and assessed for binding. TY21580, Ipilimumab, human CD80, human CD86, and mouse CD86 maintained a similar binding ability to the ADS42AAA CTLA4 mutant as compared to wild-type CTLA4 (FIG. 56A-56E). However, when the human CTLA4 CC' loop motif (42ADSQVT47) was mutated to the mouse CTLA4 CC' loop motif (42TNDQMT47), TY21580 bound two times stronger to the mutant compared to Ipilimumab, human CD80, human CD86, and mouse CD86 binding to the mutant (FIG. 56A-56E). It is consistently observed that CD80 and CD86 do not directly bind to this CC' loop motif (see e.g., FIG. 54). Although Ipilimumab is in direct contact with this motif in human CTLA4 (FIG. 54; Ramagopal et al. (2017) Proc Natl Acad Sci USA 114(21): 4223-4232), the impact of human CTLA4 binding upon mutational change of the CC' loop is minimal (see human WT vs. ADSQVT42TNDQMT in FIG. 56B). Taken together, these results suggest that the CC' loop motif does not contribute significantly to the binding affinity of Ipilimumab or TY21580 to human CTLA4.

One of the most interesting observations from the epitope mapping data is the striking difference between Ipilimumab and TY21580 binding to CTLA4 when mutations are introduced from residues 105 to 108 in human CTLA4. For example, when YL105AA and LGI106AAA were introduced into human CTLA4, Ipilimumab lost its ability to bind CTLA4 (FIG. 56B), consistent with the known contact amino acids important for Ipilimumab binding to human CTLA4, shown in FIG. 54. In addition, as shown in FIGS. 56A and 56C-56E, the binding affinity of TY21580, human CD80, human CD86, and mouse CD86 to the CTLA4 YL105AA mutant was weakened. While the binding affinity of human CD80, human CD86, and mouse CD86 with LGI106AAA was also weakened, the binding affinity of TY21580 with LGI106AAA was significantly enhanced. This is in contrast to the total loss of binding affinity of Ipilimumab with LGI106AAA.

For epitope mapping of the binding sites of CTLA4 by TY21580 and Ipilimumab, mutations were introduced into specific sites of human CTLA4. Sites that were selected for mutagenesis were known contact sites of CTLA4 by Ipilimumab, CD80, and CD86 (based on their crystal structures, see FIG. 54) which had large sequence variations between human and mouse CTLA4 sequences. For example, FIGS. 55A and 55B show the front view of the complex structures of CD80 and CD86 with human CTLA4, with I108 highlighted and shown as a ball. I108 is one of the most critical sites in contact with Ipilimumab, however it is far away from the CD80 and CD86 contact regions. The G strand contains the majority of the residues contacting Ipilimumab, CD80, and CD86 that differ significantly between human and mouse CTLA4, as shown in FIG. 54. The CC' loop motif also contains contact residues with Ipilimumab that are divergent between human and mouse CTLA4, however, the results in FIGS. 56A-56E indicated that the mutants introduced into CC' loop motif do not significantly contribute to overall binding of Ipilimumab, TY21580, CD80, or CD86 to CTLA4. Thus, to further assess the binding contribution of the G strand motif to Ipilimumab, TY21580, CD80, and CD86, the G strand of human CTLA4 (105YLGIG109) was mutated to mouse CTLA4 (105FVGMG109).

As shown in FIG. 56B, Ipilimumab suffered a severe loss of binding affinity to the YLGIG105FVGMG mutant. In contrast, TY21580, human CD80, human CD86, and mouse CD86 retained binding ability when this mutation was introduced (FIGS. 56A, 56C-56E). This indicates that TY21580 has a different binding epitope from Ipilimumab due to this difference in G strand binding between human and mouse CTLA4.

In addition, other amino acids in the G strand of human CTLA4 were replaced by the corresponding mouse sequences or other amino acids to probe their interactions with Ipilimumab, TY21580, CD80 and CD86. I108 is known to an extremely important amino acid for Ipilimumab binding. Consistent with this expectation, Ipilimumab lost its binding affinity to I108A, I108S, I108E, I108K and I108R CTLA4 mutants (FIG. 56B). In contrast, I108 mutants (I108A, I108S, I108E, I108K and I108R) had no impact on the binding affinity of TY21580, CD80 or CD86, highlighting the important differences in the binding epitope of TY21580, CD80, and CD86 compared to Ipilimumab, as shown by I108, one of the most critical binding sites of Ipilimumab (Ramagopal et al. (2017) Proc Natl Acad Sci USA 114(21): 4223-4232). The complex structure in FIGS. 55A and 55B show that I108 is indeed physically distant from the binding sites between CTLA4 and its ligands CD80 and CD86, and thus may not have a significant impact on binding between CD80/CD86 and CTLA4. Our observation confirms that TY21580 is more similar in its binding epitope with CD80/CD86, differentiated from the epitope by Ipilimumab. Therefore, TY21580 is thought to specifically bind to an epitope comprising amino acid residues Y105 and L106, but not I108 of human CTLA4.

Example 13: Effect of TY21580 and Ipilimumab on CTLA4 Ligand Binding Blockade

Figure 57A:
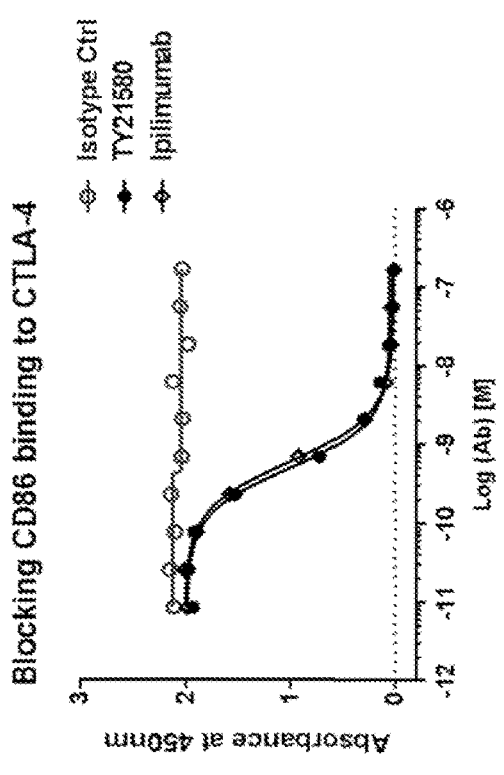
FIGS. 57A-57D depict the effect of TY21580 and Ipilimumab on receptor-ligand binding blockade between human CTLA4 and CD80 or CD86.
Figure 57B:
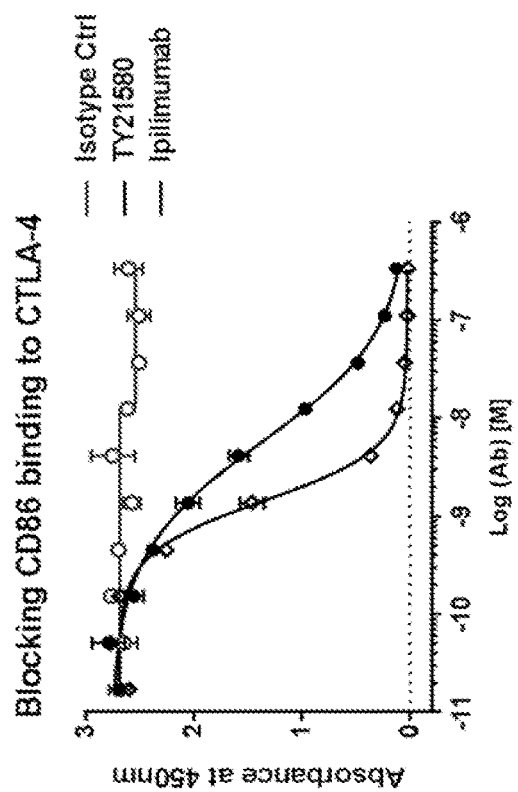
Figure 57C:
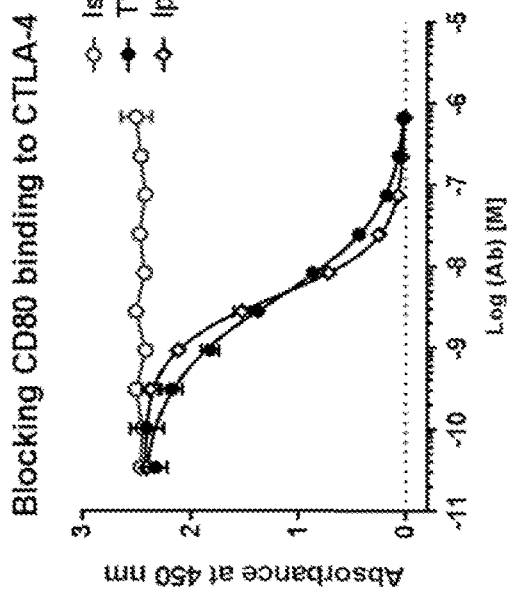
Figure 57D:
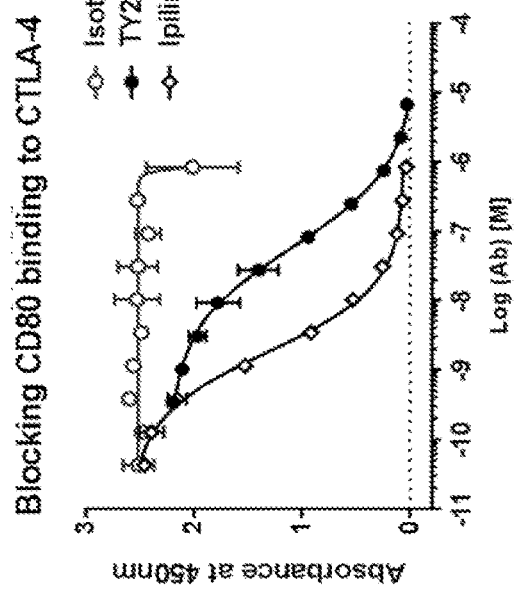

TY21580 and Ipilimumab were tested for their ability to block binding of CTLA4 to its cognate ligands CD80 and CD86 through ELISA-based experiments, as described in Example 3 (Ligand competition binding by ELISA). Briefly, in one experiment, ELISA microplates were coated with recombinant human CTLA4 proteins (1 µg/mL) and biotinylated CTLA4 ligands (CD80 at 1 µg/mL or CD86 at 2 µg/mL) were added to each well along with serial dilutions of either TY21580, Ipilimumab, or an isotype control antibody (FIGS. 57A and 57B). In another experiment, ELISA microplates were coated with recombinant CD80 or CD86 protein (1 µg/mL) and biotinylated human CTLA4 (0.2 µg/mL or 1 µg/mL) was added to each well along with serial dilutions of either TY21580, Ipilimumab, or an isotype control antibody (FIGS. 57C and 57D). In both experiments, the level of binding between human CTLA4 and either CD80 or CD86 was detected using HRP-labeled Neutravidin as described in Example 3 (Ligand competition binding by ELISA).

Figure 58:
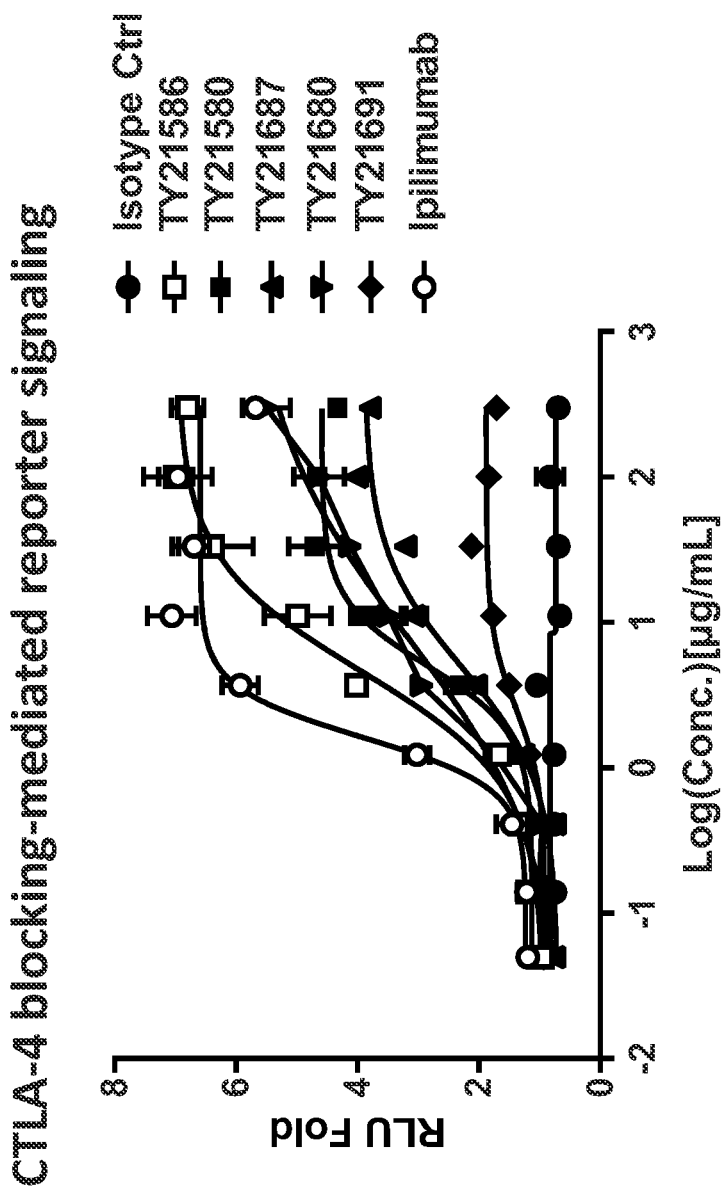
FIG. 58 depicts CTLA4 blocking-mediated reporter signaling activation of the CD28 pathway by anti-CTLA4 antibodies. Jurkat/CTLA4 and aAPC/Raji cells were co-cultured in the presence of serially diluted anti-CTLA4 antibodies, with a human IgG1 anti-HEL antibody as an isotype control. Luminescence signals were measured with Bio-Glo luciferase substrate after overnight incubation and relative luciferase units (RLU) were normalized against a blank control. Results are expressed as mean RLU fold±SEM. Experiments were performed in triplicate. Note: The data point for the top concentration of TY21580 (500 µg/mL) was excluded from analysis while fitting the curve as an apparent hook effect was observed at this point.

As shown in FIGS. 57A and 57B, when CTLA4 was immobilized onto the microplate, TY21580 and Ipilimumab blocked CD80 and CD86 binding to CTLA4 in a dose-dependent manner, whereas the isotype control antibody showed no blocking activity, indicative of assay specificity. As shown in FIGS. 57C and 57D, when CD80 or CD86 was immobilized onto the microplate, TY21580 and Ipilimumab again blocked CD80 and CD86 binding to CTLA4 in a dose-dependent manner, while the isotype control antibody displayed no blocking activity. As shown in Table 23, although TY21580 and Ipilimumab both block ligand binding to CTLA4, the dose-dependent blocking activities of TY21580 and Ipilimumab were strikingly different when human CTLA4 was immobilized onto the microplate compared to when CD80 or CD86 was immobilized onto the microplate. These results indicate that TY21580 and Ipilimumab exhibit comparable ligand blocking activities with similar IC50s under CTLA4 immobilization conditions. However, under CD80 or CD86 ligand immobilization conditions, Ipilimumab exhibited a much stronger ligand blocking activity than TY21580 for both CD80 and CD86, as shown in FIGS. 57C and 57D and Table 23. However, additional experiments suggested that a complete blockade of CTLA4's interaction with its ligands upon adding an anti-. CTLA4 antibody at a saturating concentration is not necessary for tumor rejection, meaning that TY21580 could still activate T cells and have potent anti-tumor efficacy without completely blocking CD80 or CD86. In fact, TY21586 showed complete blockage of CD80 and CD86, similar to Ipilimumab, as shown in FIG. 58. However, TY21586 and Ipilimumab have much lower ADCC reporter activity than other antibodies tested (FIG. 59), and are therefore less effective in depleting Treg cells via the ADCC effect (see also Tang et al. (2018) Cell Biosci. 8(30):1-3). Without wishing to be bound by theory, it is believed that CD28-dependent T cell activation (e.g., by blocking CTLA4 activity) is important for effective tumor rejection, however overstimulation of T cells can be detrimental. Thus, the weaker ligand blocking observed for TY21580 may be an advantage over the stronger ligand blocking activity of Ipilimumab.

TABLE 23

| Test antibody IC$_{50}$ (nM) | Plate-bound CTLA4 | | CTLA4 in solution | |
|---|---|---|---|---|
| | CD80 in solution | CD86 in solution | Plate-bound CD80 | Plate-bound CD86 |
| TY21580 | 3.809 | 0.4806 | 59.08 | 5.583 |
| Ipilimumab | 4.116 | 0.5873 | 1.789 | 1.429 |

Although the underlying mechanisms for these differences are currently unclear, the results indicate that there are inherent differences between the properties of TY21580 and Ipilimumab. Taken together, these results suggest that TY21580 can act as a ligand blocker by disrupting CD80 and CD86 binding to its inhibitory receptor CTLA4. Without wishing to be bound by theory, it is thought that relieving CD80 and CD86 from CTLA4 sequestration through weak ligand blocking allows these ligands to signal through co-stimulatory receptor CD28 during T cell activation, which can lead to increased effectiveness and safety during T cell immune activation.

Example 14: Effect of TY21580 and Ipilimumab on CTLA4 Blockade of CD28 Pathway Activation Using a cell-based CTLA4 blockade bioassay developed by Promega (CAT #JA3001 and JA3005), the CTLA4 blocking functions of TY21580 and Ipilimumab were assessed. This assay involved co-culturing two genetically engineered cell lines in the presence or absence of TY21580 or Ipilimumab, then measuring the bioluminescent signal generated by a luciferase reporter gene using the Bio-Glo™ Luciferase Assay System. The two cell lines that were co-cultured were (1) CTLA4 effector cells—Jurkat T cells expressing human CTLA4 and a luciferase reporter driven by a native promoter that responds to TCR/CD28 activation; and (2) aAPC/Raji cells—Raji cells endogenously expressing CTLA4 ligands CD80 and CD86 and additionally expressing a cell surface protein designed to activate TCRs in an antigen-independent manner. When these two cell types are co-cultured, CTLA4 competes with CD28 for CD80 and CD86 binding, which inhibits activation of the CD28 pathway and leads to low promoter-mediated luminescence. The addition of anti-CTLA4 antibodies to this system may block the interaction of CTLA4 with its ligands CD80 and CD86, resulting in higher TCR/CD28 activation and subsequent promoter-mediated luminescence.

As shown in FIG. 58, all tested antibodies activated the TCR/CD28 pathway in a dose-dependent manner, as evidenced by the increasing reporter gene signal (i.e., luminescence) as antibody concentration increased. In comparison, the isotype control antibody showed no activity. These results demonstrate a range of CTLA4 functional blocking activities by these different anti-CTLA4 antibodies. Although the EC50s of the antibodies were somewhat similar (Table 24), the magnitude of functional signaling activation stimulated by these antibodies indicated that Ipilimumab and TY21586 were the most potent CTLA4 blockers tested, followed by TY21680, TY21580, and TY21687 (FIG. 58). TY21691 had the weakest activity as a CTLA4 blocker out of the antibodies tested. These results demonstrate that all of the tested antibodies can block the interaction of CTLA4 with CD80 and CD86, resulting in downstream TCR/CD28 pathway activity in a dose-dependent manner. Without wishing to be bound by theory, the results suggest that all of the tested antibodies may increase T cell activation, which could be advantageous for the treatment of cancer. As discussed above, weaker ligand blockers such as TY21580 may be particularly effective in treating cancer because of their reduced risk of overstimulating T cells compared to strong binders.

TABLE 24

EC50s of anti-CTLA4 antibodies for TCR/CD28 pathway activation

|  | Ipilimumab | TY21580 | TY21586 | TY21687 | TY21680 | TY21691 |
| --- | --- | --- | --- | --- | --- | --- |
| $EC_{50}$ (µg/mL) | 1.62 | 5.06 | 4.66 | 5.01 | 8.21 | 2.64 |

Example 15: ADCC Activity of Anti-CTLA4 Antibodies

Antibody-dependent cell cytotoxicity (ADCC) activities of Ipilimumab, TY21580, TY21586, TY21687, TY21680, and TY21691 were tested and compared. An ADCC reporter gene assay was used to evaluate the ADCC activities of the activatable antibodies. HEK293F cells overexpressing human CTLA4 (HEK293F/hCTLA4 cells) were used as target cells; a Jurkat cell line overexpressing CD16 and NFAT-Luc (Jurkat/CD16a cells) was used as effector cells. $1.2 \times 10^5$ Jurkat/CD16a cells and $2 \times 10^4$ HEK293F/hCTLA4 cells (E:T ratio 6:1) were mixed in a 96-well tissue culture microplate in the presence or absence of serially diluted anti-CTLA4 antibodies. After incubation for 6 hours, One-Glo reagent was added to the cells, and the cells were lysed. To measure reporter gene activity, supernatants were removed for luminescence measurements using a SpectraMax i3x plate reader. A human IgG1 isotype control antibody was used as a negative control.

Figure 59:
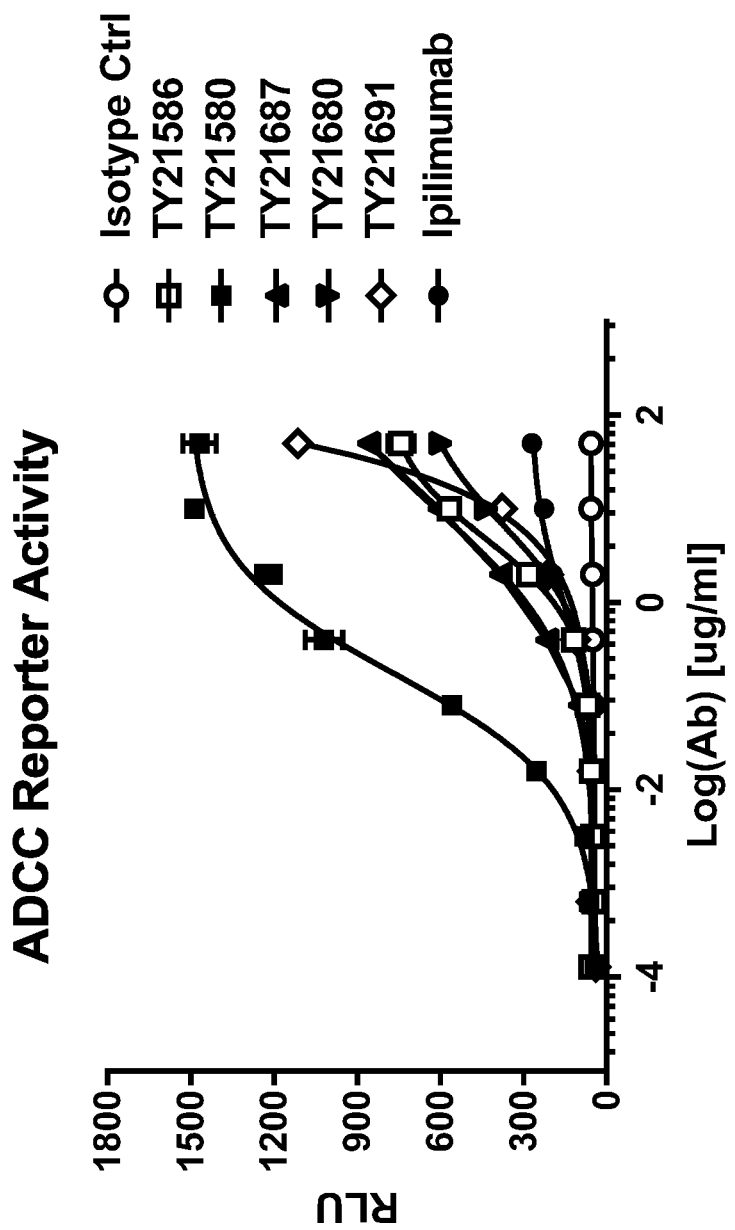
FIG. 59 depicts ADCC reporter signaling activation by anti-CTLA4 antibodies. The Jurkat/NFAT-Luc/CD16 cells and HEK293F/hCTLA4 cells were co-cultured in the presence of serially diluted anti-CTLA4 antibodies, with a human IgG1 anti-HEL antibody as isotype control. Luminescence signals were measured with ONE-Glo luciferase substrate after 6 hours incubation. Relative luciferase units (RLU) were normalized against the blank control, and the results were expressed as mean RLU±SEM. Experiments were performed in triplicate.

As shown in FIG. 59, all tested antibodies showed various degrees of ADCC signaling activation in a dose-dependent manner, whereas the isotype control showed no ADCC activity whatsoever. These results demonstrate a range of ADCC signaling/stimulatory activities by these different anti-CTLA4 antibodies. As demonstrated by both the magnitude of signaling activation (FIG. 59) and the EC50s (Table 25), TY21580 induced the most potent ADCC signaling activity of all of the antibodies tested. TY21691 was the least active antibody in inducing ADCC signaling. While earlier data demonstrated that these antibodies have similar binding affinities to human CTLA4, with KDs in the single digit nMs, these ADCC reporter results suggest that the binding epitopes of the tested antibodies likely impact ADCC activity more significantly than their binding affinities. It should be noted that although TY21586, TY21680, TY21580, TY21687, and TY21691 are cross-reactive, the above results show that their effectiveness in ligand blocking and ADCC activity is dramatically different, suggesting that subtle differences in antibody epitope binding sites may result in significant differences in anti-tumor activities.

Figure 60A:
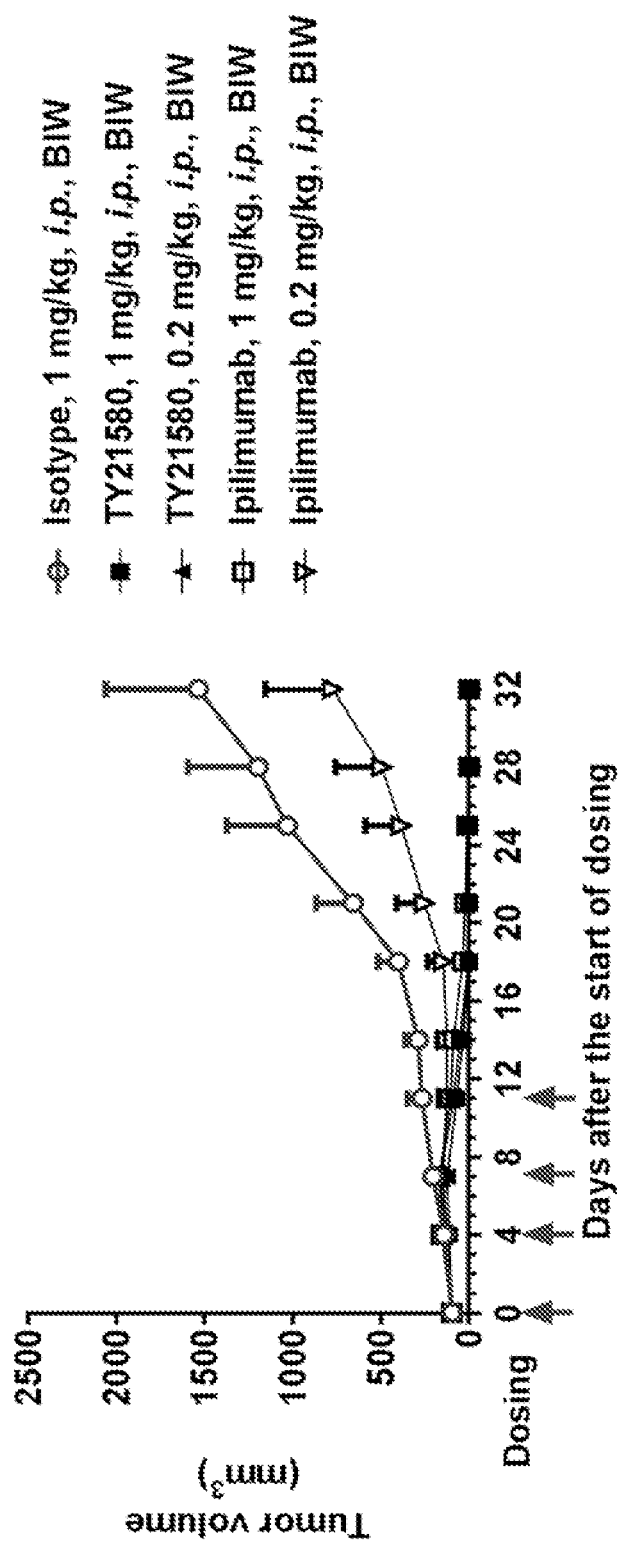
FIGS. 60A and 60B depict tumor growth curves of MC38 tumor bearing mice treated with anti-CTLA4 antibodies.
Figure 60B:
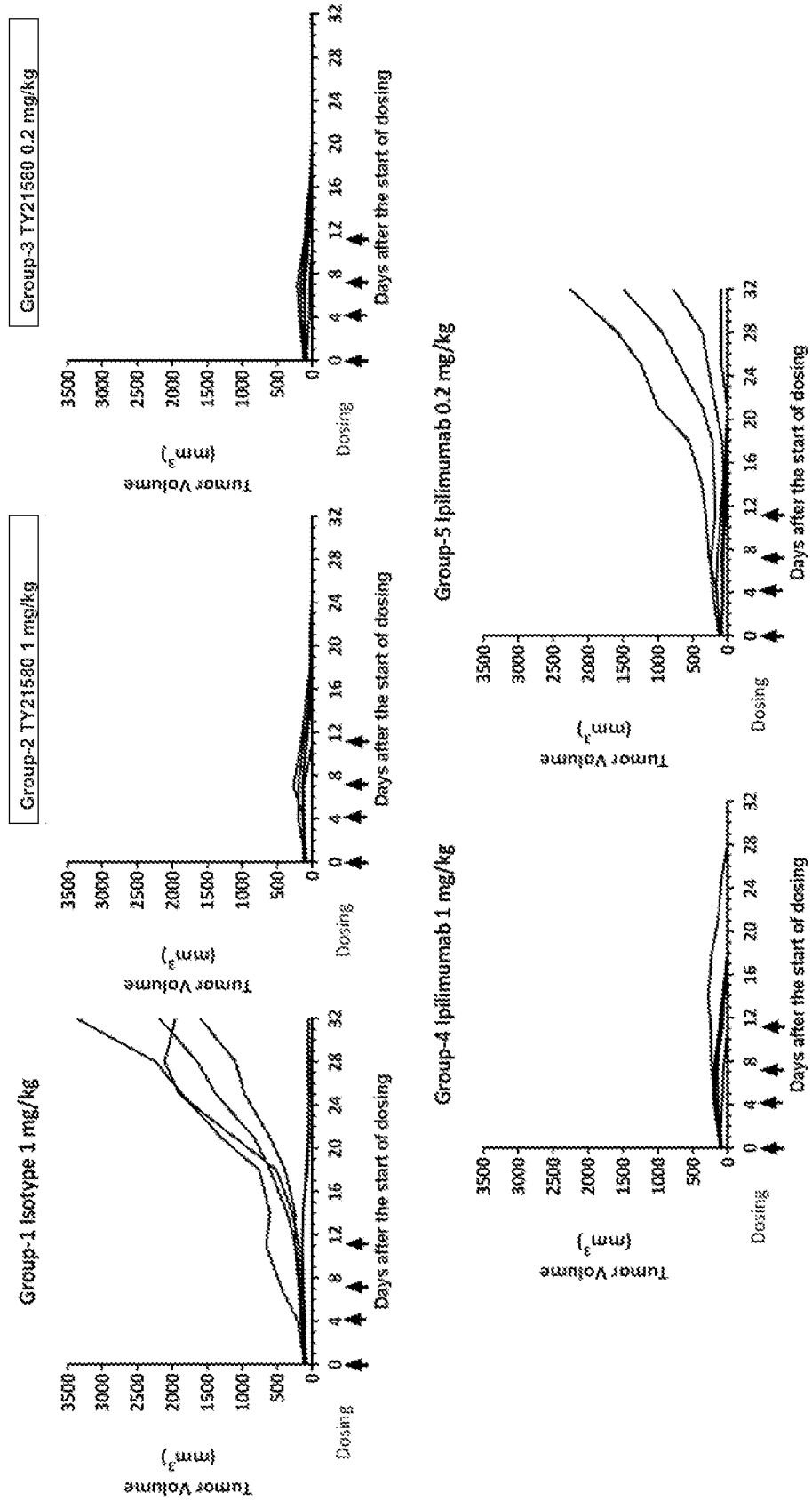

Example 16: Anti-Tumor Efficacy of TY21580 and Ipilimumab in a Murine MC38 Colorectal Tumor Model To determine the anti-tumor efficacy of TY21580 and Ipilimumab, human CTLA4 knock-in C57BL/6 mice (n=6 per group, female, 5-9 weeks old) were inoculated subcutaneously with MC38 murine colon cancer cells. When tumors were established (99 mm$^3$), mice were treated with an isotype control antibody (1 mg/kg), TY21580 (1 mg/kg or 0.2 mg/kg), or Ipilimumab (1 mg/kg or 0.2 mg/kg) by intraperitoneal injection twice a week for two weeks. Group averaged tumor growth (FIG. 60A) and individual tumor growth of each mouse in different groups (FIG. 60B) was monitored twice a week and reported as the mean tumor volume±SEM over time. As shown in FIGS. 60A and 60B, TY21580 showed a complete anti-tumor effect at doses of 1 mg/kg (Group-2) and 0.2 mg/kg (Group-3), and all tumors in these mice were completely abolished except for a very small tumor left at Day 32 post first dosing in one mouse. Ipilimumab also showed a complete anti-tumor effect at the dose of 1 mg/kg (Group-4); however, half (3/6) of the tumors treated with the lower dose of Ipilimumab (0.2 mg/kg, Group-5) escaped from tumor suppression at Day 32 post first dosing. This shows that TY21580 is more efficacious than Ipilimumab in terms of anti-tumor activity. Both TY21580 and Ipilimumab were well tolerated, no animals died during the study, and no significant body weight loss was observed in mice at the dose levels tested. In summary, these results suggest that TY21580 is a safe and effective anti-cancer agent with more potent anti-cancer activity than Ipilimumab.

Figures 61A, 61B:
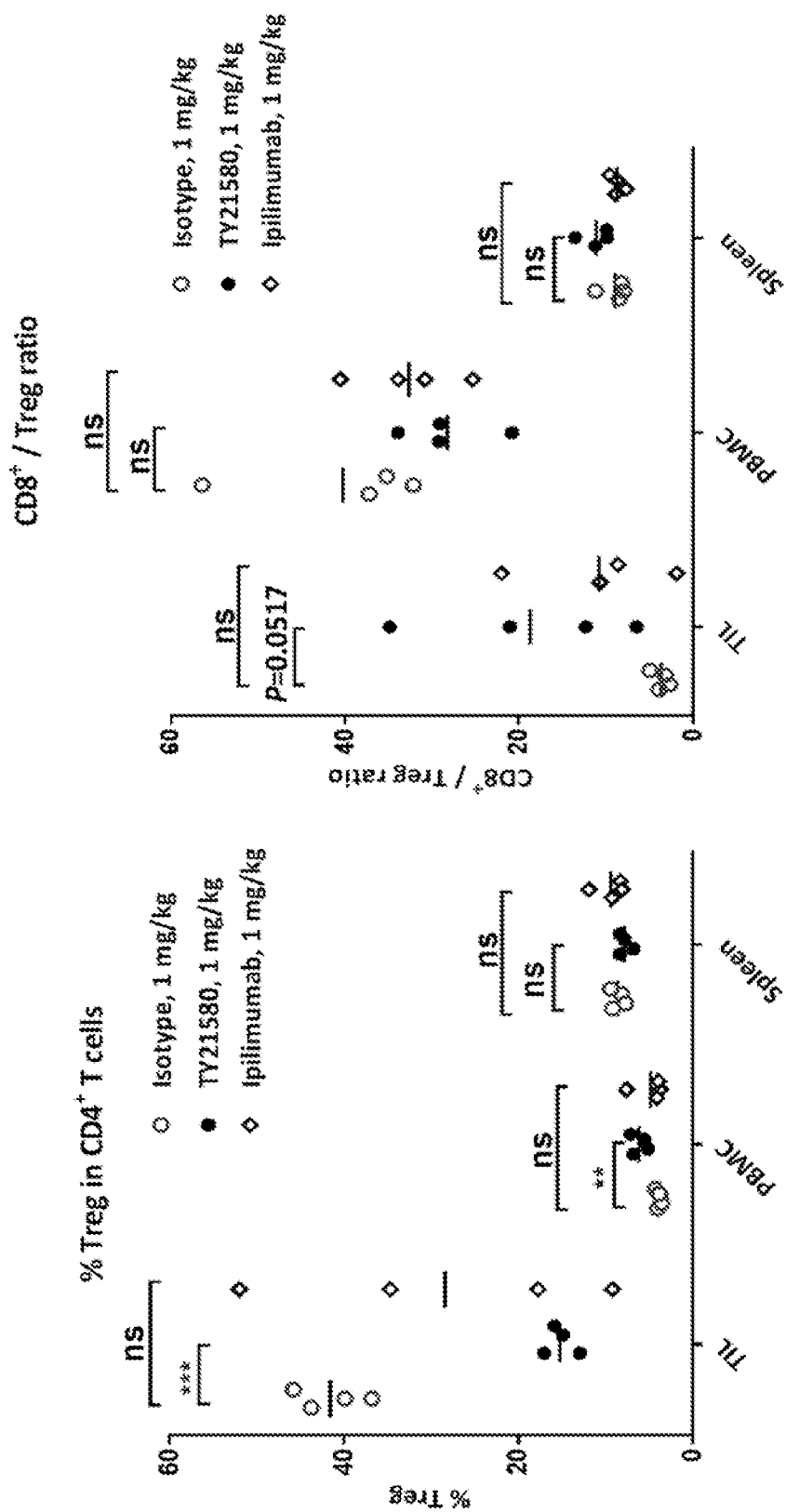
FIGS. 61A and 61B depict the effect of TY21580 and Ipilimumab on intra-tumoral regulatory T (Treg) cell levels in subcutaneous MC38 tumors from mice treated with TY21580 or Ipilimumab.

Example 17: Effect of TY21580 and Ipilimumab on Intra-Tumoral Regulatory T (Treg) Cell Levels in a Murine MC38 Colon Cancer Model The percentages of T regulatory (Treg) cells (CD4$^+$CD25$^+$) in CD4$^+$ T cell subpopulations after treatment with TY21580 or Ipilimumab were evaluated in a subcutaneous MC38 murine colon cancer syngeneic model (FIG. 61A). Tumor-bearing animals were treated with TY21580 or Ipilimumab at 1 mg/kg (Q3d×3 doses). CD4$^+$ T cells were isolated from tumors, then tumor infiltrating lymphocytes (TILs) and peripheral cells (i.e., PBMCs and spleen cells) were isolated as subpopulations from these CD4$^+$ T cells.

In the TILs, the percentage of Treg cells was significantly reduced after TY21580 treatment (15.2% for TY21580

TABLE 25

EC50s of anti-CTLA4 antibodies for ADCC reporter signaling

|  | Ipilimumab | TY21580 | TY21586 | TY21687 | TY21680 | TY21691 |
| --- | --- | --- | --- | --- | --- | --- |
| EC50 (µg/mL) | 1.08 | 0.174 | 4.69 | 9.5 | 6.76 | >10 | treatment group vs. 41.6% for isotype control group, P<0.001). There was no significant reduction of Treg cells after Ipilimumab treatment (28.4% for Ipilimumab vs. 41.6% for isotype control, P=ns). This was consistent with the observation that Ipilimumab does not significantly change or deplete FOXP3+ Treg cells within the microtumor environment (Sharma et al. (2018) Clin. Cancer Res. online publication only, PMID 30054281; Ferrara et al. (2018) Clin. Cancer Res.). In PBMCs, the percentage of Treg cells was slightly increased after TY21580 treatment (6.2% for TY21580 group vs. 3.9% for isotype control group, P=0.01), but this effect was not seen after Ipilimumab treatment (4.8% for Ipilimumab group vs. 3.9% for isotype control group). See also Ha et A PNAS (2019) 116(2):609-618. In the spleen cells, both TY21580 and Ipilimumab treatment had no effect on the percentage of Treg cells (8.6% for isotype control group; 7.8% for TY21580 group; 9.4% for Ipilimumab group).

The ratio of cytotoxic T lymphocytes (CD8$^+$ T cells) to Treg cells (i.e., the CD8$^+$/Treg ratio) was also evaluated (FIG. 61B). In the TILs, the CD8$^+$/Treg ratio increased after treatment with TY21580 (18.7 for TY21580 vs. 3.7 for isotype control; P=0.0517, close to 0.05). The effect of Ipilimumab treatment on the CD8$^+$/Treg ratio was not significant compared to the isotype control and, at best, was weaker than the effect of TY21580. In PBMCs and spleen cells, the CD8$^+$/Treg ratio was not significantly changed after TY21580 or Ipilimumab treatment. These results demonstrate that TY21580 exhibits activities that induce Treg cell depletion and increase the CD8$^+$/Treg ratio specifically in tumor infiltrating cells (i.e., TILs), but not in peripheral cells (i.e., PBMCs and spleen cells).

The regulatory activity of the TY21580 anti-CTLA4 antibody on T cells provides a mechanistic understanding for TY21580's in vivo anti-tumor efficacy. Without wishing to be bound by theory, the results suggest that TY21580 reduces immunosuppressive Treg activity and enhances cytotoxic T lymphocyte (CD8$^+$ T cell) activity in the tumor microenvironment to mediate anti-tumor responses. The quantitative differences between TY21580 and Ipilimumab in tumoral Treg depletion and in the CD8$^+$/Treg ratio also shows that TY21580 exhibits better anti-tumor activity than Ipilimumab in vivo.

Figures 62A, 62B:
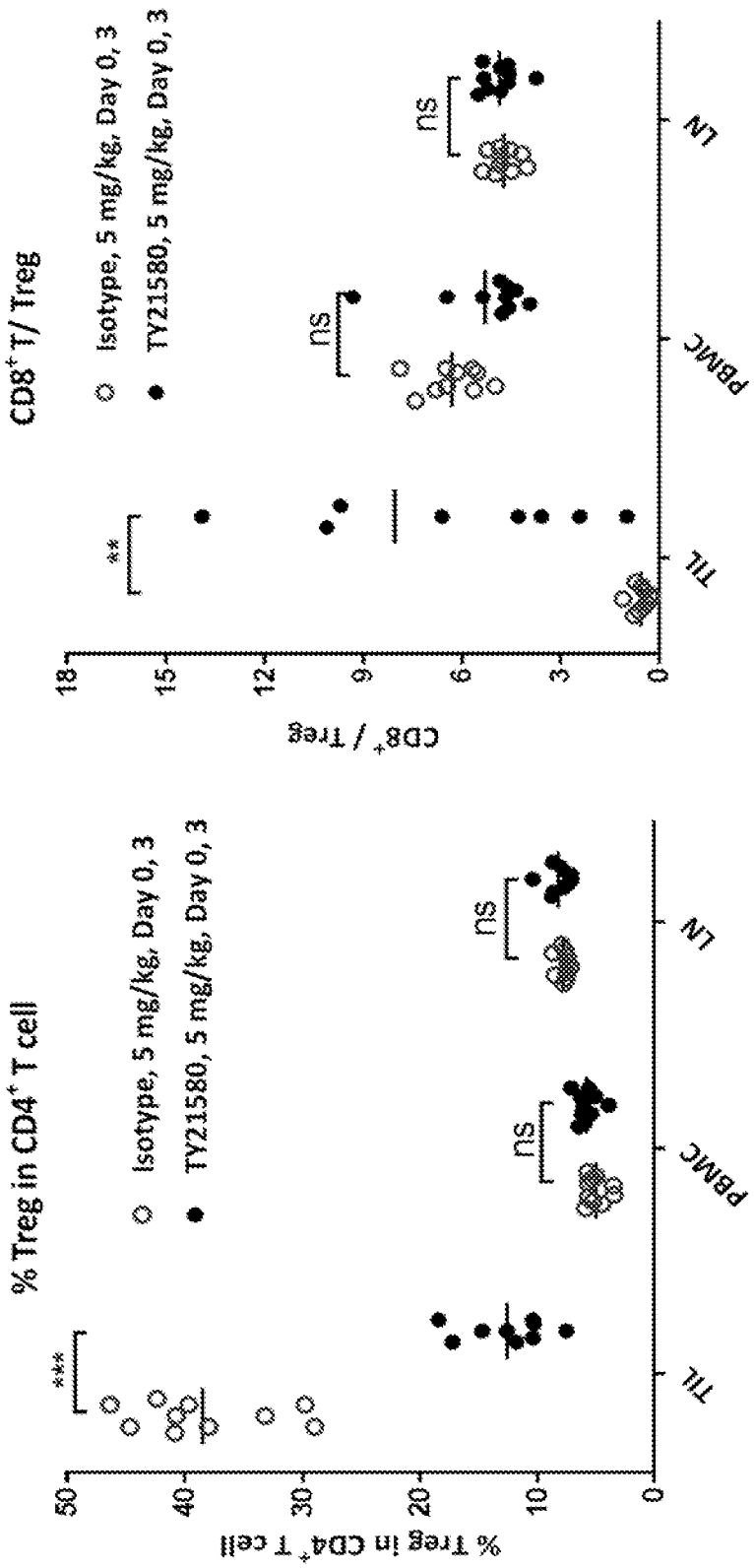
FIGS. 62A and 62B depict the effect of TY21580 and Ipilimumab on intra-tumoral regulatory T (Treg) cell levels in subcutaneous CT26 tumors from mice treated with TY21580 or Ipilimumab.

Example 18: Effect of TY21580 on Intra-Tumoral Regulatory T (Treg) Cell Levels in a Murine CT26 Colon Cancer Model The percentages of T regulatory (Treg) cells in CD4$^+$ T cell subpopulations after treatment with TY21580 was evaluated in a subcutaneous CT26 murine colon cancer syngeneic model (FIG. 62A). Tumor-bearing animals were treated with TY21580 (5 mg/kg on days 0 and 3). CD4$^+$ T cells were isolated from tumors, then tumor infiltrating lymphocytes (TILs) and peripheral cells (i.e., PBMCs and lymph node (LN) cells) were isolated as subpopulations from these CD4$^+$ T cells.

As shown in FIG. 62A, TY21580 significantly reduced the percentage of Treg cells in TILs compared to the isotype control (12.6% for TY21580 vs. 38.5% for isotype control, P<0.001). However, TY21580 did not influence the percentage of Treg cells in peripheral lymphocytes (i.e., PBMCs and lymph node (LN) cells) as compared to the isotype control. The percentage of Treg cells in PBMCs was 5.8% after TY21580 treatment vs. 4.9% after isotype control treatment (P>0.05). The percentage of Treg cells in lymph node cells was 8.1% after TY21580 treatment vs. 7.7% after isotype control treatment (P>0.05).

The ratio of cytotoxic T lymphocytes (CD8$^+$ T cells) to Treg cells (i.e., the CD8$^+$/Treg ratio) was also evaluated. As shown in FIG. 62B, TY21580 also significantly increased the CD8$^+$ T/Treg ratio in TILs compared to the isotype control (8.0% for TY21580 vs. 0.6% for isotype control, P<0.01). However, TY21580 had no significant influence on the CD8$^+$ T/Treg ratio in peripheral lymphocytes. In PBMCs, the CD8$^+$ T/Treg ratio was 5.3 after TY21580 treatment vs. 6.3 after isotype control treatment (P>0.05). In lymph node cells, the CD8$^+$ T/Treg ratio was 4.9 after TY21580 treatment vs. 4.7 after isotype control treatment (P>0.05).

Figure 63:
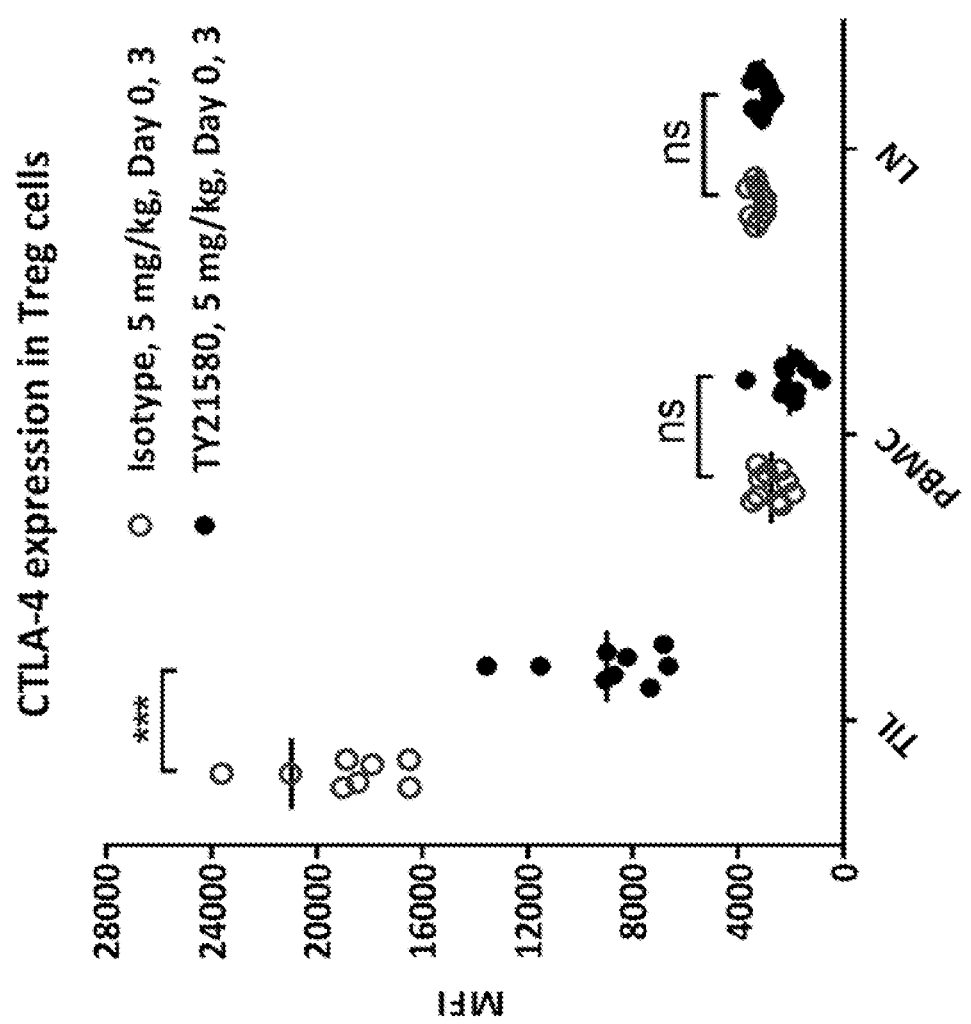
FIG. 63 depicts CTLA4 expression levels measured by mean fluorescence intensity (MFI) on FOXP3$^+$ CD4$^+$ Treg cells in CT26 tumor bearing mice treated with an isotype control antibody or TY21580. Each data point represents the data from one mouse. Statistical analyses were done with Prism 7 (GraphPad Software). P-values were calculated using Multiple T test. ns: P>0.05; : 0.001<P<0.01, *: P<0.001.

In addition, the CTLA4 expression levels in Foxp3$^+$ CD4$^+$ Treg cells from the TY21580 treatment group were significantly lower than those of the isotype control group in TILs (8985.2 MFI for TY21580 vs. 20948.0 MFI for isotype control; FIG. 63). However, CTLA4 expression levels were not changed in PBMCs (2046.7 MFI for TY21580 vs. 2740.9 MFI for isotype control) or lymph nodes (3062.0 MFI for TY21580 vs. 3247.9 MFI for isotype control). Treg cells in the TILs also displayed much higher CTLA4 expression levels than Treg cells in the peripheral cells (i.e., PBMCs and LNs), and CTLA4 expression was significantly lower in TIL Treg cells after TY21580 treatment.

Taken together, these results demonstrate that TY21580 exhibits activities that induce Treg depletion and increase the CD8$^+$/Treg ratio specifically in tumor cells (i.e., TILs), but not in peripheral cells (i.e., PBMCs or lymph node cells). Such regulatory activities of TY21580 on T cells provide a mechanistic understanding for the potent in vivo anti-tumor efficacy of TY21580. Without wishing to be bound by theory, these results suggest that TY21580 reduces immunosuppressive Treg activity and enhances cytotoxic T lymphocyte (CD8$^+$ T cell) activity in the tumor microenvironment to mediate anti-tumor responses.

Example 19: TY21580 Anti-Tumor Efficacy in a Large Established H22 Liver Tumor Model To determine the anti-tumor efficacy of TY21580 in large established tumors, female BALB/c mice were inoculated subcutaneously with mouse H22 liver cancer cells. When relatively large tumors were established at either ~500 mm$^3$ or ~800 mm$^3$, mice were treated with TY21580 at 5 mg/kg by intraperitoneal injection twice a week (BIW) for 4 doses. An isotype antibody was used as a control. Group averaged tumor growth (FIG. 64A) and individual tumor growth of each mouse in different groups (FIGS. 64B-64D) was monitored twice a week and reported as the mean tumor volume±SEM over time.

Figure 64A:
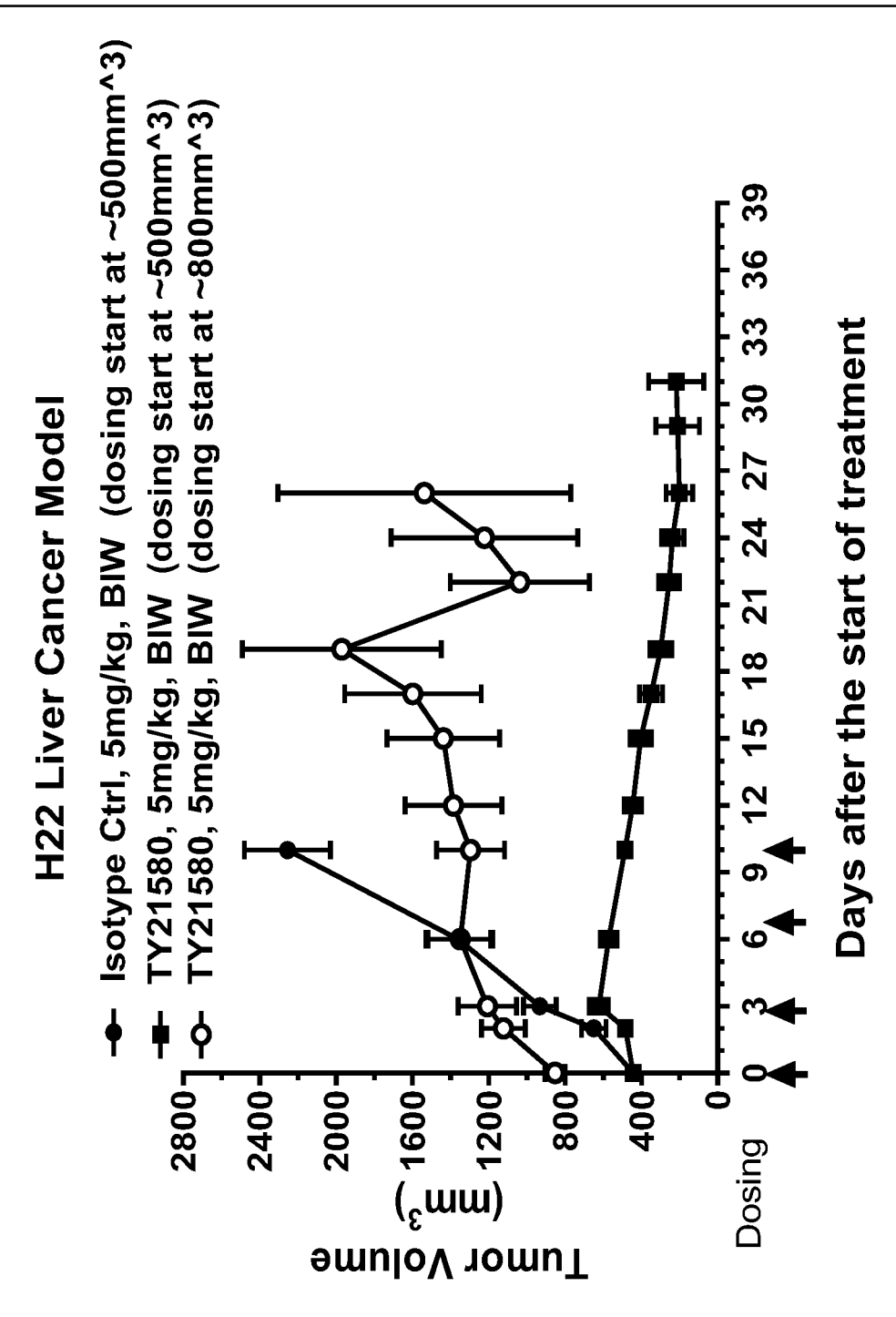
FIGS. 64A-64D depict tumor growth curves of mouse H22 liver cancer bearing mice treated with TY21580 or an isotype control antibody.
Figure 64B:
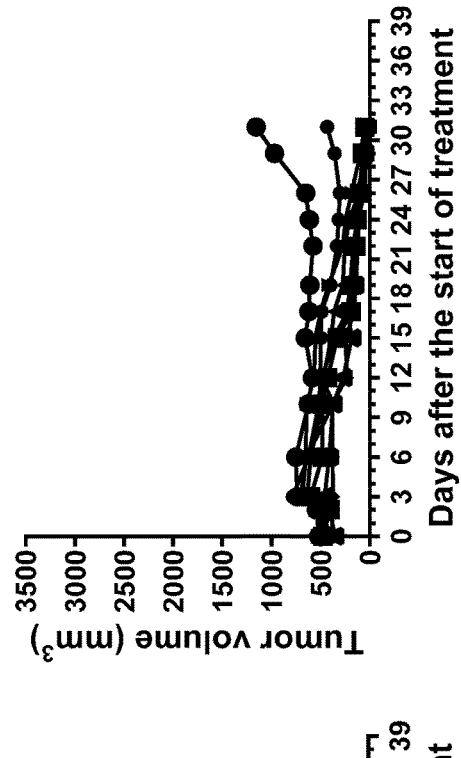
Figure 64C:
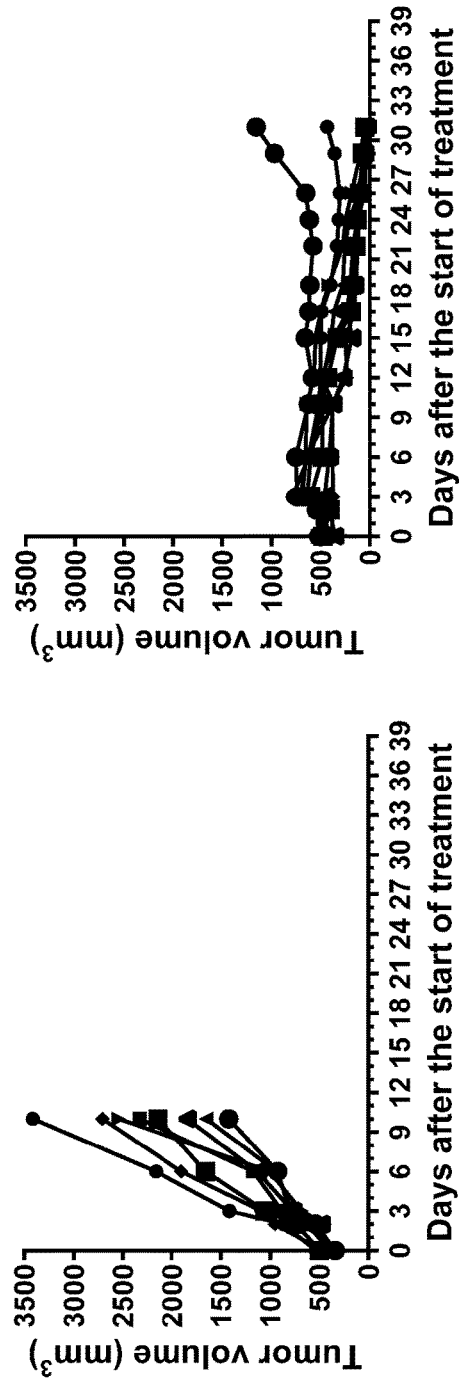
Figure 64D:
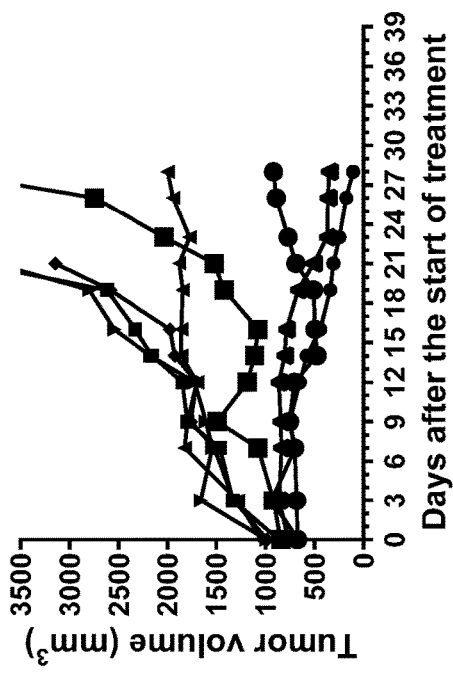

As shown in FIG. 64A for group averaged tumor growth and FIGS. 64B-64D for individual tumor growth, significant regression of the established large H22 tumors was observed in both TY21580 treatment groups (i.e., groups where treatment began when tumors reached a size of either ~500 mm$^3$ as depicted in FIGS. 64A and 64C or ~800 mm$^3$ as depicted in FIGS. 64A and 64D) as compared to the isotype control antibody treatment group (FIGS. 64A and 64B). These results demonstrate the striking efficacy of TY21580 in the suppression of large established tumors.

Example 20: Effect of the Length of Masking Peptides on Masking Efficiency

Two activatable antibodies, TY22402 and TY22404, were chosen to test the dependence of masking efficiency on the length of masking peptides to suit their specific applications. The masking peptides of TY22402 and TY22404 were shortened from 21 residues to 16 or 12 residues by removing the residues from the N-terminus, leaving only 5 or 2 residues before the first cysteine residue in the masking peptide (Table 26). These activatable antibodies were expressed and purified from mammalian cells and their masking efficiencies were measured as described in Example 8 and compared to parent antibody TY21580. Results from two experiments indicated that these activatable antibodies can be made using different masking peptides with lengths ranging from 2 to 11 residues before the first cysteine residue to modulate antibody masking efficiency (FIGS. 65A and 65B; Tables 27 and 28). This seems to suggest that the core masking motif contains the cysteine loop and its immediately adjacent residues, and is sufficient to maintain masking efficiency.

TABLE 26

Masking peptides with varying peptide lengths

| Sample ID: | Masking + cleavage peptide sequences (underlined): |
|---|---|
| TY22402 | EVGSYIVHHSDCDAFYPYCDSSGRSAGGGGTPLGLAGSGGS (SEQ ID NO: 197) |
| TY22775 | EVGHSDCDAFYPYCDSSGRSAGGGGTPLGLAGSGGS (SEQ ID NO: 198) |
| TY22864 | EDCDAFYPYCDSSGRSAGGGGTPLGLAGSGGS (SEQ ID NO: 199) |
| TY22404 | EVGSYPNPSSDCVPYYYACAYSGRSAGGGGTPLGLAGSGGS (SEQ ID NO: 200) |
| TY22776 | EVGSSDCVPYYYACAYSGRSAGGGGTPLGLAGSGGS (SEQ ID NO: 201) |
| TY22871 | EDCVPYYYACAYSGRSAGGGGTPLGLAGSGGS (SEQ ID NO: 202) |

Figure 65A:
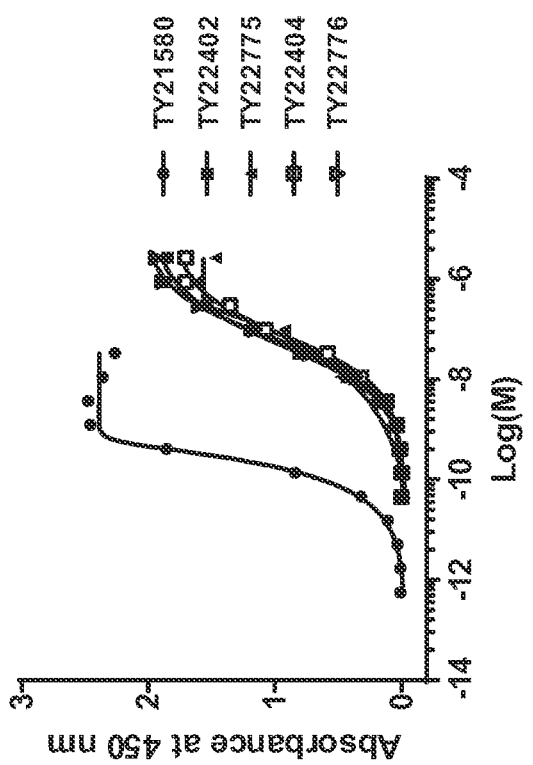
FIGS. 65A and 65B depict masking efficiencies of exemplary activatable antibodies containing masking peptides of variable lengths, as compared to the parental antibody TY21580. Masking efficiencies were determined using ELISA-based methods.
Figure 65B:
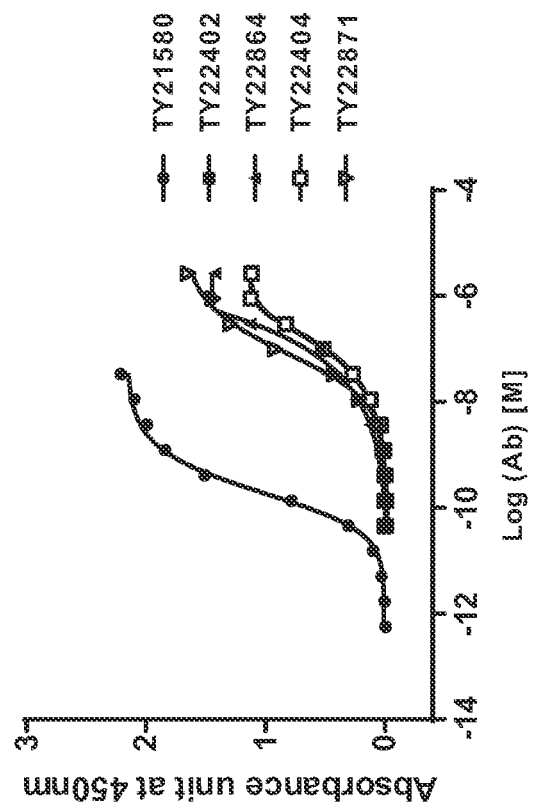

Table 27 shows the masking efficiencies of the antibodies in FIG. 65A. Table 28 shows the masking efficiencies of the antibodies in FIG. 65B.

TABLE 27

Masking efficiencies of antibodies with varying masking peptide lengths

| Sample ID | EC50 (nM) | Masking efficiency |
|---|---|---|
| TY21580 | 0.2223 | |
| TY22402 | 53.99 | 243 |
| TY22775 | 37.31 | 168 |
| TY22404 | 68.40 | 308 |
| TY22776 | 65.90 | 296 |

TABLE 28

Masking efficiencies of antibodies with varying masking peptide lengths

| Sample ID | EC50 (nM) | Masking efficiency |
|---|---|---|
| TY21580 | 0.2125 | |
| TY22402 | 115.6 | 554 |
| TY22864 | 117 | 550 |
| TY22404 | 121.5 | 572 |
| TY22871 | 88.09 | 414 |

Example 21: Effect of the Length of Cleavage Peptides on Masking Efficiency

Figure 66:
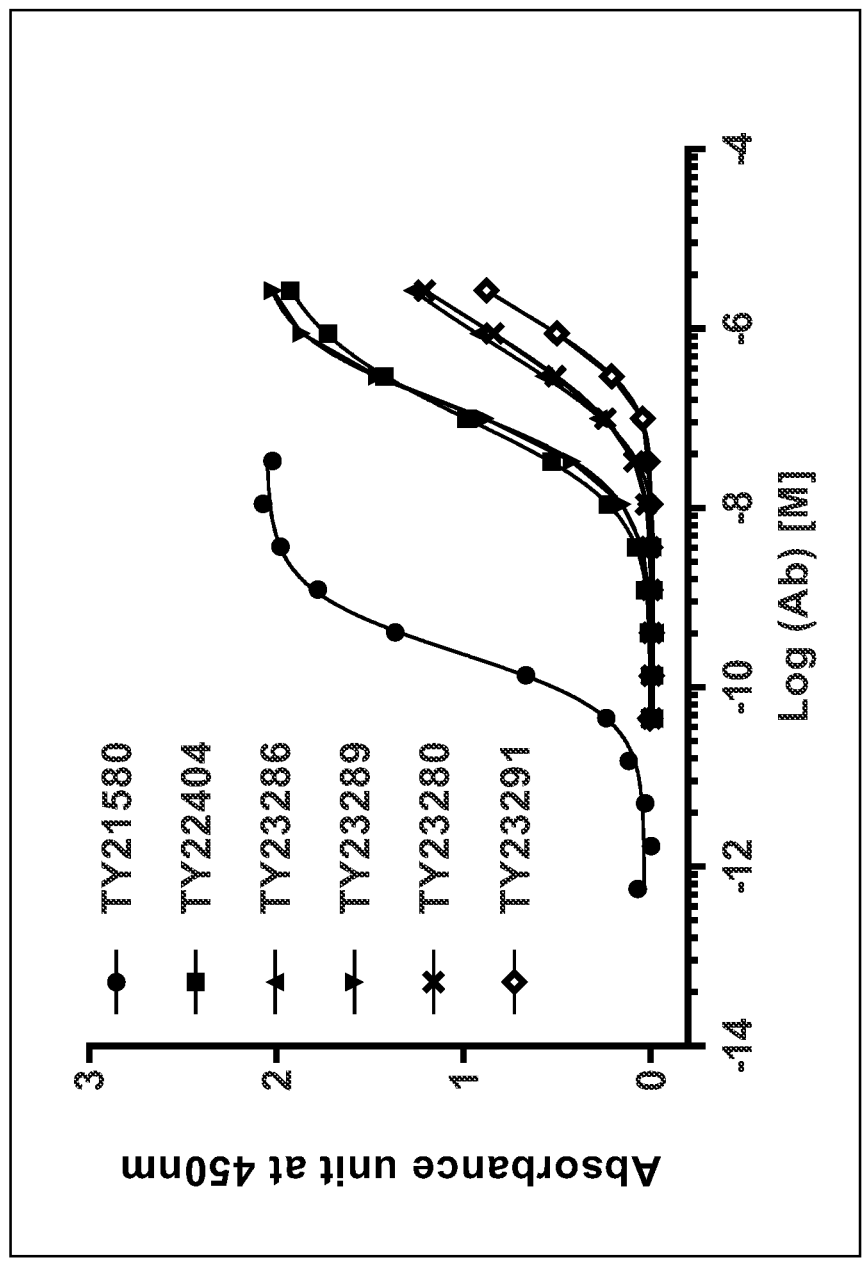
FIG. 66 depicts the masking efficiency of exemplary activatable antibodies containing cleavage peptides of varying lengths, as compared to the parental antibody TY21580. Masking efficiencies were determined using ELISA-based methods.

TY22404 was chosen to test the dependence of masking efficiency on the length of the cleavage peptide to suit their specific applications. The cleavage peptide of TY22404 was shortened to various lengths (Table 29). Activatable antibodies were expressed and purified from mammalian cells, and their masking efficiencies were measured as described in Example 8 and compared to parent antibody TY21580. As shown in FIG. 66 and Table 30, the results indicated that these activatable antibodies can be made using different cleavage peptides with their length ranging from 5 to 20 residues to modulate antibody masking efficiency. The strong correlation between masking and cleavage motifs is striking; the masking efficiency of TY23291 is enhanced at least 30-fold compared to TY22404 when the peptide length is truncated from 41 to 17 amino acids. These results indicate that several novel masking peptides can be designed and engineered. In addition, the coupling between masking and cleavage motifs could be further explored.

TABLE 29

Masking peptides with varying cleavage peptide lengths

| Sample ID | Peptide name | Masking + cleavage peptide sequences (underlined): |
|---|---|---|
| TY22404 | | EVGSYPNPSSDCVPYYYACAYSGRSAGGGGTPLGLAGSGGS (SEQ ID NO: 200) |
| TY23286 | | EVGSYPNPSSDCVPYYYACAYSGRSAPLGLA (SEQ ID NO: 209) |
| TY23289 | | EDCVPYYYACAYSGRSAPLGLA (SEQ ID NO: 210) |
| TY23280 | | EDCVPYYYACAYSGRSA (SEQ ID NO: 211) |

TABLE 29-continued

Masking peptides with varying cleavage peptide lengths

| Sample ID | Peptide name | Masking + cleavage peptide sequences (underlined): |
|---|---|---|
| TY23291 | | EDCVPYYYACAY<u>PLGLA</u> (SEQ ID NO: 212) |

Table 30 shows the masking efficiencies of the antibodies in FIG. 66.

TABLE 30

Masking efficiencies of antibodies with varying cleavage peptide lengths

| Sample ID | EC50 (nM) | Masking efficiency |
|---|---|---|
| TY21580 | 0.2505 | |
| TY22404 | 117.4 | 469 |
| TY23286 | 1496 | 5972 |
| TY23289 | 133.2 | 532 |
| TY23280 | 2952 | 11784 |
| TY23291 | 3656 | 14595 |

What is claimed is:

1. An anti-CTLA4 antibody, wherein the antibody comprises:
   a) an HVR-H1 comprising the amino acid sequence YSITSGYYWAWI (SEQ ID NO: 19), an HVR-H2 comprising the amino acid sequence VSSISGSGSTTYYADSVKGRF (SEQ ID NO: 31), an HVR-H3 comprising the amino acid sequence ARDGFGYFDY (SEQ ID NO: 41), an HVR-L1 comprising the amino acid sequence SASSSVSYVY (SEQ ID NO: 54), an HVR-L2 comprising the amino acid sequence DASSLESGV (SEQ ID NO: 67), and an HVR-L3 comprising the amino acid sequence YCVQGLQTPWT (SEQ ID NO: 71);
   b) an HVR-H1 comprising the amino acid sequence YSISSGYHWSWI (SEQ ID NO: 23), an HVR-H2 comprising the amino acid sequence LARIDWDDDKYYSTSLKSRL (SEQ ID NO: 35), an HVR-H3 comprising the amino acid sequence ARSYVYFDY (SEQ ID NO: 45), an HVR-L1 comprising the amino acid sequence RASQSVRGRFLA (SEQ ID NO: 58), an HVR-L2 comprising the amino acid sequence DASNRATGI (SEQ ID NO: 66), and an HVR-L3 comprising the amino acid sequence YCQQSSSWPPT (SEQ ID NO: 75);
   c) an HVR-H1 comprising the amino acid sequence FTFSGYAIHWV (SEQ ID NO: 26), an HVR-H2 comprising the amino acid sequence IGIISPSGGGTKYAQKFQGRV (SEQ ID NO: 37), an HVR-H3 comprising the amino acid sequence ARHPFAY (SEQ ID NO: 48), an HVR-L1 comprising the amino acid sequence RASQSVDFYGISFLD (SEQ ID NO: 61), an HVR-L2 comprising the amino acid sequence DASNRATGI (SEQ ID NO: 66), and an HVR-L3 comprising the amino acid sequence YCQQYVSSPPEYT (SEQ ID NO: 78);
   d) an HVR-H1 comprising the amino acid sequence YTFSGYAIHWV (SEQ ID NO: 28), an HVR-H2 comprising the amino acid sequence IGIISPSGGGTKYAQKFQGRV (SEQ ID NO: 37), an HVR-H3 comprising the amino acid sequence ARLYDVAY (SEQ ID NO: 50), an HVR-L1 comprising the amino acid sequence RASQSVDFHGKSFLH (SEQ ID NO: 63), an HVR-L2 comprising the amino acid sequence DASSLESGV (SEQ ID NO: 67), and an HVR-L3 comprising the amino acid sequence of YCEQSLEVPFT (SEQ ID NO: 80); or
   e) an HVR-H1 comprising the amino acid sequence FTFSDYAIHWV (SEQ ID NO: 18), an HVR-H2 comprising the amino acid sequence IGIISPSGGSTKYAQKFQGRV (SEQ ID NO: 38), an HVR-H3 comprising the amino acid sequence ARLGYGYFDV (SEQ ID NO: 51), an HVR-L1 comprising the amino acid sequence RASQSVDFYGISFLH (SEQ ID NO: 64), an HVR-L2 comprising the amino acid sequence DASSLESGV (SEQ ID NO: 67), and an HVR-L3 comprising the amino acid sequence YCVQALQLPLT (SEQ ID NO: 81).

2. The antibody of claim 1, wherein the antibody binds to human CTLA4, cynomolgus monkey CTLA4, mouse CTLA4, rat CTLA4, and dog CTLA4 with a dissociation constant ($K_D$) of about 350 nM or less.

3. The antibody of claim 2, wherein the $K_D$ is measured by surface plasmon resonance (SPR).

4. The antibody of claim 1, wherein binding of the anti-CTLA4 antibody induces antibody-dependent cell cytotoxicity (ADCC) against a CTLA4-expressing human cell or a human Treg cell, wherein the ADCC activity of the anti-CTL4 antibody is higher than the ADCC activity of ipilimumab.

5. The antibody of claim 1, wherein (a) the antibody specifically binds to an epitope comprising amino acid residues Y105 and L106 of human CTLA4 but does not comprise residue I108, wherein the numbering of the amino acid residues is according to SEQ ID NO: 207; and/or (b) the anti-CTLA4 antibody has an IC50 higher than the IC50 of ipilimumab for blocking binding of CD80 and/or CD86 to human CTLA4 in an assay wherein either when CD80 and/or CD86 are plate bound or when human CTLA4 protein is present on cell surface.

6. The antibody of claim 1, wherein the antibody comprises:
   a) a heavy chain variable region comprising the amino acid sequence of SEQ ID NO: 83, and a light chain variable region comprising the amino acid sequence of SEQ ID NO: 96;
   b) a heavy chain variable region comprising the amino acid sequence of SEQ ID NO: 87, and a light chain variable region comprising the amino acid sequence of SEQ ID NO: 100;
   c) a heavy chain variable region comprising the amino acid sequence of SEQ ID NO: 90, and a light chain variable region comprising the amino acid sequence of SEQ ID NO: 103;
   d) a heavy chain variable region comprising the amino acid sequence of SEQ ID NO: 92, and a light chain variable region comprising the amino acid sequence of SEQ ID NO: 105; or
   e) a heavy chain variable region comprising the amino acid sequence of SEQ ID NO: 93, and a light chain variable region comprising the amino acid sequence of SEQ ID NO: 106.

7. The antibody of claim 1, wherein the antibody is a human antibody.

8. The antibody of claim 1, wherein the antibody is an antibody fragment selected from the group consisting of a Fab, Fab', Fab'-SH, F(ab')$_2$, Fv and scFv fragment.

9. The antibody of claim 1, wherein the antibody comprises a human IgG1, IgG2, IgG3, or IgG4 Fc region.

10. A polynucleotide encoding the antibody of claim 1.

11. A polynucleotide comprising a sequence selected from the group consisting of SEQ ID NOS: 108-133.

12. A vector comprising the polynucleotide of claim 10.

13. A host cell comprising the polynucleotide of claim 10.

14. A pharmaceutical composition comprising the antibody of claim 1 and a pharmaceutically acceptable carrier.

15. The antibody of claim 1, wherein the antibody comprises an HVR-H1 comprising the amino acid sequence FTFSDYAIHWV (SEQ ID NO: 18), an HVR-H2 comprising the amino acid sequence IGIISPSGGST-KYAQKFQGRV (SEQ ID NO: 38), an HVR-H3 comprising the amino acid sequence ARLGYGYFDV (SEQ ID NO: 51), an HVR-L1 comprising the amino acid sequence RASQSVDFYGISFLH (SEQ ID NO: 64), an HVR-L2 comprising the amino acid sequence DASSLESGV (SEQ ID NO: 67), and an HVR-L3 comprising the amino acid sequence YCVQALQLPLT (SEQ ID NO: 81).

16. The antibody of claim 1, wherein the antibody comprises an HVR-H1 comprising the amino acid sequence YSITSGYYWAWI (SEQ ID NO: 19), an HVR-H2 comprising the amino acid sequence VSSISGSGSTTYY-ADSVKGRF (SEQ ID NO: 31), an HVR-H3 comprising the amino acid sequence ARDGFGYFDY (SEQ ID NO: 41), an HVR-L1 comprising the amino acid sequence SASSSVSYVY (SEQ ID NO: 54), an HVR-L2 comprising the amino acid sequence DASSLESGV (SEQ ID NO: 67), and an HVR-L3 comprising the amino acid sequence YCVQGLQTPWT (SEQ ID NO: 71).

17. The antibody of claim 1, wherein the antibody comprises an HVR-H1 comprising the amino acid sequence YSISSGYHWSWI (SEQ ID NO: 23), an HVR-H2 comprising the amino acid sequence LARIDWDDDKYYST-SLKSRL (SEQ ID NO: 35), an HVR-H3 comprising the amino acid sequence ARSYVYFDY (SEQ ID NO: 45), an HVR-L1 comprising the amino acid sequence RASQSVR-GRFLA (SEQ ID NO: 58), an HVR-L2 comprising the amino acid sequence DASNRATGI (SEQ ID NO: 66), and an HVR-L3 comprising the amino acid sequence YCQQSSSWPPT (SEQ ID NO: 75).

18. The antibody of claim 1, wherein the antibody comprises an HVR-H1 comprising the amino acid sequence FTFSGYAIHWV (SEQ ID NO: 26), an HVR-H2 comprising the amino acid sequence IGIISPSGGGT-KYAQKFQGRV (SEQ ID NO: 37), an HVR-H3 comprising the amino acid sequence ARHPFAY (SEQ ID NO: 48), an HVR-L1 comprising the amino acid sequence RASQSVDFYGISFLD (SEQ ID NO: 61), an HVR-L2 comprising the amino acid sequence DASNRATGI (SEQ ID NO: 66), and an HVR-L3 comprising the amino acid sequence YCQQYVSSPPEYT (SEQ ID NO: 78).

19. The antibody of claim 1, wherein the antibody comprises an HVR-H1 comprising the amino acid sequence YTFSGYAIHWV (SEQ ID NO: 28), an HVR-H2 comprising the amino acid sequence IGIISPSGGGT-KYAQKFQGRV (SEQ ID NO: 37), an HVR-H3 comprising the amino acid sequence ARLYDVAY (SEQ ID NO: 50), an HVR-L1 comprising the amino acid sequence RASQSVDFHGKSFLH (SEQ ID NO: 63), an HVR-L2 comprising the amino acid sequence DASSLESGV (SEQ ID NO: 67), and an HVR-L3 comprising the amino acid sequence of YCEQSLEVPFT (SEQ ID NO: 80).

20. The antibody of claim 1, wherein the antibody comprises a heavy chain variable region comprising the amino acid sequence of SEQ ID NO: 83, and a light chain variable region comprising the amino acid sequence of SEQ ID NO: 96.

21. The antibody of claim 1, wherein the antibody comprises a heavy chain variable region comprising the amino acid sequence of SEQ ID NO: 87, and a light chain variable region comprising the amino acid sequence of SEQ ID NO: 100.

22. The antibody of claim 1, wherein the antibody comprises a heavy chain variable region comprising the amino acid sequence of SEQ ID NO: 90, and a light chain variable region comprising the amino acid sequence of SEQ ID NO: 103.

23. The antibody of claim 1, wherein the antibody comprises a heavy chain variable region comprising the amino acid sequence of SEQ ID NO: 92, and a light chain variable region comprising the amino acid sequence of SEQ ID NO: 105.

24. The antibody of claim 1, wherein the antibody a heavy chain variable region comprising the amino acid sequence of SEQ ID NO: 93, and a light chain variable region comprising the amino acid sequence of SEQ ID NO: 106.

25. The antibody of claim 1, wherein the antibody comprises a human IgG1 Fc region comprising one or more mutations that increase antibody-dependent cellular cytotoxicity (ADCC) activity.

26. The antibody of claim 17, wherein the antibody comprises a human IgG1 Fc region comprising one or more mutations that increase antibody-dependent cellular cytotoxicity (ADCC) activity.

27. A method of treating or delaying progression of cancer in a subject in need thereof, the method comprising administering to the subject an effective amount of the antibody of claim 1.

28. A method of reducing size of a solid tumor in a subject in need thereof, wherein the solid tumor has a size of about 400-1000 mm³, the method comprises administering to the subject an effective amount of the antibody of claim 1.

* * * * *